US012589162B2

(12) United States Patent
Mejia Oneto et al.

(10) Patent No.: US 12,589,162 B2
(45) Date of Patent: Mar. 31, 2026

(54) TRANS-CYCLOOCTENE PRODRUG OF MONOMETHYL AURISTATIN E

(71) Applicant: TAMBO, INC., San Franciscso, CA (US)

(72) Inventors: Jose Manuel Mejia Oneto, San Francisco, CA (US); Nathan A. Yee, San Francisco, CA (US); Jesse M. McFarland, San Francisco, CA (US)

(73) Assignee: Tambo, Inc., San Francisco, CA (US)

( * ) Notice: Subject to any disclaimer, the term of this patent is extended or adjusted under 35 U.S.C. 154(b) by 589 days.

(21) Appl. No.: 18/020,221

(22) PCT Filed: Aug. 6, 2021

(86) PCT No.: PCT/US2021/045100
§ 371 (c)(1),
(2) Date: Feb. 7, 2023

(87) PCT Pub. No.: WO2022/032191
PCT Pub. Date: Feb. 10, 2022

(65) Prior Publication Data
US 2023/0256109 A1 Aug. 17, 2023

Related U.S. Application Data

(60) Provisional application No. 63/062,814, filed on Aug. 7, 2020.

(51) Int. Cl.
*A61K 47/68* (2017.01)
*A61K 47/06* (2006.01)
*A61K 47/54* (2017.01)
*A61K 47/64* (2017.01)
*A61P 35/00* (2006.01)

(52) U.S. Cl.
CPC .............. *A61K 47/68* (2017.08); *A61K 47/06* (2013.01); *A61K 47/542* (2017.08); *A61K 47/642* (2017.08); *A61P 35/00* (2018.01)

(58) Field of Classification Search
CPC ...... A61K 47/68; A61K 47/06; A61K 47/542; A61K 47/642
See application file for complete search history.

(56) References Cited

U.S. PATENT DOCUMENTS

| | | | |
|---|---|---|---|
| 4,689,338 | A | 8/1987 | Gerster |
| 5,770,229 | A | 6/1998 | Tanihara et al. |
| 8,552,183 | B2 | 10/2013 | Wiessler et al. |
| 9,421,274 | B2 | 8/2016 | Robillard et al. |
| 9,427,482 | B2 | 8/2016 | Rossin et al. |
| 9,463,256 | B2 | 10/2016 | Lub et al. |
| 10,046,002 | B2 | 8/2018 | Zebala et al. |
| 10,130,711 | B2 | 11/2018 | Mejia Oneto et al. |
| 10,130,723 | B2 | 11/2018 | Mejia Oneto et al. |
| 10,342,882 | B2 | 7/2019 | Mejia Oneto et al. |
| 10,487,149 | B2 | 11/2019 | Geall et al. |
| 10,806,807 | B2 | 10/2020 | Mejia Oneto et al. |
| 10,828,373 | B2 | 11/2020 | Mejia Oneto et al. |
| 11,253,600 | B2 | 2/2022 | Mejia Oneto et al. |
| 2003/0191291 | A1 | 10/2003 | Kochendoerfer et al. |
| 2005/0014197 | A1 | 1/2005 | Agnew et al. |
| 2006/0153893 | A1 | 7/2006 | Matsuno et al. |
| 2007/0048302 | A1 | 3/2007 | Theze et al. |
| 2008/0014222 | A1 | 1/2008 | Simmons et al. |
| 2009/0023916 | A1 | 1/2009 | Fox et al. |
| 2009/0304587 | A1 | 12/2009 | Rubinstein et al. |
| 2010/0016545 | A1 | 1/2010 | Wiessler et al. |
| 2010/0028435 | A1 | 2/2010 | Gavard Molliard |
| 2011/0223257 | A1 | 9/2011 | Zhao et al. |
| 2011/0268654 | A1 | 11/2011 | Hilderbrand et al. |
| 2011/0293565 | A1 | 12/2011 | Kandimalla et al. |
| 2011/0311518 | A1 | 12/2011 | Kandimalla et al. |
| 2012/0034161 | A1 | 2/2012 | Robillard et al. |
| 2012/0076727 | A1 | 3/2012 | McBride et al. |
| 2013/0281644 | A1 | 10/2013 | Kiessling et al. |
| 2013/0302246 | A1 | 11/2013 | Hilderbrand et al. |
| 2014/0093450 | A1 | 4/2014 | Robillard et al. |
| 2014/0199331 | A1 | 7/2014 | Robillard et al. |
| 2014/0205653 | A1 | 7/2014 | Dubensky, Jr. et al. |
| 2014/0303123 | A1 | 10/2014 | Baker, Jr. et al. |
| 2015/0037359 | A1 | 2/2015 | Schellenberger et al. |
| 2015/0218274 | A1 | 8/2015 | Sabatos-peyton et al. |
| 2015/0259420 | A1 | 9/2015 | Triebel et al. |
| 2016/0114046 | A1 | 4/2016 | Brudno et al. |
| 2016/0120987 | A1 | 5/2016 | Mejia Oneto et al. |

(Continued)

FOREIGN PATENT DOCUMENTS

| | | | |
|---|---|---|---|
| CN | 110496233 | A | 11/2019 |
| EP | 1867638 | A1 | 12/2007 |

(Continued)

OTHER PUBLICATIONS

Kharkar et al., "Designing degradable hydrogels for orthogonal control of cell microenvironments," Chem. Soc. Rev., vol. 42, No. 17, pp. 7335-7372 (2013).
Kojima et al., "Antitumor activity of timed-release derivative of mitomycin C, agarose bead conjugate," Chem Pharm Bull, 1978, 26(6): 1818-1824.
Koo et al., "Bioorthogonal Copper-Free Click Chemistry In Vivo for Tumor-Targeted Delivery of Nanoparticles," Angew. Chem. Int. Ed., 2012, vol. 51, pp. 11836-11840.
Korpela et al., "A simple method to introduce aldehydic function to agarose," Anal Biochem, 1976, 71 (1):322-323.

(Continued)

*Primary Examiner* — Andrea Olson
*Assistant Examiner* — Benjamin M Brandsen
(74) *Attorney, Agent, or Firm* — Michael Best & Friedrich LLP

(57) ABSTRACT 6-(Carbonyloxy)-1-methylcyclooct-4-ene-1-carbonyl)-aspartic acid conjugate of monomethyl auristatin E may be used for bioorthogonal delivery to a targeted location in a subject in the treatment of cancer and tumor growths.

4 Claims, 1 Drawing Sheet

Specification includes a Sequence Listing.

(56) References Cited

U.S. PATENT DOCUMENTS

| | | | |
|---|---|---|---|
| 2016/0287623 A1 | 10/2016 | Gajewski et al. |
| 2017/0044206 A1 | 2/2017 | Altman et al. |
| 2017/0087258 A1 | 3/2017 | Oneto et al. |
| 2017/0095580 A1 | 4/2017 | Mejia Oneto et al. |
| 2017/0189581 A1 | 7/2017 | Desai et al. |
| 2017/0233430 A1 | 8/2017 | Adams et al. |
| 2017/0333552 A1 | 11/2017 | Dubensky, Jr. et al. |
| 2018/0002369 A1 | 1/2018 | Biggadike et al. |
| 2018/0064745 A1 | 3/2018 | Katibah et al. |
| 2018/0092937 A1 | 4/2018 | Oost et al. |
| 2018/0093964 A1 | 4/2018 | Altman et al. |
| 2018/0162899 A1 | 6/2018 | Bignan et al. |
| 2018/0186828 A1 | 7/2018 | Biggadike et al. |
| 2018/0273578 A1 | 9/2018 | Oost et al. |
| 2018/0360979 A1 | 12/2018 | Mejia Oneto et al. |
| 2019/0016750 A1 | 1/2019 | Glick et al. |
| 2019/0062365 A1 | 2/2019 | Katibah et al. |
| 2019/0111163 A1 | 4/2019 | Mejia Oneto et al. |
| 2019/0151345 A1 | 5/2019 | Guiducci et al. |
| 2019/0160173 A1 | 5/2019 | Gryaznov et al. |
| 2019/0183917 A1 | 6/2019 | Birkus et al. |
| 2019/0185509 A1 | 6/2019 | Birkus et al. |
| 2019/0185510 A1 | 6/2019 | Birkus et al. |
| 2019/0185511 A1 | 6/2019 | Kanne et al. |
| 2019/0192549 A1 | 6/2019 | Yoshikawa et al. |
| 2021/0015932 A1 | 1/2021 | Mejia Oneto et al. |
| 2021/0128733 A1 | 5/2021 | Mejia Oneto et al. |
| 2022/0105191 A1 | 4/2022 | Mejia Oneto et al. |
| 2022/0168426 A1 | 6/2022 | Mejia Oneto et al. |
| 2022/0259254 A1 | 8/2022 | Mejia Oneto et al. |

FOREIGN PATENT DOCUMENTS

| | | | |
|---|---|---|---|
| EP | 2017281 | A1 | 1/2009 |
| EP | 2716662 | A1 | 4/2014 |
| EP | 2719400 | A2 | 4/2014 |
| JP | 2009513696 | A | 4/2009 |
| JP | 2010036032 | A | 2/2010 |
| WO | 2002098883 | A1 | 12/2002 |
| WO | 2003000708 | A1 | 1/2003 |
| WO | 2003084571 | A1 | 10/2003 |
| WO | 2004103272 | A2 | 12/2004 |
| WO | 2009064738 | A2 | 5/2009 |
| WO | 2010051530 | A2 | 5/2010 |
| WO | 2011095336 | A2 | 8/2011 |
| WO | 2011127149 | A1 | 10/2011 |
| WO | 2012012612 | A2 | 1/2012 |
| WO | 2012049624 | A1 | 4/2012 |
| WO | 2012074840 | A2 | 6/2012 |
| WO | 2012085789 | A1 | 6/2012 |
| WO | 2012153254 | A1 | 11/2012 |
| WO | 2012156918 | A1 | 11/2012 |
| WO | 2012156919 | A1 | 11/2012 |
| WO | 2012156920 | A1 | 11/2012 |
| WO | 2012165462 | A1 | 12/2012 |
| WO | 2012168512 | A2 | 12/2012 |
| WO | 2013187954 | A1 | 12/2013 |
| WO | 2014065860 | A1 | 5/2014 |
| WO | 2014081299 | A1 | 5/2014 |
| WO | 2014081300 | A1 | 5/2014 |
| WO | 2014081301 | A1 | 5/2014 |
| WO | 2014081303 | A1 | 5/2014 |
| WO | 2014117001 | A1 | 7/2014 |
| WO | 2014138186 | A1 | 9/2014 |
| WO | 2014189806 | A1 | 11/2014 |
| WO | 2014200767 | A1 | 12/2014 |
| WO | 2014205126 | A1 | 12/2014 |
| WO | 2014134689 | A1 | 8/2015 |
| WO | 2015117235 | A1 | 8/2015 |
| WO | 2015139025 | A1 | 9/2015 |
| WO | 2015154082 | A1 | 10/2015 |
| WO | 2016014799 | A1 | 1/2016 |
| WO | 2017004192 | A1 | 6/2016 |
| WO | 2017044983 | A1 | 3/2017 |
| WO | 2018009648 | A1 | 1/2018 |
| WO | 2018009652 | A1 | 1/2018 |
| WO | 2018013887 | A1 | 1/2018 |
| WO | 2018013908 | A1 | 1/2018 |
| WO | 2018100558 | A2 | 6/2018 |
| WO | 2018118665 | A1 | 6/2018 |
| WO | 2018138684 | A1 | 8/2018 |
| WO | 2018138685 | A2 | 8/2018 |
| WO | 2018187740 | A1 | 10/2018 |
| WO | 2018198076 | A1 | 11/2018 |
| WO | 2018208667 | A1 | 11/2018 |
| WO | 2018234805 | A1 | 12/2018 |
| WO | 2018234807 | A1 | 12/2018 |
| WO | 2018234808 | A1 | 12/2018 |
| WO | 2019027858 | A1 | 2/2019 |
| WO | 2019046511 | A1 | 3/2019 |
| WO | 2019051488 | A1 | 3/2019 |
| WO | 2019051489 | A1 | 3/2019 |
| WO | 2019092660 | A1 | 5/2019 |
| WO | 2019115402 | A1 | 6/2019 |
| WO | 2019118839 | A1 | 6/2019 |
| WO | 2019125974 | A1 | 6/2019 |
| WO | 2021007160 | A1 | 1/2021 |

OTHER PUBLICATIONS

Koshy et al., "Click-Crosslinked Injectable Gelatin Hydrogels," Advanced Healthcare Materials, 2016, DOI: 10.1002/adhm.201500757, 7 pages.

Kroemer, G., et al. "Immunogenic cell death in cancer therapy." Annual review of immunology 31 (2013): 51-72.

Landa et al., "Effect of Injectable Alginate Implant on Cardiac Remodeling and Function After Recent and Old Infarcts in Rat," Circulation, 2008, vol. 117, pp. 1388-1396.

Li et al., "Designing hydrogels for controlled drug delivery," Nature Reviews Materials, 2016, 1(12): 38 pages.

Li et al., "Diels-Alder reaction-triggered bioorthogonal protein decaging in living cells," Natural Chemical Biology, Advanced Online Publication, 2014, vol. 10, 5 pages.

Li et al., "Monodispersed PEG-DOTA Conjugated Anti-Tag-72 Diabody Has Low Kidney Uptake and High Tumor to Blood Ratios Resulting in Inproved 64Cu PET Imaging," J. Nucl. Med., 2010, vol. 51, No. 7, pp. 1139-1146.

Li, A., et al. "Activating cGAS-STING pathway for the optimal effect of cancer immunotherapy." Journal of hematology & oncology 12.1 (2019): 1-12.

Lucey, D.R. et al. "Type 1 and type 2 cytokine dysregulation in human infectious, neoplastic, and inflammatory diseases." Clinical microbiology reviews 9.4 (1996): 532-562.

Lueckgen et al., "Hydrolytically-degradable click-crosslinked alginate hydrogels," Biomaterials, 2018, 181: 189-198.

Maggi, A., et al. "Development of a novel antibody-tetrazine conjugate for bioorthogonal pretargeting." Organic & Biomolecular Chemistry 14.31 (2016): 7544-7551.

Matikonda et al., "Bioorthogonal prodrug activation driven by a strain-promoted 1,3-dipolar cycloaddition," Chem. Sci., 2015, vol. 6, pp. 1212-1218.

Medler, T.R. et al. "Immune response to cancer therapy: mounting an effective antitumor response and mechanisms of resistance." Trends in cancer 1.1 (2015): 66-75.

Mejia Oneto et al., "Implantable biomaterial based on click chemistry for targeting small molecules," Acta Biomaterialia, 2014, vol. 10, pp. 5099-5105.

Mejia Oneto et al: In Vivo Bioorthogonal Chemistry Enables Local Hydrogel and Systemic Pro-Drug to Treat Soft Tissue Sarcoma11 , ACS Central Science, vol. 2, No. 7, Jul. 13, 2016 (Jul. 13, 2016), pp. 476-482.

Molica Poeta, V. et al. "Chemokines and chemokine receptors: new targets for cancer immunotherapy." Frontiers in immunology 10 (2019): 379.

Nejadmoghaddam, M.-R., et al. "Antibody-drug conjugates: possibilities and challenges." Avicenna journal of medical biotechnology 11.1 (2019): 3-23.

(56) References Cited

OTHER PUBLICATIONS

Neves et al., "Imaging Cell Surface Glycosylation in Vivo Using "Double Click" Chemistry," Bioconjugate Chem., May 5, 2013, vol. 24, pp. 934-941.
Niska et al., "Vancomycin-rifampin combination therapy has enhanced efficacy against an experimental *Staphylococcus aureus* prosthetic joint infection," Antimicrob Agents Chemother, 2013, 57(10):5080-5086.
Patterson et al., "Finding the Right (Bioorthogonal) Chemistry," ACS Chem. Biol., 2014, vol. 9, pp. 592-605.
Pretze et al., "Recent Trends in Bioorthogonal Click-Radiolabeling Reactions Using Fluorine-18," Molecules, vol. 18, 2013, pp. 8618-8665; doi:I0.3390/molecules18078618.
Ravasi, T., et al. (2007). Systems biology of transcription control in macrophages. Bioessays, 29(12), 1215-1226.
Reiner et al., "The inverse electron demand Diels-Alder click reaction in radiochemistry," J. Labelled Comp. Radiopharm., 2014, vol. 57, No. 4, pp. 285-290.
Roach, J. C., et al. "Transcription factor expression in lipopolysaccharide-activated peripheral-blood-derived mononuclear cells." Proceedings of the National Academy of Sciences 104.41 (2007): 16245-16250.
Roers, A. et al. "Recognition of endogenous nucleic acids by the innate immune system." Immunity 44.4 (2016): 739-754.
Rohatagi et al., "Pharmacokinetic and Pharmacodynamic Evaluation of Triamcinolone Acetonide After Intravenous, Oral, and Inhaled Administration," J. Clin. Pharmacol., 1995, 35: 1187-1193.
Rondon, A. et al. "Antibody pretargeting based on bioorthogonal click chemistry for cancer imaging and targeted radionuclide therapy." Bioconjugate Chemistry 31.2 (2019): 159-173.
Rossin et al., "Chemically triggered drug release from an antibody-drug conjugate leads to potent antitumour activity in mice," Nat Commun, 2018, 9:1484, Supplementary Information Included, 120 pages.
Rossin et al., "Highly reactive trans-cyclooctene tags with improved stability for Diels-Alder chemistry in living systems." Bioconjugate chemistry 24.7 (2013): 1210-1217.
Rossin et al., "In vivo chemistry for pretargeted tumor imaging in live mice." Angewandte Chemie 122.19 (2010): 3447-3450.
Rossin et al., "Triggered Drug Release from an Antibody-Drug Conjugate Using Fast "Click-to-Release" Chemistry in Mice," Bioconjugate Chemistry, 2016, vol. 27, pp. 1697-1706.
Rossin et al., Supplementary Information for "Tetrazine-triggered drug release from an antibody-drug conjugate leads to potent antitumour activity in mice," Nat Commun, 2018, 109 pages.
Rossin et al., Supporting Information for "In Vivo Chemistry for Pretargeted Tumor Imagining in Live Mice," Sections S1-S6, pp. S2-S21 (2010).
Royzen et al., "A Photochemical Synthesis of Functionalized trans-Cyclooctenes Driven by Metal Complexation," J. Am. Chem. Soc., vol. 130, pp. 3760-3761 (2008).
Scott, A.M. et al. "Monoclonal antibodies in cancer therapy." Cancer immunity 12.1 (2012) 1-8.
Seif-Naraghi et al., "Safety and Efficacy of an Injectable Extracellular Matrix Hydrogel for Treating Myocardial Infarction," Science Translation Medicine, 2013, vol. 5, Issue 173, 10 pages.
Selvaraj et al., "Tetrazine-tans-cyclooctene ligation for the rapid construction of integrin avβ3 targeted PET tracer based on a cyclic RGD peptide," Bioorg. Med. Chem. Lett., 2011; 21 (17), pp. 5011-5014; doi:10.1016/j.bmcl.2011.04.116.
Selvaraj et al., "trans-Cyclooctene—a stable, voracious dienophile for bioorthogonal labeling", Current Opinion in Chemical Biology, vol. 17, Issue 5, 2013, pp. 753-760; doi: 10.1016/j.cbpa.2013.07.031.
Shelke et al., "Polysaccharide biomaterials for drug delivery and regenerative engineering," Polym. Adv. Technol., 2014, vol. 25, pp. 448-460.
Shuyi, Y., et al. "A critical role of CCR7 in invasiveness and metastasis of SW620 colon cancer cell in vitro and in vivo." Cancer biology & therapy 7.7 (2008): 1037-1043.
Sluyterman et al., "Chromatofocusing: a preparative protein separation method," TIBS, 1982, pp. 168-170.
Strieter, R. M., et al. "The functional role of the ELR motif in CXC chemokine-mediated angiogenesis." Journal of Biological Chemistry 270.45 (1995): 27348-27357.
Tamamis, P. et al. "Elucidating a key component of cancer metastasis: CXCL12 (SDF-1α) binding to CXCR4." Journal of chemical information and modeling 54.4 (2014): 1174-1188.
Tesniere et al., "Immunogenic cancer cell deaths: a key-lock paradigm", Curr. Op. Immunol, 2008, vol. 20, pp. 504-511.
Thalhammer et al., "Reaktivitat Einfacher Offenkettiger Und Cyclischer Dienophile Bei Diels-Alder-Reaktionen Mit Inversem Elektronenbedarf," Tetrahedron Letters, 1990, vol. 31, No. 47, pp. 6851-6854.
ThermoFisher Scientific. Sulfhyryl-reactive Crosslinker Chemistry. Article. Version dated Apr. 1, 2020. Available online at See https://wwhttps://web.archive.org/web/20200401201454/https://www.thermofisher.com/us/en/home/life-science/protein-biology/protein-biology-learning-center/protein-biology-resource-library/pierce-protein-methods/sulfhydryl-reactive-crosslinker-chemistry.html (8 pages).
Thomas et al., "Polyvalent Dendrimer-Methotrexate as a Folate Receptor-Targeted Cancer Therapeutic" Molecular Pharmaceutics, 2012, vol. 9 pp. 2669-2676.
Al-Dubai et al., "Biocompatible medical implant materials with binding sites for a biodegradable drug-delivery system," Nanotechnology, Science and Applications, vol. 2011, No. 4, pp. 87-94 (2011).
Alge et al., "Synthetically tractable click hydrogels for three-dimensional cell culture formed using tetrazine-norbornene chemistry," Biomacromolecules, 2013, 14(4):949-953.
Altin et al., "Fabrication of "Clickable" Hydrogels via Dendron-Polymer Conjugates," Macromolecules, 2010, vol. 43, No. 8, pp. 3801-3808.
Antoci et al., "The inhibition of *Staphylococcus epidermidis* biofilm formation by vancomycin-modified titanium alloy and implications for the treatment of periprosthetic infection," Biomaterials, vol. 29, pp. 4684-4690 (2008).
Arenberg, D. A., et al. "Epithelial-neutrophil activating peptide (ENA-78) is an important angiogenic factor in non-small cell lung cancer." The Journal of clinical investigation 102.3 (1998): 465-472.
Arenberg, D. A., et al. "Inhibition of interleukin-8 reduces tumorigenesis of human non-small cell lung cancer in SCID mice." The Journal of clinical investigation 97.12 (1996): 2792-2802.
Barber GN. Sting: infection, inflammation and cancer. Nat Rev Immunol. 2015; 15(12):760-770.
Berge et al., "Pharmaceutical Salts," J. Pharm. Sci., 1977, vol. 66, pp. 1-19.
Berger, G. et al. "Pharmacological modulation of the Sting pathway for cancer immunotherapy." Trends in molecular medicine 25.5 (2019): 412-427.
Berraondo, P., et al. "Cytokines in clinical cancer immunotherapy." British journal of cancer 120.1 (2019): 6-15.
Blackman et al., "Tetrazine Ligation: Fast Bioconjugation Based on Inverse-Electron-Demand Diels-Alder Reactivity," J. Am. Chem. Soc., 2008, vol. 130, pp. 13518-13519.
Brinton, L. T., et al. "Metastatic biomarker discovery through proteomics." Cancer genomics & proteomics 9.6 (2012): 345-355.
Brudno et al., "In Vivo Targeting through Click Chemistry," Chem. Med. Chem., 2015, vol. 10, pp. 617-620.
Brudno et al., "On-demand drug delivery from local depots," J. Control. Release, 2015, http://dx.doi.org/10.1016/j.jconrel.2015.09.011, 10 pages.
Brudno et al., "Refilling drug delivery depots through the blood," PNAS, 2014, 111(35): 12722-12727.
Brudno et al., "Replenishable drug depot to combat post-resection cancer recurrence," Biomaterials, 2018, 178:373-382.
Burdick et al., "Acellular Biomaterials: An Evolving Alternative to Cell-Based Therapies," Science Translation Medicine, Mar. 13, 2013, vol. 5, Issue 176, 4 pages.

(56) References Cited

OTHER PUBLICATIONS

Carlson et al., "Unraveling Tetrazine-Triggered Bioorthogonal Elimination Enables Chemical Tools for Ultrafast Release and Universal Cleavage," J. Am. Chem. Soc., 2018, 140(10):3603-3612.
Chi, B.-J., et al. "Silencing of CCR7 inhibits the growth, invasion and migration of prostate cancer cells induced by VEGFC." International journal of clinical and experimental pathology 8.10 (2015): 12533.
Chung et al., "Ubiquitous Detection of Gram-Positive Bacteria with Bioorthogonal Magnetofluorescent Nanoparticles," ACS Nano, 2011, vol. 5, No. 11, pp. 8834-8841, Supporting Documentation Included.
Click Chemistry Tools. Sulfhydryl Reactive. Version dated Sep. 27, 2020. Available online at https://web.archive.org/web/20200927065750/https://clickchemistrytools.com/product-category/tco-reagents/sulfhydryl-reactive-tco-reagents/ (1 page).
Cok et al., "Synthesis of Model Network Hydrogels via Tetrazine-Olefin Inverse Electron Demand Diels-Alder Cycloaddition," Macromol Symp, 2013, 329:108-112.
Coviello et al., "Polysaccharide hydrogels for modified release formulations," Journal of Controlled Release, 2007, vol. 119, pp. 5-24.
Czuban, M., et al. "Bio-orthogonal chemistry and reloadable biomaterial enable local activation of antibiotic prodrugs and enhance treatments against *Staphylococcus aureus* infections." With Supporting Information, ACS central science 4.12 (2018): 1624-1632.
De Clercq, E . . . "Mozobil®(Plerixafor, AMD3100), 10 years after its approval by the US Food and Drug Administration." Antiviral Chemistry and Chemotherapy 27 (2019): 2040206619829382.
Deforest et al., "Sequential click reactions for synthesizing and patterning three-dimensional cell microenvironments," Nature materials: Letters, 2009, vol. 8, pp. 659-664.
Desai et al., "Versatile click alginate hydrogels crosslinked via tetrazine-norbornene chemistry," Biomaterials, 2015, vol. 50, pp. 30-37.
Devaraj et al., "Fast and Sensitive Pretargeted Labeling of Cancer Cells through a Tetrazine/trans-Cyclooctene Cycloaddition," Angew. Chem. Int. Ed., 2009, vol. 48, pp. 7013-7016.
Devaraj et al., "Reactive polymer enables efficient in vivo bioorthogonal chemistry," PNAS, 2012, vol. 109, No. 13, pp. 4762-4767.
Dondelinger, M., et al. "Understanding the significance and implications of antibody numbering and antigen-binding surface/residue definition." Frontiers in immunology 9 (2018): 2278.
Dougan, S. K., et al. "Regulation of innate and adaptive antitumor immunity by IAP antagonists." Immunotherapy 10.9 (2018): 787-796.
Eckhouse et al., "Local Hydrogel Release of Recombinant TIMP-3 Attenuates Adverse Left Ventricular Remodeling After Experimental Myocardial Infarction," Science Translation Medicine, 2014, vol. 6, Issue 223, 10 pages.
Eschenhagen et al., "Physiological aspects of cardiac tissue engineering," Am. J. Physiol. Heart Circ. Physiol., vol. 30, 2012, pp. H133-H143.
Fox, E., et al. "Indoximod: an immunometabolic adjuvant that empowers T cell activity in cancer." Frontiers in oncology 8 (2018): 370.
Ganesan, A., et al. "Comprehensive in vitro characterization of PD-L1 small molecule inhibitors." Scientific reports 9.1 (2019): 12392.
Gilchrist, M., et al. "Systems biology approaches identify ATF3 as a negative regulator of Toll-like receptor 4." Nature 441.7090 (2006): 173-178.
Godoy et al., "Enhanced activity of an immobilized lipase promoted by site-directed chemical modification with polymers," Process Biochemistry, 2010, 45(4):534-541.
Guo H. et al: "Functional alginate nanoparticles for efficient intracellular release of doxorubicin and hepatoma carcinoma cell targeting therapy", International Journal of Pharmaceutics, ELS EV I ER, N L, vol. 451, No. 1, Apr. 22, 2013 (Apr. 22, 2013), pp. 1-11.
Haghnegahdar, H., et al. "The tumorigenic and angiogenic effects of MGSA/GRO proteins in melanoma." Journal of leukocyte biology 67.1 (2000): 53-62.
Hashida et al., "Timed-Release of Mitomycin C from Its Agarose Bead Conjugate," Chem Pharm Bull, 1977, 25:2456-2458.
Haun et al., "Bioorthogonal chemistry amplifies nanoparticle binding and enhances the sensitivity of cell detection", Nature Nanotechnology, 2010, vol. 5, No. 9, pp. 660-665.
Hermanto, S., et al. "Molecular dynamic simulation of Trastuzumab F (ab') 2 structure in corporation with HER2 as a theranostic agent of breast cancer." Journal of Physics: Conference Series. vol. 835. No. 1. IOP Publishing, 2017.
Hofmann et al., "Targeted delivery of vancomycin to *Staphylococcus epidermidis* biofilms using a fibrinogen-derived peptide," J Biomed Mater Res A, 2012, 100(9):2517-2525.
Horita, S., et al. "High-resolution crystal structure of the therapeutic antibody pembrolizumab bound to the human PD-1." Scientific reports 6.1 (2016): 35297.
Hu et al., "Mitochondria-Targeted Cancer Therapy Using a Light-Up Probe with Aggregation-Induced-Emission Characteristics," Angew. Chem. Int. Ed., 2014, 53:14225-14229.
Inoue, K., et al. "Interleukin 8 expression regulates tumorigenicity and metastases in androgen-independent prostate cancer." Clinical Cancer Research 6.5 (2000): 2104-2119.
International Preliminary Report on Patentability for Application No. PCT/US2021/045100 dated Feb. 7, 2023 (12 pages).
International Search Report and Written Opinion for Application No. PCT/US2021/045100 dated Nov. 26, 2021 (22 pages).
IUPAC 1974 Recommendations for Section E, Fundamental Stereochemistry, in Pure Appl. Chem., 1976, 45: 13-30.
Ju, G., et al. "Structure-function analysis of human interleukin-2. Identification of amino acid residues required for biological activity." Journal of Biological Chemistry 262.12 (1987): 5723-5731.
TJWA, "Budesonide inhaled via Turbuhaler: a more effective treatment for asthma than beclomethasone dipropionate via Rotahaler," Ann. Allergy Asthma Immunol., 1995, 75(2): 107-111.
Triton et al., "The anticancer agent adriamycin can be actively cytotoxic without entering cells," Science, 1982, 217 (4556):248-250.
Van De Graaff, M. J., et al. "Conditionally controlling human TLR2 activity via trans-cyclooctene caged ligands." Bioconjugate chemistry 31.6 (2020): 1685-1692.
Van Der Gracht, AMF, et al. "Chemical control over T-cell activation in vivo using deprotection of trans-cyclooctene-modified epitopes." ACS chemical biology 13.6 (2018): 1569-1576.
Verbeke et al., "Multicomponent Injectable Hydrogels for Antigen-Specific Tolerogenic Immune Modulation," Adv Healthc Mater, 2017, 6 (6), 34 pages.
Versteegen et al., "Click to Release: Instantaneous Doxorubicin Elimination upon Tetrazine Ligation," Angew. Chem. Int. Ed., 2013, vol. 52, pp. 14112-14116.
Versteegen et al., "Click-to-Release from trans-Cyclooctenes: Mechanistic Insights and Expansion of Scope from Established Carbamate to Remarkable Ether Cleavage," Angew. Chem. Int. Ed., 2018, 57:10494-10499.
Wang, K., et al. "Post-synthesis DNA modifications using a trans-cyclooctene click handle." Organic & biomolecular chemistry 13.3 (2015): 909-915.
Wu, J. et al. "Immunogenic chemotherapy: dose and schedule dependence and combination with immunotherapy." Cancer letters 419 (2018): 210-221.
Xu, Z., et al. "Novel HER2-targeting antibody-drug conjugates of trastuzumab beyond T-DM1 in breast cancer: trastuzumab deruxtecan (DS-8201a) and (Vic−) trastuzumab duocarmazine (SYD985)." European journal of medicinal chemistry 183 (2019): 111682.
Yoneda, J., et al. "Expression of angiogenesis-related genes and progression of human ovarian carcinomas in nude mice." JNCI: Journal of the National Cancer Institute 90.6 (1998): 447-454.
Zeglis et al., "A Pretargeted PET Imaging Strategy Based on Bioorthogonal Diels-Alder Click Chemistry," J. Nucl. Med., 2013, vol. 54, No. 8, pp. 1389-1396.

(56) References Cited

OTHER PUBLICATIONS

Zeglis et al., "Building Blocks for the Construction of Bioorthogonally Reactive Peptides via Solid-Phase Peptide Synthesis," Chemistry Open Communications, 2014, vol. 3, pp. 48-53, DOI: 10.1002/open.201402000.
Zeglis et al., "Modular Strategy for the Construction of Radiometalated Antibodies for Positron Emission Tomography Based on Inverse Electron Demand Diels-Alder Click Chemistry," Bioconjugate Chemistry, 2011, vol. 22, pp. 2048-2059.
Zhang et al., "An ionically crosslinked hydrogel containing vancomycin coating on a porous scaffold for drug delivery and cell culture," International Journal of Pharmaceutics, 2008, vol. 353, pp. 74-87.
Zhang, H., et al. "Interfacial bioorthogonal cross-linking." ACS macro letters 3.8 (2014): 727-731.
European Patent Office, European Search Report for Application No. 23207387.4, dated Jan. 31, 2024 (7 pages).
Srinivasan, S., et al. "SQ3370 Activates Cytotoxic Drug via Click Chemistry at Tumor and Elicits Sustained Responses in Injected and Non-Injected Lesions." Advanced therapeutics 4.3 (2021): 2000243.
Japanese Patent Office. Notification of Reasons for Rejection for Application No. 2023-508513, dated Jun. 25, 2025 (7 pages with translation).
U.S. Appl. No. 19/323,247, filed Sep. 9, 2025, by McFarland et al. (pursuant to the waiver of 37 C.F. R. § 1.98(a)(2)(iii) issued by the Office on Oct. 19, 2004).

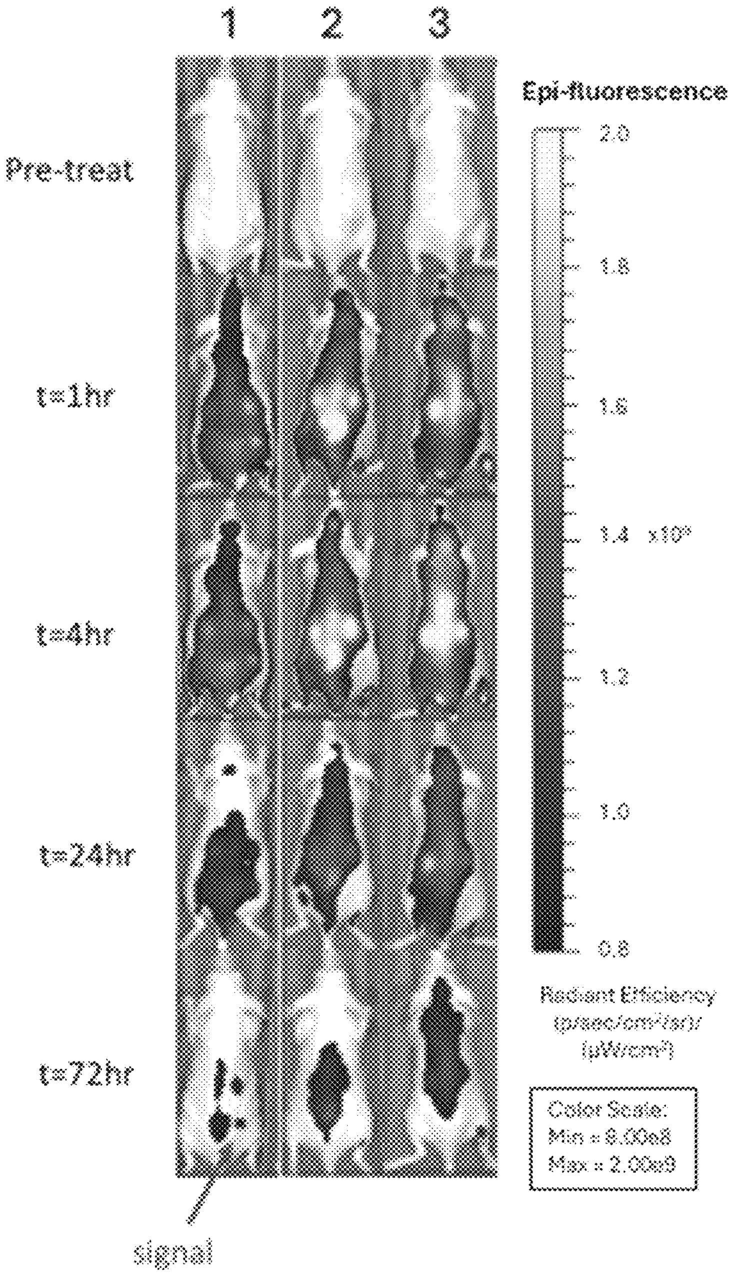
1
2
3
Pre-treat
t=1hr
t=4hr
t=24hr
t=72hr
signal
Epi-fluorescence
2.0
1.8
1.6
1.4 x10⁹
1.2
1.0
0.8
Radiant Efficiency
(p/sec/cm²/sr)/
(μW/cm²)
Color Scale:
Min = 8.00e8
Max = 2.00e9

TRANS-CYCLOOCTENE PRODRUG OF MONOMETHYL AURISTATIN E

RELATED APPLICATIONS

This patent application is the U.S. national stage entry, under 35 U.S.C. § 371, of International Application Number PCT/US2021/045100, filed Aug. 6, 2021, which claims priority to U.S. Provisional Application No. 63/062,814, filed Aug. 7, 2020, the entire contents of each of which are hereby incorporated by reference.

SEQUENCE LISTING

The sequence listing is filed with the application and is incorporated by reference herein. The sequence listing text file "7-G206463PM_Sequence_Listing.txt" was created on Jan. 24, 2023, and is 751 bytes in size.

TECHNICAL FIELD

The present disclosure provides trans-cyclooctene derivatives and use for bioorthogonal delivery in a subject for cancer and/or immunotherapy.

BACKGROUND

Immunotherapy to boost the immune system against tumor growth and dissemination of cancer has been clinically validated. Immunotherapy strategies harness immune cells and include monoclonal antibodies against tumor antigens, immune checkpoint inhibitors, vaccination, adoptive cell therapies (e.g., CAR-T cells) and cytokine administration.

Bioorthogonal conjugation or click reactions are selective and orthogonal (non-interacting with) functionalities found in biological systems, and have found use in various applications in the fields of chemistry, chemical biology, molecular diagnostics, and medicine, where they can be used to facilitate the selective manipulation of molecules, cells, particles and surfaces, and the tagging and tracking of biomolecules in vitro and in vivo. These reactions include the Staudinger ligation, the azide-cyclooctyne cycloaddition, and the inverse-electron-demand Diels-Alder reaction.

SUMMARY

The present disclosure provides a conjugate comprising an immunomodulatory agent payload, a monoclonal antibody payload, or a therapeutic protein payload linked to one or more bioorthogonal moieties, wherein the immunomodulatory agent payload is selected from the group consisting of a cytokine, chemokine, chemokine antagonist, and immune checkpoint inhibitor payload; or a pharmaceutically acceptable salt thereof.

In one aspect, the invention provides conjugates of formula (I), or a pharmaceutically acceptable salt thereof, $$(G-L^1)_m-D^1 \qquad \text{(I)}$$

wherein

G is the bioorthogonal moiety, and G, at each occurrence, is independently

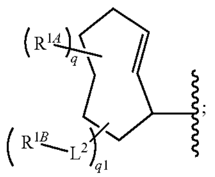

$L^1$, at each occurrence, is independently a linker;

m is an integer from 1-150;

$D^1$ is the immunomodulatory agent payload, a monoclonal antibody payload, or a therapeutic protein payload;

$R^{1A}$, at each occurrence, is independently selected from the group consisting of $C_{1-4}$alkyl, $C_{1-4}$haloalkyl, and $C_{1-4}$alkoxy;

q is 0, 1 or 2;

q1 is 0 or 1;

$R^{1B}$, at each occurrence, is independently selected from the group consisting of $G^1$, OH, $-NR^{1c}-C_{1-4}$alkylene-$G^1$, $-NR^{1c}-C_{1-4}$alkylene-$N(R^{1d})_2$, $-NR^{1c}-C_{1-6}$alkylene-$N(C_{1-4}alkyl)_3^+$, $-N(R^{1c})CHR^{1e}CO_2H$, $-N(R^{1e})-C_{1-6}$alkylene-$CO_2H$, $-N(R^{1f})-C_{2-4}$alkylene-$(N(C_{1-4}$alkylene-. $CO_2H)-C_{2-4}alkylene)_n$-$N(C_{1-4}$alkylene-$CO_2H)_2$, $-N(R^{1c})CHR^{1e}C(O)OC_{1-6}$alkyl, $-N(R^{1c})-C_{1-6}$alkylene-$C(O)OC_{1-6}$alkyl, $-N(R^{1f})-C_{2-4}$alkylene-$(N(C_{1-4}$alkylene-$C(O)OC_{1-6}$ alkyl)-$C_{2-4}alkylene)_n$-$N(C_{1-4}$alkylene-$C(O)OC_{1-6}alkyl)_2$, $-N(R^{1c})-C_{1-6}$alkylene-$SO_3H$, $-N(R^{1c})-(CH_2CH_2O)_{1-3}-CH_2CH_2N((CH_2CH_2O)_{1-3}-C_{1-6}$alkylene-$CO_2H)_2$, and $-N(R^{1c})CH(CH_2O-(CH_2CH_2O)_{0-2}-C_{1-6}$alkylene-$CO_2H)_2$;

$R^{1c}$ and $R^{1d}$, at each occurrence, are independently hydrogen or $C_{1-4}$alkyl;

$R^{1e}$, at each occurrence, is independently $-C_{1-4}$alkylene-$CO_2H$; $-C_{1-4}$alkylene-$CONH_2$, or $-C_{1-4}$alkylene-OH;

$R^{1f}$, at each occurrence, is independently hydrogen, $C_{1-6}$alkyl, or $C_{1-4}$alkylene-$CO_2H$;

n, at each occurrence, is independently 0, 1, 2, or 3;

$L^2$, at each occurrence, is independently selected from the group consisting of $-C(O)-$ and $C_{1-3}$alkylene; and $G^1$, at each occurrence, is independently an optionally substituted heterocyclyl.

In another aspect, the invention provides a pharmaceutical composition comprising the conjugate, or a pharmaceutically acceptable salt thereof, and a pharmaceutically acceptable carrier.

In another aspect, the invention provides a method of treating cancer or enhancing or eliciting an immune response, the method comprising administering to a subject in need thereof, a therapeutically effective amount of the conjugate, or a pharmaceutically acceptable salt or composition thereof, and a therapeutic support composition, the therapeutic support composition comprising a biocompatible support and a tetrazine-containing group of formula

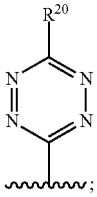;
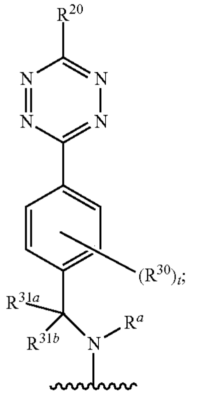
or
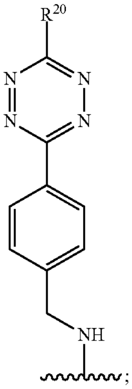;

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R''', SC(═O)R''', OC(═S)R''', SC(═S)R''', S(═O)R', $S(═O)_2R'''$; $S(═O)_2NR'R''$, C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O)SR'', NR'C(═S)SR'', OC(═O)NR'R'', SC(═O)NR'R'', OC(═S)R'R', SC(═S)R'R'', NR'C(═O)NR''R'', and NR'C(═S)NR''R'';

R' and R'' at each occurrence are independently selected from hydrogen, aryl and alkyl;

R''' at each occurrence is independently selected from aryl and alkyl;

$R^{30}$ is halogen, cyano, nitro, hydroxy, alkyl, haloalkyl; alkenyl, alkynyl, alkoxy; haloalkoxy; heteroalkyl, aryl, heteroaryl, heterocycle, cycloalkyl, or cycloalkenyl;

$R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In another aspect, the invention provides a pharmaceutical combination comprising the conjugate, or a pharmaceutically acceptable salt, or composition thereof; and a therapeutic support composition, the therapeutic support composition comprising a biocompatible support and a tetrazine-containing group of formula

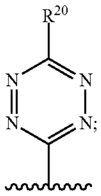
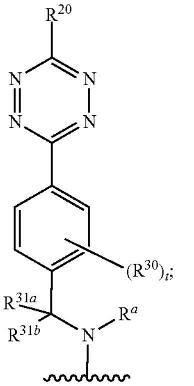
or

-continued

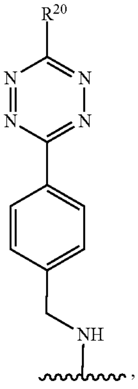, as defined herein for use in treating cancer or enhancing or eliciting an immune response.

In another aspect, the invention provides the use of a combination comprising conjugate, or a pharmaceutically acceptable salt, or composition thereof; and a therapeutic support composition, the therapeutic support composition comprising a biocompatible support and a tetrazine-containing group of formula

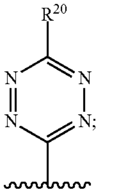
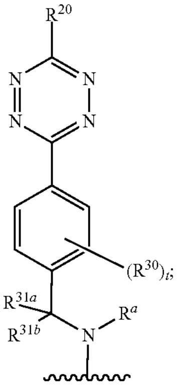
or
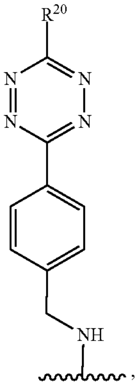, as defined herein in the manufacture of a medicament for treating cancer or enhancing or eliciting an immune response.

Aspects of the present disclosure include a method for delivering an effective amount of the immunomodulatory agent to a target location in a subject, where the method includes administering to the subject a therapeutic support composition and conjugate, as defined herein.

Aspects of the present disclosure also include a kit comprising the conjugate, a therapeutic support composition as defined herein, and optionally a compound of formula (III), as defined herein.

BRIEF DESCRIPTION OF THE FIGURE

FIG. 1 shows fluorescence images of 3 mice injected subcutaneously in the right flank with: (1) SQL70 biopolymer, followed by IV via tail vein injection (TVI) with TCO-Fab-Cy5.5 (Cy-5.5-modified TCO-modified Ranibizumab) one hour later at 10 mg/kg (Group 1), (2) SQL70 biopolymer, followed by IV via tail vein injection (TVI) with Fab-Cy5.5 (Cy-5.5-modified Ranibizumab) one hour later at 10 mg/kg (Group 2), and (3) control unmodified HA biopolymer, followed by IV via tail vein injections (TVI) with TCO-Fab-Cy5.5 (Cy-5.5-modified TCO-modified Ranibizumab) one hour later at 10 mg/kg (Group 3).

DETAILED DESCRIPTION

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

A. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry,* 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkoxy" as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy and tert-butoxy.

The term "alkyl" as used herein, means a straight or branched, saturated hydrocarbon chain containing from 1 to 30 carbon atoms. The term "lower alkyl" or "$C_1$-$C_6$-alkyl" means a straight or branched chain hydrocarbon containing from 1 to 6 carbon atoms. The term "$C_1$-$C_3$-alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a hydrocarbon chain containing from 2 to 30 carbon atoms with at least one carbon-carbon double bond. The alkenyl group may be substituted or unsubstituted. For example, the alkenyl group may be substituted with an aryl group, such as a phenyl.

The term "alkynyl," as used herein, refers to straight or branched monovalent hydrocarbyl groups having from 2 to 30 carbon atoms, such as 2 to 20, or 2 to 10 carbon atoms and having at least 1 site of triple bond unsaturation. The term "alkyne" also includes non-aromatic cycloalkyl groups of from 5 to 20 carbon atoms, such as from 5 to 10 carbon atoms, having single or multiple rings and having at least one triple bond. Examples of such alkynyl groups include, but are not limited to, acetylenyl (—C≡CH), and propargyl ($—CH_2C≡CH$), and cycloalkynyl moieties, such as, but not limited to, substituted or unsubstituted cyclooctyne moieties.

The term "alkoxyalkyl" as used herein, refers to an alkoxy group, as defined herein, appended to the parent molecular moiety through an alkyl group, as defined herein.

The term "alkylene" as used herein, refers to a divalent group derived from a straight or branched chain hydrocarbon of 1 to 30 carbon atoms, for example, of 2 to 10 carbon atoms. Representative examples of alkylene include, but are not limited to, $—CH_2—$, $—CH(CH_3)—$, $—C(CH_3)_2—$, $—CH_2CH_2—$, $—CH(CH_3)CH_2—$, $—C(CH_3)_2CH_2—$, $—CH_2CH_2CH_2—$, $—CH(CH_3)CH_2CH_2—$, $—C(CH_3)_2CH_2CH_2—$, $—CH_2C(CH_3)_2CH_2—$, $—CH_2CH_2CH_2CH_2—$, and $—CH_2CH_2CH_2CH_2CH_2—$.

The term "amino acid" refers to both natural and unnatural amino acids, protected natural and unnatural amino acids, as well as amino acid analogs and amino acid mimetics that function in a manner similar to the naturally occurring amino acids. Naturally encoded amino acids include 20 common amino acids (alanine, arginine, asparagine, aspartic acid, cysteine, glutamine, glutamic acid, glycine, histidine, isoleucine, leucine, lysine, methionine, phenylalanine, proline, serine, threonine, Tryptophan, tyrosine and valine) and pyrrolidine and selenocysteine. Amino acid analogs refer to compounds having the same basic chemical structure as a naturally occurring amino acid, i.e., by way of example only, an α-carbon attached to a hydrogen, carboxyl group, amino group, and R group. Such analogs can have a modified R group (e.g., norleucine as an example) or retain a modified peptide backbone while retaining the same basic chemical structure as a natural amino acid. Non-limiting examples of amino acid analogs include citrulline, homoserine, norleucine, methionine sulfoxide, methionine methylsulfonium.

The term "aryl" as used herein, refers to a phenyl group, or bicyclic aryl or tricyclic aryl fused ring systems. Bicyclic fused ring systems are exemplified by a phenyl group appended to the parent molecular moiety and fused to a phenyl group. Tricyclic fused ring systems are exemplified by a phenyl group appended to the parent molecular moiety and fused to two other phenyl groups. Representative examples of bicyclic aryls include, but are not limited to, naphthyl. Representative examples of tricyclic aryls include, but are not limited to, anthracenyl. The monocyclic, bicyclic, and tricyclic aryls are connected to the parent molecular moiety through any carbon atom contained within the rings, and can be unsubstituted or substituted.

The term "azide" as used herein, refers to the functional group $—N_3$.

The term "cycloalkyl" as used herein, refers to a carbocyclic ring system containing three to ten carbon atoms, zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl and cyclodecyl. "Cycloalkyl" also includes carbocyclic ring systems in which a cycloalkyl group is appended to the parent molecular moiety and is fused to an aryl group as defined herein, a heteroaryl group as defined herein, or a heterocycle as defined herein.

The term "cycloalkenyl" as used herein, means a non-aromatic monocyclic or multicyclic ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "cyclooctene" as used herein, refers to a substituted or unsubstituted non-aromatic cyclic alkyl group of 8 carbon atoms, having a single ring with a double bond. Examples of such cyclooctene groups include, but are not limited to, substituted or unsubstituted trans-cyclooctene (TCO).

The term "fluoroalkyl" as used herein, means an alkyl group, as defined herein, in which one, two, three, four, five, six, seven or eight hydrogen atoms are replaced by fluorine. Representative examples of fluoroalkyl include, but are not limited to, 2-fluoroethyl, 2,2,2-trifluoroethyl, trifluoromethyl, difluoromethyl, pentafluoroethyl, and trifluoropropyl such as 3,3,3-trifluoropropyl.

The term "alkoxyfluoroalkyl" as used herein, refers to an alkoxy group, as defined herein, appended to the parent molecular moiety through a fluoroalkyl group, as defined herein.

The term "fluoroalkoxy" as used herein, means at least one fluoroalkyl group, as defined herein, is appended to the parent molecular moiety through an oxygen atom. Representative examples of fluoroalkyloxy include, but are not limited to, difluoromethoxy, trifluoromethoxy and 2,2,2-trifluoroethoxy.

The term "halogen" or "halo" as used herein, means Cl, Br, I, or F.

The term "haloalkyl" as used herein, means an alkyl group, as defined herein, in which one, two, three, four, five, six, seven or eight hydrogen atoms are replaced by a halogen.

The term "haloalkoxy" as used herein, means at least one haloalkyl group, as defined herein, is appended to the parent molecular moiety through an oxygen atom.

The term "heteroalkyl" as used herein, means an alkyl group, as defined herein, in which one or more of the carbon atoms has been replaced by a heteroatom selected from S, Si, O, P and N. The heteroatom may be oxidized. Representative examples of heteroalkyls include, but are not limited to, alkyl ethers, secondary and tertiary alkyl amines, and alkyl sulfides.

The term "heteroaryl" as used herein, refers to an aromatic monocyclic ring or an aromatic bicyclic ring system or an aromatic tricyclic ring system. The aromatic monocyclic rings are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl groups are exemplified by a monocyclic heteroaryl ring appended to the parent molecular moiety and fused to a monocyclic cycloalkyl group, as defined herein, a monocyclic aryl group, as defined herein, a monocyclic heteroaryl group, as defined herein, or a monocyclic heterocycle, as defined herein. The tricyclic heteroaryl groups are exemplified by a monocyclic heteroaryl ring appended to the parent molecular moiety and fused to two of a monocyclic cycloalkyl group, as defined herein, a monocyclic aryl group, as defined herein, a monocyclic heteroaryl group, as defined herein, or a monocyclic heterocycle, as defined herein. Representative examples of monocyclic heteroaryl include, but are not limited to, pyridinyl (including pyridin-2-yl, pyridin-3-yl, pyridin-4-yl), pyrimidinyl, pyrazinyl, thienyl, furyl, thiazolyl, thiadiazolyl, isoxazolyl, pyrazolyl, and 2-oxo-1,2-dihydropyridinyl. Representative examples of bicyclic heteroaryl include, but are not limited to, chromenyl, benzothienyl, benzodioxolyl, benzotriazolyl, quinolinyl, thienopyrrolyl, thienothienyl, imidazothiazolyl, benzothiazolyl, benzofuranyl, indolyl, quinolinyl, imidazopyridine, benzooxadiazolyl, and benzopyrazolyl. Representative examples of tricyclic heteroaryl include, but are not limited to, dibenzofuranyl and dibenzothienyl. The monocyclic, bicyclic, and tricyclic heteroaryls are connected to the parent molecular moiety through any carbon atom or any nitrogen atom contained within the rings, and can be unsubstituted or substituted.

The term "heterocycle" or "heterocyclic" as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, 1,3-dimethylpyrimidine-2,4(1H,3H)-dione, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), and oxa-adamantane (2-oxatricyclo[3.3.1.1$^{3,7}$]decane). The monocyclic, bicyclic, and tricyclic heterocycles are connected to the parent molecular moiety through any carbon atom or any nitrogen atom contained within the rings, and can be unsubstituted or substituted.

The term "hydroxyl" as used herein, means an —OH group.

The term "hydroxyalkyl" as used herein, means an alkyl group, as defined herein, in which one, two, three, four, five, six, seven or eight hydrogen atoms are replaced by a hydroxyl group.

In some instances, the number of carbon atoms in a hydrocarbyl substituent (e.g., alkyl or cycloalkyl) is indicated by the prefix "$C_x$-$C_y$-" or "$C_{x-y}$," wherein x is the minimum and y is the maximum number of carbon atoms in the substituent. Thus, for example, "$C_1$-$C_3$-alkyl" and "$C_{1-3}$alkyl" refer to an alkyl substituent containing from 1 to 3 carbon atoms. The two conventions "$C_x$-$C_y$-" and "$C_{x-y}$" are used interchangeably and have the same meaning.

The term "substituted" refers to a group that may be further substituted with one or more non-hydrogen substituent groups. Substituent groups include, but are not limited to, halogen, =O, =S, cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

The term "tetrazine" refers to a substituted or unsubstituted aromatic cyclic group of 2 carbon atoms and 4 nitrogen atoms, having a single ring with three double bonds. Examples of tetrazine groups include 1,2,3,4-tetrazine and 1,2,4,5-tetrazine. As used herein, 1,2,4,5-tetrazine is referred to as a "Tz" group.

The term "selectively delivering" refers to delivering an agent (e.g., a payload) to an organ or tissue (or portion thereof) in need of treatment or diagnosis, without significant binding to other non-target organs or tissues (or portions thereof).

The term "payload" refers to an agent for delivery to a target site in a subject. Payloads include therapeutic agents.

A "payload moiety" as used herein refers to a payload D or $D^1$ minus the payload's nucleophilic group such as NH, $NC_{1-4}$alkyl, O, or S that attaches to a linker or minus the payload's electrophilic group such as C(O) that attaches to a linker, i.e., the remainder of the payload.

The term "therapeutic agent" refers to an agent capable of treating and/or ameliorating a condition or disease, or one or more symptoms thereof, in a subject. Therapeutic agents of the present disclosure also include prodrug forms of therapeutic agents.

The term "diagnostic agent" refers to agents that assist in diagnosing conditions or diseases. Representative diagnostic agents include imaging agents such as paramagnetic agents, optical probes, radionuclides, and the like. Paramagnetic agents are imaging agents that are magnetic under an externally applied field. Examples of paramagnetic agents include, but are not limited to, iron particles including iron nanoparticles and iron microparticles. Optical probes are fluorescent compounds that can be detected by excitation at one wavelength of radiation and detection at a second, different, wavelength of radiation. Optical probes of the present disclosure include, but are not limited to, Cy5.5, Alexa 680, Cy5, DiD (1,1'-dioctadecyl-3,3,3',3'-tetramethylindodicarbocyanine perchlorate) and DiR (1,1'-dioctadecyl-3,3,3',3'-tetramethylindotricarbocyanine iodide). Other optical probes include quantum dots. Radionuclides are elements that undergo detectable radioactive decay. Radionuclides useful in embodiments of the present disclosure include, but are not limited to, $^{3}$H, $^{11}$C, $^{13}$N, $^{18}$F, $^{19}$F, $^{60}$Co, $^{64}$Cu, $^{67}$Cu, $^{68}$Ga, $^{82}$Rb, $^{90}$Sr, $^{90}$Y, $^{99}$Tc, $^{99}$mTc, $^{111}$In, $^{123}$I, $^{124}$I, $^{125}$I, $^{129}$I, $^{131}$I, $^{137}$Cs, $^{177}$Lu, $^{186}$Re, $^{188}$Re, $^{211}$At, Rn, Ra, Th, U, Pu and $^{241}$Am.

The term "targeting agent" refers to a chemical or biological agent that specifically binds to a target (e.g., a targeted organ or tissue), thereby forming a stable association between the targeting agent and the specific target. By "stably associated" or "stable association" is meant that a moiety is bound to or otherwise associated with another moiety or structure under standard physiological conditions. Bonds may include covalent bonds and non-covalent interactions, such as, but not limited to, ionic bonds, hydrophobic interactions, hydrogen bonds, van der Waals forces (e.g., London dispersion forces), dipole-dipole interactions, and the like. A targeting agent may be a member of a specific binding pair, such as, but are not limited to: a member of a receptor/ligand pair; a ligand-binding portion of a receptor; a member of an antibody/antigen pair; an antigen-binding fragment of an antibody; a hapten; a member of a lectin/carbohydrate pair; a member of an enzyme/substrate pair; biotin/avidin; biotin/streptavidin; digoxin/antidigoxin; a member of a DNA or RNA aptamer binding pair; a member of a peptide aptamer binding pair; and the like. Targeting agents include ligands that specifically bind (or substantially specifically bind) a particular clinically-relevant target receptor or cell surface target. The ligand can be an antibody, peptide, nucleic acid, phage, bacteria, virus, or other molecule with a specific affinity for a target receptor or cell surface target. Examples of receptors and cell surface targets include, but are not limited to, PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, LT4-human mAb directed against the inhibitory immune checkpoint receptor immunoglobulin-like transcript 4 (ILT4; leukocyte immunoglobulin-like receptor subfamily B member 2, LILRB2, lymphocyte immunoglobulin-like receptor 2, LIR2, monocyte/macrophage immunoglobulin-like receptor 10, MIR-10, CD85d, or other cellular receptors or cell surface targets.

The term "targeted organ or tissue" refers to an organ or tissue that is being targeted for delivery of the payload. Representative organs and tissues for targeting include those that can be targeted by chemical or biological targeting agents, as well as those organs and tissues that cannot be targeted by chemical or biological targeting agents.

The term "implanting" refers to surgical implantation into a subject's body.

The term "contacting" or "contact" refers to the process of bringing into contact at least two distinct species such that they can interact with each other, such as in a non-covalent or covalent binding interaction or binding reaction. It should be appreciated, however, the resulting complex or reaction product can be produced directly from an interaction or a reaction between the added reagents or from an intermediate from one or more of the added reagents or moieties, which can be produced in the contacting mixture.

The term "binding agent" refers to an agent having a functional group capable of forming a covalent bond to a complementary functional group of another binding agent in a biological environment. Binding between binding agents in a biological environment may also be referred to as bioconjugation. Binding agents include bioorthogonal binding agents, which are binding agents having bioorthogonal functional groups. Bioorthogonal functional groups of bioorthogonal binding agents selectively react with a complementary bioorthogonal functional group of another bioorthogonal binding partner. Selective reaction between bioorthogonal binding partners can minimize side reactions with other binding agents, biological compounds, or other non-complementary bioorthogonal binding agents or non-complementary bioorthogonal functional groups. Bioorthogonal moieties or functional groups of bioorthogonal binding agents include, but are not limited to, an azide and alkyne for formation of a triazole via Click-chemistry reactions, trans-cyclooctene (TCO) and tetrazine (Tz) (e.g., 1,2,4,5-tetrazine), and others. The binding agents useful in the present disclosure may have a high reactivity with the corresponding binding agent so that the reaction is rapid.

The term "functionalized" refers to a moiety having a functional group attached to the moiety, such as for example a moiety having a binding agent functional group (e.g., a bioorthogonal functional group) attached thereto.

The term "administering" refers to any suitable route of administration to a subject, such as, but not limited to, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

The term "parenterally," as used herein, refers to modes of administration which include intravenous, intramuscular, intraperitoneal, intrasternal, subcutaneous and intraarticular injection and infusion.

The term "leaving group" refers to an atom (or a group of atoms) with electron withdrawing ability that can be displaced as a stable species, taking with it the bonding electrons. Examples of suitable leaving groups include halides (e.g., Br, Cl, I), sulfonate esters (e.g., triflate, mesylate, tosylate, and brosylate), and nitrophenols.

The term "pharmaceutically effective amount" and "therapeutically effective amount" refer to an amount of a compound sufficient to treat a specified disorder or disease or one or more of its symptoms and/or to prevent or reduce the risk of the occurrence or reoccurrence of the disease or disorder or symptom(s) thereof. In reference to tumorigenic proliferative disorders, a pharmaceutically or therapeutically effective amount comprises an amount sufficient to, among other things, cause the tumor to shrink or decrease the growth rate of the tumor.

As used herein, the term "subject," "patient," or "organism" includes humans and mammals (e.g., mice, rats, pigs, cats, dogs, and horses). Typical subjects to which an agent(s) of the present disclosure may be administered may include mammals, particularly primates, especially humans. For veterinary applications, suitable subjects may include, for example, livestock such as cattle, sheep, goats, cows, swine, and the like; poultry such as chickens, ducks, geese, turkeys, and the like; and domesticated animals particularly pets such as dogs and cats. For diagnostic or research applications, suitable subjects may include mammals, such as rodents (e.g., mice, rats, hamsters), rabbits, primates, and swine such as inbred pigs and the like.

The term "treating" or "treatment" as used herein means the treating or treatment of a disease or medical condition or symptom(s) thereof in a patient, such as a mammal (particularly a human) that includes: (a) ameliorating the disease or medical condition or symptom(s) thereof, such as, eliminating or causing regression of the disease or medical condition or symptom(s) thereof in a patient; (b) suppressing the disease or medical condition or symptom(s) thereof, for example by, slowing or arresting the development of the disease or medical condition or symptom(s) thereof in a patient; or (c) alleviating a symptom of the disease or medical condition or symptom(s) thereof in a patient.

The term "physiological conditions" is meant to encompass those conditions compatible with living cells, e.g., predominantly aqueous conditions of a temperature, pH, salinity, etc. that are compatible with living cells.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The compounds may exist as stereoisomers wherein asymmetric or chiral centers are present. The stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45:13-30. The disclosure contemplates various stereoisomers and mixtures thereof, and these are specifically included within the scope of this invention. Stereoisomers include enantiomers and diastereomers and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography, and optional liberation of the optically pure product from the auxiliary as described in Furniss, Hannaford, Smith, and Tatchell, "Vogel's Textbook of Practical Organic Chemistry," 5$^{th}$ edition (1989), Longman Scientific & Technical, Essex CM20 2JE, England, or (2) direct separation of the mixture of optical enantiomers on chiral chromatographic columns, or (3) fractional recrystallization methods.

It should be understood that the compounds may possess tautomeric forms as well as geometric isomers, and that these also constitute an aspect of the invention.

The present disclosure also includes isotopically-labeled compounds, which are identical to those recited herein, but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to, $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Substitution with heavier isotopes such as deuterium, i.e., 2H, can afford certain therapeutic advantages resulting from greater metabolic stability, for example increased in vivo half-life or reduced dosage requirements, and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I), (II), or (III) are $^{11}C$, $^{13}N$, $^{15}O$, and $^{18}F$. Isotopically-labeled compounds disclosed herein can generally be prepared by conventional techniques known to those skilled in the art or by processes analogous to those described in the accompanying Examples using appropriate isotopically-labeled reagent in place of non-isotopically-labeled reagent.

B. CONJUGATES

In the following, embodiments of the invention are disclosed. The first embodiment is denoted E1, subsequent embodiments are denoted E1.1, E1.1A, E1.2, and so forth.

E1. A conjugate comprising an immunomodulatory agent payload linked to one or more bioorthogonal moieties, wherein the immunomodulatory agent payload is selected from the group consisting of a cytokine, chemokine, chemokine antagonist, therapeutic monoclonal antibody, and immune checkpoint inhibitor payload; or a pharmaceutically acceptable salt thereof. The bioorthogonal moiety comprises a bioorthogonal functional group such as a trans-cyclooctene, tetrazine, azide, or alkyne. Bioorthogonal functional groups are well-known in the art, as described in Randon, 2020, *Bioconjugate Chem.,* 31(2): 159-173).

E1.1. A conjugate comprising an immunomodulatory agent payload linked to one or more bioorthogonal moieties, wherein the immunomodulatory agent payload is an inhibitor of a cytokine payload, or a pharmaceutically acceptable salt thereof.

E1.1A. The conjugate of E1.1, or a pharmaceutically acceptable salt thereof, wherein the inhibitor of a cytokine payload is a payload of an inhibitor of TNF-α, infliximab, certolizumab, TGF-β, galunisertib, fresolimumab, M7824, CSF-1, pexidartinib, or cabiralizumab.

E1.2. A conjugate comprising a monoclonal antibody payload linked to one or more bioorthogonal moieties, or a pharmaceutically acceptable salt thereof.

E1.3. A conjugate comprising a therapeutic protein payload linked to one or more bioorthogonal moieties, or a pharmaceutically acceptable salt thereof.

E1.3A. The conjugate of E1.3, or a pharmaceutically acceptable salt thereof, wherein the therapeutic protein payload is a payload of an antibody-based drug, Fc fusion protein, anticoagulant, blood factor, bone morphogenetic protein, engineered protein scaffold, enzyme, growth factor, hormone, interferon, interleukin, or thrombolytic.

E1.3B. The conjugate of E1.3, or a pharmaceutically acceptable salt thereof, wherein the therapeutic protein payload is a payload of a cytokine, chemokine, growth factor, hormone, antibody, or antigen.

E1.3C. The conjugate of E1.3, or a pharmaceutically acceptable salt thereof, wherein the therapeutic protein payload is a payload of erythropoietin (EPO, e.g., native EPO or synthetic EPO (see, e.g., US 2003/0191291), such as, but not limited to, e.g., PROCRIT®, EPREX®, or EPOGEN® (epoetin-α), ARANESP® (darbepoietin-α), NEORECORMON®, EPOGIN® (epoetin-β), and the like); a growth hormone (e.g., a somatotropin, e.g., GENOTROPIN®, NUTROPIN®, NORDITROPIN®, SAIZEN®, SEROSTIM®, HUMATROPE®, etc.); theraputic monoclonal antibody (e.g. Atezolizumab, Avelumab, Bevacizumab, Cemiplimab, Cetuximab, Daratumumab, Dinutuximab, Durvalumab, Elotuzumab, Ipilimumab, Isatuximab, Mogamulizumab, Necitumumab, Nivolumab, Obinutuzumab, Ofatumumab, Olaratumab, Panitumumab, Pembrolizumab, Pertuzumab, Ramucirumab, Rituximab, Trastuzumab etc.); human growth hormone (hGH); bovine growth hormone (bGH); follicle stimulating hormone (FSH); interferon (e.g., IFN-γ, IFN-α, IFN-β, IFN-ω; IFN-τ, consensus interferon, and the like); insulin (e.g., Novolin, Humulin, Humalog, Lantus, Ultralente, etc.), insulin-like growth factor (e.g., IGF-I, IGF-II); blood factors (e.g., Factor X, tissue plasminogen activator (TPA), and the like, such as, but not limited to, e.g., ACTIVASE® (alteplase) tissue plasminogen activator, NOVOSEVEN® (recombinant human factor Vila), Factor Vila, Factor VIII (e.g., KOGENATE®), Factor IX, β-globin, hemoglobin, and the like); colony stimulating factors (e.g., granulocyte-CSF (G-CSF, e.g., NEUPOGEN® (filgrastim)), macrophage-CSF (M-CSF), granulocyte-macrophage-CSF (GM-CSF), Neulasta (pegfilgrastim), granulocyte-monocyte colony stimulating factor, megakaryocyte colony stimulating factor, and the like), transforming growth factors (e.g., TGF-beta, TGF-alpha); interleukins (e.g., IL-1, IL-2 (e.g., Proleukin®), IL-3, IL-4, IL-5, IL-6, IL-7, IL-8, IL-9, IE-12, and the like); a growth factor (e.g., epidermal growth factor (EGF), platelet-derived growth factor (PDGF, e.g., REGRANEX® (beclapermin)), fibroblast growth factors (FGFs, e.g., aFGF, bFGF, such as FIB LAST® (trafermin)), glial cell line-derived growth factor (GDNF), nerve growth factor (NGF), stem cell factor (e.g., STEMGEN® (ancestim)), keratinocyte growth factor, a hepatocyte growth factor, and the like); a soluble receptor (e.g., a TNF-α-binding soluble receptor such as ENBREL® (etanercept), a soluble VEGF receptor, a soluble interleukin receptor, a soluble γ/δ T cell receptor, and the like); an enzyme (e.g., α-glucosidase, CERAZYME® (imiglucarase, β-glucocerebrosidase, CEREDASE® (alglucerase); an enzyme activator (e.g., tissue plasminogen activator); a chemokine (e.g., IP-10, Mig, Groα/IL-8, regulated and normal T cell expressed and secreted (RANTES), MIP-1α, MIP-1ρ, MCP-1, PF-4, and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; or an IL-1 receptor antagonist (e.g., Kineret® (anakinra)); and the like E2. The conjugate of any of E1-E1.3C, or a pharmaceutically acceptable salt thereof, wherein each bioorthogonal moiety independently comprises a trans-cyclooctene or a tetrazine.

E3. The conjugate of any of E1-E2 of formula (I), or a pharmaceutically acceptable salt thereof, $$(G—L^1)_m—D^1 \qquad (I)$$

wherein

G is the bioorthogonal moiety, and G, at each occurrence, is independently

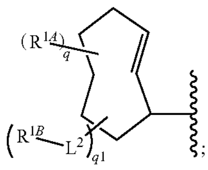

;

$L^1$, at each occurrence, is independently a linker;

m is an integer from 1-150;

$D^1$ is the immunomodulatory agent payload, a monoclonal antibody payload, or a therapeutic protein payload;

$R^{1A}$, at each occurrence, is independently selected from the group consisting of $C_{1-4}$alkyl, $C_{1-4}$haloalkyl, and $C_{1-4}$alkoxy;

q is 0, 1 or 2;

q1 is 0 or 1;

$R^{1B}$, at each occurrence, is independently selected from the group consisting of $G^1$, OH, —$NR^{1c}$—$C_{1-4}$alkylene-$G^1$, —$NR^{1c}$—$C_{1-4}$alkylene-$N(R^{1d})_2$, —$NR^{1c}$—$C_{1-6}$alkylene-$N(C_{1-4}alkyl)_3^+$, —$N(R^{1c})CHR^{1e}CO_2H$, —$N(R^{1c})$—$C_{1-6}$alkylene-$CO_2H$, —$N(R^{1f})$—$C_{2-4}$alkylene-($N(C_{1-4}$alkylene-$CO_2H)$—$C_{2-4}$alkylene$)_n$-$N(C_{1-4}$alkylene-$CO_2H)_2$, —$N(R^{1c})CHR^{1e}C(O)OC_{1-6}$alkyl, —$N(R^{1c})$—$C_{1-6}$alkylene-$C(O)OC_{1-6}$alkyl, —$N(R^{1f})$—$C_{2-4}$alkylene-($N(C_{1-4}$alkylene-C(O)

$OC_{1-6}$alkyl)-$C_{2-4}$alkylene$)_n$-N($C_{1-4}$alkylene-C(O)$OC_{1-6}$ alkyl$)_2$, —N($R^{1c}$)—$C_{1-6}$alkylene-$SO_3H$, —N($R^{1c}$)—($CH_2CH_2O)_{1-3}$—$CH_2CH_2N((CH_2CH_2O)_{1-3}$—$C_{1-6}$alkylene-$CO_2H)_2$, and —N($R^{1c}$)—CH($CH_2O$—($CH_2CH_2O)_{0-2}$—$C_{1-6}$ alkylene-$CO_2H)_2$;

$R^{1c}$ and $R^{1d}$, at each occurrence, are independently hydrogen or $C_{1-4}$alkyl;

$R^{1e}$, at each occurrence, is independently —$C_{1-4}$alkylene-$CO_2H$, —$C_{1-4}$alkylene-$CONH_2$, or —$C_{1-4}$alkylene-OH;

$R^{1f}$, at each occurrence, is independently hydrogen, $C_{1-6}$alkyl, or $C_{1-4}$alkylene-$CO_2H$; n, at each occurrence, is independently 0, 1, 2, or 3;

$L^2$, at each occurrence, is independently selected from the group consisting of —C(O)— and $C_{1-3}$alkylene; and $G^1$, at each occurrence, is independently an optionally substituted heterocyclyl.

E3.1. The conjugate of E3 of formula (I), or a pharmaceutically acceptable salt thereof $$(G—L^1)_m D^1 \qquad (I)$$

wherein

G is the bioorthogonal moiety, and G, at each occurrence, is independently

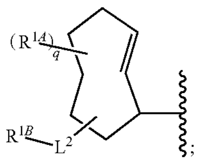

$L^1$, at each occurrence, is independently a linker;

m is an integer from 1-150;

$D^1$ is the immunomodulatory agent payload;

$R^{1A}$, at each occurrence, is independently selected from the group consisting of $C_{1-4}$alkyl, $C_{1-4}$haloalkyl, and $C_{1-4}$alkoxy;

q is 0 or 1;

$R^{1B}$, at each occurrence, is independently selected from the group consisting of $G^1$, OH, —$NR^{1c}$—$C_{1-4}$alkylene-$G^1$, —$NR^{1c}$—$C_{1-4}$alkylene-N($R^{1d})_2$, —N($R^{1c}$)CH$R^{1e}CO_2H$, —N($R^{1c}$)—$C_{1-6}$alkylene-$CO_2H$, —N($R^{1f}$)—$C_{2-4}$alkylene-(N($C_{1-4}$alkylene-$CO_2H$)—$C_{2-4}$alkylene$)_n$-N($C_{1-4}$alkylene-$CO_2H)_2$, —N($R^{1c}$)CH$R^{1e}$C(O)$OC_{1-6}$alkyl, —N($R^{1c}$)—$C_{1-6}$alkylene-C(O)$OC_{1-6}$alkyl, and —N($R^{1f}$)—$C_{2-4}$alkylene-(N($C_{1-4}$ alkylene-C(O)$OC_{1-6}$alkyl)-$C_{2-4}$alkylene$)_n$-N($C_{1-4}$alkylene-C(O)$OC_{1-6}$alkyl$)_2$;

$R^{1c}$ and $R^{1d}$, at each occurrence, are independently hydrogen or $C_{1-4}$alkyl;

$R^{1e}$, at each occurrence, is independently —$C_{1-4}$alkylene-$CO_2H$, —$C_{1-4}$alkylene-$CONH_2$, or —$C_{1-4}$alkylene-OH;

$R^{1f}$, at each occurrence, is independently hydrogen, $C_{1-6}$alkyl, or $C_{1-4}$alkylene-$CO_2H$; n, at each occurrence, is independently 0, 1, 2, or 3;

$L^2$, at each occurrence, is independently selected from the group consisting of —C(O)— and $C_{1-3}$alkylene; and $G^1$, at each occurrence, is independently an optionally substituted heterocyclyl.

E3.1A. The conjugate of E3 or E3.1, or a pharmaceutically acceptable salt thereof, wherein G, at each occurrence, is independently

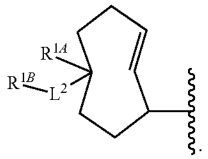

E3.1B. The conjugate of E3.1A, or a pharmaceutically acceptable salt thereof, wherein G, at each occurrence, is independently

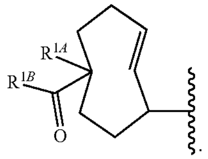

E3.2. The conjugate of any of E1 or E2-E3.1B, or a pharmaceutically acceptable salt thereof, wherein the immunomodulatory agent payload is an antibody payload.

E4. The conjugate of any of E1 or E2-E3.2, or a pharmaceutically acceptable salt thereof, wherein the immunomodulatory agent payload is the immune checkpoint inhibitor payload.

E4.1. The conjugate of E4, or a pharmaceutically acceptable salt thereof, wherein the immune checkpoint inhibitor payload is a payload of pidilizumab, sintilimab, AMP-224, atezolizumab, durvalumab, BMS-936559, tremelimumab, indoximod, epacadostat, a TIGIT inhibitor (e.g., LAG-3, such as an anti-LAG-3 antibody; TIM-3, such as an anti-TIM-3 antibody), a B7 molecule, or a BTLA pathway antagonist.

E5. The conjugate of E4, or a pharmaceutically acceptable salt thereof, wherein the immune checkpoint inhibitor payload is an immune checkpoint inhibitor antibody payload.

E6. The conjugate of E5, or a pharmaceutically acceptable salt thereof, wherein the immune checkpoint inhibitor antibody payload is a PD-1 inhibitor payload.

E7. The conjugate of E6, or a pharmaceutically acceptable salt thereof, wherein the PD-1 inhibitor payload is a nivolumab, pembrolizumab, pidilizumab, sintilimab, or AMP-224 payload.

E8. The conjugate of E5, or a pharmaceutically acceptable salt thereof, wherein the immune checkpoint inhibitor antibody payload is a PD-L1 inhibitor payload.

E9 The conjugate of E8, or a pharmaceutically acceptable salt thereof, wherein the PD-L1 inhibitor payload is an atezolizumab, avelumab, durvalumab, or BMS-936559 payload.

E10. The conjugate of E5, or a pharmaceutically acceptable salt thereof, wherein the immune checkpoint inhibitor antibody payload is a CTLA4 inhibitor payload.

E11. The conjugate of E10, or a pharmaceutically acceptable salt thereof, wherein the CTLA4 inhibitor payload is an ipilimumab or tremelimumab payload.

E12. The conjugate of E4, or a pharmaceutically acceptable salt thereof, wherein the immune checkpoint inhibitor payload is an indoleamine 2,3-dioxygenase (IDO) inhibitor payload.

E13. The conjugate of E12, or a pharmaceutically acceptable salt thereof, wherein the IDO inhibitor payload is an indoximod or epacadostat payload.

E14. The conjugate of any of E1 or E2-E3.2, or a pharmaceutically acceptable salt thereof, wherein the immunomodulatory agent payload is a cytokine payload.

E15. The conjugate of E14, or a pharmaceutically acceptable salt thereof, wherein the cytokine payload is an interferon, interleukin, tumor necrosis factor, erythropoietin, MIP3a, ICAM, macrophage colony stimulating factor, Erythropoietin (EPO), granulocyte colony stimulating factor (GCSF), or granulocyte-macrophage colony stimulating factor payload.

E15.1. The conjugate of E14, or a pharmaceutically acceptable salt thereof, wherein the interleukin payload is chosen from IL-1 to IL-40.

E15.2. The conjugate of E14, or a pharmaceutically acceptable salt thereof, wherein the interleukin payload is IL-2, IL-7, IL-12, IL-15, IL-18, or IL-21.

E15.3. The conjugate of E14, or a pharmaceutically acceptable salt thereof, wherein the immunomodulatory agent payload is a type 1 cytokine. (IL-2, IL-12, TNF-B, IFN-g).

E15.4. The conjugate of E14, or a pharmaceutically acceptable salt thereof, wherein the cytokine payload is selected from the group consisting of IFN-alpha, IFN-beta, IFN-gamma, pegylated IFN-α, and apolipoprotein A-I fusion protein with IFN-α, interleukin, IL-2, IL-2 covalently bound to immunoglobulins (e.g., cergutuzumab amunaleukin, RO6874281), IL-2 covalently bound to PEG molecules (e.g., NKTR-214), IL-10, PEGylated IL-10 (e.g., pegilodecakin), IL-7, IL-12, IL-15, recombinant aglycosylated IL-15, fusion protein of IL-15 with the binding domain of IL-15Rα (e.g., RLI), triple fusion protein comprising human IL-15, the binding domain of IL-15Rα and apolipoprotein A-I, ALT-803 (IL-15 fused to IgG1 Fc domain), IL-18, IL-21, tumor necrosis factor, TNF-alpha, TNF-beta), erythropoietin (EPO), MIP3a, ICAM, macrophage colony stimulating factor (M-CSF), granulocyte colony stimulating factor (GCSF), granulocyte-macrophage colony stimulating factor (GM-CSF), GM-CSF, and talimogene laherparepvec.

E16: The conjugate of any of E1 or E2-E3.2, or a pharmaceutically acceptable salt thereof, wherein the immunomodulatory agent payload is the chemokine payload.

E17. The conjugate of E16, or a pharmaceutically acceptable salt thereof, wherein the chemokine payload is a CCL27, CCL28, CCL2, CCL3, CCL5, CXCL1, CXCL2, CXCL3, CXCL5, CXCL6, CXCL8, CXCL9, CXCL10, CXCL11, CXCL12, or CXCL14 payload.

E18. The conjugate of any of E1 or E2-E3.2, or a pharmaceutically acceptable salt thereof, wherein the immunomodulatory agent payload is the chemokine antagonist payload.

E19. The conjugate of E18, or a pharmaceutically acceptable salt thereof, wherein the chemokine antagonist payload is a plerixafor payload.

E19.1. The conjugate of any of E1 or E2-E3.2, or a pharmaceutically acceptable salt thereof, wherein the immunomodulatory agent is a monoclonal antibody specific to a cytokine or a cytokine receptor.

E20. The conjugate of any of E1, E2-E18, or E19.1, or a pharmaceutically acceptable salt thereof, wherein the immunomodulatory agent payload comprises a polypeptide.

E21. The conjugate of E20, or a pharmaceutically acceptable salt thereof, wherein the polypeptide comprises one or more lysine residues.

E21.1. The conjugate of E20, or a pharmaceutically acceptable salt thereof, wherein the polypeptide comprises one or more lysine, serine, threonine, or tyrosine residues.

E22. The conjugate of E21, or a pharmaceutically acceptable salt thereof, wherein the bioorthogonal moiety, at each occurrence, is linked to one of the one or more lysine residues.

E22.1. The conjugate of E21.1, or a pharmaceutically acceptable salt thereof, wherein the bioorthogonal moiety, at each occurrence, is independently linked to one or more lysine, serine, threonine, or tyrosine residues.

E22.2. The conjugate of any of E20-E22.1, or a pharmaceutically acceptable salt thereof, wherein the polypeptide comprises an N-terminal amino acid, wherein an occurrence of the bioorthogonal moiety is linked to the N-terminal amino acid.

E23. The conjugate of any of E3-E22.2, or a pharmaceutically acceptable salt thereof, wherein m is 1-20.

In the conjugates described herein, linker L may have 1 to 100 linking atoms, and may include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms, or from 1 to 40 linking atoms, or from 1 to 30 linking atoms, or from 1 to 20 linking atoms, or from 1 to 10 linking atoms, or from 1 to 5 linking atoms, or from 5 to 30 linking atoms, or from 10 to 30 linking atoms, or from 5 to 40 linking atoms, or from 5 to 50 linking atoms, or from 10 to 50 linking atoms.

The linker in formula (I) may comprise one or more (e.g., 1-10 or 1-5) chain heteroatoms (e.g., O, N, S) and one or more (e.g., 1-10 or 1-5) alkylene, alkenylene, alkynylene, arylene, heteroarylene, cycloalkylene or heterocycloalkylene moieties; wherein each alkylene, alkenylene, alkynylene, arylene, heteroarylene, cycloalkylene or heterocycloalkylene moiety, may be independently optionally substituted with one to five substituents independently selected from oxo, halo, $C_{1-4}$ alkyl, $C_{1-4}$ alkoxy, and $C_{1-4}$ haloalkyl.

In formula (I), the linker may be of the formula:

$$—Y^{10}—(CH_2)_{n'}—Y^{20}—(CH_2)_{m'}—Y^{30}—$$

wherein:

each of $Y^{10}$, $Y^{20}$, and $Y^{30}$ are independently a bond, $—NR^{110}—$, $—O—$, $—S(O)_{0-2}—$, $—NR^{110}C(O)—$, $—C(O)NR^{110}—$, $—NR^{110}S(O)_2—$, $—S(O)_2NR^{110}—$, $—CR^{120}{=}N—NR^{110}—$, $—NR^{110}—N{=}CR^{120}—$, $—C(O)—$, $—OC(O)—$, $—OC(O)O—$, alkylene, alkenylene, alkynylene, arylene, heteroarylene, cycloalkylene or heterocycloalkylene; wherein each alkylene, alkenylene, alkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and m" are each independently 0, 1, 2, 3, 4, 5, 6, 7, or 8.

In certain embodiments, the linker is not a bond. In certain embodiments, each $R^{110}$ is independently hydrogen, $C_{1-4}$ alkyl, $C_1$-4 haloalkyl, aryl, heteroaryl, cycloalkyl or heterocyclyl; and each $R^{120}$ is independently hydrogen, $C_{1-4}$ alkyl, $C_{1-4}$ haloalkyl, aryl, heteroaryl, cycloalkyl or heterocyclyl.

Representative linkers include, but are not limited to, those shown below:

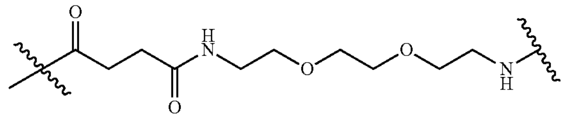

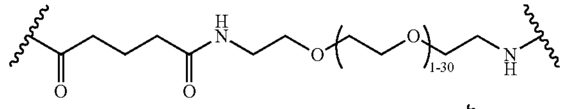

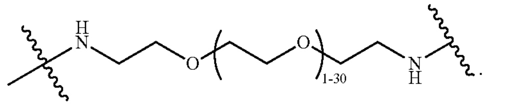

Representative linkers include, but are not limited to, those shown below:

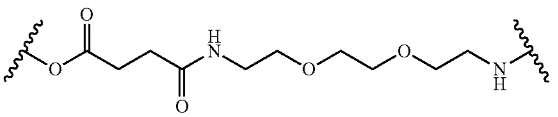

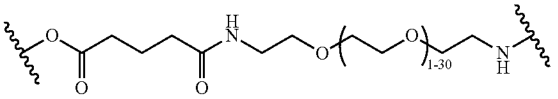

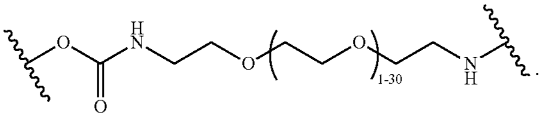

The linker in formula (I) may comprise one or more of polyethylene glycol (e.g., PEG having an average molecular weight of from 300 g/mol to 10,000 g/mol), ethylene-1,2-diylbis(methylcarbamate, an arylene (e.e., phenylene), ethylene-oxy, amine, ester, amide, carbamate, ketone (i.e., formyl), or carbonate. The linker in formula (I) may comprise

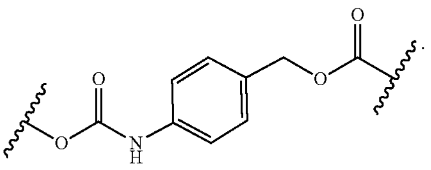 [SMILES: *OC(=O)Nc1ccc(COC(*)=O)cc1]

In formula (I), the linker may comprise one or more natural or unnatural amino acids, which may be referred to as a peptide linker. Where the drug ($D^1$) comprises an amino moiety, the linker may be bound thereto using a peptide linker made up of a carboxylic acyl unit, and one or more amino acids making up a protein or peptide sequence. The linker may also contain a self-immolating spacer which spaces the drug and the protein peptide sequence.

In formula I, the linker L may be a peptide linker represented by "A-Y—Z—X—W" in which "A" is the carboxylic acyl unit, "Y" and "Z" are each one or more natural or unnatural amino acids and together form a peptide sequence, and "X" and "W" are optional additional linkers having from 1 to 50 linking atoms, or from 5 to 10 linking atoms, or from 1 to 10 linking atoms which spaces the peptide and the drug, $D^1$, or the bioorthogonal moiety. In certain embodiments, one or more of the amino acids in the peptide linker is N-methylated.

In formula (I), Y may be at least one amino acid selected from the group consisting of alanine, valine, leucine, isoleucine, methionine, phenylalanine, tryptophan and proline. Y may be at least one amino acid selected from the group consisting of phenylalanine, alanine, and valine.

In formula (I), Z may be at least one amino acid selected from the group consisting of alanine, lysine, lysine protected with acetyl or formyl, arginine, arginine protected with tosyl or nitro groups, histidine, ornithine, ornithine protected with acetyl or formyl, and citrulline. Z may be at least one amino acid selected from the group consisting of alanine, lysine and citrulline.

Preferred Y—Z combinations include Valine-Citrulline; Valine-Alanine; and Alanine-Alanine.

In certain embodiments, A is —OC(O)—.

In certain embodiments, X is —OC(O)—.

In certain embodiments, W is —OC(O)—. In certain embodiments, X is absent and W is —OC(O)—.

In certain embodiments, —X—W is

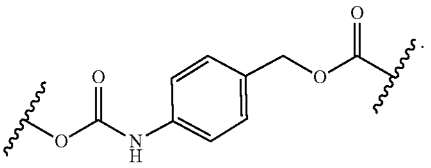 [SMILES: *OC(=O)Nc1ccc(COC(*)=O)cc1]

In certain embodiments, —X—W is

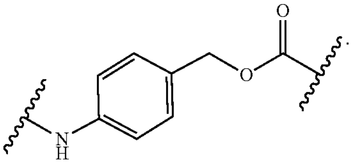 [SMILES: *Nc1ccc(COC(*)=O)cc1]

In certain embodiments, the peptide linker is specifically tailored so that it will be selectively cleaved (e.g., enzymatically cleaved) releasing the drug, such as by one or more of the tumor-associated proteases.

In certain embodiments, the peptide linker has a chain length of two to four amino acid residues (i.e., a di-, tri-, or tetra-peptide). It will be understood, however, that peptide linkers up to five, six, seven, or eight amino acid residues may also suitably be employed.

In certain embodiments, the peptide linker is Phe-Lys, Val-Lys, Val-Ala, Ala-Ala, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly [SEQ ID NO: 1], Ala-Leu-Ala-Leu [SEQ ID NO:2], Phe-$N^9$-tosyl-Arg, or Phe-$N^9$-Nitro-Arg. In certain embodiments, the peptide linker is Phe-Lys, Val-Lys, Val-Ala, Ala-Ala, Val-Val, Val-Cit, or D-Phe-L-Phe-Lys. In certain embodiments, the peptide linker is Val-Cit, Val-Ala, or Ala-Ala.

In certain embodiments, the linker L in formula (I) is:
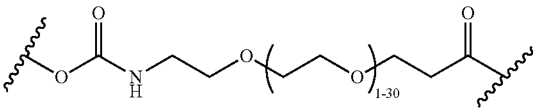
(e.g.,
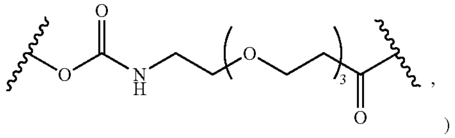
)
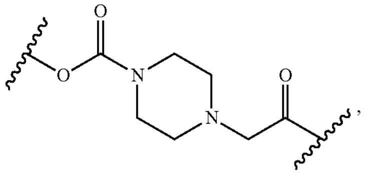
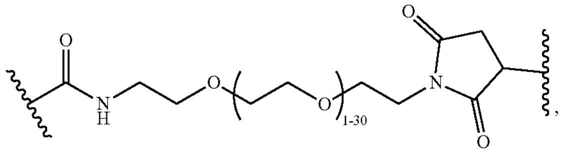
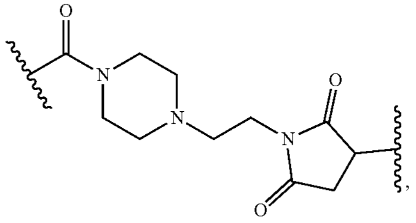
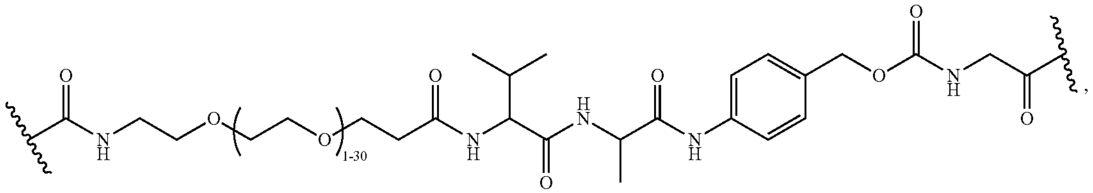
or
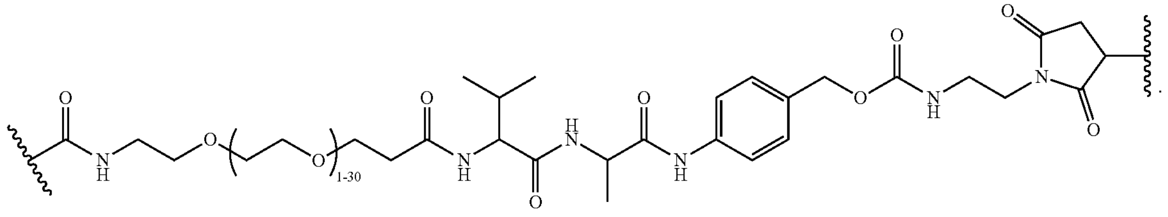

The foregoing linkers may attach on the right-hand side to amino acid side chains of $D^1$ such lysine or cysteine (e.g.,

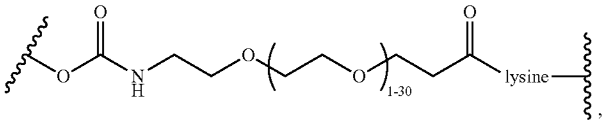
,
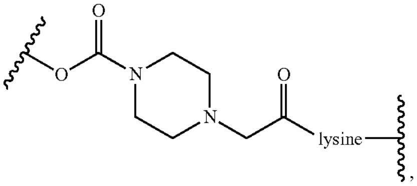
,
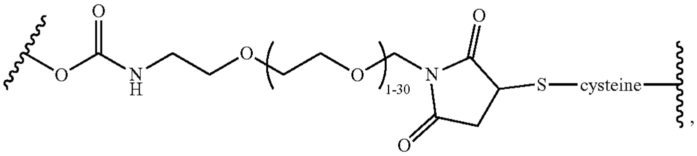
,
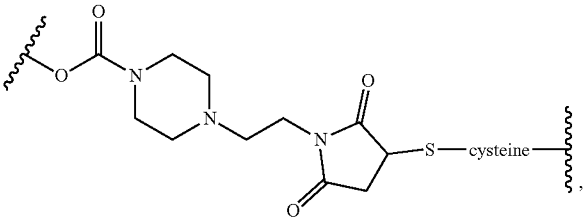
,
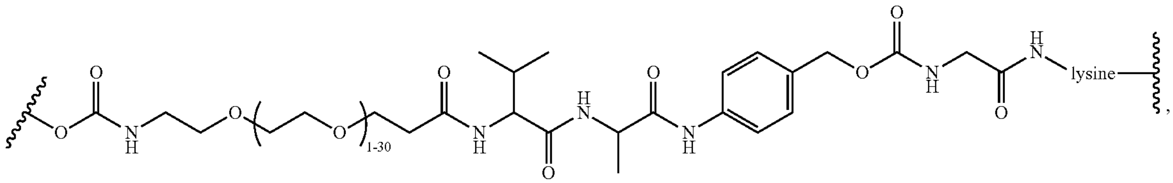
,
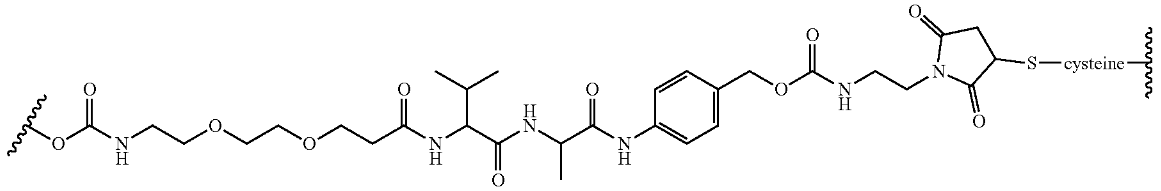
.
)

E24, The conjugate of any of E3-E23, or a pharmaceutically acceptable salt thereof, wherein $L^1$ is —OC(O)$L^4$- or —$OC_{1-6}$alkyleneC(O)$L^4$-;

$L^4$ is a bond, —N($R^{12}$)—$C_{2-3}$alkylene-N($R^{13}$)C(O)—, —CH(NHC(O)$R^{14}$)$C_{1-4}$alkylene-S—S—$C_{1-4}$alkylene-OC(O)—, —NHNHC(O)CH(NHC(O)$R^{15}$)$CH_2$C(O)—, —$C_{1-6}$alkylene-CH($G^x$)OC(O)—

,
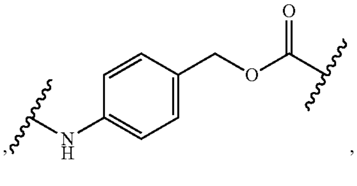
,

-continued

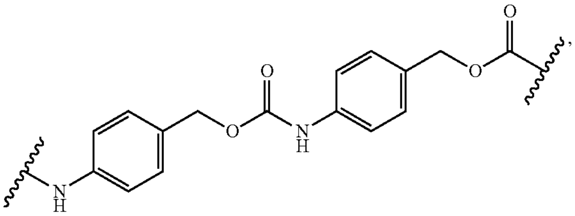
,
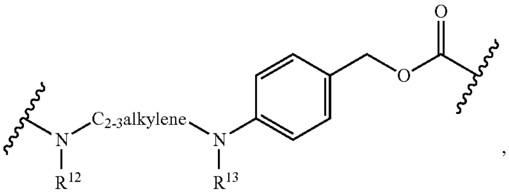
,

-continued

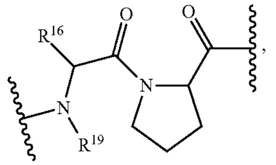

, or

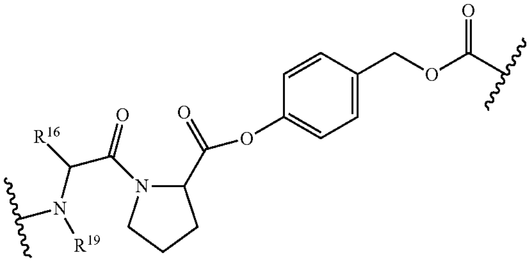

;

$R^{12}$, $R^{13}$, $R^{14}$, $R^{15}$, and $R^{19}$ are each independently hydrogen or $C_{1-4}$alkyl;

$R^{16}$ is hydrogen, $C_{1-4}$alkyl, —$C_{1-4}$alkylene-OH, —$C_{1-4}$ alkylene-O$C_{1-4}$alkyl, —$C_{1-4}$alkylene-$CO_2H$, or —$C_{1-4}$ alkylene-$CONH_2$; and $G^x$ is phenyl optionally substituted with 1-5 substituents independently selected from the group consisting of halogen, $C_{1-4}$alkyl, $C_{1-4}$haloalkyl, $C_{1-4}$alkoxy, cyano, and nitro.

E25. The conjugate of claim E24, or a pharmaceutically acceptable salt thereof, wherein:

G-$L^1$, at each occurrence, is independently

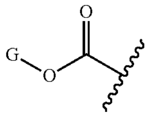

,

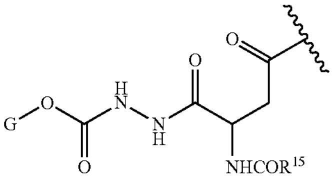

,

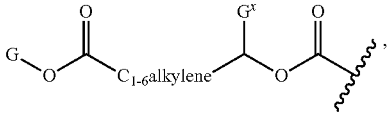

,

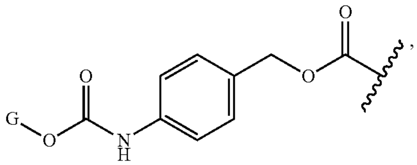

,

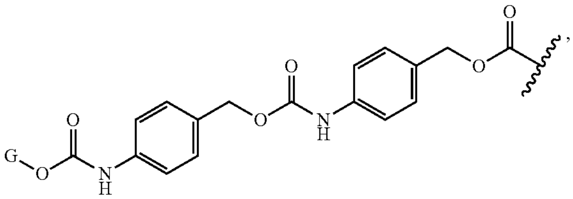

,

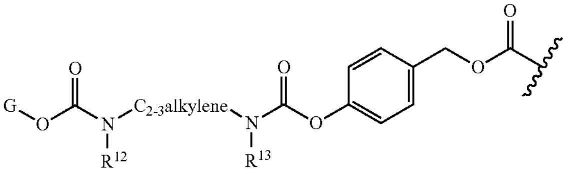

,

-continued

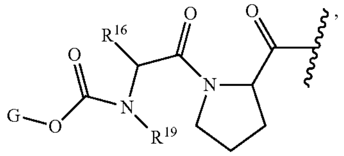

, or

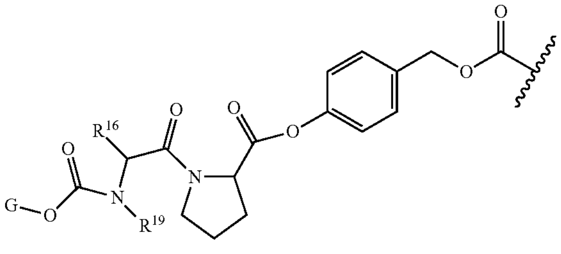

.

E26. The conjugate of E25, or a pharmaceutically acceptable salt thereof, wherein G-$L^1$, at each occurrence, is independently

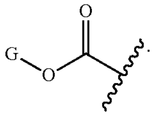

.

When attached to a lysine residue, the conjugate may have formula

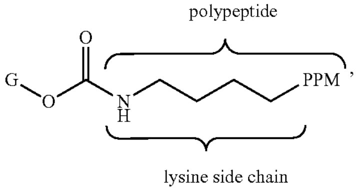

, wherein PPM is a polypeptide moiety having the lysine residue and lysine side chain and the PPM may also have additional lysines, or other amino acid side chains conjugated to the group

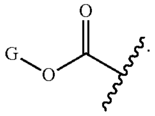

.

E27. The conjugate of any of E3-E26, or a pharmaceutically acceptable salt thereof, wherein:

$R^{1B}$ is selected from the group consisting of $G^1$, OH, —$NR^{1c}$—$C_{1-4}$alkylene-$G^1$, —$NR^{1c}$—$C_{1-4}$alkylene-N$(R^{1d})_2$, —$N(R^{1e})CHR^{1e}CO_2H$, —$N(R^{1c})CH_2CO_2H$, and —$N(R^{1f})$—$CH_2CH_2$—$(N(CH_2CO_2H)CH_2CH_2)_n$—$N(CH_2CO_2H)_2$;

$R^{1e}$ is —$CH_2CO_2H$, —$CH_2CH_2CO_2H$, —$CH_2CONH_2$, —$CH_2CH_2CONH_2$, —$CH_2OH$, or —$CH(CH_3)OH$; and $R^{1f}$ is hydrogen or $CH_2CO_2H$.

E27.1. The conjugate of any of E3-E26, or a pharmaceutically acceptable salt thereof, wherein:

$R^{1B}$ is selected from the group consisting of $—NR^{1c}—C_{2-4}alkylene-N(C_{1-4}alkyl)_3^+$, $—N(R^{1c})—C_{1-6}alkylene-SO_3H$, $—N(R^{1c})—(CH_2CH_2O)_{1-3}—CH_2CH_2N((CH_2CH_2O)_{1-3}—C_{1-6}alkylene-CO_2H)_2$, and $—N(R^{1c})—CH(CH_2O—(CH_2CH_2O)_{0-2}—C_{1-6}alkylene-CO_2H)_2$.

E27.2. The conjugate of E27.1, or a pharmaceutically acceptable salt thereof, wherein $R^{1B}$ is selected from the group consisting of $—NR^{1c}—CH_2CH_2—N(CH_3)_3^+$, $—N(R^{1c})CH_2CH_2—SO_3H$, $—N(R^{1c})—(CH_2CH_2O)_3—CH_2CH_2N((CH_2CH_2O)_3—CH_2CH_2—CO_2H)_2$, and $—N(R^{1e})—CH(CH_2O—CH_2CH_2—CO_2H)_2$.

E27.3. The conjugate of any of E27-E27.2, or a pharmaceutically acceptable salt thereof, wherein $R^{1A}$ is $C_{1-4}alkyl$.

E27.4. The conjugate of E27.3, or a pharmaceutically acceptable salt thereof, wherein $R^{1A}$ is $CH_3$.

E27.5. The conjugate of any of E27-E27.4, or a pharmaceutically acceptable salt thereof, wherein $R^{1c}$ is hydrogen.

E28. The conjugate of any of E3-E26, or a pharmaceutically acceptable salt thereof, wherein $R^{1A}$ is $C_{1-4}alkyl$;

$R^{1B}$ is selected from the group consisting of $G^1$, OH, $—NR^{1c}—C_{1-4}alkylene-G^1$, $—NR^{1c}—C_{1-4}alkylene-N(R^{1d})_2$, $—N(R^{1e})CHR^{1e}CO_2H$, $—N(R^{1c})CH_2CO_2H$, and $—N(R^{1f})CH_2CH_2—(N(CH_2CO_2H)CH_2CH_2)_n—N(CH_2CO_2H)_2$;

$R^{1e}$ is $—C_{1-4}alkylene-CO_2H$;

$R^{1f}$ is hydrogen or $C_{1-4}alkylene-CO_2H$;

$G_1$ is a 4- to 8-membered monocyclic heterocyclyl containing a first nitrogen and optionally one additional heteroatom selected from nitrogen, oxygen, and sulfur, $G^1$ being attached at the first nitrogen and optionally substituted with 1-4 substituents independently selected from the group consisting of $C_{1-4}alkyl$, $C_{1-4}haloalkyl$, halo, cyano, OH, $—OC_{1-4}alkyl$, and oxo; and n is 0, 1, or 2.

E29. The conjugate of E28, or a pharmaceutically acceptable salt thereof, wherein $R^{1A}$ is $CH_3$;

$R^{1e}$ is $—CH_2CO_2H$;

$R^{1f}$ is hydrogen or $CH_2CO_2H$; and $G^1$ is a piperazinyl, morpholinyl, piperidinyl, azepanyl, or pyrrolidinyl, attached through a ring nitrogen atom and optionally substituted with 1-4 substituents independently selected from the group consisting of $C_{1-4}alkyl$, $C_{1-4}haloalkyl$, halo, cyano, OH, $—OC_{1-4}alkyl$, and oxo.

E30. The conjugate of any of E3-E29, or a pharmaceutically acceptable salt thereof, wherein $L^2$ is —C(O)—.

E31. The conjugate of E30, or a pharmaceutically acceptable salt thereof, wherein $R^{1B}$ is selected from the group consisting of OH, $N(H)CH_2CO_2H$, $—N(H)CHR^{1e}CO_2H$, $—N(H)—CH_2CH_2—(N(CH_2CO_2H)CH_2CH_2)_n—N(CH_2CO_2H)_2$, and $—N(CH_2CO_2H)—CH_2CH_2—N(CH_2CO_2H)_2$; and $R^{1e}$ is $—CH_2CO_2H$.

E32. The conjugate of any of E1-E31, or a pharmaceutically acceptable salt thereof wherein the bioorthogonal moiety is

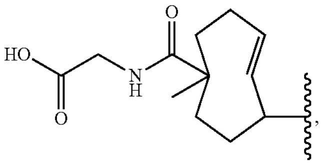

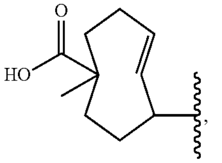

or

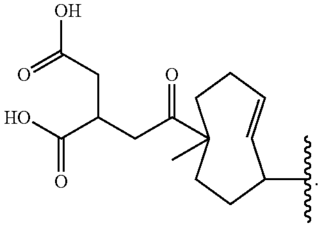

E32.1. The conjugate of any of E1-E31, or a pharmaceutically acceptable salt thereof wherein the bioorthogonal moiety is

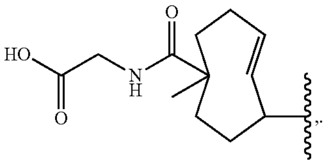 [SMILES: *C1/C=C/CCC(C)(C(=O)NCC(=O)O)CC1]

E32.2. The conjugate of any of E1-E31, or a pharmaceutically acceptable salt thereof wherein the bioorthogonal moiety is

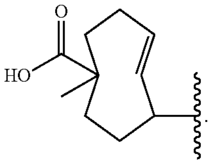 [SMILES: *C1/C=C/CCC(C)(C(=O)O)CC1]

E32.3. The conjugate of any of E1-E31, or a pharmaceutically acceptable salt thereof wherein the bioorthogonal moiety is

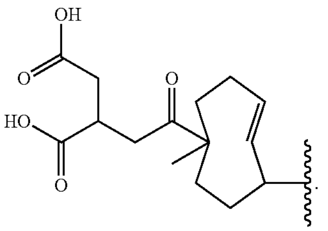 [SMILES: *C1/C=C/CCC(C)(C(=O)CC(CC(=O)O)C(=O)O)CC1]

E32.4. The conjugate of any of E1-E31, or a pharmaceutically acceptable salt thereof wherein the bioorthogonal moiety is

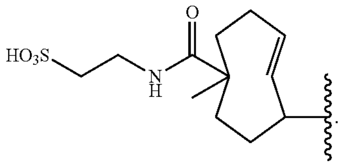 [SMILES: *C1/C=C/CCC(C)(C(=O)NCCS(=O)(=O)O)CC1]

E32.5. The conjugate of any of E1-E31, or a pharmaceutically acceptable salt thereof wherein the bioorthogonal moiety is

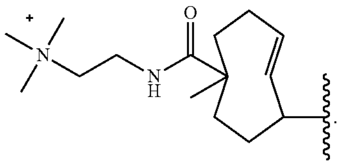

E32.6. The conjugate of any of E1-E31, or a pharmaceutically acceptable salt thereof wherein the bioorthogonal moiety is

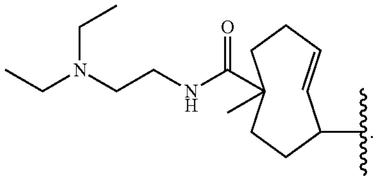 [SMILES: *C1/C=C/CCC(C)(C(=O)NCCN(CC)CC)CC1]

E32.7. The conjugate of any of E1-E31, or a pharmaceutically acceptable salt thereof wherein the bioorthogonal moiety is

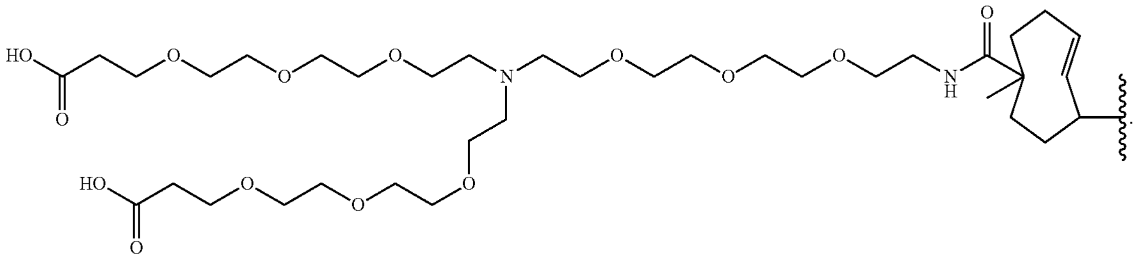 [SMILES: *C1/C=C/CCC(C)(C(=O)NCCOCCOCCOCCN(CCOCCOCCOCCC(=O)O)CCOCCOCCOCCC(=O)O)CC1]

E32.8. The conjugate of any of E1-E31, or a pharmaceutically acceptable salt thereof wherein the bioorthogonal moiety is

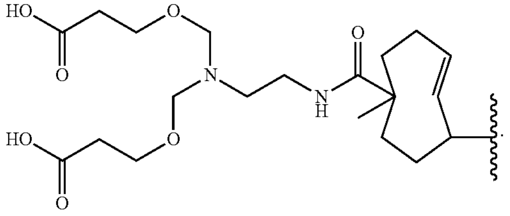 [SMILES: *C1/C=C/CCC(C)(C(=O)NCCN(COCCC(=O)O)COCCC(=O)O)CC1]

E32.9. The conjugate of any of E1-E31, or a pharmaceutically acceptable salt thereof wherein the bioorthogonal moiety is

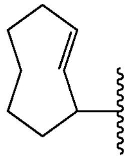 [SMILES: *C1/C=C/CCCCC1]

(i.e., q is 0 and q1 is 0 in formula (I)).

E33. A pharmaceutical composition comprising the conjugate of any of E1-32.9, or a pharmaceutically acceptable salt thereof, and a pharmaceutically acceptable carrier.

E34. A method of treating cancer or enhancing or eliciting an immune response, the method comprising administering to a subject in need thereof, a therapeutically effective amount of the conjugate of any of E 1-E32.9, or a pharmaceutically acceptable salt thereof, or the pharmaceutical composition of E33, and a therapeutic support composition, the therapeutic support composition comprising a biocompatible support and a tetrazine-containing group of formula

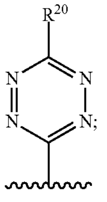

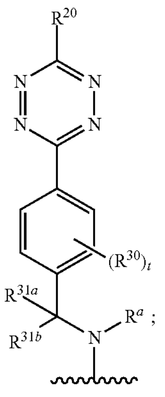

or

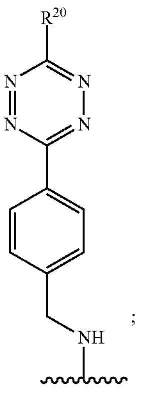

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R", SC(═O)R'", OC(═S)R'", SC(═S)R'", S(═O)R', $S(═O)_2R'"$, $S(═O)_2NR'R"$, C(═O)O—R', C(═O)S—R', C(═S)O—R', C(═S)S—R', C(═O)NR'R", C(═S)NR'R", NR'R", NR'C(═O)R", NR'C(═S)R", NR'C(═O)OR", NR'C(═S)OR", NR'C(═O)SR", NR'C(═S)SR", OC(═O)NR'R", SC(═O)NR'R", OC(═S)R'R', SC(═S)R'R", NR'C(═O)NR"R", and NR'C(═S)NR"R";

R' and R" at each occurrence are independently selected from hydrogen, aryl and alkyl;

R'" at each occurrence is independently selected from aryl and alkyl;

$R^{30}$ is halogen, cyano, nitro, hydroxy, alkyl, haloalkyl; alkenyl, alkynyl, alkoxy; haloalkoxy; heteroalkyl, aryl, heteroaryl, heterocycle, cycloalkyl, or cycloalkenyl;

$R^a$, $R^{31a}$ and $R^{31b}$ are each independently hydrogen, $C_1$-$C_6$-alkyl, or $C_1$-$C_6$-haloalkyl; and is 0, 1, 2, 3, or 4.

E35. The method of E34, wherein the tetrazine-containing group is linked or directly bonded to a hyaluronic acid biocompatible support.

E36. The method of E34 or E35, wherein the therapeutic support composition comprises substituted hyaluronic acid units of formula (II), (II)

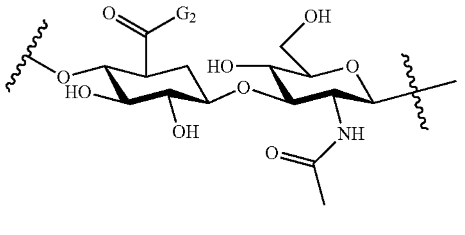

wherein $G^2$ is

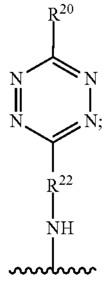

and $R^{22}$ is a linker of 1 to 100 linking atoms.

E37. The method of E36, wherein:

$G^2$ is

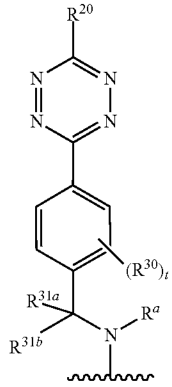

or

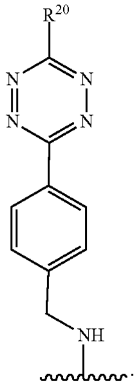

E38. The method of E37, wherein G2 is

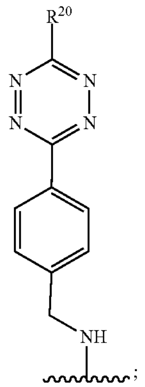

and $R^{20}$ is hydrogen or $C_{1-4}$alkyl.

E39. The method of any of E34-E38, wherein the method is a method of treating cancer.

E39.1. The method of E39, wherein the cancer is metastatic.

E40. The method of E39 or E39.1, wherein the cancer is melanoma, renal cancer, prostate cancer, ovarian cancer, endometrial carcinoma, breast cancer, glioblastoma, lung cancer, soft tissue sarcoma, fibrosarcoma, osteosarcoma, pancreatic cancer, gastric carcinoma, squamous cell carcinoma of head/neck, anal/vulvar carcinoma, esophageal carcinoma, pancreatic adenocarcinoma, cervical carcinoma, hepatocellular carcinoma, kaposi's sarcoma, Non-Hodgkins lymphoma, Hodgkins lymphoma Wilm's tumor/neuroblastoma, bladder cancer, thyroid adenocarcinoma, pancreatic neuroendocrine tumors, prostatic adencocarcinoma, nasopharyngeal carcinoma, or cutaneous T-cell lymphoma.

E40.1. The method of E39 or E39.1, wherein the cancer is a melanoma, renal cancer, prostate cancer, ovarian cancer, breast cancer, glioma, lung cancer, soft tissue carcinoma, soft tissue sarcoma, osteosarcoma, or pancreatic cancer.

E41. The method of any of E39-E40.1, wherein the cancer is a solid tumor.

E42. The method of any of E39-E40.1, wherein the cancer is a soft tissue sarcoma.

E43. The method of E42, wherein the soft tissue sarcoma is a fibrosarcoma, rhabdomyosarcoma, or Ewing's sarcoma.

E44. The method of any of E34-E38, wherein the method is a method of enhancing or eliciting an immune response.

E45. The method of E44, wherein the immune response is an increase in one or more of leukocytes, lymphocytes, monocytes, and eosinophils.

E46. The method of any of E34-E45, further comprising administering a therapeutically effective amount of an additional therapeutic agent selected from the group consisting of an anticancer agent, an immunomodulatory agent, or a trans-cyclooctene prodrug thereof. Anticancer agents, immunomodulatory agents, and their trans-cyclooctene prodrugs are known in the art, as described herein below and which are incorporated by reference in E46.

E47. A kit comprising the conjugate of any of E1-E32.9, or a pharmaceutically acceptable salt thereof, or the pharmaceutical composition of E33, and instructions for use thereof.

E48. The kit of E45, further comprising the therapeutic support composition as defined in any of E34-E38.

E49. A method for delivering an effective amount of the immunomodulatory agent payload of any of E1-E22.2 to a target location in a subject, the method comprising administering to the subject at the target location the therapeutic support composition of any of E34-E38 and administering to the subject the conjugate, or the pharmaceutically acceptable salt or composition thereof, of any E1-E33.

1. Therapeutic Proteins

Therapeutic proteins for use in the conjugates disclosed herein are generally intended to be a large molecule comprised of a long chain of amino acids that is folded into a three-dimensional shape. In general, therapeutic proteins can be categorized based on their pharmacological activity, they can be divided into five groups: (a) replacing a protein that is deficient or abnormal; (b) augmenting an existing pathway; (c) providing a novel function or activity; (d) interfering with a molecule or organism; and (e) delivering other compounds or proteins, such as a radionuclide, cytotoxic drug, or effector proteins. Therapeutic proteins can also be grouped based on their molecular type, where exemplary types include antibody-based drugs, Fc fusion proteins, anticoagulants, blood factors, bone morphogenetic proteins, engineered protein scaffolds, enzymes, growth factors, hormones, interferons, interleukins, or thrombolytics. Therapeutic proteins may also be classified based on their molecular mechanism of activity, such as (a) binding non-covalently to target, e.g., mAbs; (b) affecting covalent bonds, e.g., enzymes; or (c) exerting activity without specific interactions, e.g., serum albumin.

Examples of classes of therapeutic proteins include those that are cytokines, chemokines, growth factors, hormones, antibodies, and antigens. Further examples include, but are not limited to, the following: erythropoietin (EPO, e.g., native EPO or synthetic EPO (see, e.g., US 2003/0191291), such as, but not limited to, e.g., PROCRIT®, EPREX®, or EPOGEN® (epoetin-α), ARANESP® (darbepoietin-α), NEORECORMON®, EPOGIN® (epoetin-β), and the like); a growth hormone (e.g., a somatotropin, e.g., GENOTROPIN®, NUTROPIN®, NORDITROPIN®, SAIZEN®, SEROSTIM®, HUMATROPE®, etc.); theraputic monoclonal antibody (e.g. Atezolizumab, Avelumab, Bevacizumab, Cemiplimab, Cetuximab, Daratumumab, Dinutuximab, Durvalumab, Elotuzumab, Ipilimumab, Isatuximab, Mogamulizumab, Necitumumab, Nivolumab, Obinutuzumab, Ofatumumab, Olaratumab, Panitumumab, Pembrolizumab, Pertuzumab, Ramucirumab, Rituximab, Trastuzumab etc.); human growth hormone (hGH); bovine growth hormone (bGH); follicle stimulating hormone (FSH); interferon (e.g., IFN-γ, IFN-α, IFN-β, IFN-ω; IFN-τ, consensus interferon, and the like); insulin (e.g., Novolin, Humulin, Humalog, Lantus, Ultralente, etc.), insulin-like growth factor (e.g., IGF-I, IGF-II); blood factors (e.g., Factor X, tissue plasminogen activator (TPA), and the like, such as, but not limited to, e.g., ACTIVASE® (alteplase) tissue plasminogen activator, NOVOSEVEN® (recombinant human factor Vila), Factor Vila, Factor VIII (e.g., KOGENATER), Factor IX, β-globin, hemoglobin, and the like); colony stimulating factors (e.g., granulocyte-CSF (G-CSF, e.g., NEUPOGEN® (filgrastim)), macrophage-CSF (M-CSF), granulocyte-macrophage-CSF (GM-CSF), Neulasta (pegfilgrastim), granulocyte-monocyte colony stimulating factor, megakaryocyte colony stimulating factor, and the like), transforming growth factors (e.g., TGF-beta, TGF-alpha); interleukins (e.g., IL-1, IL-2 (e.g., Proleukin®), IL-3, IL-4, IL-5, IL-6, IL-7, IL-8, IL-9, IE-12, and the like); a growth factor (e.g., epidermal growth factor (EGF), platelet-derived growth factor (PDGF, e.g., REGRANEX® (beclapermin)), fibroblast growth factors (FGFs, e.g., aFGF, bFGF, such as FIB LAST® (trafermin)), glial cell line-derived growth factor (GDNF), nerve growth factor (NGF), stem cell factor (e.g., STEMGEN® (ancestim)), keratinocyte growth factor, a hepatocyte growth factor, and the like); a soluble receptor (e.g., a TNF-α-binding soluble receptor such as ENBREL® (etanercept), a soluble VEGF receptor, a soluble interleukin receptor, a soluble γ/δ T cell receptor, and the like); an enzyme (e.g., α-glucosidase, CERAZYME® (imiglucarase, β-glucocerebrosidase, CEREDASE® (alglucerase); an enzyme activator (e.g., tissue plasminogen activator); a chemokine (e.g., IP-10, Mig, Groα/IL-8, regulated and normal T cell expressed and secreted (RANTES), MIP-1α, MIP-1ρ, MCP-1, PF-4, and the like); an angiogenic agent (e.g., vascular endothelial growth factor (VEGF); an anti-angiogenic agent (e.g., a soluble VEGF receptor); a protein vaccine; a neuroactive peptide such as bradykinin, cholecystokinin, gastin, secretin, oxytocin, gonadotropin-releasing hormone, beta-endorphin, enkephalin, substance P, somatostatin, galanin, growth hormone-releasing hormone, bombesin, warfarin, dynorphin, neurotensin, motilin, thyrotropin, neuropeptide Y, luteinizing hormone, calcitonin, insulin, glucagon, vasopressin, angiotensin II, thyrotropin-releasing hormone, vasoactive intestinal peptide, a sleep peptide, etc.; other proteins such as a thrombolytic agent, an atrial natriuretic peptide, bone morphogenic protein, thrombopoietin, relaxin, glial fibrillary acidic protein, follicle stimulating hormone, a human alpha-1 antitrypsin, a leukemia inhibitory factor, a transforming growth factor, a tissue factor, an insulin-like growth factor, a luteinizing hormone, a follicle stimulating hormone, a macrophage activating factor, tumor necrosis factor, a neutrophil chemotactic factor, a nerve growth factor, a tissue inhibitor of metalloproteinases; a vasoactive intestinal peptide, angiogenin, angiotropin, fibrin; hirudin; a leukemia inhibitory factor; an IL-1 receptor antagonist (e.g., Kineret® (anakinra)); and the like. It will be readily appreciated that native forms of the above therapeutic proteins are also of interest as payloads in the present disclosure.

2. Cytokines

Cytokines may limit tumor cell growth by a direct anti-proliferative or pro-apoptotic activity, or indirectly by stimulating the cytotoxic activity of immune cells against tumor cells. Cytokines are sometimes classified as type 1 or type 2, as described by Lucey et al., Clin Microbiol Rev. 1996; 9(4):532-62. In this nomenclature, a type 1 response is defined as a strong cellular immune response with normal or increased levels of IL-2, IFN-γ, TNF-β, and/or IL-12 while a type 2 response is defined as an impaired cellular response with an increase in one or more B-cell activities (e.g., hypergammaglobulinemia, autoantibody production, or hyperIgE) and an increase in the level of IL-4, IL-5, IL-6, IL-10, and/or IL-13. Generally, type 1 cytokines have been shown to mediate anti-tumor responses. Cytokines that may be used as immunomodulatory agents include, but are not limited to, IFN-alpha, IFN-beta, and IFN-gamma, interleukins (e.g., IL-1 to IL-40, in particular, IL-7, IL-12, IL-15, IL-18, and IL-21), tumor necrosis factors (e.g., TNF-alpha and TNF-beta), erythropoietin (EPO), MIP3a, ICAM, macrophage colony stimulating factor (M-CSF), granulocyte colony stimulating factor (GCSF) and granulocyte-macrophage colony stimulating factor (GM-CSF) as described in US 2008/0014222. In embodiments of the invention, the cytokine is IL-2, IL-2 covalently bound to immunoglobulins (e.g., cergutuzumab amunaleukin, RO6874281) or PEG molecules (e.g., NKTR-214), IL-10, PEGylated IL-10 (e.g., pegilodecakin), IL-12, IL-15, recombinant aglycosylated IL-15, fusion protein of IL-15 with the binding domain of IL-15Rα (e.g., RLI), triple fusion protein comprising human IL-15, the binding domain of IL-15Rα and apolipoprotein A-I, ALT-803 (il-15 fused to IgG1 Fc domain), IL-21, GM-CSF, talimogene laherparepvec, IFN-α, pegylated IFN-α, apolipoprotein A-I fusion protein with IFN-α.

The inhibitors of certain cytokines, their cognate receptor agonists and/or antagonists may also be used as cancer therapy. Cytokines are secreted or membrane-bound proteins that act as mediators of intercellular signaling to regulate homeostasis of the immune system. They are produced by cells of innate and adaptive immunity in response to microbes, self-antigens and tumor antigens. Inhibitors of TNF-α (e.g., infliximab, certolizumab) particularly in the context of PD-1 pathway blockade, TGF-B (e.g., galunisertib, fresolimumab, M7824), and CSF-1 (e.g., pexidartinib, cabiralizumab) may be used in the methods of the invention.

Immunotherapy with cytokines and cytokine inhibitors is described by Berraondo et al., British Journal of Cancer (2019) 120, 6-15, which is incorporated herein by reference.

3. Chemokines

Chemokines and/or chemokine receptor inhibitors may be used as immunomodulatory agents; they are chemotactic proteins that have the potential to attract macrophages, T-cells, eosinophils, basophils, and other cells to sites of inflammation, infection and/or tumor growth. These proteins are usually of low molecular mass (7-9 kD). Chemokines form four main structural subclasses (C, CC, CXC, and CX3C) categorized through their primary amino acid structure, which contain various combinations of conserved cysteine residues.

Immunomodulatory chemokines that may be suitable are CCL27 and CCL28, CC (CCL2, CCL3, CCL5) and CXC (CXCL1, CXCL2, CXCL5, CXCL6, CXCL8, CXCL9, CXCL10, CXL12).

ELRCXC chemokines, including IL-8, GROα, GROβ, GROγ, NAP-2, and ENA-78 (Strieter, 1995, *J Biol Chem,* 270:27348-57), have also been implicated in the induction of tumor angiogenesis (new blood vessel growth). Angiogenic activity is due to ELRCXC-chemokine binding to, and activation of CXCR2, and possibly CXCR1 for IL-8, expressed on the surface of vascular endothelial cells (ECs) in surrounding vessels. Many different types of tumors have been shown to produce ELRCXC chemokines. Chemokine production has been correlated with a more aggressive phenotype (Inoue, 2000, *Clin Cancer Res,* 6:2104-2119) and poor prognosis (Yoneda, 1998, *J Nat Cancer Inst,* 90:447-54). Chemokines are potent chemotactic factors and the ELRCXC chemokines, in particular, have been shown to induce EC chemotaxis. Thus, these chemokines are thought to induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg, 1996, *J Clin Invest,* 97:2792-802), ENA-78 (Arenberg, 1998, *J Clin Invest,* 102:465-72), and GROα (Haghnegandar, 2000, *J Leukoc Biology,* 67:53-62). CXC chemokine inhibitors include

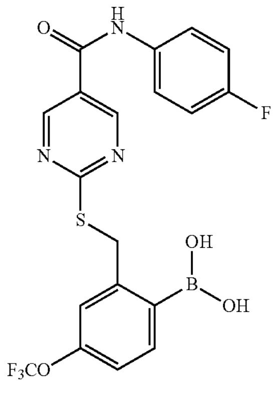

and

-continued

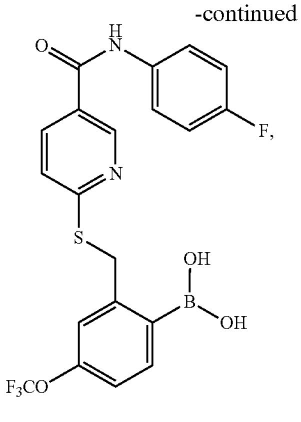

as described in U.S. Pat. No. 10,046,002, which is incorporated herein by reference.

4. Chemokine Antagonists

Immunomodulatory agents suitable for use with the methods of the present invention include chemokine or chemokine receptor antagonists that inhibit the recruitment of suppressive immune cells into the tumor microenvironment. For example, but not exclusively, the methods of the present invention may use a CCR1, CCR2 or CCR5 antagonist that reduces the infiltration of myeloid suppressor cells and regulatory T cells.

Suitable CCR, CXCR, and CCL inhibitors include inhibitors of CCR1 (e.g., CCX721, BL5923), CCR2 (e.g., CCX9588, PF-04136309, CCX872, RDC018, 747, iCCR2), CCL2 (e.g., CNTO 888), CCR4 (e.g., Affi 5, AF399/420/1802), CCR5 (e.g. Maraviroc), CCR7 (e.g., siRNA, MSM R707), CXCR2 (e.g., Navarixin, SB225002, Reparixin, SB265610, AZD5069), CXCR4 (e.g., AMD3100, AMD3465, LY2510924, BKT140, BMS-936564, PF-06747143, PRX177561, POL5551, USL311, CTCE-9908), as described by Poeta et al., Frontiers in Immunology (2019), Article 379, doi: 10.3389/fimmu.2019.00379; Yu et al., Cancer Biol. Ther. (2008) 7:1037-43; and Chi et al., Int. J Clin Exp Pathol. (2015) 8:12533-40.

5. Immune Checkpoint Inhibitors

Immune checkpoint inhibitors include but are not limited to PD-1 inhibitors (e.g. nivolumab, pembrolizumab, pidilizumab, sintilimab, AMP-224), PD-L1 inhibitors (e.g. atezolizumab, avelumab, durvalumab, BMS-936559), CTLA4 inhibitors (e.g. ipilimumab, tremelimumab) IDO inhibitors (e.g. indoximod, epacadostat), TIGIT inhibitors (e.g., LAG-3, such as an anti-LAG-3 antibody described in US2015/0259420, which is incorporated herein by reference; TIM-3, such as an anti-TIM-3 antibody described in US2015/0218274, which is incorporated herein by reference), and a BTLA pathway antagonist.

6. Cytokine Inhibitors

Cytokine inhibitors are a heterogeneous group of drugs which 1) decrease the synthesis of cytokines; 2) decrease their concentration in free active form: 3) block their interaction with specific receptors, or 4) interfere with the signaling of cytokine receptors. Cytokine inhibitors include antagonists, soluble receptors, cytokine-binding proteins, and cytokines that block other cytokines. These agents include, but are not limited to, small molecules, peptides, and larger proteins such as mAbs.

In some embodiments, the immune response is modulated using a xenobiotic agent, biologic agent, natural or artificially-derived adjuvants, cell-based therapy and/or checkpoint inhibitors including but not limited to the inhibitors of PD-1, PD-L1, CTLA-4, B7 molecules, TIGIT, Tim-3 and/or Lag-3, indoleamine 2,3-dioxygenase (IDO).

An additional therapeutic agent may be an immune checkpoint inhibitor. Immune checkpoint inhibitors include PD-1 inhibitors (e.g. nivolumab, pidilizumab, sintilimab), PD-L1 inhibitors (e.g. atezolizumab, avelumab, durvalumab, BMS-936559), CTLA4 inhibitors (e.g. ipilimumab, tremelimumab) or IDO inhibitors (e.g. indoximod, epacadostat).

C. THERAPEUTIC SUPPORT COMPOSITIONS

The therapeutic support composition comprises a support. Supports may be biocompatible supports compositions, i.e., compatible with the subject's body. In some instances, a support is non-toxic to the subject and does not substantially react with tissue or biological compounds in the subject. For example, the support can be a hydrogel, among others. A support is capable of implantation into a subject's body and supporting binding agents (e.g., tetrazine-containing group), as well as payloads after the binding agents conjugate. Representative supports include, but are not limited to polymers, viscous or non-viscous liquid materials, gels, hydrogels, polysaccharide hydrogels, a cross-linked polymer matrix, a metal, a ceramic, a plastic, a bone graft material, alginate, cellulose, chitosan, hyaluronic acid, chondroitin sulfate, heparin, and the like. Supports also include particles, such as nanoparticles, microparticles, and the like.

Hydrogels may be polysaccharide hydrogels, alginate, cellulose, hyaluronic acid, chitosan, chitosin, chitin, hyaluronic acid, chondroitin sulfate, heparin, and the like. Other suitable sugar-based biomaterials include those described in *Polymer Advanced Technology,* 2014, 25, 448-460. Polymers that may be used as the support can include, but are not limited to, polyphosphazenes, polyanhydrides, polyacetals, poly(ortho esters), polyphosphoesters, polycaprolactones, polyurethanes, polylactides, polycarbonates, polyamides, and polyethers, and blends/composites/copolymers thereof. Representative polyethers include, but are not limited to, poly(ethylene glycol) (PEG), polypropylene glycol) (PPG), triblock Pluronic ($[PEG]_n$-$[PPG]_m$-[PEG]n), PEG diacrylate (PEGDA), and PEG dimethacrylate (PEGDMA). The support can also include proteins and other poly(amino acids), such as collagen, gelatin, elastin and elastin-like polypeptides, albumin, fibrin, poly(gamma-glutamic acid), poly(L-lysine), poly(L-glutamic acid), poly (aspartic acid), and the like.

In some embodiments, the support is a hydrogel. In some embodiments, the support is an alginate. In some embodiments, the support is chitin. In some embodiments, the support is a hyaluronic acid (e.g., a non-hydrogel hyaluronic acid substantially without crosslinks). In some embodiments, the support is chitosin.

In certain embodiments, the support is a particle. Particles of the present disclosure can have a diameter that is 2 cm or less, such as 1.5 cm or less, or 1 cm or less, or 0.5 cm or less. For example, the particles can be nanoparticles or microparticles. Nanoparticles include particles having average dimensions in the nanometer scale (e.g., 1000 nm or less). Microparticles are particles having average dimensions in the micrometer scale (e.g., 1000 μm or less). By "average" is meant the arithmetic mean. In some embodiments, the nanoparticles have a diameter ranging from 1 nm to 1 μm, such as from 10 nm to 1 μm, or 25 nm to 1 μm, or 50 nm to 1 μm, or 75 nm to 1 μm, or 100 nm to 1 μm, or 150 nm to 1 μm, or 200 nm to 1 μm, or 250 nm to 1 μm, or 300 nm to 1 μm, or 350 nm to 1 μm, or 400 nm to 1 μm, or 450 nm to 1 μm, or 500 nm to 1 μm. In other embodiments, the microparticles have a diameter ranging from 1 μm to 1 mm, such as from 10 μm to 1 mm, or 25 μm to 1 mm, or 50 μm to 1 mm, or 75 μm to 1 mm, or 100 μm to 1 mm, or 150 μm to 1 mm, or 200 μm to 1 mm, or 250 μm to 1 mm, or 300 μm to 1 mm, or 350 μm to 1 mm, or 400 μm to 1 mm, or 450 μm to 1 mm, or 500 μm to 1 mm. In further embodiments, small particles on the order of 10-100 nm in diameter may be assembled to form larger complexes, such as clusters or assemblies on the order of 1-10 μm. Particles of the present disclosure may be substantially spherical, such that the particles have a substantially circular cross-section. Other particle shapes may also be used, such as, but not limited to, ellipsoid, cubic, cylindrical, conical, needle, or other irregular shapes.

A "particle" may take the form of any fabricated material, a molecule, cryptophan, a virus, a phage, etc. The particle may be composed of a material, such as, but not limited to, a metal, a ceramic, a plastic, a glass, a composite, a polymer, a hydrogel, and the like. For example, the particles may be made of an inert material, such as alginate or iron oxide. In some examples, the particles may be magnetic and can be formed from a paramagnetic, super-paramagnetic or ferromagnetic material, or other material that responds to a magnetic field. Further, a particle may be of any shape, for example, spheres, rods, non-symmetrical shapes, etc. The particles, or a group of several particles in a complex, may be functionalized with a receptor that has a specific affinity to bind to or interact with a clinically relevant substrate. The receptor may be inherent to the particle itself. For example, the particle itself may be a virus or a phage with an inherent affinity for certain substrates. Additionally or alternatively, the particles can be functionalized by covalently or otherwise attaching or associating a receptor that specifically binds or otherwise recognizes a particular clinically relevant substrate. The functionalized receptor can be an antibody, peptide, nucleic acid, phage, bacteria, virus, or any other molecule with a defined affinity for a target substrate. Examples of material that may be used for the "particles" and/or "carrier" include polylactic acid, polyglycolic acid, PLGA polymers, alginates and alginate derivatives, gelatin, collagen, fibrin, hyaluronic acid, laminin rich gels, agarose, natural and synthetic polysaccharides, polyamino acids, polypeptides, polyesters, poly anhydrides, polyphosphazines, poly(vinyl alcohols), poly(alkylene oxides), poly(allylamines) (PAM), poly(acrylates), modified styrene polymers, pluronic polyols, polyoxamers, poly(uronic acids), poly(vinylpyrrolidone) and copolymers or graft copolymers of any of the above. These examples do not limit their concentration, their cross-linking with different agents, their method of administration, their tailored degradation profiles and other characteristics known to those skilled in the art.

The particles, or a group of several particles in a complex, may be functionalized with a targeting agent (e.g., a ligand or antibody) that specifically binds (or substantially specifically binds) to a target (e.g., a target receptor or a cell surface target, such as a clinically relevant receptor or cell surface target (e.g., antigen)). The targeting agent may be attached directly to the particle itself. The targeting agent can be an antibody, peptide, nucleic acid, phage, bacteria, virus, or any other molecule with a specific affinity for a target receptor or cell surface target. In some instances, the receptor or cell surface target is PD-1, CTLA-4, HER2/neu, HER1/EGFR, VEGFR, BCR-ABL, SRC, JAK2, MAP2K, EML4-ALK, BRAF V600E, 4-1BB, GITR, GSK3beta, or other cellular receptors or cell surface targets. Other compounds or molecules, such as fluorophores or autofluorescent or luminescent markers, which may assist in detecting the particles (e.g., in vivo detection), may also be attached to the particles. The ligands and/or detectable labels may be attached directly to the particle or attached to the particle through bioorthogonal functional groups as described herein.

In certain embodiments, the support is a bone graft material, such as a bone graft substitute material. A bone graft substitute material is a material structurally similar to bone. In some instances, a bone graft substitute material is bioresorbable such that the bone graft substitute material can dissolve or be absorbed in the body over time. A bone graft substitute material can be osteoconductive, such that it facilitates blood vessel and new bone formation into the bone graft substitute material. In some instances, the bone graft substitute material is osteoinductive, such that facilitates the formation of new bone through active recruitment of mesenchymal stem cells from the surrounding tissue. For example, growth factors, such as bone morphogenetic proteins, may be included in the bone graft substitute material. Bone graft substitute materials include, but are not limited to, hydroxyapatite, tricalcium phosphate, demineralized bone matrix, bovine collagen, calcium sulfate, calcium phosphate, cancellous bone chips, and the like, and combinations thereof.

Therapeutic support compositions of the present disclosure include a support and a first binding agent covalently linked to the support. The binding agent may be attached to the support on a surface of the support, such as a solvent-accessible surface of the support (e.g., a surface of the support that is in contact with the surrounding solvent). In some cases, the binding agent is attached directly to the support. For example, the binding agent may be covalently attached to the surface of the support, e.g., through a covalent bond, such as an amide, amine, ester, carbamate, urea, thioether, thiocarbamate, thiocarbonate, thiourea, etc. In some instances, the binding agent is covalently attached to the support through an amide bond. In other instances, the binding agent may be linked to the support via a linker. Any suitable linker can be used to link the binding agent to the support. Representative linkers can have from 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms. Representative linkers include, but are not limited to, those shown below:

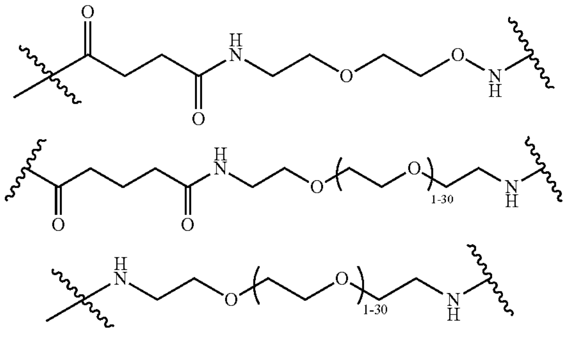

In certain embodiments, the therapeutic support compositions comprise a support and a tetrazine-containing group of formula:

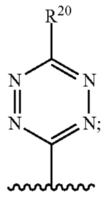

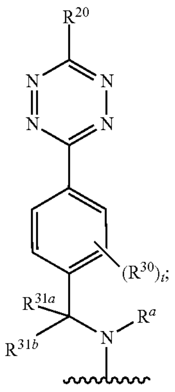

or

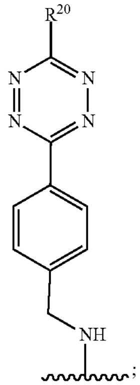

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R'', SC(═O)R''', OC(═S)R''', SC(═S)R''', S(═O)R', S(═O)$_2$R''', S(═O)$_2$NR'R'', C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O)SR'', NR'C(═S)SR'', OC(═O)NR'R'', SC(═O)NR'R'', OC(═S)R'R''', SC(═S)R'R'', NR'C(═O)NR''R'', and NR'C(═S)NR''R''; R' and R'' at each occurrence are independently selected from hydrogen, aryl and alkyl; and R''' at each occurrence is independently selected from aryl and alkyl; $R^{30}$ is halogen, cyano, nitro, hydroxy, alkyl, haloalkyl; alkenyl, alkynyl, alkoxy; haloalkoxy; heteroalkyl, aryl, heteroaryl, heterocycle, cycloalkyl, or cycloalkenyl; Ra, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the therapeutic support compositions have formula:

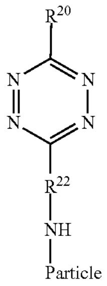

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R'', SC(═O)R', OC(═S)R''', SC(═S)R''', S(═O)R', S(═O)$_2$R'', S(═O)$_2$NR'R'', C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O)SR'', NR'C(═S)SR'', OC(═O)NR'R'', SC(═O)NR'R'', OC(═S)R'R', SC(═S)R'R'', NR'C(═O)NR''R'', and NR'C(═S)NR''R''; R' and R'' at each occurrence are independently selected from hydrogen, aryl and alkyl; R'' at each occurrence is independently selected from aryl and alkyl; and $R^{22}$ is a linker of 1 to 100 linking atoms, and can include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms.

In certain embodiments, the therapeutic support compositions have formula:

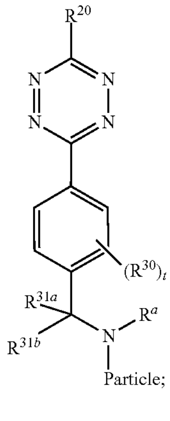

or

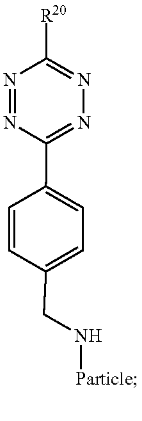

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R''', SC(═O)R''', OC(═S)R', SC(═S)R''', S(═O)R', S(═O)$_2$R''', S(═O)$_2$NR'R'', C(═O)O—R', C(═O)S—R', C(═S)O—R', C(═S)S—R', C(═O)NR'R'', C(═S)NR'R'', NR'R'', NR'C(═O)R'', NR'C(═S)R'', NR'C(═O)OR'', NR'C(═S)OR'', NR'C(═O)SR'', NR'C(═S)SR'', OC(═O)NR'R'', SC(═O)NR'R'', OC(=S)R'R''', SC(=S)R'R", NR'C(=O)NR"R", and NR'C(=S)NR"R"; R' and R" at each occurrence are independently selected from hydrogen, aryl and alkyl; R''' at each occurrence is independently selected from aryl and alkyl; $R^{30}$ is halogen, cyano, nitro, hydroxy, alkyl, haloalkyl; alkenyl, alkynyl, alkoxy; haloalkoxy; heteroalkyl, aryl, heteroaryl, heterocycle, cycloalkyl, or cycloalkenyl; $R^a$, $R^{31a}$ and $R^{31b}$ are each independently hydrogen, $C_1$-$C_6$-alkyl, or $C_1$-$C_6$-haloalkyl; and t is 0, 1, 2, 3, or 4.

In certain embodiments, the therapeutic support compositions comprise substituted alginate having units of formula:

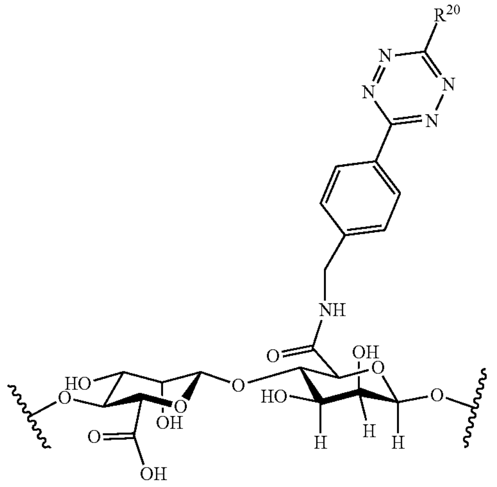

and/or

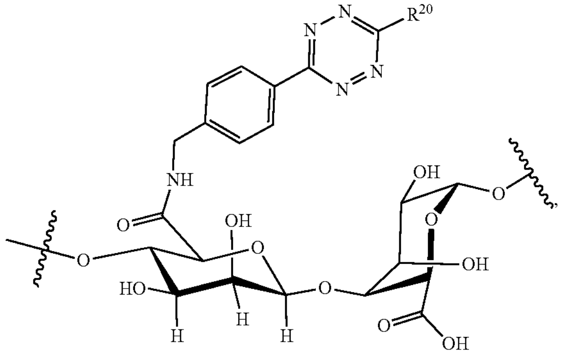

, or a salt thereof, wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(=O)R', C(=S)R', OC(=O)R', SC(=O)R', OC(=S)R''', SC(=S)R''', S(=O)R', $S(=O)_2R"$, $S(=O)_2NR'R"$, C(=O)O—R', C(=O)S—R', C(=S)O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)R'R''', SC(=S)R'R", NR'C(=O)NR"R", and NR'C(=S)NR"R"; R' and R" at each occurrence are independently selected from hydrogen, aryl and alkyl; and R" at each occurrence is independently selected from aryl and alkyl.

In certain embodiments, the therapeutic support compositions comprise units of formula:

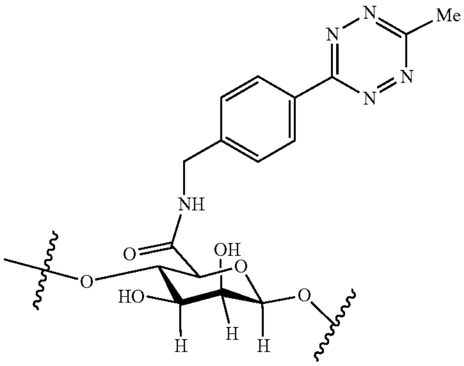

or

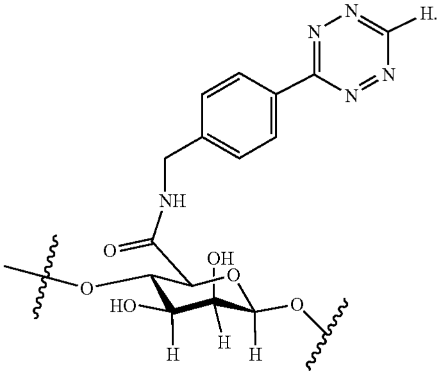

.

In some embodiments, the therapeutic support compositions comprise units of formula:

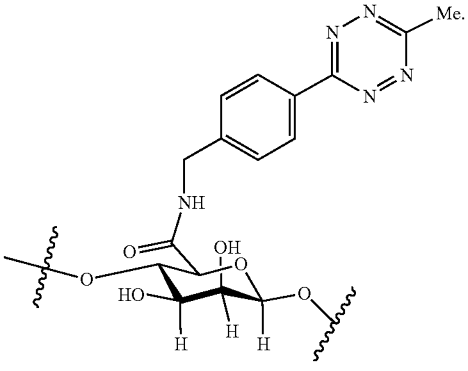

.

In some embodiments, the therapeutic support compositions comprise units of formula:

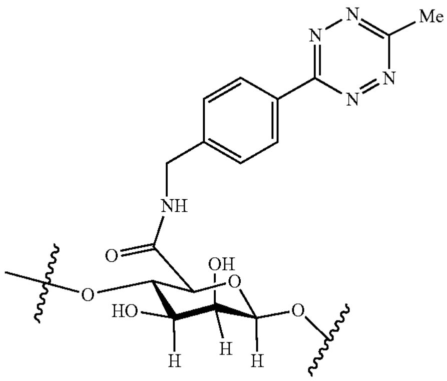

and

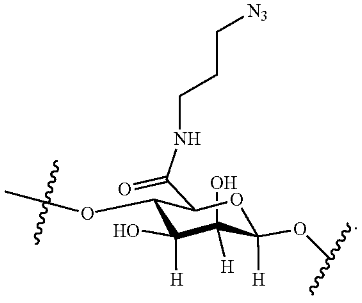

In some embodiments, the therapeutic support compositions comprise substituted hyaluronic acid having units of formula (II):

(II)

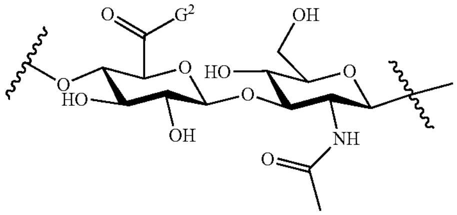

wherein $G^2$ is

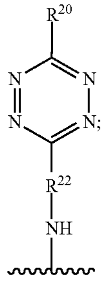

$R^{22}$ is a linker of 1 to 100 linking atoms; and $R^{20}$ is as defined herein.

In further embodiments, $G^2$ is

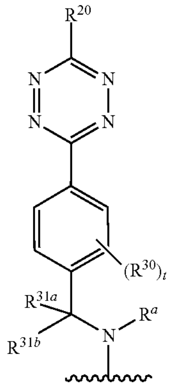

or

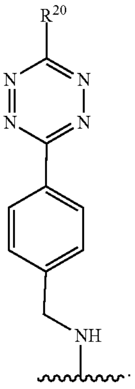

In still further embodiments, $G^2$ is

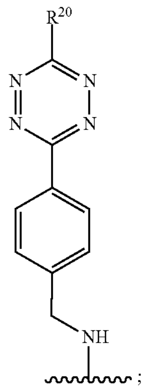

and $R^{20}$ is hydrogen or $C_{1-4}$alkyl.

Compounds of formula (II) include compounds of formula (II-A):

(II-A)

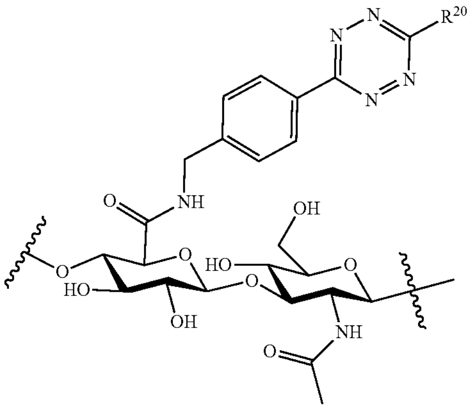

wherein $R^{20}$ is selected from the group consisting of hydrogen, halogen, cyano, nitro, alkyl, alkenyl, alkynyl, heteroalkyl, aryl, heteroaryl, heterocycle, cycloalkyl, cycloalkenyl, $CF_3$, $CF_2$—R', $NO_2$, OR', SR', C(═O)R', C(═S)R', OC(═O)R''', SC(═O)R''', OC(═S)R''', SC(═S)R''', S(═O)R', $S(═O)_2R''$, $S(═O)_2NR'R''$, C(═O)O—R', C(═O)S—R', C(═S)

O—R', C(=S)S—R', C(=O)NR'R", C(=S)NR'R", NR'R", NR'C(=O)R", NR'C(=S)R", NR'C(=O)OR", NR'C(=S)OR", NR'C(=O)SR", NR'C(=S)SR", OC(=O)NR'R", SC(=O)NR'R", OC(=S)R'R'", SC(=S)R'R", NR'C(=O)NR"R", and NR'C(=S) NR"R"; R' and R" at each occurrence are independently selected from hydrogen, aryl and alkyl; and R'" at each occurrence is independently selected from aryl and alkyl. In further embodiments according to formula (II-A), $R^{20}$ is hydrogen or $C_{1-4}$alkyl.

In some embodiments, the therapeutic support compositions comprise units of formula:

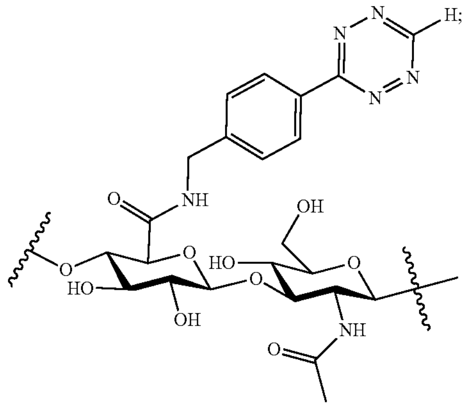

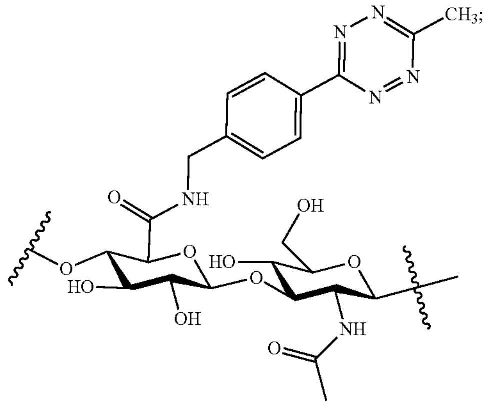

or

-continued

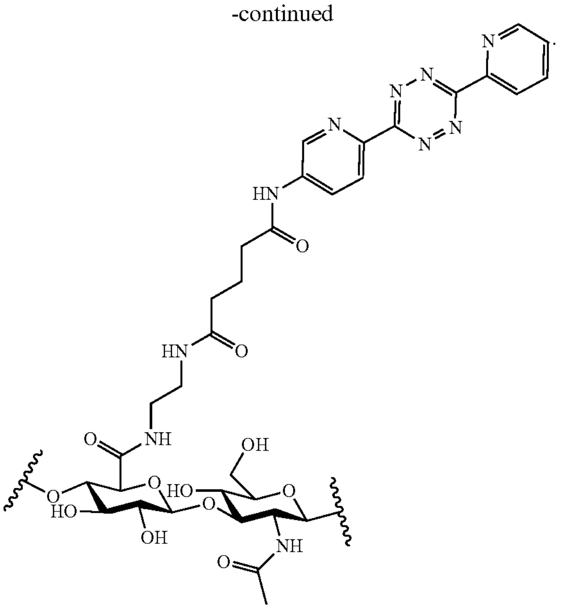

Additional therapeutic support compositions are exemplified in WO2017/044983, WO/2015/139025A1, and WO/2014/205126A1, the entire contents of each of which is incorporated herein by reference in their entirety.

The hyaluronic acid derivative includes a hyaluronic acid having a plurality of glucuronic acid units and a tetrazine-containing group linked or directly bonded to a glucuronic acid unit of the hyaluronic acid. The hyaluronic acid may also have a plurality of N-acetylglucosamine units. In certain embodiments, the N-acetylglucosamine units of the hyaluronic acid are not linked or conjugated to the tetrazine-containing group.

The tetrazine-containing group can be linked or directly bonded through a carboxylic acid of a glucuronic acid unit. The tetrazine-containing group can be incorporated into the hyaluronic acid from about 0.1% to about 80% as measured by the % of carboxylic acids being linked or conjugated to the tetrazine-containing group, such as about 1% to about 75%, about 5% to about 75%, about 10% to about 50%, or about 40% to about 75% as measured by the % of carboxylic acids being linked or conjugated to the tetrazine-containing group.

D. METHODS OF TREATMENT

Aspects of the present disclosure include methods for delivering a payload to a target location in a subject. In certain embodiments, the method includes selectively delivering a payload to the target location in a subject. Selective delivery of the payload includes delivering the payload to the target location (e.g., an organ or tissue, or portion thereof), without targeting other locations in the subject (e.g., other organs or tissues, or portions thereof) that do not need administration of the payload. Selective delivery of the payload may be achieved through use of the support compositions and the functionalized payloads described herein.

In some instances, a support composition of the present disclosure may be localized to a desired target location in a subject. For example, methods of the present disclosure may include administering to a subject a support composition as described herein. The support composition may be administered to the subject at a desired target location in the subject. In some instances, the support composition may be implanted into the subject at the desired target location in the subject. In some embodiments, the support composition may be attached to a targeting agent as described herein, and the method may include administering the support composition to the subject (e.g., administered systemically). In these embodiments, the support composition that is attached to a targeting agent may localize at a desired target location in the subject through specific binding of the targeting agent to its target (e.g., antibody-antigen interaction, and the like), or may localize on the surface of a desired target (e.g., a cell surface) through specific binding of the targeting agent to its target (e.g., antibody-antigen interaction, and the like).

As described herein, selective binding between bioorthogonal binding partners (e.g., between a tetrazine binding agent of the support composition and its complementary trans-cyclooctene binding agent of a functionalized payload) may occur. Due to the localized administration of the support composition to a desired location in the subject as described above, the selective binding between the binding agent of the support composition and its complementary binding agent of the functionalized payload will localize the payload to the desired target location. Accordingly, in certain embodiments, the method includes administering to the subject a functionalized payload such that the functionalized payload binds to the support composition to form a support complex. For example, the functionalized payload may be administered systemically to the subject. Upon administration of the functionalized payload to the subject, contact between the binding agent of the support composition and the complementary binding agent of the functionalized payload may occur, such that the binding agent and its complementary binding agent bind to one another to form a support complex, thereby selectively delivering the payload to the target location in the subject. In some embodiments, selective delivery of the functionalized payload results in a concentration of the payload at the target location that is greater than the concentration of the payload elsewhere in the subject (e.g., at non-targeted areas in the subject).

Indications for this approach include cancer, both hematological and solid cancers. In certain embodiments, the approach can be used for the treatment and/or diagnosis of soft tissue sarcomas: rhabdomyosarcoma, fibrosarcoma, Ewing's sarcoma, and all the different subtypes of soft tissue sarcoma as well as osteosarcoma. The compositions can be for the treatment and/or diagnosis of pigmented vilonodular synovitis.

The compositions of the present disclosure find use in treatment and/or diagnosis of a condition or disease in a subject that is amenable to treatment or diagnosis by administration of the payload (e.g., the parent drug (i.e., the drug prior to conjugation to the composition)). By "treatment" is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition. Treatment may include inhibition, that is, arresting the development or further development of clinical symptoms, e.g., mitigating or completely inhibiting an active disease. Treatment may include relief, that is, causing the regression of clinical symptoms. For example, in the context of cancer, the term "treating" includes any or all of: reducing growth of a solid tumor, inhibiting replication of cancer cells, reducing overall tumor burden, prolonged survival and ameliorating one or more symptoms associated with a cancer.

The subject to be treated can be one that is in need of therapy, where the subject to be treated is one amenable to treatment using the parent drug. Accordingly, a variety of subjects may be amenable to treatment using the compositions disclosed herein. Generally, such subjects are "mammals," with humans being of interest. Other subjects can include domestic pets (e.g., dogs and cats), livestock (e.g., cows, pigs, goats, horses, and the like), rodents (e.g., mice, guinea pigs, and rats, e.g., as in animal models of disease), as well as non-human primates (e.g., chimpanzees, and monkeys).

In certain embodiments, the functionalized payloads, therapeutic support compositions, additional therapeutic agents, and methods can be used for the treatment, prevention, and/or diagnosis of solid tumors, including but not limited to, melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), endometrial carcinoma, breast cancer (e.g., triple negative breast cancer), glioblastoma (e.g., glioblastoma multiforme), and lung cancer (e.g., non-small cell lung cancer), soft tissue sarcoma, fibrosarcoma, osteosarcoma, pancreatic cancer, gastric carcinoma, squamous cell carcinoma of head/neck, anal/vulvar carcinoma, esophageal carcinoma, pancreatic adenocarcinoma, cervical carcinoma, hepatocellular carcinoma, kaposi's sarcoma, Non-Hodgkins lymphoma, Hodgkins lymphoma Wilm's tumor/neuroblastoma, bladder cancer, thyroid adenocarcinoma, pancreatic neuroendocrine tumors, prostatic adencocarcinoma, nasopharyngeal carcinoma, cutaneous T-cell lymphoma, among others. The disclosed approach lends itself well as an adjuvant/neoadjuvant system. For example, particles as disclosed herein could be placed during the biopsy, once the results from the study come back, the practitioner could deliver the appropriate cocktail to the desired site in the body. This would minimize the size of the tumor particularly in the context of a surgically resectable tumor. Then at the end of the surgery, the surgeon could place more particles around the surgical cavity and treat the patient with further doses of treatment (e.g. chemotherapy through the disclosed approach) to minimize the risk of any cancer cells that may have been missed in the surgical margins.

In certain embodiments, the disclosed methods provide the ability to place particles as disclosed herein at the time of the biopsy. When the results return, the practitioner can deliver through to the biopsy site immunomodulatory agents such as TLR agonists, STING agonists, chemokines (agents that attract cancerous cells and/or immune cells) and adjuvants to enhance the immune system with fewer side effects as well as the chemotherapeutics agents combined with immunotherapy agents. This combination approach would be beneficial to patients. The chemotherapy agent would treat the solid tumor or specific location, while the enhanced response of the immunotherapy would help with distant metastatic sites. For example, in certain embodiments, the disclosed compositions and methods could employ or be used with anthracyclines, taxanes, gemcitabine and other agents to enhance the efficacy of one or more immunomodulatory agents such as ipilimumab, nivolumab, pembrolizumab, avelumab (also known as MSB0010718C; Pfizer).

1. Cancer

The disclosed methods may be used to treat or prevent cancer, including metastatic cancer. Cancer is a group of related diseases that may include sustained proliferative signaling, evasion of growth suppressors, resistance to cell death, enablement of replicative immortality, induction of angiogenesis, and the activation of invasion and metastasis. The disclosed methods may enhance or elicits an immune response against a cancer in the subject. The immune response may lead to an increase in one or more of leukocytes, lymphocytes, monocytes, and eosinophils.

Cancer that may be treated by the disclosed methods, includes, but is not limited to, astrocytoma, adrenocortical carcinoma, appendix cancer, basal cell carcinoma, bile duct cancer, bladder cancer, bone cancer, brain cancer, brain stem cancer, brain stem glioma, breast cancer, cervical cancer, colon cancer, colorectal cancer, cutaneous T-cell lymphoma, diffuse intrinsic pontine glioma, ductal cancer, endometrial cancer, ependymoma, Ewing's sarcoma, esophageal cancer, eye cancer, fibrosarcoma, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, soft tissue carcinoma, soft tissue sarcoma, solid tumor, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor.

In some embodiments, the cancer that may be treated by the disclosed methods is melanoma, renal cancer, prostate cancer, ovarian cancer, breast cancer, glioma, lung cancer, soft tissue carcinoma, soft tissue sarcoma, osteosarcoma, or pancreatic cancer. In some embodiments, the cancer is a solid tumor. In some embodiments, the cancer is a soft tissue carcinoma. In some embodiments, the cancer is afibrosarcoma. In some embodiments, the cancer is diffuse intrinsic pontine glioma. In some embodiments, the cancer is a metastatic cancer.

Without being bound by a particular theory, local release of certain anti-cancer agents using the compounds and methods of the invention may produce or contribute to immunogenic cell death (ICD). For example, certain anti-cancer agents (e.g., anthracyclines, cyclophosphamide, oxaliplatin) have been reported to induce ICD. Kroemer et al. Annu. Rev. Immunol. 2013 (31), 51-72. Immunogenic apoptosis of cancer cells can induce an effective antitumor immune response through activation of dendritic cells (DCs) and consequent activation of specific T cell response. ICD is characterized by secretion of damage-associated molecular patterns (DAMPs). Three important DAMPs which are exposed to the cell surface during ICD. Calreticulin (CRT), one of the DAMP molecules, which is normally in the lumen of endoplasmic reticulum (ER), is translocated after the induction of immunogenic apoptosis to the surface of dying cell where it functions as an "eat me" signal for professional phagocytes. Other important surface exposed DAMPs are heat-shock proteins (HSPs), namely HSP70 and HSP90, which are under stress condition also translocated to the plasma membrane. On the cell surface they have an immunostimulatory effect, based on their interaction with number of antigen-presenting cell (APC) surface receptors like CD91 and CD40 and also facilitate crosspresentation of antigens derived from tumor cells on MHC class I molecule, which than leads to the CD8+ T cell response. Other important DAMPs, characteristic for ICD are secreted amphoterin (HMGB1) and ATP. HMGB1 is considered to be late apoptotic marker and its release to the extracellular space seems to be required for the optimal release and presentation of tumor antigens to dendritic cells. It binds to several pattern recognition receptors (PRRs) such as Toll-like receptor (TLR) 2 and 4, which are expressed on APCs. The most recently found DAMP released during immunogenic cell death is ATP, which functions as a "find-me" signal for monocytes when secreted and induces their attraction to the site of apoptosis. Kroemer et. al. Curr. Op. Immunol. 2008 (20), 504-511.

Thus, local release of ICD inducers using the compounds and methods of the invention may be beneficially combined with one or more immunomodulatory agents.

In certain embodiments, the functionalized payloads, therapeutic support compositions, and methods can be used for the treatment, prevention, and/or diagnosis of solid tumors, including but not limited to, melanoma (e.g., unresectable, metastatic melanoma), renal cancer (e.g., renal cell carcinoma), prostate cancer (e.g., metastatic castration resistant prostate cancer), ovarian cancer (e.g., epithelial ovarian cancer, such as metastatic epithelial ovarian cancer), breast cancer (e.g., triple negative breast cancer), glioblastoma (e.g., glioblastoma multiforme), and lung cancer (e.g., non-small cell lung cancer), soft tissue sarcoma, fibrosarcoma, osteosarcoma, pancreatic cancer, among others.

The disclosed approach lends itself well as an adjuvant/neoadjuvant system. For example, therapeutic support compositions as disclosed herein could be placed during the biopsy, once the results from the study come back, the practitioner could administer the appropriate cocktail to deliver treatment to the desired site in the body (compound of formula (I) and optional additional therapeutic agent(s)). The results of the biopsy may indicate the amount and type of treatment to deliver to the site of a tumor. For example, chemokines (agents that attract cancerous cells and/or immune cells) and adjuvants to enhance the immune system with fewer side effects as well as the chemotherapeutics agents could be delivered and combined with immunotherapy agents.

The disclosed compounds and compositions may be administered prior to surgical resection. The disclosed methods may minimize the size of the tumor prior to surgical resection. This would minimize the size of the tumor particularly in the context of a surgically resectable tumor. The disclosed conjugates, compounds and compositions may be administered during surgical resection. The disclosed conjugates, compounds and compositions may be administered after surgical resection. Therapeutic support composition may be placed around the surgical cavity at the end of surgical resection and the subject may then be treated with further doses of a treatment to minimize the risk of any cancer cells that may have been missed in the surgical margins.

The disclosed methods may include multiple systemic doses of functionalized payload that focus at one location. The disclosed methods may be used to deliver a second payload. The disclosed methods may be used to administer a second functionalized payload if the tumor is resistant to the first payload. A second payload may be a TCO-labeled payload of gemcitabine or docetaxel. The TCO-labeled payload of gemcitabine or docetaxel may be administered in combination with doxorubicin. The second functionalized payload may be activated by the therapeutic support composition used for the first prodrug.

The functionalized payloads disclosed herein may function as adjuvants. This combination approach would be beneficial to patients. The chemotherapy agent would treat the solid tumor or specific location and may enhance or elicit an immune response, while the enhanced response of the immunotherapy of the functionalized payload and/or separate agent may help with distant metastatic sites. For example, in certain embodiments, the disclosed compositions and methods could employ or be used with anthracyclines, taxanes, gemcitabine and other agents to enhance the efficacy of ipilimumab, nivolumab, pembrolizumab, avelumab (also known as MSB0010718C; Pfizer).

The disclosed methods may be used to treat diffuse intrinsic pontine gliomas. Diffuse intrinsic pontine gliomas (DIPG) are pediatric brainstem tumors that may be highly malignant and may be difficult to treat. There is no known curative treatment for DIPG, and survival odds have remained dismal over the past four decades. DIPG patients have a median overall survival of just 11 months, with a two-year survival rate below 10%. DIPG account for 75-80% of brainstem tumors in children, affecting an estimated 200-300 children in the U.S. each year. The rarity of this devastating disease and previous lack of experimental model systems has impeded research, and over the past four decades survival odds have remained the same. Diagnosis of DIPG may begin with clinical symptoms and may be confirmed by MRI. The disease may begin with several months of generalized symptoms, including behavioral changes and difficulties in school, double vision, abnormal or limited eye movements, an asymmetric smile, loss of balance, and weakness. Alternately, severe neurologic deterioration may happen more quickly, with symptoms present for less than a month prior to diagnosis. Clinical examination may reveal the triad of multiple cranial neuropathies, long tract signs such as hyperreflexia and clonus, as well as ataxia. Expansion of the pons section of the brainstem may cause obstructive hydrocephalus and increased intracranial pressure.

Nuclei critical for life-sustaining function such as breathing and heartbeat in are located in the pons and without treatment, breathing and heartbeat may be damaged by DIPG.

The disclosed methods may be used to deliver molecular payloads to the site of a DIPG. The disclosed methods may include delivering drugs systemically that are only activated at the tumor site. The disclosed methods may be used as a neoadjuvant or adjuvant therapy. The biomaterial may be placed during a biopsy. The results of the biopsy may indicate the amount and type of treatment to deliver to the site of a tumor. The disclosed compounds and compositions may be administered prior to surgical resection. The disclosed methods may minimize the size of the tumor prior to surgical resection. The disclosed compounds and compositions may be administered during surgical resection. The disclosed compounds and compositions may be administered after surgical resection. Biomaterial may be placed around the surgical cavity at the end of surgical resection and the subject may then be treated with further doses of a treatment. The disclosed biodegradable gel may be implanted at the time of biopsy or surgery. The disclosed methods may not require an additional invasive procedure to deliver additional doses of the disclosed compounds and compositions.

The disclosed methods may include multiple systemic doses of functionalized payload that focus at one location. The disclosed methods may be used to deliver a second payload. The disclosed methods may be used to administer a second functionalized payload if the tumor is resistant to the first payload. A second payload may be a TCO-labeled payload of gemcitabine J or docetaxel. The TCO-labeled payload of gemcitabine or docetaxel may be administered in combination with doxorubicin. The second functionalized payload may be activated by the therapeutic support composition used for the first prodrug.

2. Modes of Administration

Methods of treatment may include any number of modes of administering a disclosed conjugate, compound or composition. Modes of administration may include tablets, pills, dragees, hard and soft gel capsules, granules, pellets, skin patches, skin creams, skin gels, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the conjugate, compound or compositions disclosed herein may be admixed with adjuvants and excipients, such as gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire®). In the pharmaceutical composition, the conjugate, compound or compositions disclosed herein may also be dispersed in a microparticle, e.g. a nanoparticulate composition.

For parenteral administration, the conjugates, compounds or compositions disclosed herein may be dissolved or suspended in a physiologically acceptable diluent, such as water, buffer, oils with or without solubilizers, surface-active agents, dispersants or emulsifiers. Suitable oils may include, for example, olive oil, peanut oil, cottonseed oil, soybean oil, castor oil and sesame oil. For parenteral administration, the conjugates, compounds or compositions disclosed herein may be administered in the form of an aqueous, lipid, oily or other kind of solution or suspension, or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

Therapeutic support compositions are preferably administered locally at the site of a tumor, such as by injection or implantation. Functionalized payloads, such as conjugates or compounds of formula (I) or (III), may be administered by any convenient route, in view of a subject's condition and judgment of medical professionals. Parenteral administration is a suitable means of administering conjugates or compounds of formula (I) or (III).

The amount of composition administered to a subject can be initially determined based on guidance of a dose and/or dosage regimen of the parent drug. In general, the compositions can provide for targeted delivery and/or enhanced serum half-life of the bound drug, thus providing for at least one of reduced dose or reduced administrations in a dosage regimen. Thus, the compositions can provide for reduced dose and/or reduced administration in a dosage regimen relative to the parent drug prior to being conjugated in a composition of the present disclosure.

The compositions of the present disclosure can be delivered by any suitable means, including oral, parenteral and topical methods. For example, transdermal administration methods, by a topical route, can be formulated as applicator sticks, solutions, suspensions, emulsions, gels, creams, ointments, pastes, jellies, paints, powders, and aerosols.

The pharmaceutical formulation may be provided in unit dosage form. In such form the pharmaceutical formulation may be subdivided into unit doses containing appropriate quantities of the compositions of the present disclosure. The unit dosage form can be a packaged preparation, the package containing discrete quantities of the preparation, such as packeted tablets, capsules, and powders in pouches, vials or ampoules. Also, the unit dosage form can be a capsule, tablet, dragee, cachet, or lozenge, or it can be the appropriate number of any of these in packaged form.

Compositions of the present disclosure can be present in any suitable amount, and can depend on various factors including, but not limited to, weight and age of the subject, state of the disease, etc. Suitable dosage ranges for the composition of the present disclosure include from 0.1 mg to 10,000 mg, or 1 mg to 1000 mg, or 10 mg to 750 mg, or 25 mg to 500 mg, or 50 mg to 250 mg. For instance, suitable dosages for the composition of the present disclosure include 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg or 1000 mg.

In some embodiments, multiple doses of a composition are administered. The frequency of administration of a composition can vary depending on any of a variety of factors, e.g., severity of the symptoms, condition of the subject, etc. For example, in some embodiments, a composition is administered once per month, twice per month, three times per month, every other week (qow), once per week (qw), twice per week (biw), three times per week (tiw), four times per week, five times per week, six times per week, every other day (qod), daily (qd), twice a day (qid), or three times a day (tid).

The compositions of the present disclosure can be administered at any suitable frequency, interval and duration. For example, the composition of the present disclosure can be administered once an hour, or two, three or more times an hour, once a day, or two, three, or more times per day, or once every 2 days, 3 days, 4 days, 5 days, 6 days, or 7 days, so as to provide the desired dosage level to the subject. When the composition of the present disclosure is administered more than once a day, representative intervals include 5 min, 10 min, 15 min, 20 min, 30 min, 45 min and 60 minutes, as well as 1 hr, 2 hr, 4 hr, 6 hr, 8 hr, 10 hr, 12 hr, 16 hr, 20 hr, and 24 hours. The composition of the present disclosure can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The compositions of the present disclosure can be co-administered with another active agent. Co-administration includes administering the composition of the present disclosure and active agent within 0.5 hr, 1 hr, 2 hr, 4 hr, 6 hr, 8 hr, 10 hr, 12 hr, 16 hr, 20 hr, or 24 hours of each other. Co-administration also includes administering the composition of the present disclosure and active agent simultaneously or approximately simultaneously (e.g., within about 1 min, 5 min, 10 min, 15 min, 20 min, or 30 minutes of each other), or sequentially in any order. In addition, the composition of the present disclosure and the active agent can each be administered once a day, or two, three, or more times per day so as to provide the desired dosage level per day.

Co-Administration can be Accomplished by Coimplantation or Coinjection.

In some embodiments, co-administration can be accomplished by co-formulation, e.g., preparing a single pharmaceutical formulation including both the composition of the present disclosure and the active agent. In other embodiments, the composition of the present disclosure and the active agent can be formulated separately and co-administered to the subject.

The composition of the present disclosure and the active agent can be present in a formulation in any suitable weight ratio, such as from 1:100 to 100:1 (w/w), or 1:50 to 50:1, or 1:25 to 25:1, or 1:10 to 10:1, or 1:5 to 5:1 (w/w). The composition of the present disclosure and the other active agent can be present in any suitable weight ratio, such as 1:100 (w/w), 1:75, 1:50, 1:25, 1:10, 1:5, 1:4, 1:3, 1:2, 1:1, 2:1, 3:1, 4:1, 5:1, 10:1, 25:1, 50:1, 75:1, or 100:1 (w/w). Other dosages and dosage ratios of the composition of the present disclosure and the active agent are suitable in the formulations and methods described herein.

3. Combination Therapies

In one aspect, the invention provides a method of treating cancer or enhancing or eliciting an immune response comprising administering to a subject in need thereof: a therapeutically effective amount of a conjugate of the invention (e.g., formula (I)), or a pharmaceutically acceptable salt or composition thereof; a therapeutic support composition, as described herein; and a therapeutically effective amount of an additional therapeutic agent selected from the group consisting of an anticancer agent, an immunomodulatory agent, or a trans-cyclooctene prodrug thereof.

The invention also provides a pharmaceutical combination comprising a conjugate described herein, or a pharmaceutically acceptable salt, or composition thereof; a therapeutic support composition, as described herein; and an additional therapeutic agent selected from the group consisting of an anticancer agent, an immunomodulatory agent, or a trans-cyclooctene prodrug thereof, for use in the treatment or prevention of a cancer or for use in enhancing or eliciting an immune response.

The invention also provides the use of a pharmaceutical combination comprising a conjugate described herein, or a pharmaceutically acceptable salt, or composition thereof; a therapeutic support composition; and a therapeutically effective amount of an additional therapeutic agent selected from the group consisting of an anticancer agent, an immunomodulatory agent, or a trans-cyclooctene prodrug thereof for the treatment or prevention of a cancer or for use in enhancing or eliciting an immune response.

In the methods and uses described herein, the components of the pharmaceutical combinations may be administered/used simultaneously, separately, or sequentially, and in any order, and the components may be administered separately or as a fixed combination. For example, the delay of progression or treatment of diseases according to the invention may comprise administration of the first active ingredient in free or pharmaceutically acceptable salt form and administration of the second active ingredient in free or pharmaceutically acceptable salt form, simultaneously or sequentially in any order, in jointly therapeutically effective amounts or effective amounts, e.g. in daily dosages corresponding to the amounts described herein. The individual active ingredients of the combination can be administered separately at different times during the course of therapy or concurrently in divided or single dosage forms. The instant invention is therefore to be understood as embracing all such regimes of simultaneous or alternating treatment and the term "administering" is to be interpreted accordingly. Thus, a pharmaceutical combination, as used herein, defines either a fixed combination in one dosage unit form or separate dosages forms for the combined administration where the combined administration may be independently at the same time or at different times. As a further example, the therapeutic support composition and conjugate may be administered/used simultaneously (e.g., through coinjection or coimplantation), separately, or sequentially, followed by administration of the additional therapeutic agent selected from the group consisting of an anticancer agent, an immunomodulatory agent, or a trans-cyclooctene prodrug thereof.

The methods and uses in treating cancer include administering/localizing the therapeutic support composition at a tumor. In the methods and uses disclosed herein, the administration of the conjugate, or a pharmaceutically acceptable salt, or composition thereof; the therapeutic support composition; and the additional therapeutic agent may inhibit the growth of the tumor.

Additional therapeutic agent(s) may be administered simultaneously or sequentially with the disclosed conjugates and compositions. Sequential administration includes administration before or after the disclosed conjugates and compositions. An additional therapeutic agent may be administered before the disclosed conjugates and compositions. An additional therapeutic agent may be administered after the disclosed conjugates and compositions. An additional therapeutic agent may be administered at the same time as the disclosed conjugates and compositions. In some embodiments, the additional therapeutic agent or agents may be administered in the same composition as the disclosed conjugates. In other embodiments, there may be an interval of time between administration of the additional therapeutic agent and the disclosed conjugates or compositions. In some embodiments, administration of an additional therapeutic agent with a disclosed conjugate or composition may allow lower doses of the other therapeutic agents and/or administration at less frequent intervals. When used in combination with one or more other active ingredients, the conjugates or compositions of the present invention and the other active ingredients may be used in lower doses than when each is used singly. Accordingly, the pharmaceutical compositions of the present invention include those that contain one or more other active ingredients, in addition to a conjugates of the present disclosure.

a. Anticancer Agents

Exemplary anti-cancer agents include, but are not limited to, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride), Adrucil (Fluorouracil), Afatinib Dimaleate, Afinitor (Everolimus), Aldara (Imiquimod), Aldesleukin, Alemtuzumab, Alimta (Pemetrexed Disodium), Aloxi (Palonosetron Hydrochloride), Ambochlorin (Chlorambucil), Amboclorin (Chlorambucil), Aminolevulinic Acid, Anastrozole, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Avastin (Bevacizumab), Axitinib, Azacitidine, BEACOPP, Bendamustine Hydrochloride, BEP, Bevacizumab, Bexarotene, Bexxar (Tositumomab and I 131 Iodine Tositumomab), Bicalutamide, Bleomycin, Bortezomib, Bosulif (Bosutinib), Bosutinib, Brentuximab Vedotin, Busulfan, Busulfex (Busulfan), Cabazitaxel, Cabozantinib-S-Malate, CAF, Campath (Alemtuzumab), Camptosar (Irinotecan Hydrochloride), Capecitabine, CAPOX, Carboplatin, Carboplatin-Taxol, Carfilzomib, Casodex (Bicalutamide), CeeNU (Lomustine), Cerubidine (Daunorubicin Hydrochloride), Cervarix (Recombinant HPV Bivalent Vaccine), Cetuximab, Chlorambucil, Chlorambucil-Prednisone, CHOP, Cisplatin, Clafen (Cyclophosphamide), Clofarabine, Clofarex (Clofarabine), Clolar (Clofarabine), CMF, Cometriq (Cabozantinib-S-Malate), COPP, COPP-ABV, Cosmegen (Dactinomycin), Crizotinib, CVP, Cyclophosphamide, Cyfos (Ifosfamide), Cytarabine, Cytarabine, Liposomal, Cytosar-U (Cytarabine), Cytoxan (Cyclophosphamide), Dabrafenib, Dacarbazine, Dacogen (Decitabine), Dactinomycin, Dasatinib, Daunorubicin Hydrochloride, Decitabine, Degarelix, Denileukin Diftitox, Denosumab, DepoCyt (Liposomal Cytarabine), DepoFoam (Liposomal Cytarabine), Dexrazoxane Hydrochloride, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Efudex (Fluorouracil), Elitek (Rasburicase), Ellence (Epirubicin Hydrochloride), Eloxatin (Oxaliplatin), Eltrombopag Olamine, Emend (Aprepitant), Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Etopophos (Etoposide Phosphate), Etoposide, Etoposide Phosphate, Evacet (Doxorubicin Hydrochloride Liposome), Everolimus, Evista (Raloxifene Hydrochloride), Exemestane, Fareston (Toremifene), Faslodex (Fulvestrant), FEC, Femara (Letrozole), Filgrastim, Fludara (Fludarabine Phosphate), Fludarabine Phosphate, Fluoroplex (Fluorouracil), Fluorouracil, Folex (Methotrexate), Folex PFS (Methotrexate), Folfiri, Folfiri-Bevacizumab, Folfiri-Cetuximab, Folfirinox, Folfox (Leucovorin, Fluorouracil, Oxaliplatin), Folotyn (Pralatrexate), FU-LV, Fulvestrant, Gardasil (Recombinant HPV Quadrivalent Vaccine), Gazyva (Obinutuzumab), Gefitinib, Gemcitabine Hydrochloride, Gemcitabine-Cisplatin, Gemcitabine-Oxaliplatin, Gemtuzumab Ozogamicin, Gemzar (Gemcitabine Hydrochloride), Gilotrif (Afatinib Dimaleate), Gleevec (Imatinib Mesylate), Glucarpidase, Goserelin Acetate, Halaven (Eribulin Mesylate), Herceptin (Trastuzumab), HPV Bivalent Vaccine, Recombinant, HPV Quadrivalent Vaccine, Recombinant, Hycamtin (Topotecan Hydrochloride), Hyper-CVAD, Ibritumomab Tiuxetan, Ibrutinib, ICE, Iclusig (Ponatinib Hydrochloride), Ifex (Ifosfamide), Ifosf amide, Ifosfamidum (Ifosfamide), Imatinib Mesylate, Imbruvica (Ibrutinib), Imiquimod, Inlyta (Axitinib), Intron A (Recombinant Interferon Alfa-2b), Iodine 131 Tositumomab and Tositumomab, Ipilimumab, Iressa (Gefitinib), Irinotecan Hydrochloride, Istodax (Romidepsin), Ixabepilone, Ixempra (Ixabepilone), Jakafi (Ruxolitinib Phosphate), Jevtana (Cabazitaxel), Kadcyla (Ado-Trastuzumab Emtansine), Keoxifene (Raloxifene Hydrochloride), Kepivance (Palifermin), Kyprolis (Carfilzomib), Lapatinib Ditosylate, Lenalidomide, Letrozole, Leucovorin Calcium, Leukeran (Chlorambucil), Leuprolide Acetate, Levulan (Aminolevulinic Acid), Linfolizin (Chlorambucil), LipoDox (Doxorubicin Hydrochloride Liposome), Liposomal Cytarabine, Lomustine, Lupron (Leuprolide Acetate), Lupron Depot (Leuprolide Acetate), Lupron Depot-Ped (Leuprolide Acetate), Lupron Depot-3 Month (Leuprolide Acetate), Lupron Depot-4 Month (Leuprolide Acetate), Marqibo (Vincristine Sulfate Liposome), Matulane (Procarbazine Hydrochloride), Mechlorethamine Hydrochloride, Megace (Megestrol Acetate), Megestrol Acetate, Mekinist (Trametinib), Mercaptopurine, Mesna, Mesnex (Mesna), Methazolastone (Temozolomide), Methotrexate, Methotrexate LPF (Methotrexate), Mexate (Methotrexate), Mexate-AQ (Methotrexate), Mitomycin C, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Nelarabine, Neosar (Cyclophosphamide), Neupogen (Filgrastim), Nexavar (Sorafenib Tosylate), Nilotinib, Nolvadex (Tamoxifen Citrate), Nplate (Romiplostim), Obinutuzumab, Ofatumumab, Omacetaxine Mepesuccinate, Oncaspar (Pegaspargase), Ontak (Denileukin Diftitox), OEPA, OPPA, Oxaliplatin, Paclitaxel, Paclitaxel Albumin-stabilized Nanoparticle Formulation, Palifermin, Palonosetron Hydrochloride, Pamidronate Disodium, Panitumumab, Paraplat (Carboplatin), Paraplatin (Carboplatin), Pazopanib Hydrochloride, Pegaspargase, Peginterferon Alfa-2b, PEG-Intron (Peginterferon Alfa-2b), Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Pralatrexate, Prednisone, Procarbazine Hydrochloride, Proleukin (Aldesleukin), Prolia (Denosumab), Promacta (Eltrombopag Olamine), Provenge (Sipuleucel-T), Purinethol (Mercaptopurine), Radium 223 Dichloride, Raloxifene Hydrochloride, Rasburicase, R-CHOP, R-CVP, Recombinant HPV Bivalent Vaccine, Recombinant HPV Quadrivalent Vaccine, Recombinant Interferon Alfa-2b, Regorafenib, Revlimid (Lenalidomide), Rheumatrex (Methotrexate), Rituxan (Rituximab), Rituximab, Romidepsin, Romiplostim, Rubidomycin (Daunorubicin Hydrochloride), Ruxolitinib Phosphate, Sclerosol Intrapleural Aerosol (Talc), Sipuleucel-T, Sorafenib Tosylate, Sprycel (Dasatinib), Stanford V, Sterile Talc Powder (Talc), Steritalc (Talc), Stivarga (Regorafenib), Sunitinib Malate, Sutent (Sunitinib Malate), Sylatron (Peginterferon Alfa-2b), Synovir (Thalidomide), Synribo (Omacetaxine Mepesuccinate), Tafinlar (Dabrafenib), Talc, Tamoxifen Citrate, Tarabine PFS (Cytarabine), Tarceva (Erlotinib Hydrochloride), Targretin (Bexarotene), Tasigna (Nilotinib), Taxol (Paclitaxel), Taxotere (Docetaxel), Temodar (Temozolomide), Temozolomide, Temsirolimus, Thalidomide, Thalomid (Thalidomide), Toposar (Etoposide), Topotecan Hydrochloride, Toremifene, Torisel (Temsirolimus), Tositumomab and 1 131 Iodine Tositumomab, Totect (Dexrazoxane Hydrochloride), Trametinib, Trastuzumab, Treanda (Bendamustine Hydrochloride), Trisenox (Arsenic Trioxide), Tykerb (Lapatinib Ditosylate), Vandetanib, VAMP, Vectibix (Panitumumab), VelP, Velban (Vinblastine Sulfate), Velcade (Bortezomib), Velsar (Vinblastine Sulfate), Vemurafenib, VePesid (Etoposide), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, Vismodegib, Voraxaze (Glucarpidase), Vorinostat, Votrient (Pazopanib Hydrochloride), Wellcovorin (Leucovorin Calcium), Xalkori (Crizotinib), Xeloda (Capecitabine), Xelox, Xgeva (Denosumab), Xofigo (Radium 223 Dichloride), Xtandi (Enzalutamide), Yervoy (Ipilimumab), Zaltrap (Ziv-Aflibercept), Zelboraf (Vemurafenib), Zevalin (Ibritumomab Tiuxetan), Zinecard (Dexrazoxane Hydrochloride), Ziv-Aflibercept, Zoladex (Goserelin Acetate), Zoledronic Acid, Zolinza (Vorinostat), Zometa (Zoledronic Acid), and Zytiga (Abiraterone Acetate).

The anticancer agent may be a PBD dimer, calicheamicin, speromycin, tubulysin B, rhizoxin, dolastatin, didemnin B, camptothecin, CBI, temsirolimus, actinomycin D, epothilone B, taxol, cryptophycin, SN38, velcade, bruceantin, DAVLBH, DM1, Phyllanthoside, Alimta, T2 Toxin, MMC, vantalanib, vinorelbine, brefeldin, sunitinib, daunomycin, semaxanib, tarceva, iressa, irinotecan, LY-541503, geldanomycin, gemcitabine, methotrexate, gleevec, topotecan, bleomycin, doxorubicin, cisplatin, N-mustards, etoposide, or 5-FU.

In certain embodiments, an anticancer agent is an anthracycline. In certain embodiments, anticancer agent is a taxane. In certain embodiments, anticancer agent is gemcitabine. In certain embodiments, anticancer agent is doxorubicin. In certain embodiments, anticancer agent is docetaxel. In certain embodiments, anticancer agent is SN38. In certain embodiments, anticancer agent is monomethyl auristatin E.

b. Immunomodulatory Agents

An additional therapeutic agent may be a TLR or STING agonist. Other immunomodulatory agents include cytokines, chemokines, chemokine antagonists, and immune checkpoint inhibitors.

i. TLR Agonists

TLR agonists are immunomodulatory agents. TLR-mediated signaling in response to pathogen-associated molecular patterns (PAMPs) is a sequential cascade of transcriptional regulatory events that vary depending on the TLR agonists, cell types involved and pathogenicity of the antigen. Individual genes (notably proinflammatory cytokines, e.g., IL-1 (alpha and beta), IL-6, IL-18, TNF-C.) are induced transiently reflecting the ability that the innate immune system has to interpret the infection and orchestrate appropriate responses while promoting resolution (T. Ravasi, C. A. Wells, D. A. Hume, Bioessays 29, 1215 (Nov. 15, 2007); J. C. Roach et al., Proc Natl Acad Sci USA 104, 16245 (Oct. 9, 2007); M. Gilchrist et al., Nature 441, 173 (May 11, 2006)).

TLR agonists include but are not limited to agonists of TLR1/2 heterodimer (e.g., Pam3CSK4, i.e., Trispalmitoyl-CysSerLysLysLysLys), TLR3 (e.g., Poly I:C, Poly ICLC), TLR4 (e.g., monophosphoryl lipid A, lipopolysaccharide, GLA-SE, G100), TLR5 (e.g. flagellin), TLR2/6 heterodimer (e.g., diacyl lipopetides of gram positive bacteria, mycoplasma and fungi), TLR7 (e.g., imidazo[4,5-c]quinolin-4-amines such as imiquimod and as described in U.S. Pat. No. 4,689,338, which is incorporated herein by reference and polyriboinosinic-polyribocytidylic acid (Poly I:C)) TLR3 (Polyadenylic-polyuridylic acid (Poly A:U)), TLR2 (peptidoglycan), TLR2 and TLR4 (e.g. is *Bacillus* Calmette-Guerin (BCG)), imiquimod

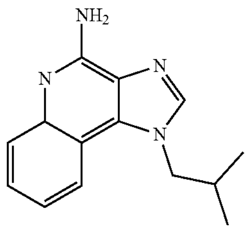

TLR7/8 (e.g., loxoribine; imidazo[4,5-c]quinolin-4-amines such as resiquimod (R848) and MEDI9197),

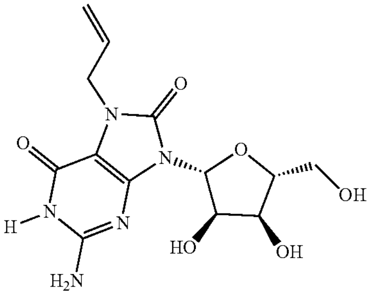

loxoribine

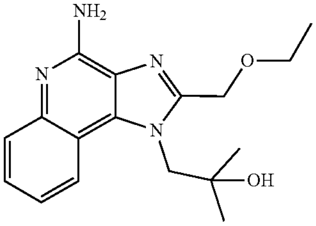

resiquimod

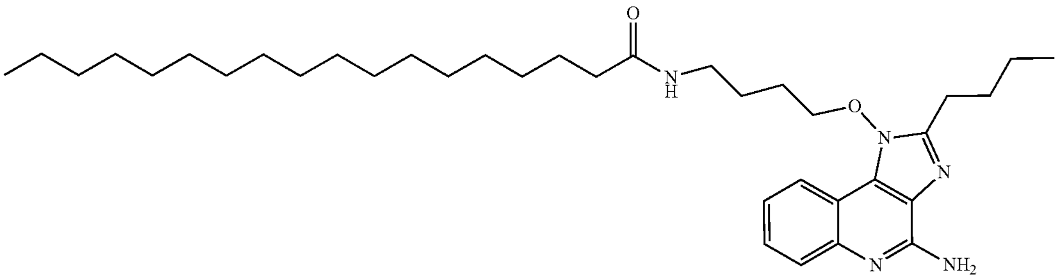

MEDI9197

TLR8 (e.g., VTX-2337)

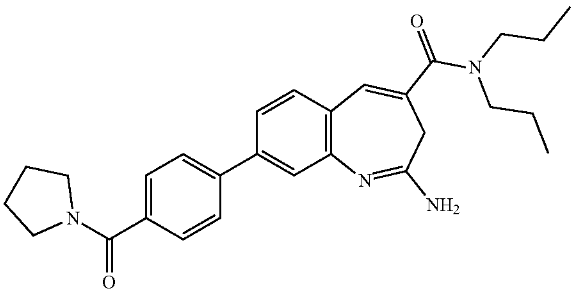

VTX-2337 and TLR9 (e.g., CpG ODNs such as ODN D-SL01, MGN1703, CPG7909, SD-101, EMD 1201081). CpG ODNs are short synthetic single-stranded DNA molecules containing unmethylated CpG dinucleotides in particular sequence contexts (CpG motifs). CpG ODNs possess a partially or completely phosphorothioated (PS) backbone, as opposed to the natural phosphodiester (PO) backbone found in genomic bacterial DNA. Three major classes of stimulatory CpG ODNs have been identified based on structural characteristics and activity on human peripheral blood mononuclear cells (PBMCs), in particular B cells and plasmacytoid dendritic cells (pDCs). CpG-A ODNs are characterized by a PO central CpG-containing palindromic motif and a PS-modified 3' poly-G string. They induce high IFN-α production from pDCs but are weak stimulators of TLR9-dependent NF-κB signaling and pro-inflammatory cytokine (e.g. IL-6) production. CpG-B ODNs contain a full PS backbone with one or more CpG dinucleotides. They strongly activate B cells and TLR9-dependent NF-κB signaling but weakly stimulate IFN-α secretion. CpG-C ODNs combine features of both classes A and B. They contain a complete PS backbone and a CpG-containing palindromic motif. C-Class CpG ODNs induce strong IFN-α production from pDC as well as B cell stimulation.

Further TLR9 agonists are described in WO2019/115402, EP2017281, US2019/0160173, US2019/0151345, US2011/0311518, US2011/0293565, each of which is incorporated herein by reference.

Single and double-stranded RNA may function as a TLR agonist, as described by Roers et al. in Immunity (2016) 44, 739-754, which is incorporated herein by reference.

ii. STING Agonists

STING agonists are immunomodulatory agents responsible for controlling numerous pro-inflammatory host defense genes, including type I inteferons, and pro-inflammatory cytokines, following the recognition of cyclic dinucleotides in the cytosol of a cell. These signals can then stimulate the adaptive immune system through cross presentation of antigen and T-cell priming, along with other mechanisms (Barber GN. STING: infection, inflammation and cancer. Nat Rev Immunol. 2015; 15(12):760-70) TLR and STING agonists are also capable of promoting anti-tumor immune responses in solid cancers and cancers being treated with immunotherapy (Berger G, Marloye M, Lawler S E. Immunotherapy. Trends Mol Med. 2019; 25(5):412-427).

STING agonists include ADU-S100 and 2'3'-cG$^{S}$A$^{S}$MP. STING agonists include cyclic dinucleotides and analogs thereof, such as c-di-AMP

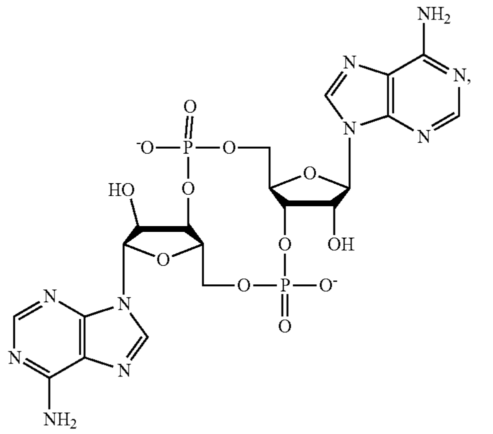

c-di-GMP

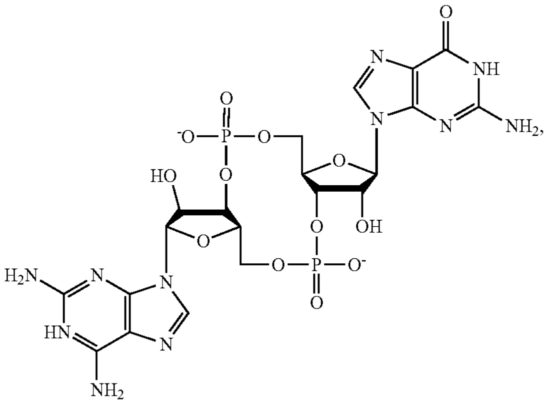

3'3'-cGAMP

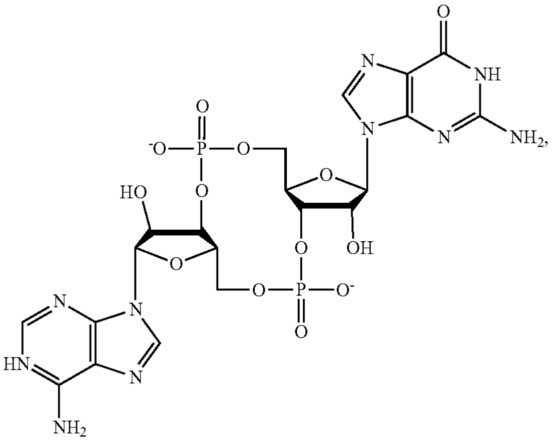

-continued

2'3'-cGAMP

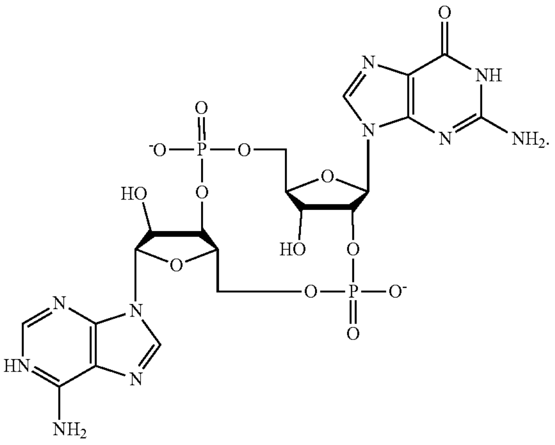

STING agonists further include modified cyclic dinucleotides. In some embodiments, the modified cyclic dinucleotide may not occur in nature or may be chemically synthesized. In some embodiments, the modified cyclic dinucleotide is a compound of the formula:

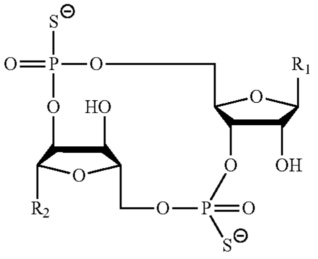

In some embodiments, $R_1$ and $R_2$ may each independently be 9-purine, 9-adenine, 9-guanine, 9-hypoxanthine, 9-Xanthine, 9-uric acid, or 9-isoguanine, the structures of which are shown below, the structures of which are:

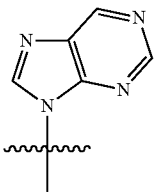

9-purine

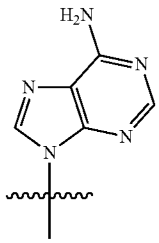

9-adenine

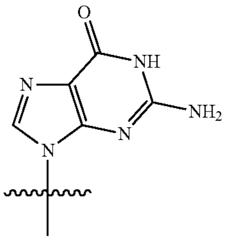

9-guanine

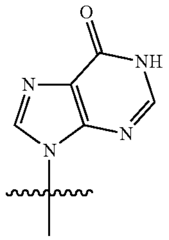

9-hypoxanthine

-continued

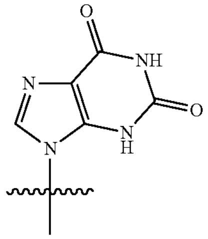

9-xanthine

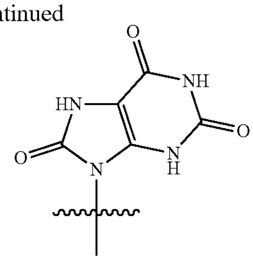

9-uric acid

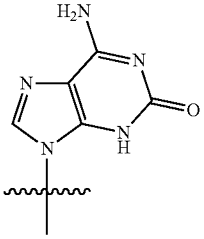

9-isoguanine $R_1$ and $R_2$ may be identical or different. In some embodiments, the compound may be provided in the form of predominantly Rp·Rp or Rp·Sp. stereoisomers, or prodrugs, or pharmaceutically acceptable salts thereof, as described in US 2016/0287623, which is incorporated herein by reference. In some embodiments, the compound may be provided in the form of predominantly Rp·Rp stereoisomers. In particular embodiments, the compound may be a compound of the formula below or in the form of predominantly Rp·Rp stereoisomers thereof:

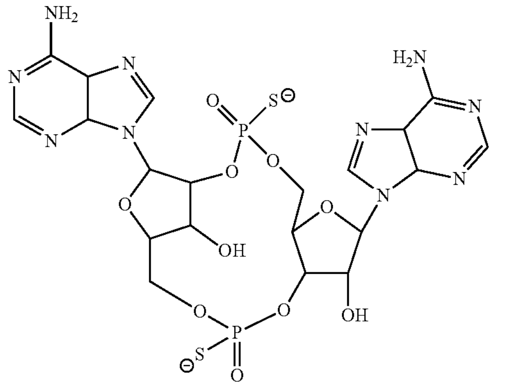 [SMILES: NC1=NC=NC2C1N=CN2C1OC2COP(=O)([S-])OC3C(O)C(COP(=O)([S-])OC2C1O)OC3N1C=NC2C(N)=NC=NC21]

STING agonists may include compounds of formula

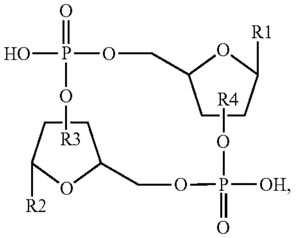

as described in US2017/0333552, which is incorporated herein by reference.

STING agonists may include compounds of formula

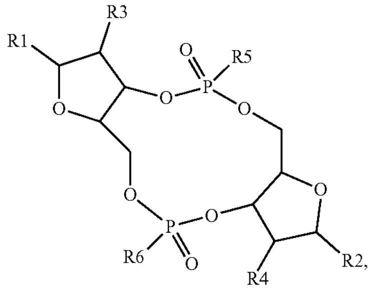

as described in US2018/0064745, which is incorporated herein by reference.

STING agonists may include compounds of formula

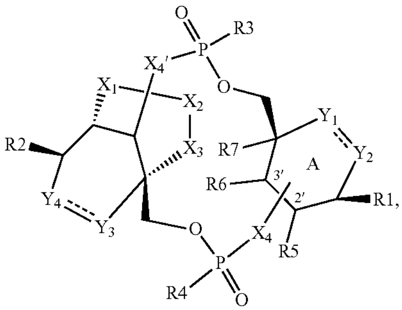

as described in US2019/0185511, which is incorporated herein by reference.

STING agonists may include compounds of formula

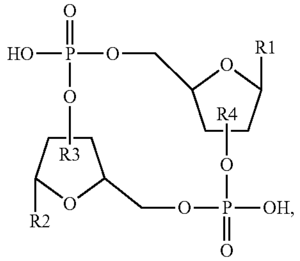

as described in WO2014/189806, which is incorporated herein by reference.

STING agonists may include compounds of formula

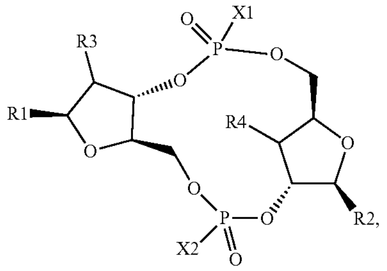

as described in US2019/0062365, which is incorporated herein by reference.

STING agonists may include compounds of formula

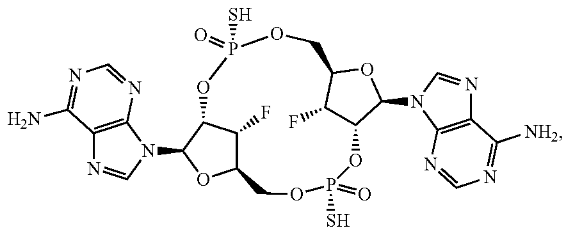 [SMILES: Nc1ncnc2c1ncn2[C@@H]1O[C@@H]2CO[P@@](=O)(S)O[C@@H]3[C@H](F)[C@@H](CO[P@@](=O)(S)O[C@@H]1[C@@H]2F)O[C@H]3n1cnc2c(N)ncnc21]

as described in WO2018/198076, which is incorporated herein by reference.

STING agonists may include compounds of formula

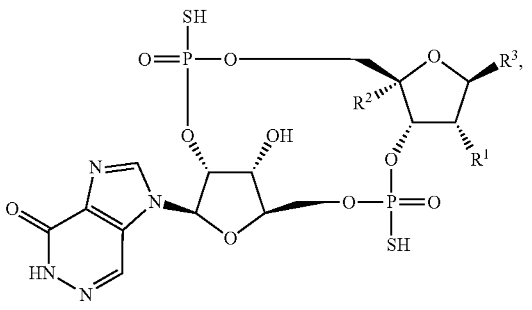

as described in US2018/0092937, which is incorporated herein by reference.

STING agonists may include compounds of formula

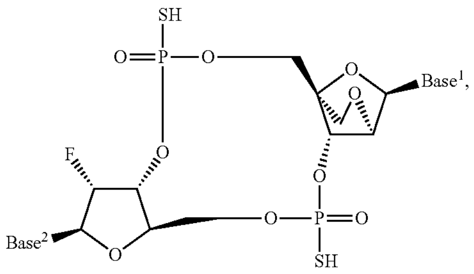

as described in US2018/0273578, which is incorporated herein by reference.

STING agonists may include compounds of formula

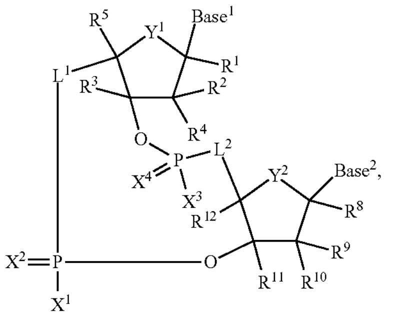

as described in US2019/0183917, which is incorporated herein by reference.

STING agonists may include compounds of formula

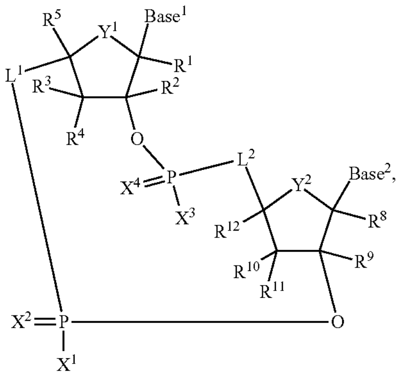

as described in US2019/0185509, which is incorporated herein by reference.

STING agonists may include compounds of formula

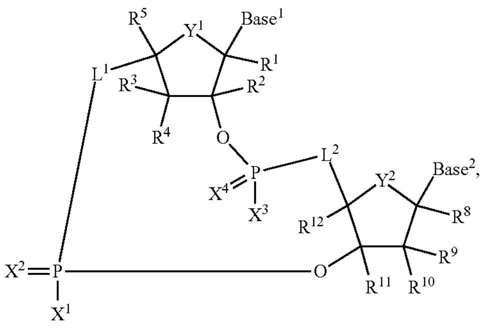

as described in US2019/0185510, which is incorporated herein by reference.

STING agonists may include compounds of formula

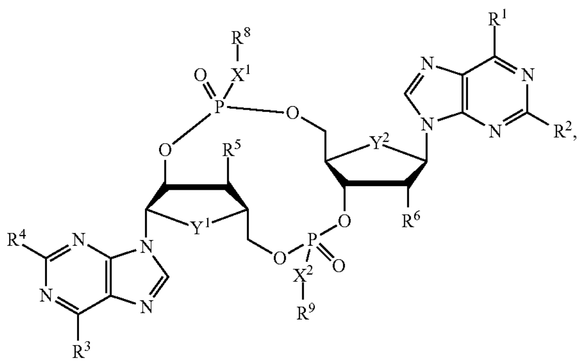

as described in US2017/0233430, which is incorporated herein by reference.

STING agonists may include compounds of formula

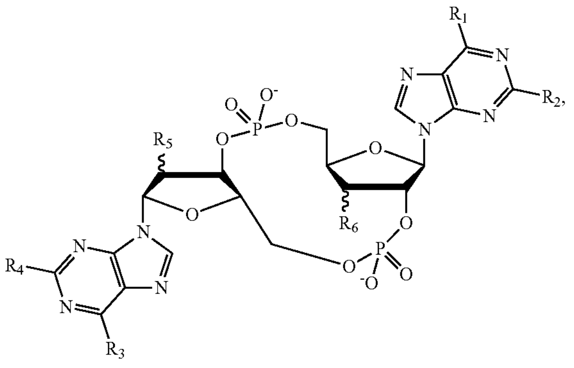

as described in US2018/0002369, which is incorporated herein by reference.

STING agonists may include compounds of formula

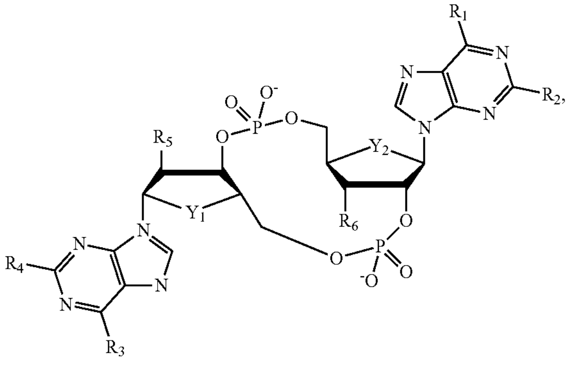

as described in US2018/0186828, which is incorporated herein by reference.

STING agonists may include compounds of formula

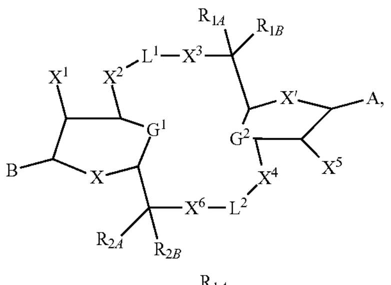

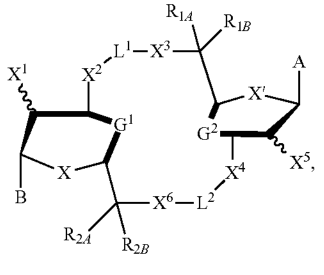

-continued

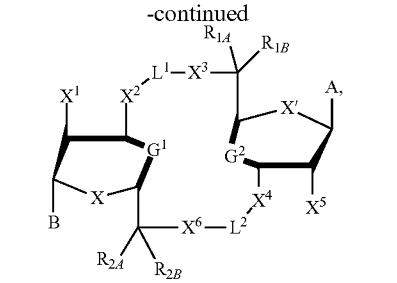

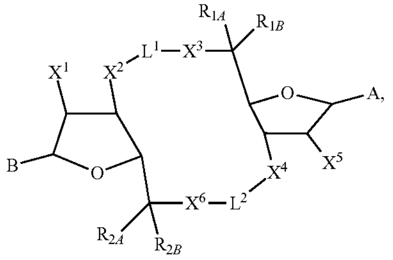

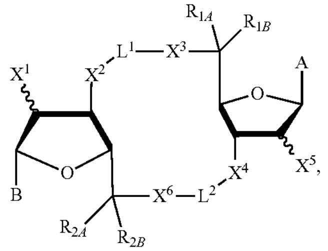

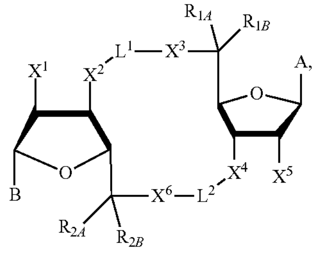

as described in US2019/0016750, which is incorporated herein by reference.

STING agonists may include compounds of formula

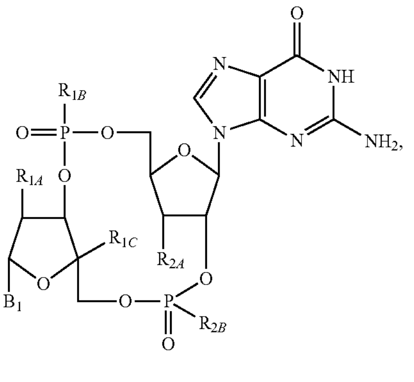

as described in US2018/0162899, which is incorporated herein by reference.

STING agonists may include compounds of formula

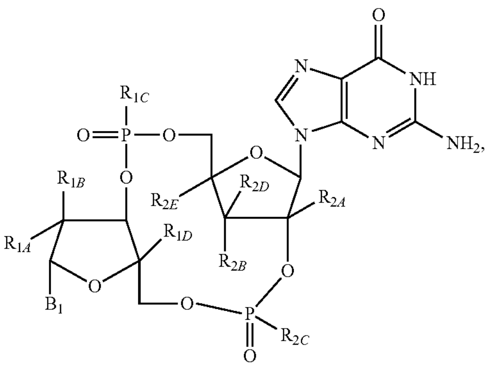

as described in WO2018/138684, which is incorporated herein by reference.

STING agonists may include compounds of formula

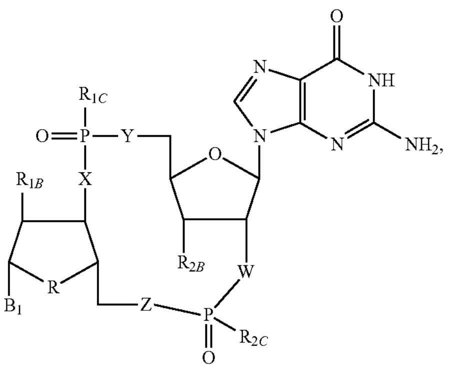

as described in WO2018/138685, which is incorporated herein by reference.

STING agonists may include compounds of formula

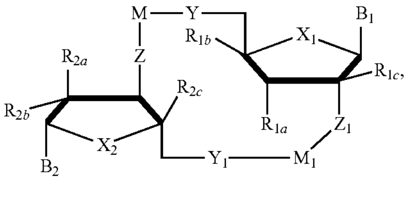

as described in WO2019/118839, which is incorporated herein by reference.

STING agonists may include compounds of formula

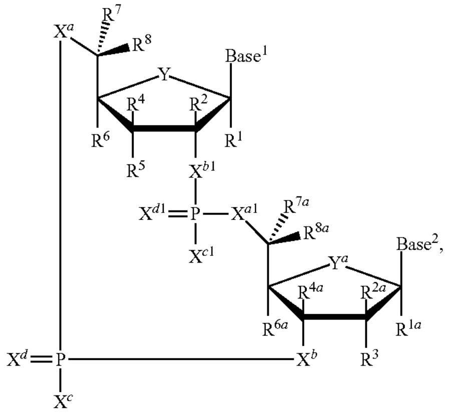

as described in US2017/0044206, which is incorporated herein by reference.

STING agonists may include compounds of formula

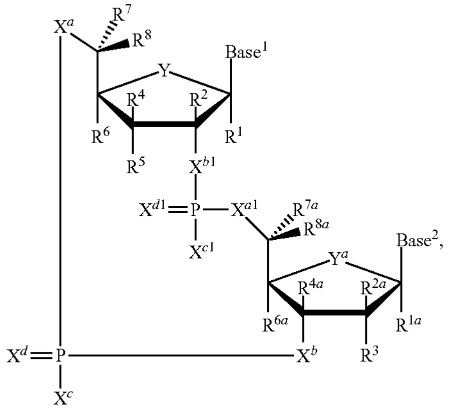

as described in WO2018/118665, which is incorporated herein by reference.

STING agonists may include compounds of formula

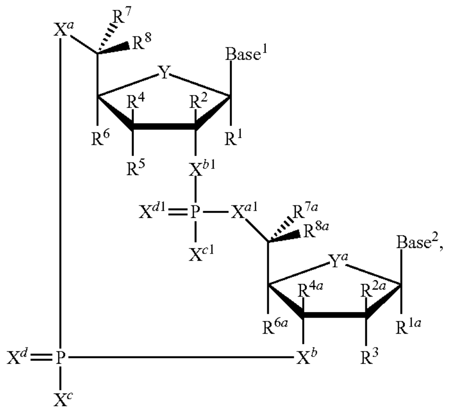

as described in WO2018/208667, which is incorporated herein by reference.

STING agonists may include compounds of formula

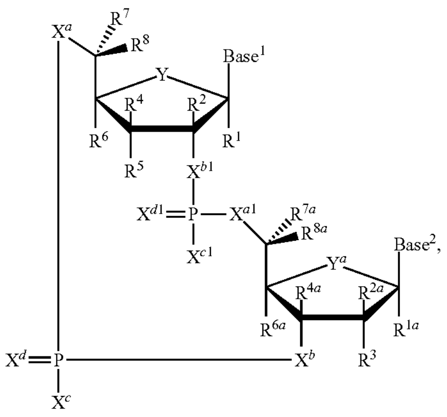

as described in WO2019/125974, which is incorporated herein by reference.

STING agonists may include compounds of formula

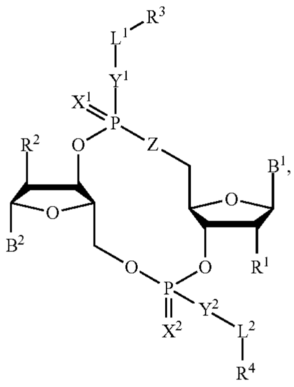

as described in WO2018/009648, which is incorporated herein by reference.

STING agonists may include compounds of formula

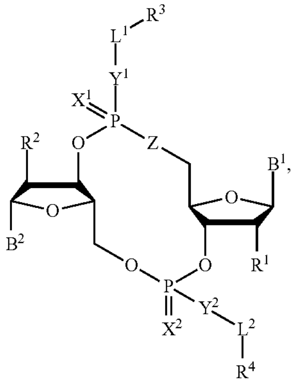

as described in WO2018/009652, which is incorporated herein by reference.

STING agonists may include compounds of formula

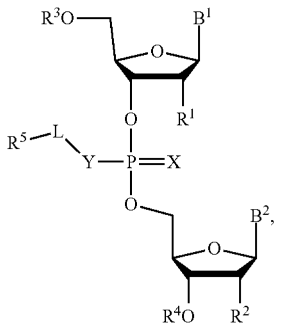

as described in WO2018/013887, which is incorporated herein by reference.

STING agonists may include compounds of formula

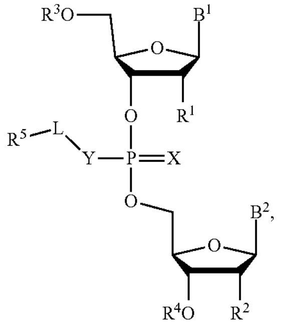

as described in WO2018/013908, which is incorporated herein by reference.

STING agonists may include compounds of formula

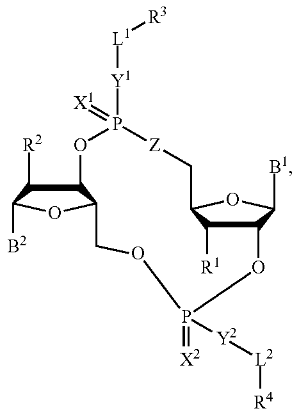

as described in WO2019/046511, which is incorporated herein by reference.

STING agonists may include compounds of formula

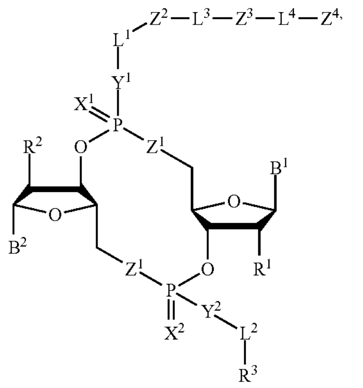

as described in WO2019/051488, which is incorporated herein by reference.

STING agonists may include compounds of formula

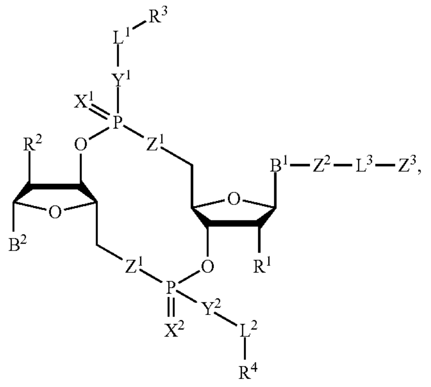

as described in WO2019/051489, which is incorporated herein by reference.

STING agonists may include compounds of formula

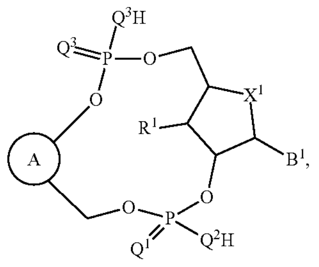

as described in US2019/0192549, which is incorporated herein by reference.

STING agonists may include compounds of formula

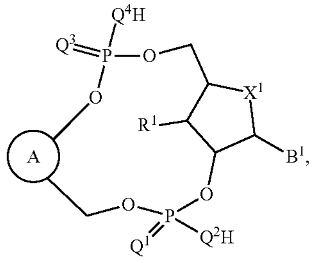

as described in WO2018/100558, which is incorporated herein by reference.

STING agonists may include compounds of formula

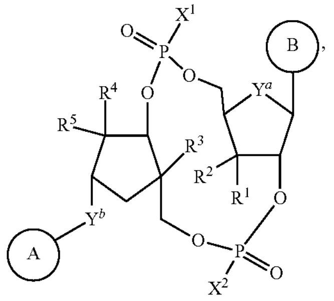

as described in WO2019/092660, which is incorporated herein by reference.

STING agonists may include compounds of formula

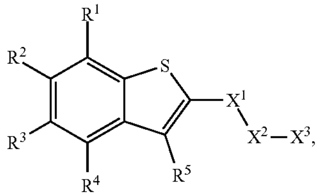

as described in WO2019/027858, which is incorporated herein by reference.

STING agonists may include compounds of formula

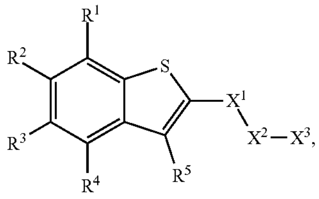

as described in US2018/0093964, which is incorporated herein by reference.

STING agonists may include compounds of formula

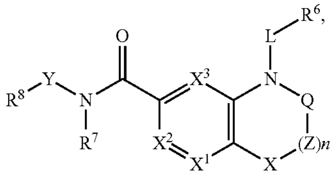

wherein X, $X^1$-$X^3$, L, Q, Z, Y, n, and $R^6$-$R^8$ are as described in WO2018/234805, which is incorporated herein by reference.

STING agonists may include compounds of formula

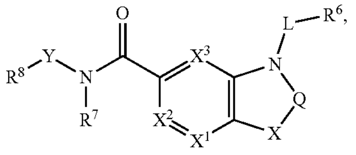

wherein X, $X^1$-$X^3$, L, Q, Y, and $R^6$-$R^8$ are as described in WO2018/234807, which is incorporated herein by reference.

STING agonists may include compounds of formula

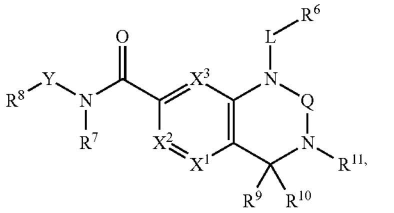

wherein $X^1$-$X^3$, L, Q, Y, and $R^6$-$R^{11}$ are as described in WO2018/234808, which is incorporated herein by reference.

STING agonists include, for example, the compound DMXAA:

DMXAA

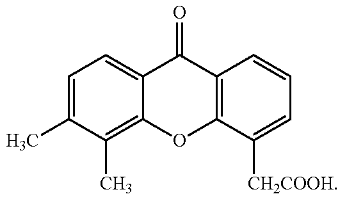

STING agonists include di-amidobenimidazoles, such as

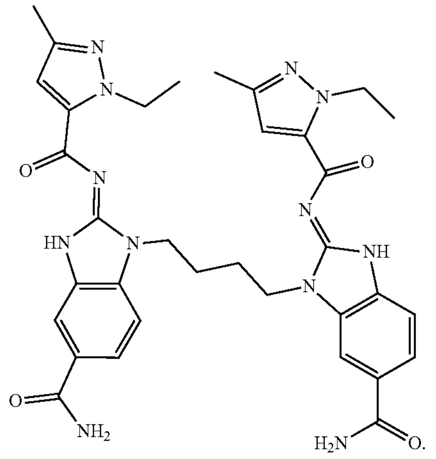 [SMILES: CCn1nc(C)cc1C(=O)/N=c1\[nH]c2cc(C(N)=O)ccc2n1CCCCn1/c(=N/C(=O)c2cc(C)nn2CC)[nH]c2ccc(C(N)=O)cc21]

c. Trans-Cyclooctene Functionalized Prodrugs

Trans-cyclooctene functionalized prodrugs are known in the art, including prodrugs of anticancer agents, as described in WO2018/187740, WO2014/205126, WO2015/139025, and WO2017/044983, which are incorporated herein by reference. Further embodiments using trans-cyclooctene functionalized prodrugs follow.

E46.1A. The method of E46, wherein the trans-cyclooctene functionalized prodrug has formula (III)

(III)

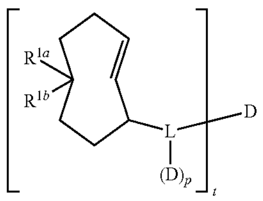

or a pharmaceutically acceptable salt thereof, wherein $R^{1a}$, at each occurrence, is independently selected from the group consisting of hydrogen, $C_{1-4}$alkyl, and $C_{1-4}$haloalkyl;

$R^{1b}$, at each occurrence, is independently selected from the group consisting of hydrogen, $C_{1-4}$alkyl, $C_{1-4}$haloalkyl, C(O)OH, C(O)O$C_{1-4}$alkyl, C(O)N($R^{1e}$)CH$R^{1e}$$CO_2$H, C(O)N($R^{1c}$)CH$R^{1e}$C(O)O$C_{1-4}$alkyl, C(O)N($R^{1c}$)—$C_{1-6}$alkylene-$CO_2$H, and C(O)N($R^{1c}$)—$C_{1-6}$alkylene-C(O)O$C_{1-4}$alkyl;

$R^{1c}$, at each occurrence, is independently hydrogen or $C_{1-4}$alkyl;

$R^{1e}$, at each occurrence, is independently —$C_{1-4}$alkylene-$CO_2$H, —$C_{1-4}$alkylene-$CONH_2$, or —$C_{1-4}$alkylene-OH;

D, at each occurrence, is independently a payload selected from the group consisting of an anticancer agent payload, a toll-like receptor (TLR) agonist payload and a stimulator of interferon genes (STING) agonist payload;

L, at each occurrence, is independently a linker;

t, at each occurrence, is independently 1, 2, or 3; and p, at each occurrence, is independently 0, 1, or 2.

E46.1B. A compound of formula (III) or a compound of formula (III) for use in the method of E46, wherein the trans-cyclooctene functionalized prodrug has formula (III)

(III)

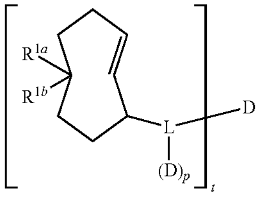

or a pharmaceutically acceptable salt thereof, wherein $R^{1a}$, at each occurrence, is independently selected from the group consisting of hydrogen, $C_{1-4}$alkyl, and $C_{1-4}$haloalkyl;

$R^{1b}$, at each occurrence, is independently selected from the group consisting of $C(O)N(R^{1e})$—$C_{1-6}$alkylene-$SO_3H$, $C(O)N(R^{1c})$—$C_{2-6}$alkylene-$N(C_{1-4}alkyl)_3^+$, $C(O)N(R^{1c})$—$(CH_2CH_2O)_{1-3}$—$CH_2CH_2N((CH_2CH_2O)_{1-3}$—$C_{1-6}$alkylene-$CO_2H)_2$, and $C(O)N(R^{1c})$—$CH(CH_2O$—$(CH_2CH_2O)_{0-2}$—$C_{1-6}$alkylene-$CO_2H)_2$;

$R^{1c}$, at each occurrence, is independently hydrogen or $C_{1-4}$alkyl;

D, at each occurrence, is independently a payload selected from the group consisting of an anticancer agent payload, a toll-like receptor (TLR) agonist payload and a stimulator of interferon genes (STING) agonist payload;

L, at each occurrence, is independently a linker;

t, at each occurrence, is independently 1, 2, or 3; and p, at each occurrence, is independently 0, 1, or 2.

E46.2. The method of E46.1A, the compound, or pharmaceutically acceptable salt, of E46.1B, or the compound, or pharmaceutically acceptable salt, for use in the method of E46.1B, wherein $R^{1a}$ is hydrogen.

E46.3. The method of E46.1A, the compound, or pharmaceutically acceptable salt, of E46.1B, or the compound, or pharmaceutically acceptable salt, for use in the method of E46.1B, wherein $R^{1a}$ is $C_{1-4}$alkyl.

E46.4. The method of E46.1A, the compound, or pharmaceutically acceptable salt, of E46.1B, or the compound, or pharmaceutically acceptable salt, for use in the method of E46.1B, wherein $R^{1a}$ is $CH_3$.

E46.5. The method of any of E46.1A or E46.2 to E46.4, wherein $R^{1b}$ is selected from the group consisting of C(O)OH, $C(O)OC_{1-4}$alkyl, $C(O)N(R^{1c})CHR^{1e}CO_2H$, $C(O)N(R^{1c})CHR^{1e}C(O)OC_{1-4}$alkyl, $C(O)N(R^{1c})$—$C_{1-6}$ alkylene-$CO_2H$, and $C(O)N(R^{1c})$—$C_{1-6}$alkylene-$C(O)OC_{1-4}$alkyl.

E46.6A. The method of any of E46.1A or E46.2 to E46.4, wherein $R^{1b}$ is selected from the group consisting of C(O)OH, $C(O)N(R^{1e})CHR^{1e}CO_2H$, and $C(O)N(R^{1e})CH_2CO_2H$.

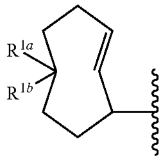

is

E46.6B. The compound, or pharmaceutically acceptable salt, of any of E46.1B to E46.4, or the compound, or pharmaceutically acceptable salt, for use in the method of any of E46.1B to E46.4, wherein $R^{1b}$ is selected from the group consisting of —$NR^{1c}$—$CH_2CH_2$—$N(CH_3)_3^+$, —$N(R^{1c})$—$CH_2CH_2$—$SO_3H$, —$N(R^{1c})$—$(CH_2CH_2O)_3$—$CH_2CH_2N((CH_2CH_2O)_3$—$CH_2CH_2$—$CO_2H)_2$, and —$N(R^{1c})CH(CH_2O$—$CH_2CH_2$—$CO_2H)_2$.

E46.6C. The compound, or pharmaceutically acceptable salt of E46.1B, or the compound, or pharmaceutically acceptable salt, for use in the method of E46.1B, wherein

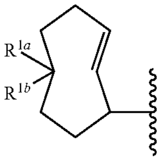

is

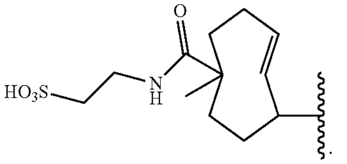

.

E46.6D. The compound, or pharmaceutically acceptable salt of E46.1B, or the compound, or pharmaceutically acceptable salt, for use in the method of E46.1B, wherein

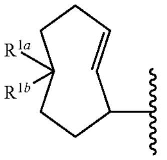

is

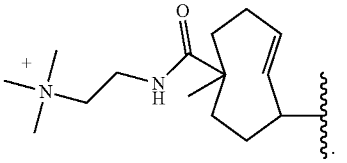

.

E46.6E. The compound, or pharmaceutically acceptable salt of E46.1B, or the compound, or pharmaceutically acceptable salt, for use in the method of E46.1B, wherein -continued

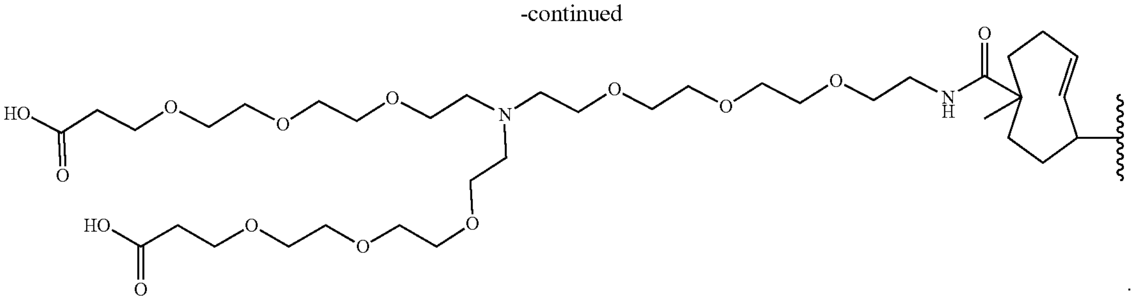

E46.6F. The compound, or pharmaceutically acceptable salt of E46.1B, or the compound, or pharmaceutically acceptable salt, for use in the method of E46.1B, wherein

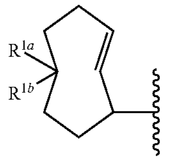

is

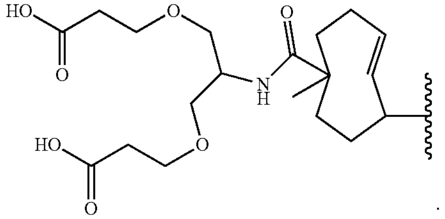

E46.7. The method of E46.5 or E46.6A, wherein $R^{1e}$ is $—CH_2CO_2H$, $—CH_2CH_2CO_2H$, $—CH_2CONH_2$, $—CH_2CH_2CONH_2$, $—CH_2OH$, or $—CH(CH_3)OH$.

E46.8. The method of E46.5 or E46.6A, wherein $R^{1e}$ is $—C_{1-4}$alkylene-$CO_2H$.

E46.9. The method of E46.5 or E46.6A, wherein $R^{1e}$ is $—CH_2CO_2H$.

E46.10. The method of any of E46.1A or E46.2 to E46.4, wherein $R^{1b}$ is $C(O)N(R^{1e})—C_{1-6}$alkylene-$CO_2H$.

E46.11. The method of any of E46.1A or E46.2 to E46.4, wherein $R^{1b}$ is $C(O)N(R^{1c})CH_2CO_2H$.

E46.12. The method of any of E46.1A to E46.11, wherein $R^{1c}$ is hydrogen.

E46.13. The method of any of E46.1A or E46.2 to E46.4, wherein $R^{1b}$ is hydrogen.

E46.14. The method of any of E46.1A or E46.2 to E46.4, wherein $R^{1b}$ is C(O)OH.

In the compounds described herein, linker L may have 1 to 100 linking atoms, and may include ethylene-oxy groups, amines, esters, amides, carbamates, carbonates, and ketone functional groups. For example, linkers may have from 1 to 50 linking atoms, or from 5 to 50 linking atoms, or from 10 to 50 linking atoms, or from 1 to 40 linking atoms, or from 1 to 30 linking atoms, or from 1 to 20 linking atoms, or from 1 to 10 linking atoms, or from 1 to 5 linking atoms, or from 5 to 30 linking atoms, or from 10 to 30 linking atoms, or from 5 to 40 linking atoms, or from 5 to 50 linking atoms, or from 10 to 50 linking atoms.

The linker in formula (III) may comprise one or more (e.g., 1-10 or 1-5) chain heteroatoms (e.g., O, N, S) and one or more (e.g., 1-10 or 1-5) alkylene, alkenylene, alkynylene, arylene, heteroarylene, cycloalkylene or heterocycloalkylene moieties; wherein each alkylene, alkenylene, alkynylene, arylene, heteroarylene, cycloalkylene or heterocycloalkylene moiety, may be independently optionally substituted with one to five substituents independently selected from oxo, halo, $C_{1-4}$ alkyl, $C_{1-4}$ alkoxy, and $C_{1-4}$ haloalkyl.

In formula (III), the linker may be of the formula:

$$—Y^{10}—(CH_2)_{n'}—Y^{20}—(CH_2)_{m''}—Y^{30}—$$

wherein:

each of $Y^{10}$, $Y^{20}$, and $Y^{30}$ are independently a bond, $—NR^{110}—$, $—O—$, $—S(O)_{0-2}—$, $—NR^{110}C(O)—$, $—C(O)NR^{110}—$, $—NR^{110}S(O)_2—$, $—S(O)_2NR^{110}—$, $—CR^{120}{=}N—NR^{110}$, $—NR^{110}—N{=}CR^{120}—$, $—C(O)—$, $—OC(O)—$, $—OC(O)O—$, alkylene, alkenylene, alkynylene, arylene, heteroarylene, cycloalkylene or heterocycloalkylene; wherein each alkylene, alkenylene, alkynylene, arylene, heteroarylene, cycloalkylene or heterocycloalkylene is independently optionally substituted with one to five substituents independently selected from oxo, halo, $C_{1-4}$ alkyl, $C_{1-4}$ alkoxy, and $C_{1-4}$ haloalkyl;

each $R^{110}$ is independently hydrogen, $C_{1-4}$ alkyl, $C_{1-4}$ haloalkyl, aryl, heteroaryl, cycloalkyl or heterocyclyl;

each $R^{120}$ is independently hydrogen, $C_{1-4}$ alkyl, $C_{1-4}$ haloalkyl, aryl, heteroaryl, cycloalkyl or heterocyclyl; and n' and m" are each independently 0, 1, 2, 3, 4, 5, 6, 7, or 8.

In certain embodiments, the linker is not a bond. In certain embodiments, each $R^{110}$ is independently hydrogen, $C_{1-4}$ alkyl, $C_{1-4}$ haloalkyl, aryl, heteroaryl, cycloalkyl or heterocyclyl; and each $R^{120}$ is independently hydrogen, $C_{1-4}$ alkyl, $C_{1-4}$ haloalkyl, aryl, heteroaryl, cycloalkyl or heterocyclyl.

Representative linkers include, but are not limited to, those shown below:

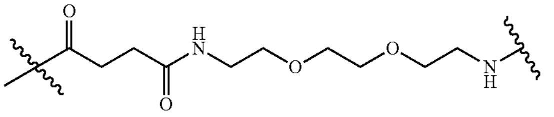

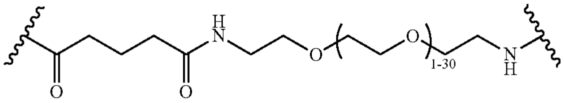

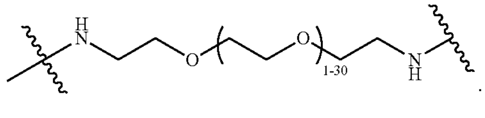

Representative linkers include, but are not limited to, those shown below:

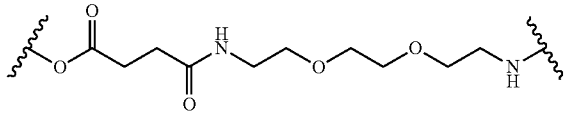

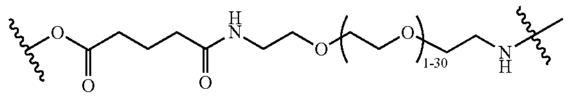

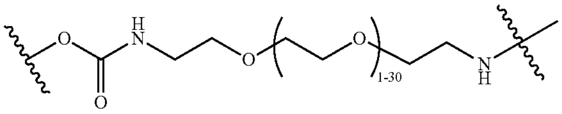

The linker in formula (III) may comprise one or more of polyethylene glycol (e.g., PEG having an average molecular weight of from 300 g/mol to 10,000 g/mol), ethylene-1,2-diylbis(methylcarbamate, an arylene (e.e., phenylene), ethylene-oxy, amine, ester, amide, carbamate, ketone (i.e., formyl), or carbonate. The linker in formula (III) may comprise

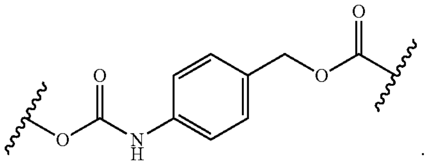 [SMILES: *OC(=O)Nc1ccc(COC(*)=O)cc1]

In formula (III), the linker may comprise one or more natural or unnatural amino acids, which may be referred to as a peptide linker. Where the drug (D) comprises an amino moiety, the linker may be bound thereto using a peptide linker made up of a carboxylic acyl unit, and one or more amino acids making up a protein or peptide sequence. The linker may also contain a self-immolating spacer which spaces the drug and the protein peptide sequence.

In formula III, the linker L may be a peptide linker represented by "A-Y—Z—X—W" in which "A" is the carboxylic acyl unit, "Y" and "Z" are each one or more natural or unnatural amino acids and together form a peptide sequence, and "X" and "W" are optional additional linkers having from 1 to 50 linking atoms, or from 5 to 10 linking atoms, or from 1 to 10 linking atoms which spaces the peptide and the drug, D, or the bioorthogonal moiety. In certain embodiments, one or more of the amino acids in the peptide linker is N-methylated.

In formula (III), Y may be at least one amino acid selected from the group consisting of alanine, valine, leucine, isoleucine, methionine, phenylalanine, tryptophan and proline. Y may be at least one amino acid selected from the group consisting of phenylalanine, alanine, and valine.

In formula (III), Z may be at least one amino acid selected from the group consisting of alanine, lysine, lysine protected with acetyl or formyl, arginine, arginine protected with tosyl or nitro groups, histidine, ornithine, ornithine protected with acetyl or formyl, and citrulline. Z may be at least one amino acid selected from the group consisting of alanine, lysine and citrulline.

Preferred Y—Z combinations include Valine-Citrulline; Valine-Alanine; and Alanine-Alanine.

In certain embodiments, A is —OC(O)—.

In certain embodiments, X is —OC(O)—.

In certain embodiments, W is —OC(O)—. In certain embodiments, X is absent and W is —OC(O)—.

In certain embodiments, —X—W is

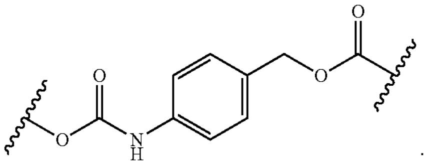 [SMILES: *OC(=O)Nc1ccc(COC(*)=O)cc1]

In certain embodiments, —X—W is

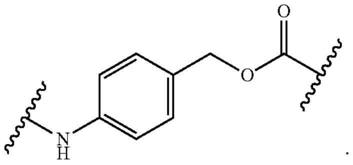 [SMILES: *Nc1ccc(COC(*)=O)cc1]

In certain embodiments, the peptide linker is specifically tailored so that it will be selectively cleaved (e.g., enzymatically cleaved) releasing the drug, such as by one or more of the tumor-associated proteases.

In certain embodiments, the peptide linker has a chain length of two to four amino acid residues (i.e., a di-, tri-, or tetra-peptide). It will be understood, however, that peptide linkers up to five, six, seven, or eight amino acid residues may also suitably be employed.

In certain embodiments, the peptide linker is Phe-Lys, Val-Lys, Val-Ala, Ala-Ala, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly [SEQ ID NO: 1], Ala-Leu-Ala-Leu [SEQ ID NO:2], Phe-$N^9$-tosyl-Arg, or Phe-$N^9$-Nitro-Arg. In certain embodiments, the peptide linker is Phe-Lys, Val-Lys, Val-Ala, Ala-Ala, Val-Val, Val-Cit, or D-Phe-L-Phe-Lys. In certain embodiments, the peptide linker is Val-Cit, Val-Ala, or Ala-Ala.

In certain embodiments, the linker L in formula (III) is:

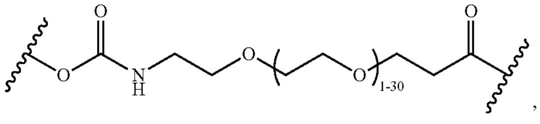,

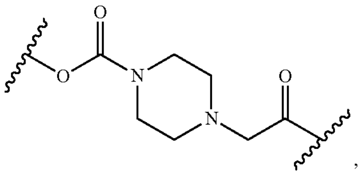,

-continued
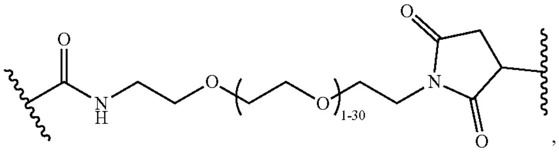
,
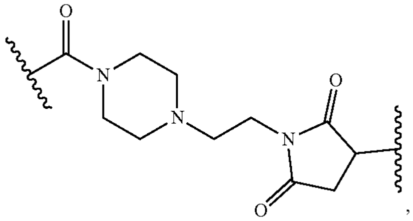
,
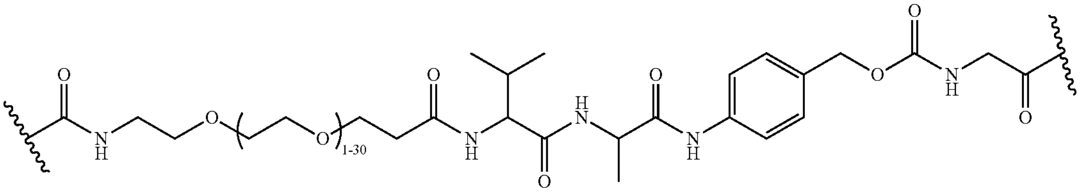
, or
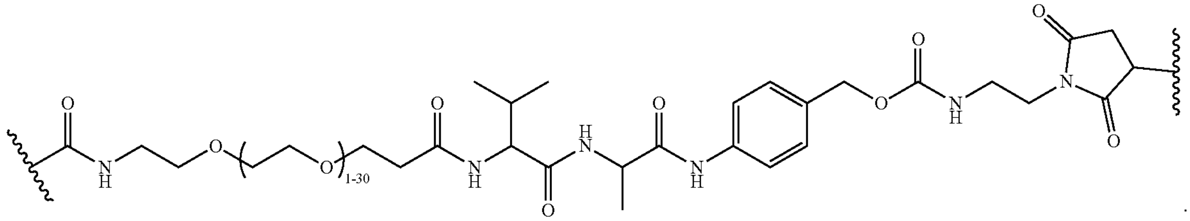
.
The foregoing linkers may attach on the right-hand side to amino acid side chains of D such lysine or cysteine (e.g.,
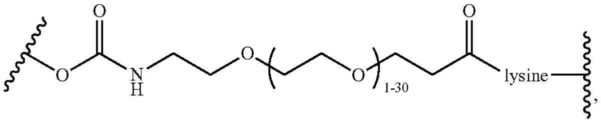
,
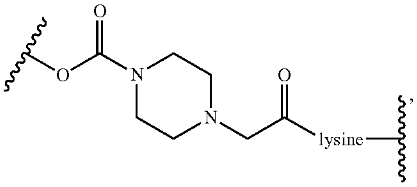
,
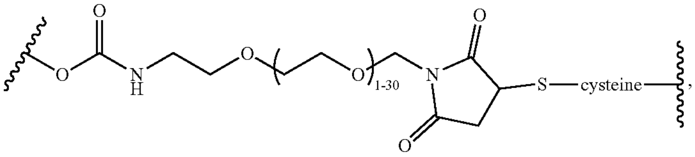
,
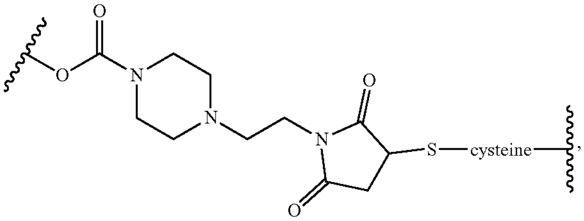
,
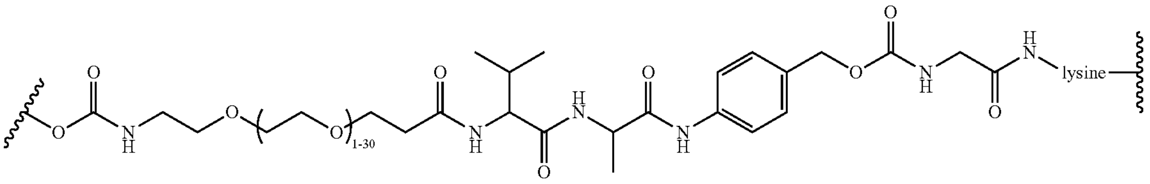
, -continued

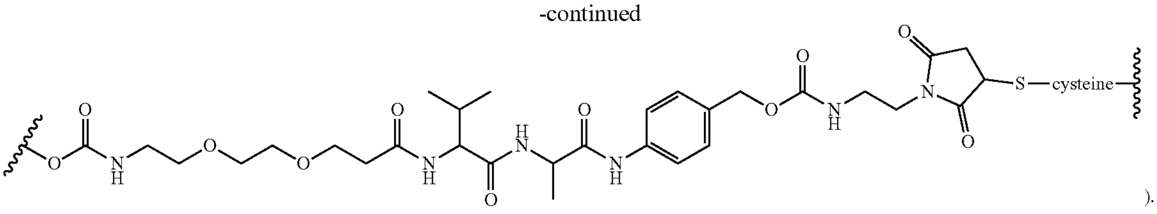

).

In some instances, the therapeutic agent is covalently attached to the linker through an amide bond; e.g., the therapeutic agent may be an amine-containing therapeutic agent for attachment of the therapeutic agent to a carbonyl group of the linker, or, in other cases, the therapeutic agent may be a carboxyl-containing therapeutic agent for attachment of the therapeutic agent to an amine group of the linker. In some instances, the therapeutic agent and linker, together form a carbamate group; e.g., the therapeutic agent may be an amine-containing therapeutic agent for attachment of the therapeutic agent to an acyloxy group of the linker. In some instances, the therapeutic agent and linker, together form a carbonate group; e.g., the therapeutic agent may be a hydroxy-containing therapeutic agent for attachment of the therapeutic agent to an acyloxy group of the linker.

E46.15A. The method of any of E46.1A, E46.2 to E46.6, or E46.7 to E46.14, the compound, or pharmaceutically acceptable salt, of any of E46.1B to E46.4 or E46.6B to E46.6F, or the compound, or pharmaceutically acceptable salt, for use in the method of any of E46.1B to E46.4 or E46.6B to E46.6F, wherein L is

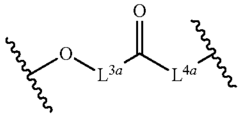

or —O—;

$L^{3a}$ is a bond or $C_{1-6}$alkylene;

$L^{4a}$ is a bond, —NHN, —$N(R^{10})C_{2-6}$alkylene-$N(R^{11})$—, —$N(R^{12})$—$C_{2-3}$alkylene-$N(R^{13})C(O)$—, —$N(R^{10})$—$C_{1-6}$alkylene-C(O)NHN, —NHNHC(O)$C_{1-6}$alkylene-C(O)NHN, —CH(NHC(O)$R^{14}$)$C_{1-4}$alkylene-S—S—$C_{1-4}$alkylene-OC(O)—, —NHNHC(O)CH(NHC(O)$R^{15}$)$CH_2C(O)$—, —$C_{1-6}$alkylene-CH($G^x$)OC(O)—,

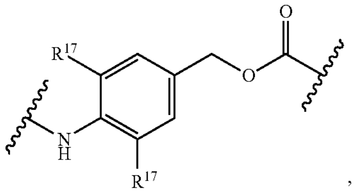

,

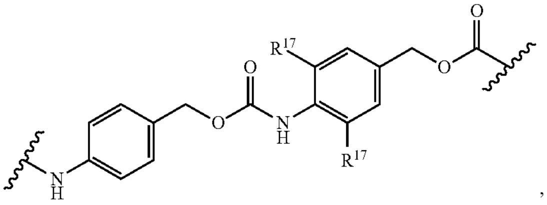

,

-continued

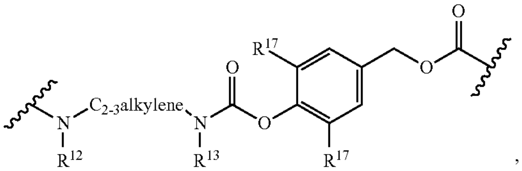

,

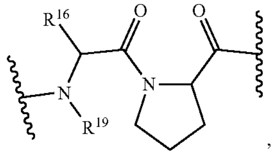

, or

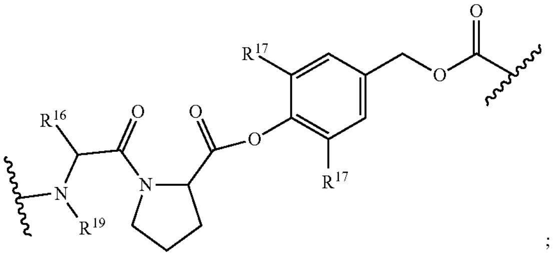

;

$R^{10}$, $R^{11}$, $R^{12}$, $R^{13}$, $R^{14}$, $R^{15}$, and $R^{19}$ are each independently hydrogen or $C_{1-4}$alkyl;

$R^{16}$ is hydrogen, $C_{1-4}$alkyl, —$C_{1-4}$alkylene-OH, —$C_{1-4}$alkylene-O$C_{1-4}$alkyl, —$C_{1-4}$alkylene-$CO_2H$, or —$C_{1-4}$alkylene-$CONH_2$;

$R^{17}$, at each occurrence, is independently hydrogen or —$CH_2OC(O)$—; and $G^x$ is phenyl optionally substituted with 1-5 substituents independently selected from the group consisting of halogen, $C_{1-4}$alkyl, $C_{1-4}$haloalkyl, $C_{1-4}$alkoxy, cyano, and nitro.

E46.15B. The method of any of E46.1A, E46.2 to E46.6, or E46.7 to E46.14, the compound, or pharmaceutically acceptable salt, of any of E46.1B to E46.4 or E46.6B to E46.6F, or the compound, or pharmaceutically acceptable salt, for use in the method of any of E46.1B to E46.4 or E46.6B to E46.6F, wherein L is

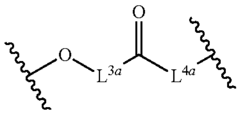

;

$L^{3a}$ is a bond;

$L^{4a}$ is

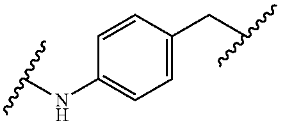

or

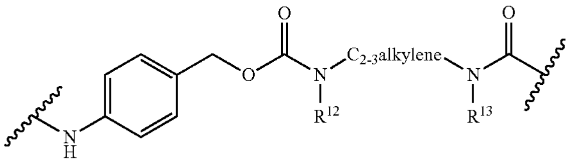

;

and $R^{12}$ and $R^{13}$ are each independently hydrogen or $C_{1-4}$alkyl.

E46.16. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein t is 1.

E46.17A. The method of E46.16, the compound, or pharmaceutically acceptable salt, of E46.16, or the compound, or pharmaceutically acceptable salt, for use in the method of E46.16, wherein

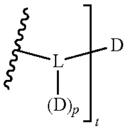

is

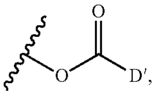

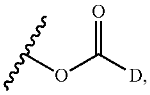

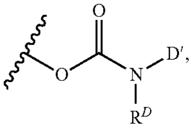

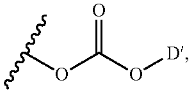

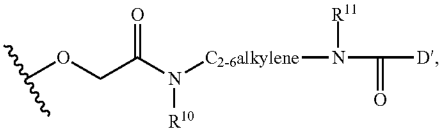

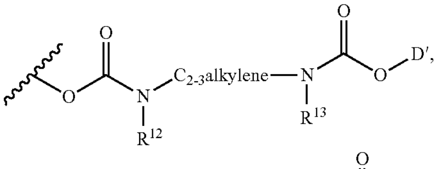

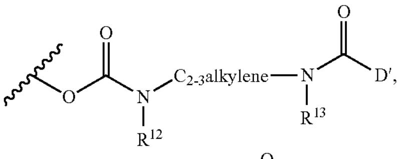

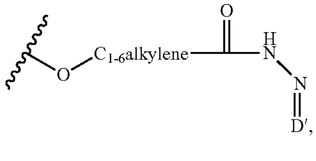

-continued

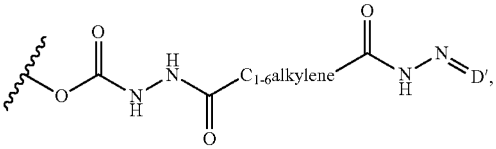

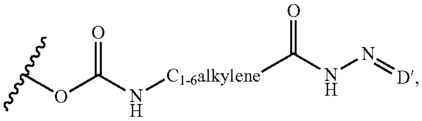

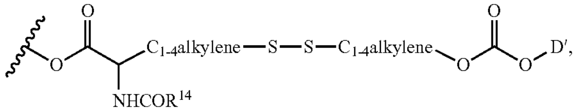

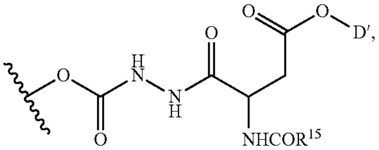

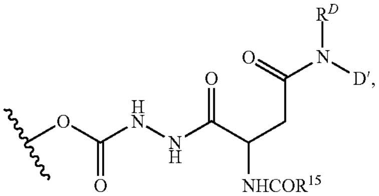

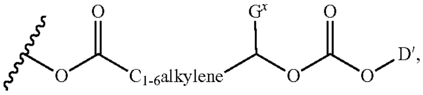

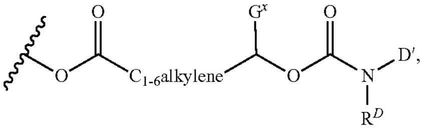

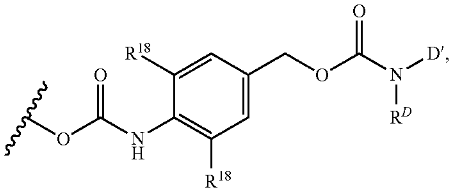

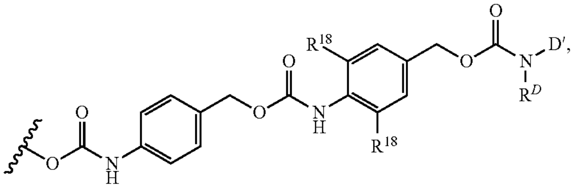

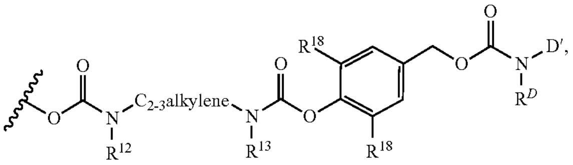

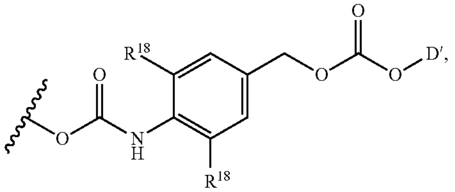

-continued

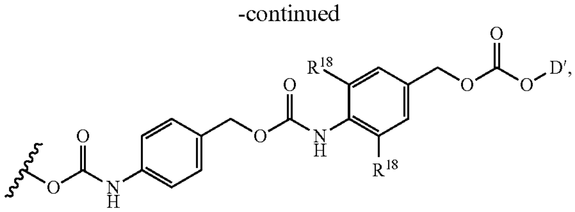

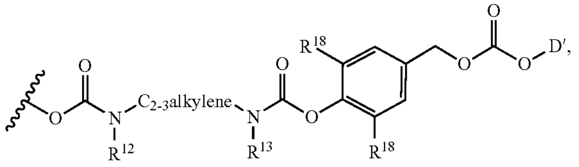

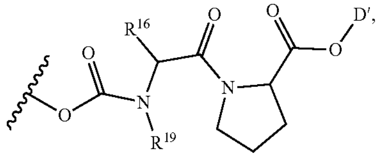

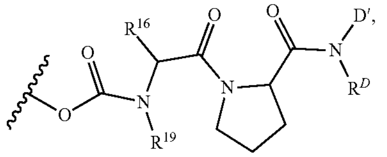

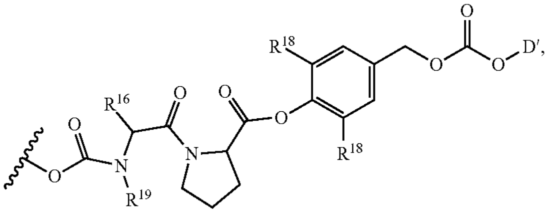

or

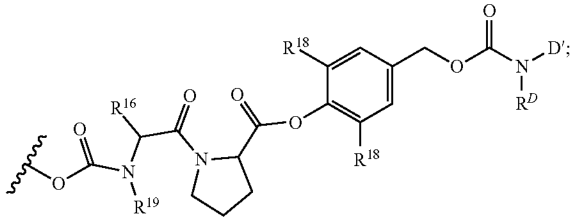

$R^{18}$, at each occurrence, is independently hydrogen or $—CH_2OC(O)NHD'$;

$R^D$ is hydrogen or $C_{1-4}$alkyl on a nitrogen atom of the payload; and

D' is a payload moiety (e.g., cyclic dinucleotide payload moiety, imidazo[4,5-c]quinolin-4-amine payload moiety, TLR agonist payload moiety, STING agonist payload moiety, anticancer agent payload moiety).

E46.17B. The method of E46.16, the compound, or pharmaceutically acceptable salt, of E46.16, or the compound, or pharmaceutically acceptable salt, for use in the method of E46.16, wherein

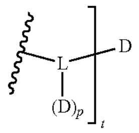

is

-continued

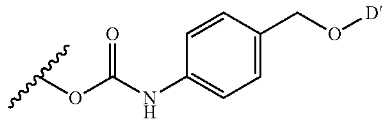

or

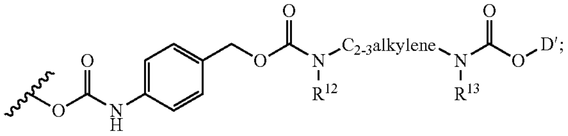

$R^{12}$ and $R^{13}$ are each independently hydrogen or $C_{1-4}$alkyl; and

D' is a payload moiety (e.g., anticancer agent payload moiety).

E46.18. The method of any of E46.1A, E46.2 to E46.6A, or E46.7 to E46.17B, the compound, or pharmaceutically acceptable salt of any of E46.1B to E46.4, E46.6B to E46.6F, or E46.15A to E46.17B, or the compound, or pharmaceutically acceptable salt, for use in the method of any of E46.1B to E46.4, E46.6B to E46.6F, or E46.15A to E46.17B, wherein p is 0.

E46.19. The method of E46.18, the compound, or pharmaceutically acceptable salt of E46.18, or the compound, or pharmaceutically acceptable salt, for use in the method of E46.18, wherein t is 2 or 3.

E46.20. The method of E46.19, the compound, or pharmaceutically acceptable salt of E46.19, or the compound, or pharmaceutically acceptable salt, for use in the method of E46.19, wherein t is 2 and

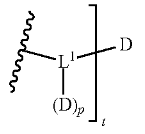

is

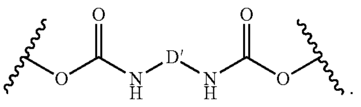

The person skilled in the art will recognize that a payload D bonded to a linker does not refer to a payload molecule per se, but refers to the portion of the payload molecule bonded to the linker. Release of the payload D from a prodrug, releases the payload per se.

D may be an anticancer agent payload of any of the anticancer agents described herein.

D may be a TLR agonist payload of any of the TLR agonists described herein. Preferably, D is an imidazo [4,5-c]quinolin-4-amine, such as

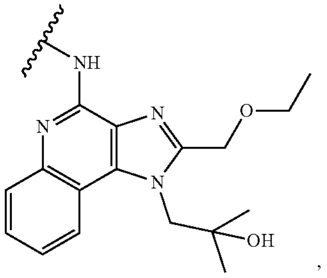

,

-continued

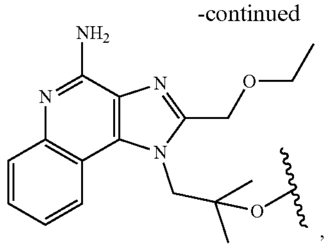

, and

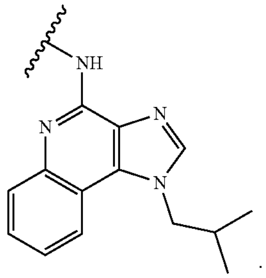

.

D may be a STING agonist payload of any of the STING agonists described herein. D may be a cyclic dinucleotide payload, such as

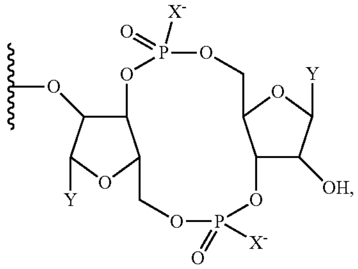

wherein Y is a nucleobase and X is O or S, and as illustrated below. A nucleobase includes naturally-occurring purine and pyrimidine bases, as well as modified purine and pyrimidine bases and other heterocyclic bases which have been modified. Such modifications include methylated purines or pyrimidines, acylated purines or pyrimidines, and the like. Nucleobase modifications may include, for example, deazapurines, N-1-methylguanosine, isoguanine, 2-aminopurine, 1,3-diaza-2-oxophenothiazine, 1,3-diaza-2-oxophenoxazine, 7-nitro-1,3-diaza-2-oxophenothiazine, 2,6-diaminopurine, purine, 6-thioguanine, hypoxanthine, 2-pyrimidinone, 2-pyridone, 4-thiouridine, imidazole-4-carboxamide, N-substituted 5-(carboxyamide) uridines such as 5-(N-benzylcarboxyamide)-uridine, or 5-fluoro-deoxyuridine. The payload D may be

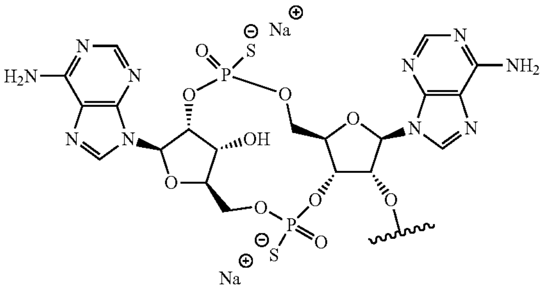

or

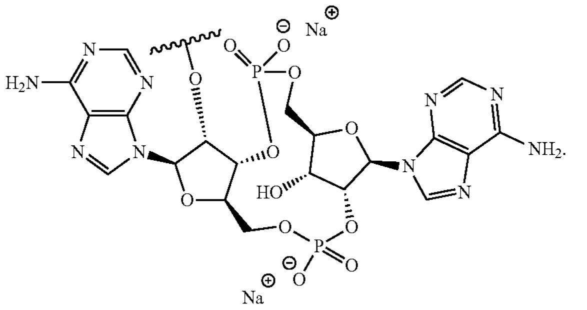

E46.21A. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

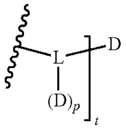

is

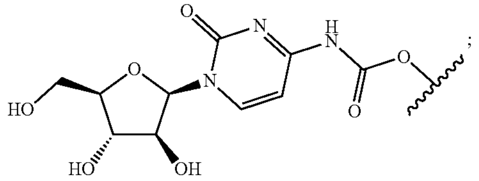

;

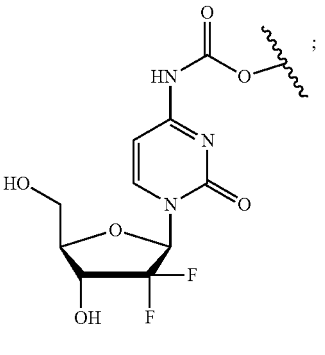

;

-continued
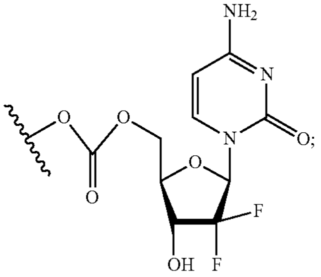
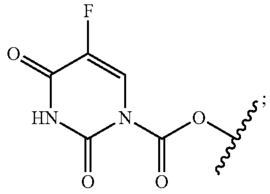
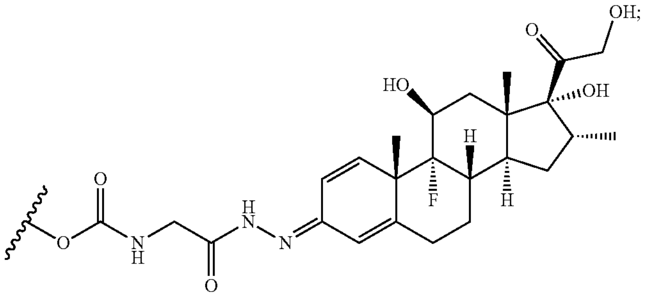
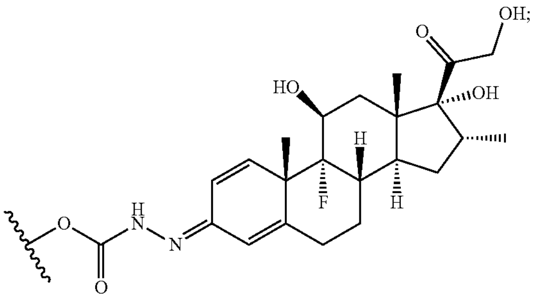
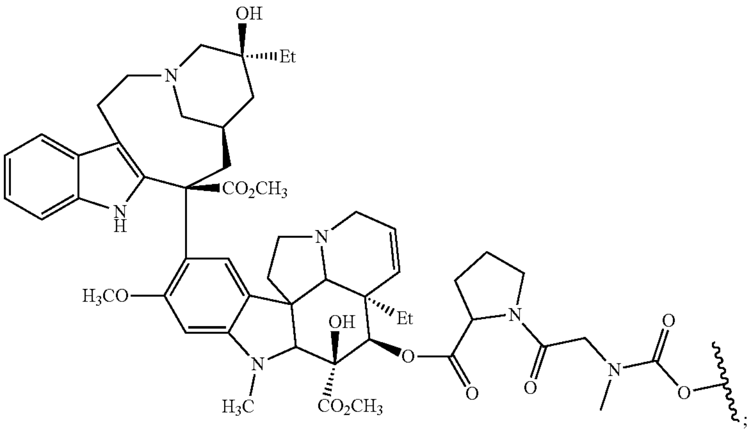

-continued
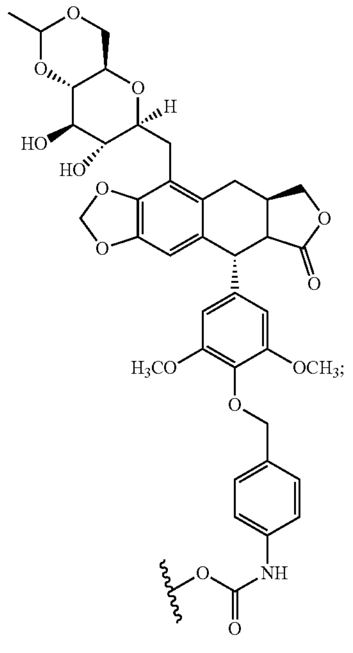
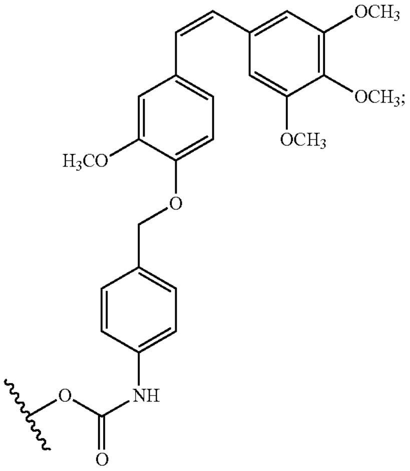
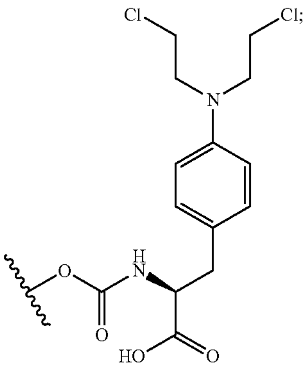
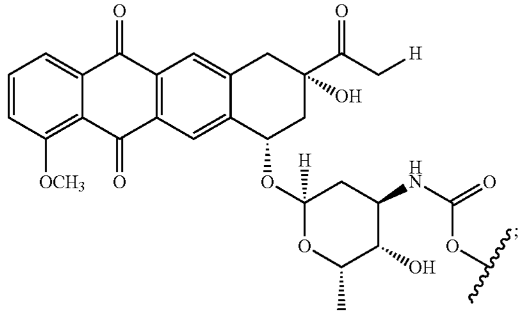
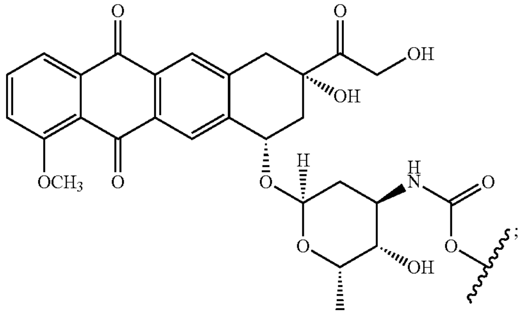
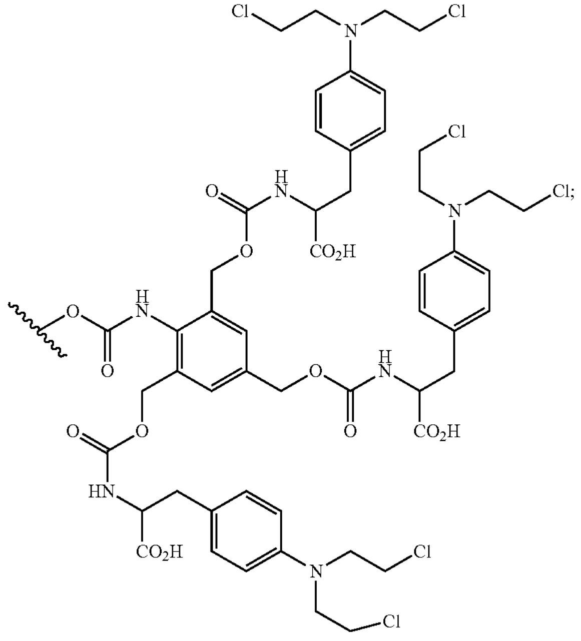
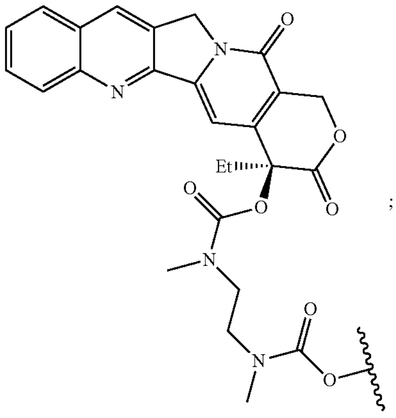
;

-continued
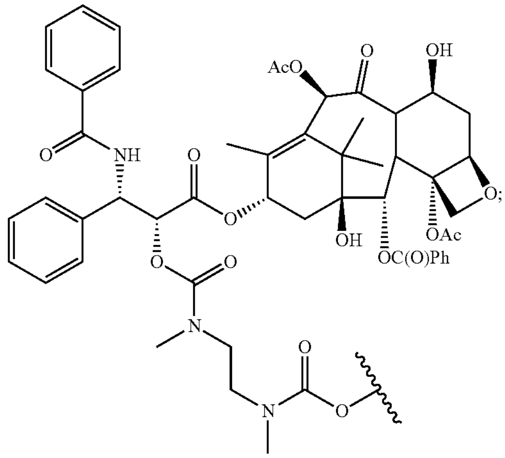
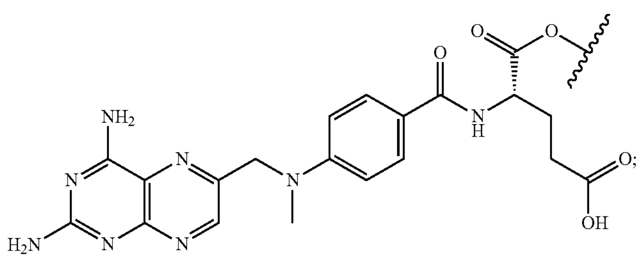
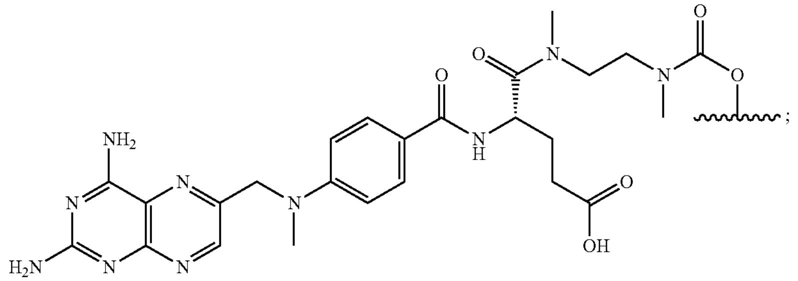
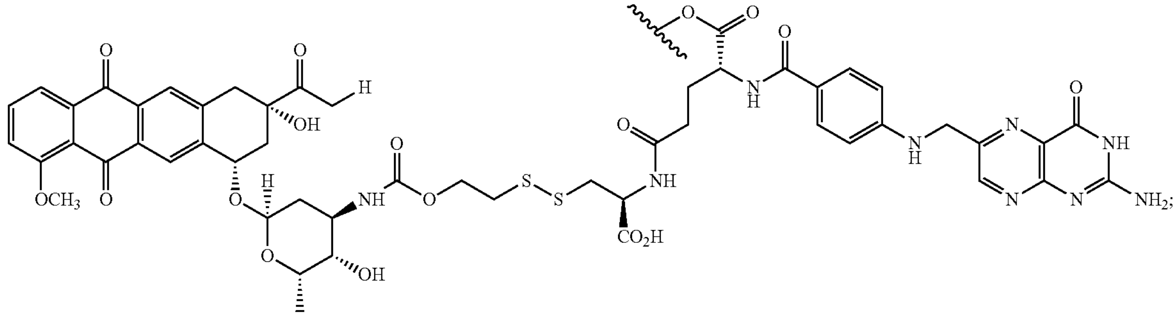
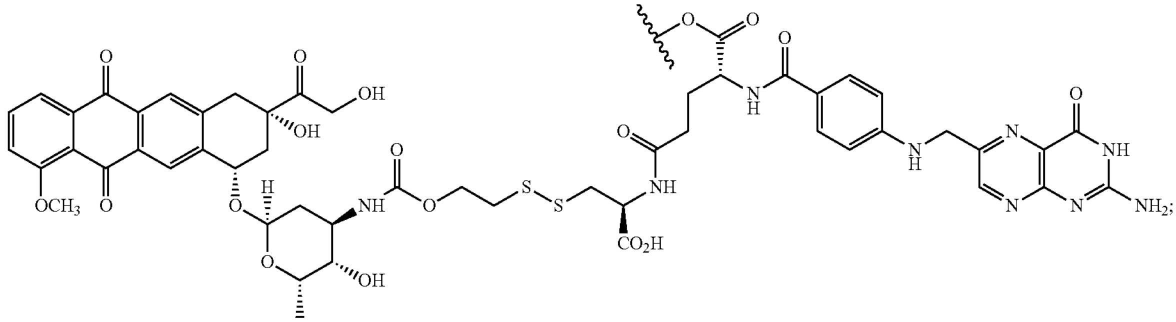
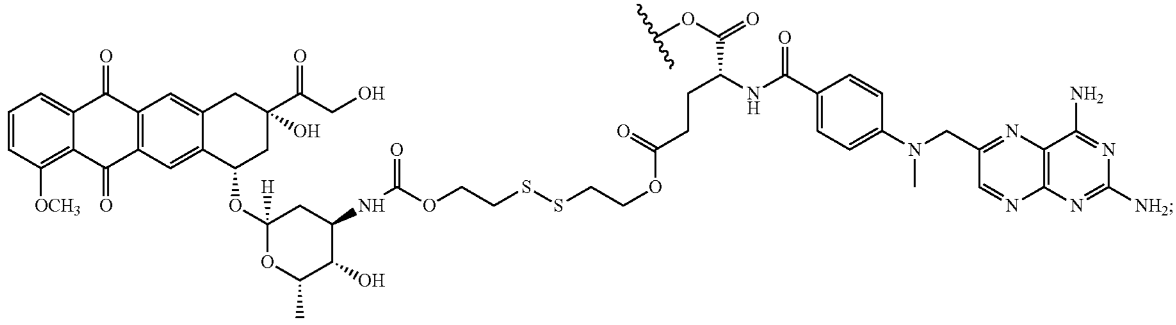

-continued
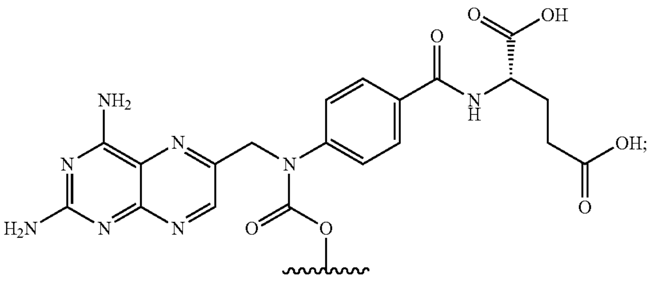
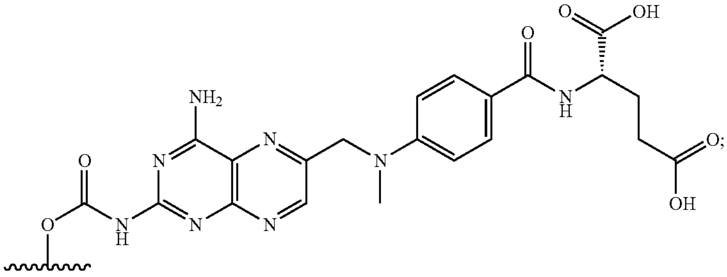
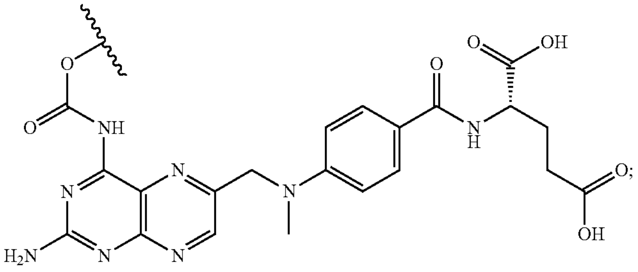
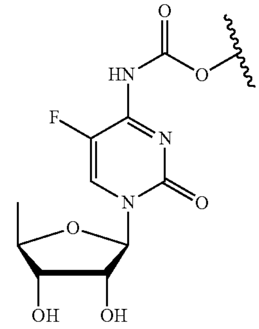
;
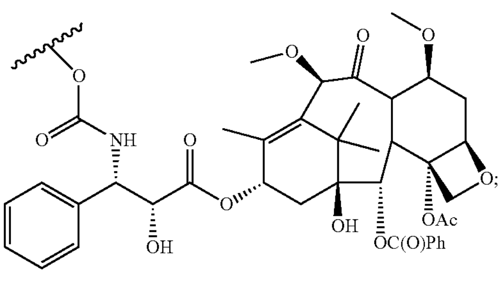
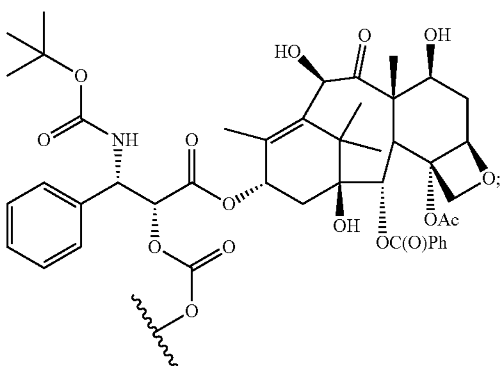

-continued
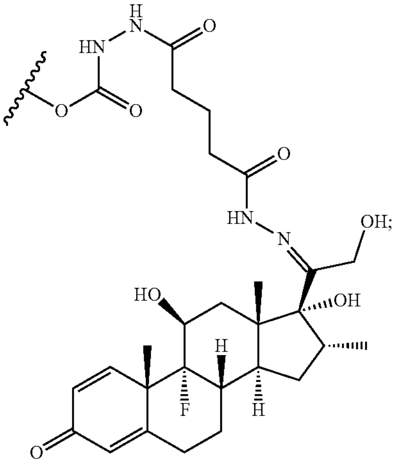
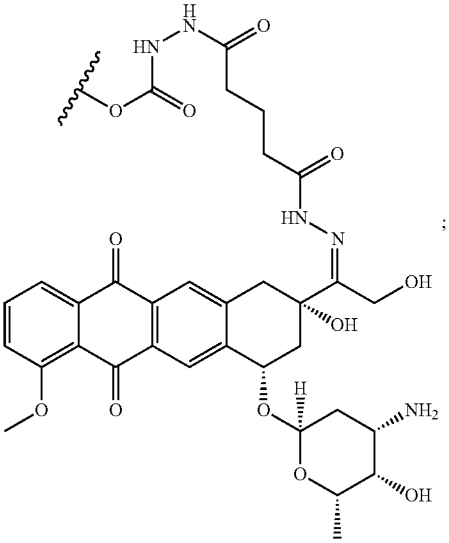
;
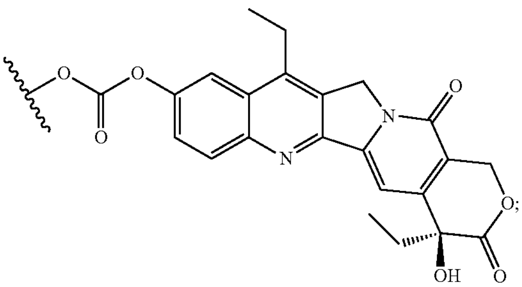
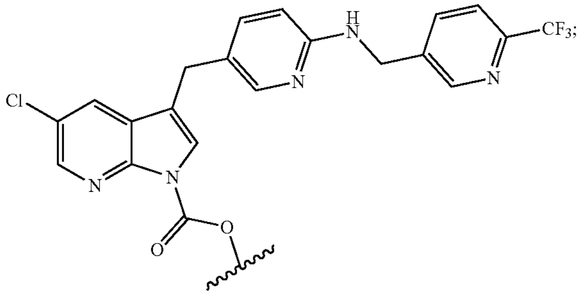
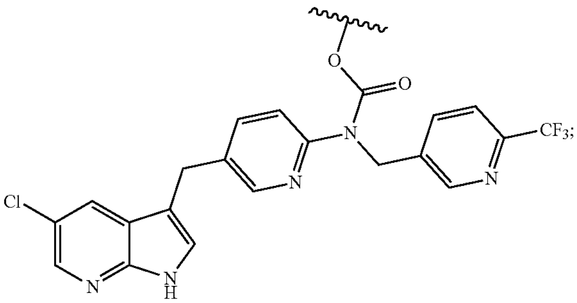
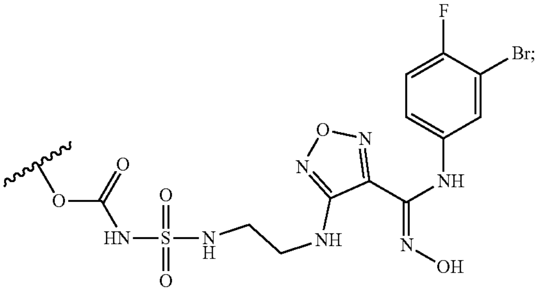

-continued
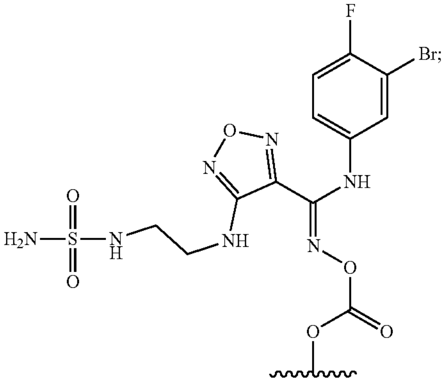
;
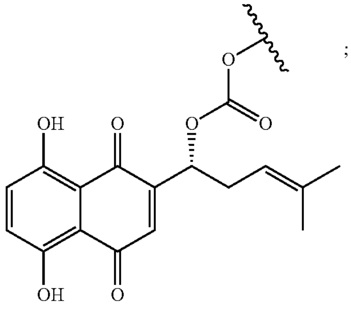
;
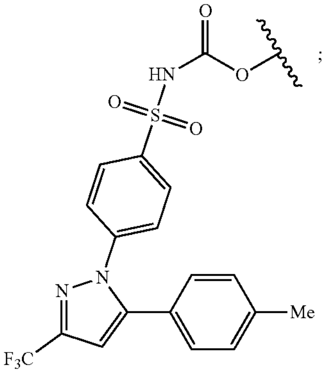
;
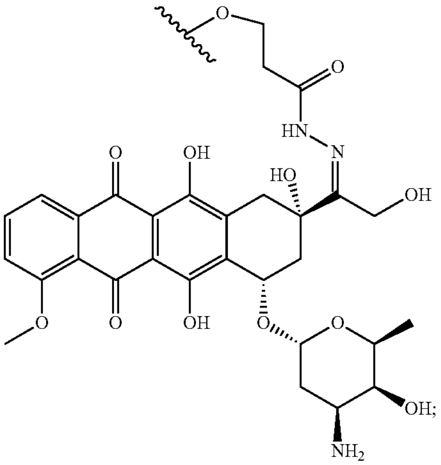
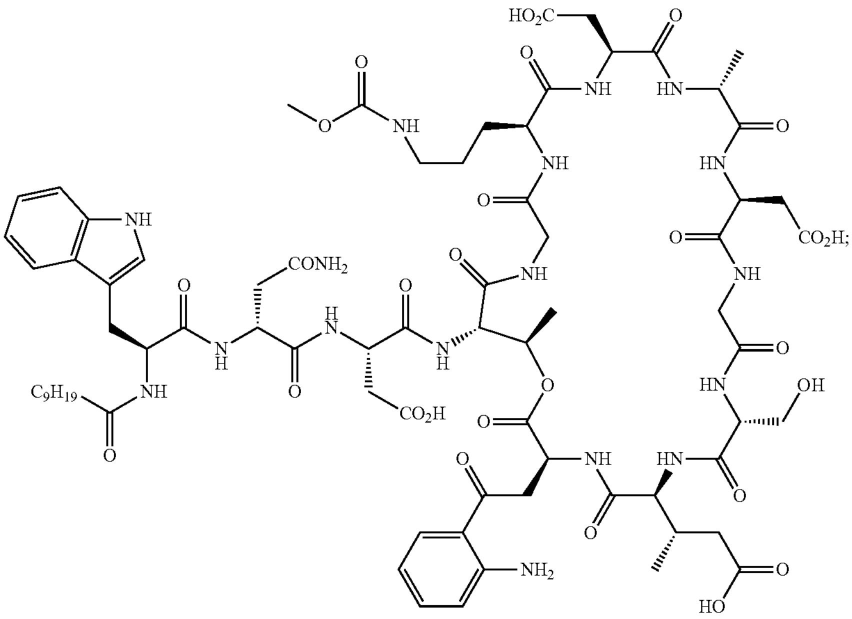

-continued
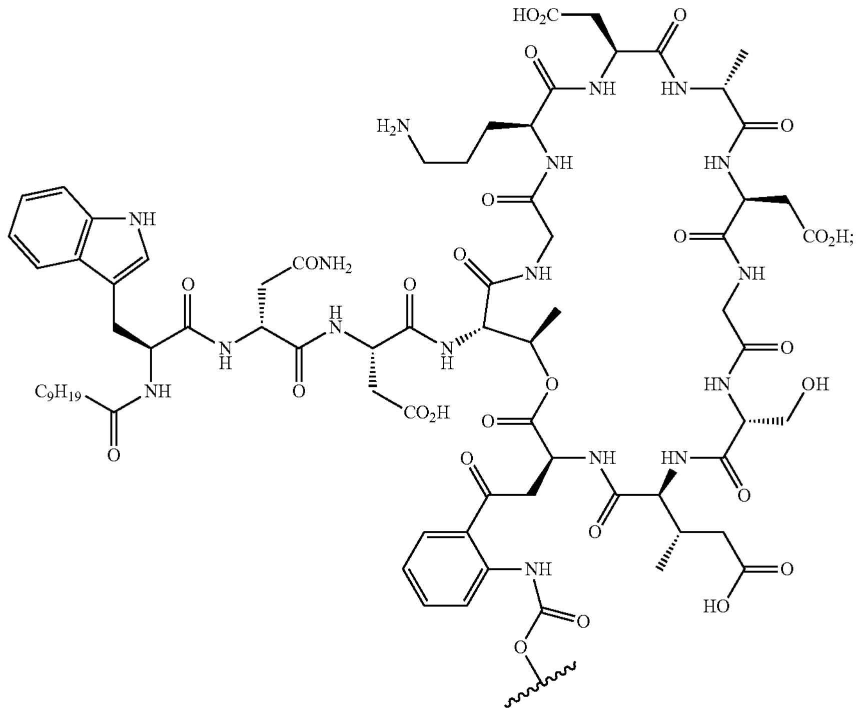
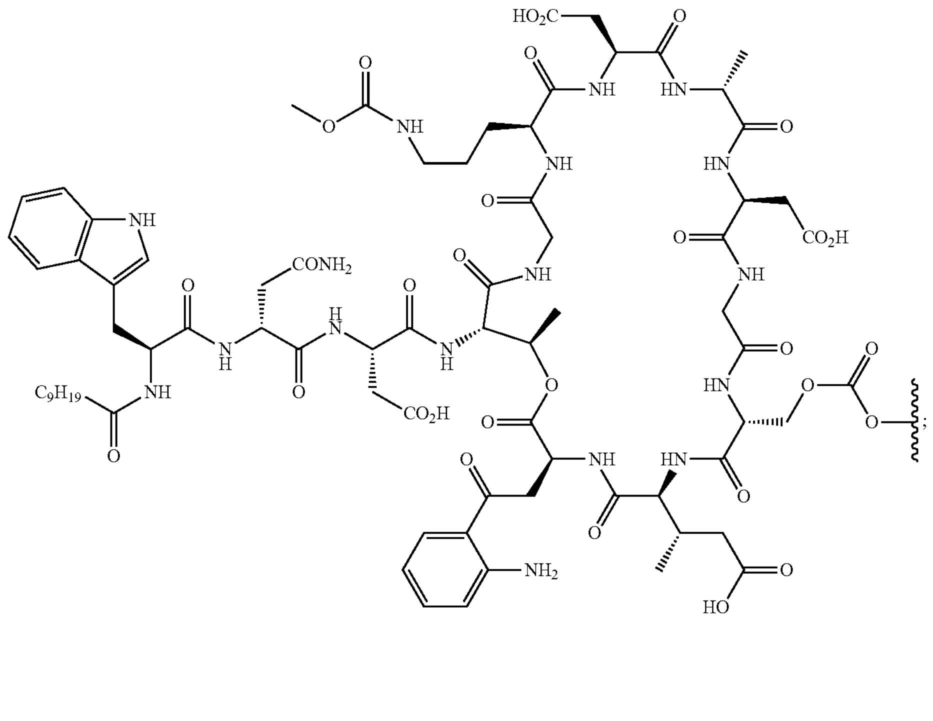

-continued
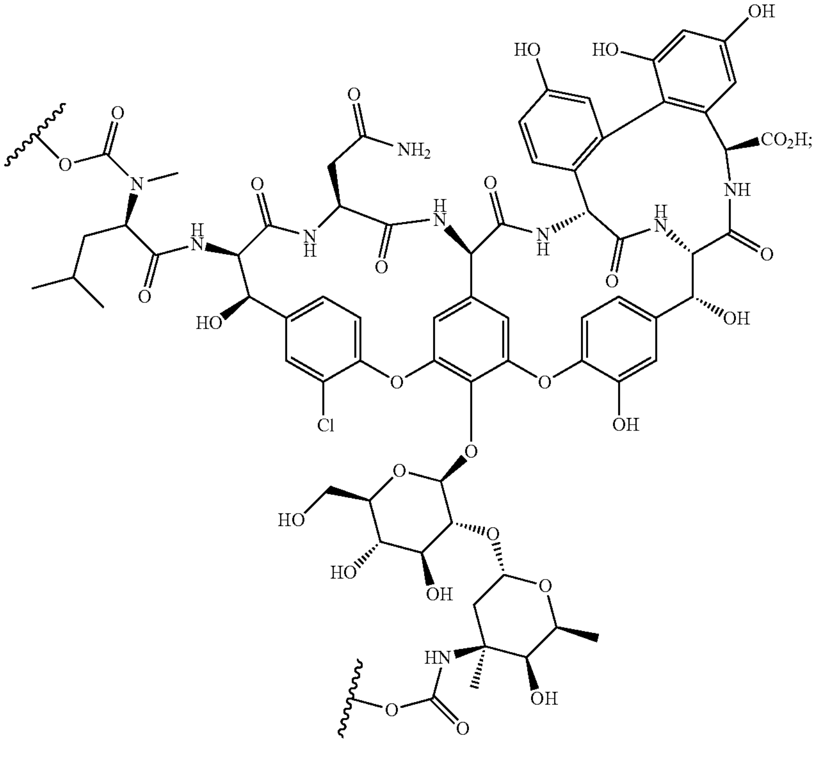
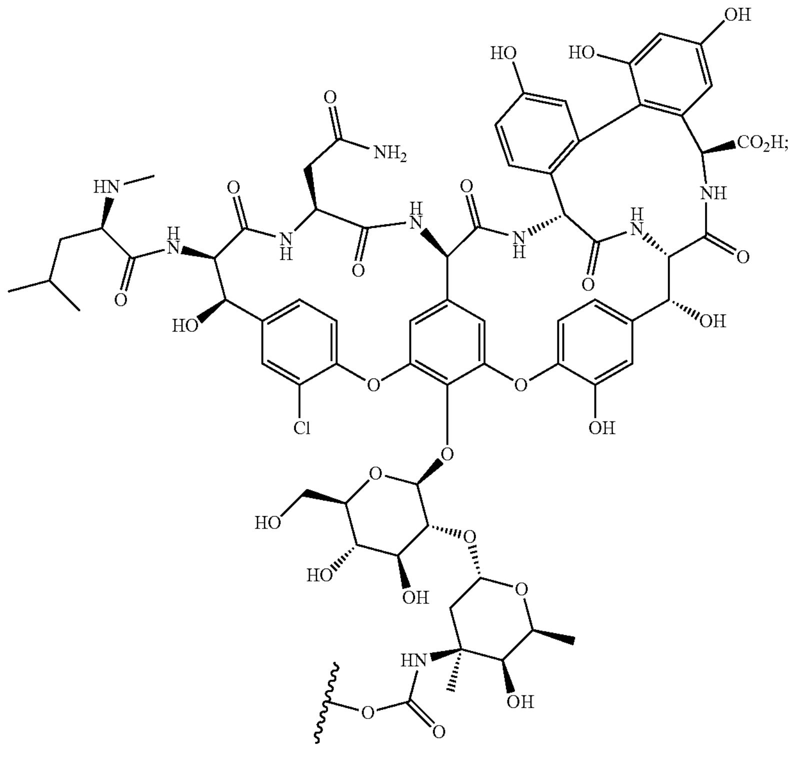

-continued
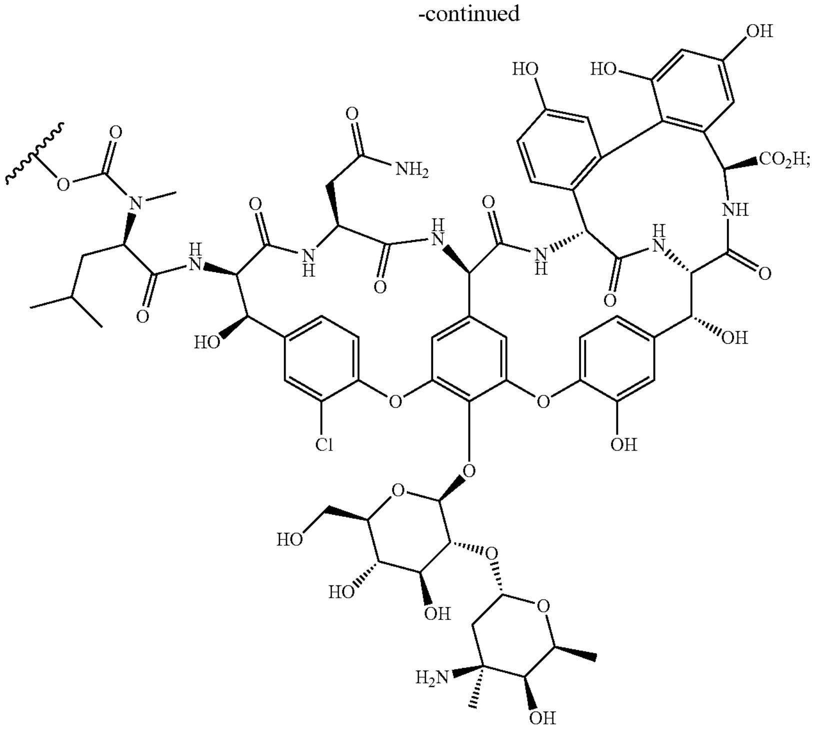
or
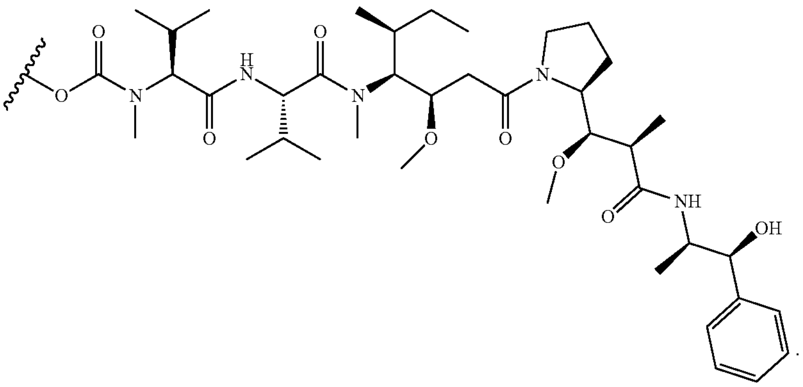
E46.21B. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein
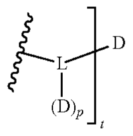
is
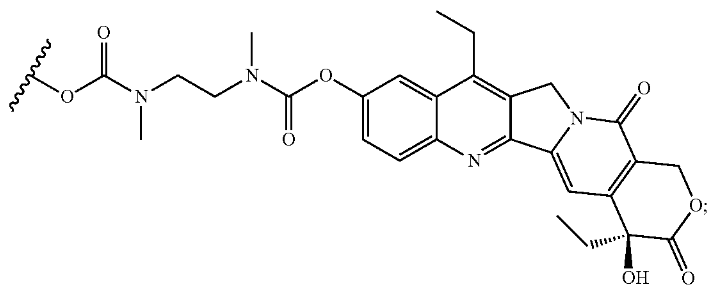

-continued
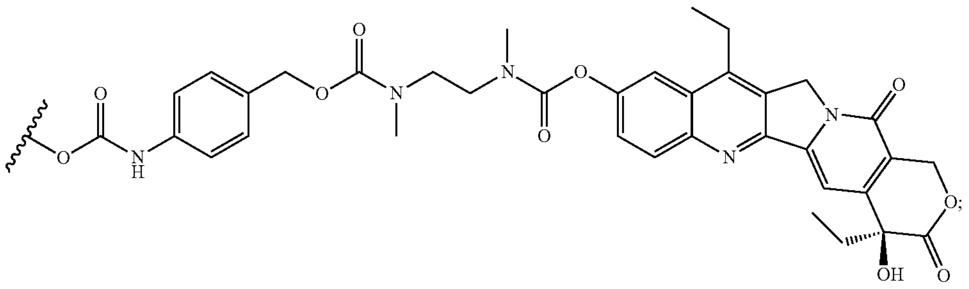
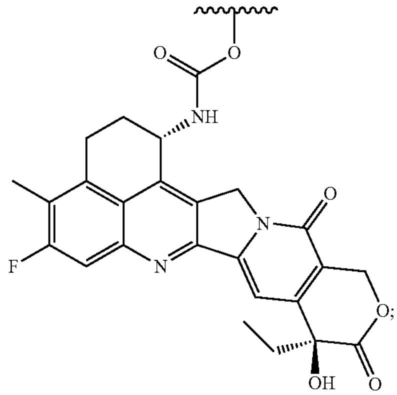
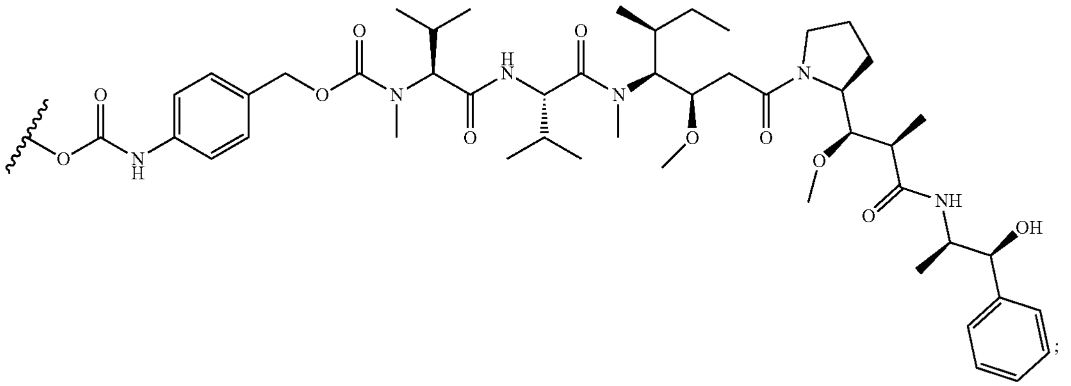
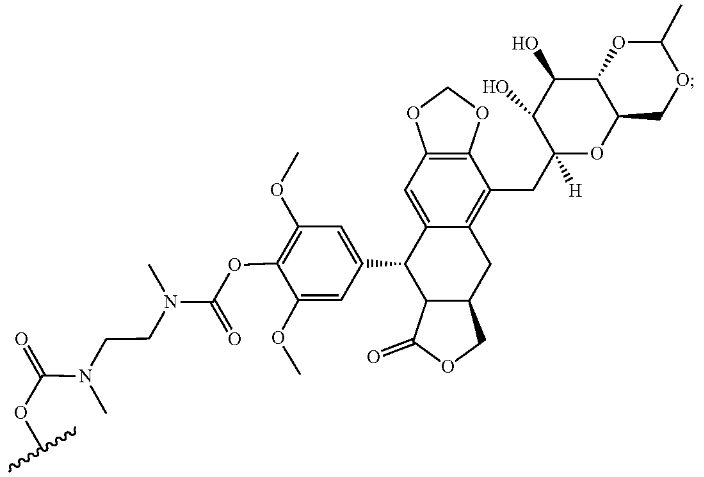

-continued
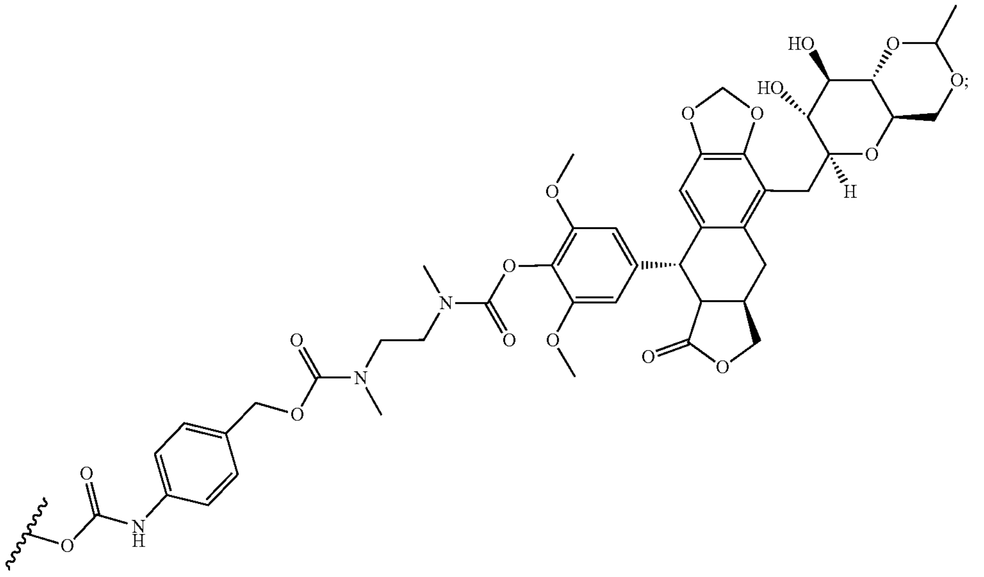
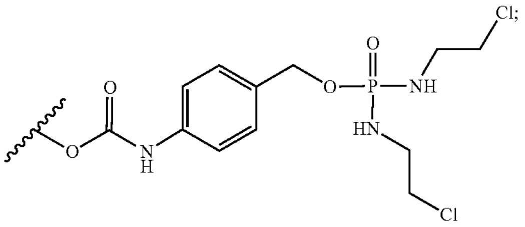
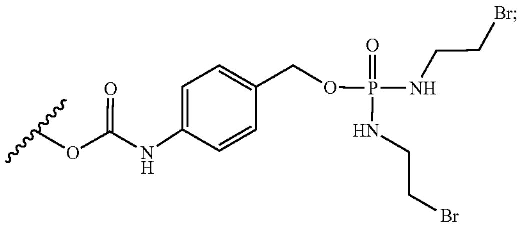
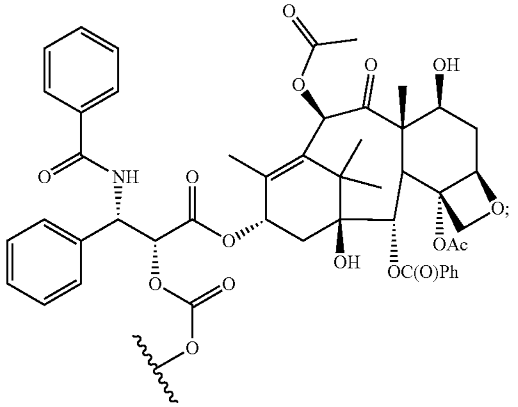
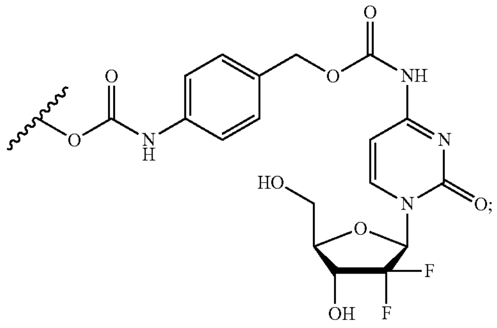
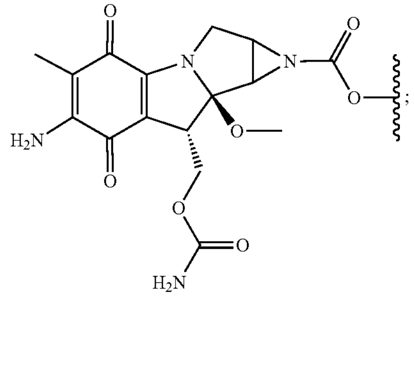
or
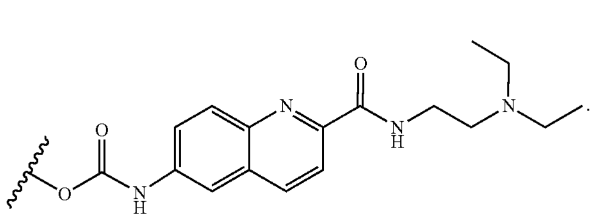

E46.22. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein.
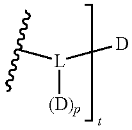
is
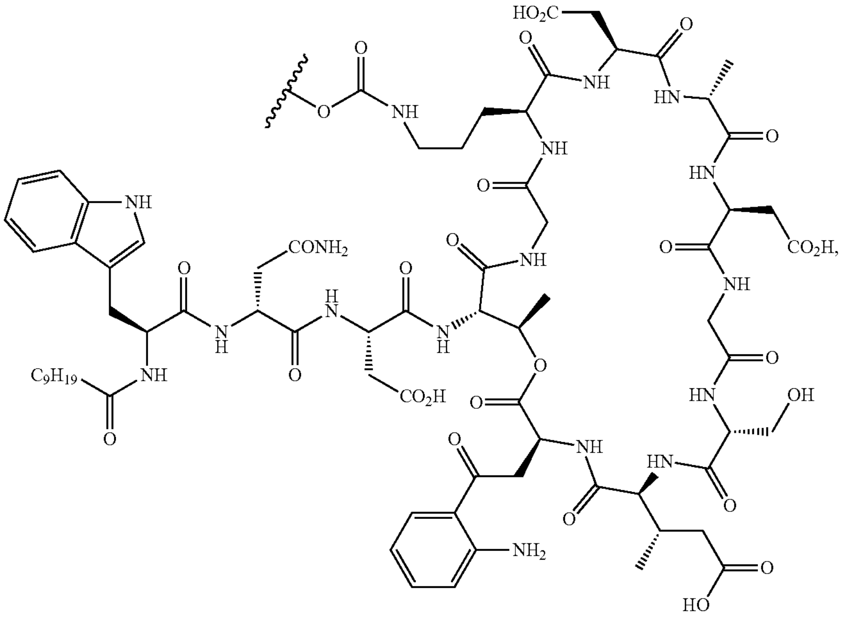
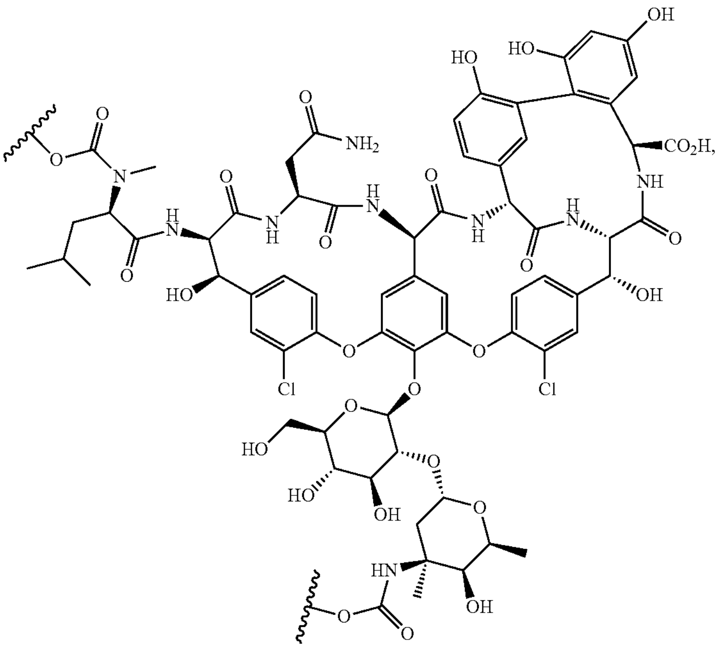

-continued

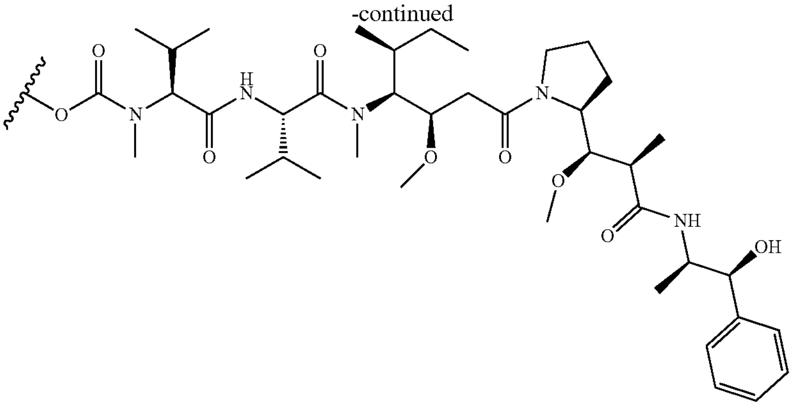

, or

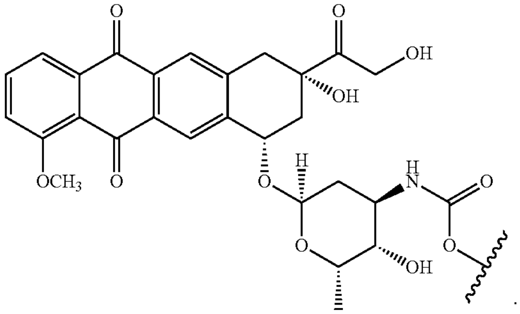

.

E46.23. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

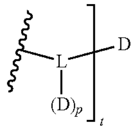

is

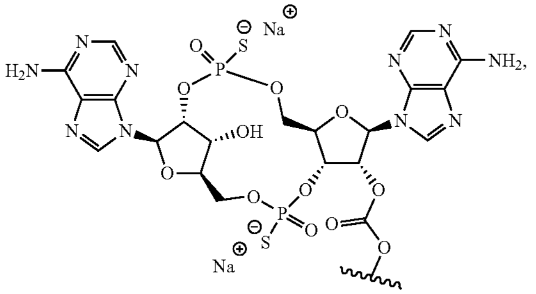

, or

-continued

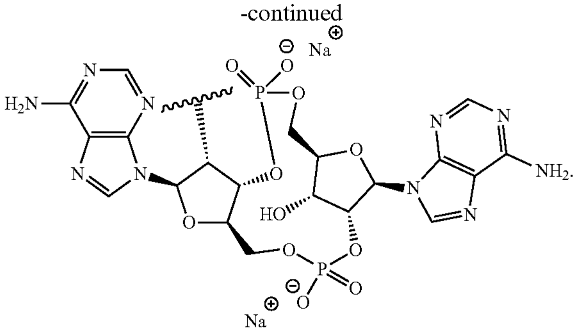

In E46.23, p is 0 and L is —OC(O)—.

E46.24. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

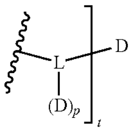

is

-continued

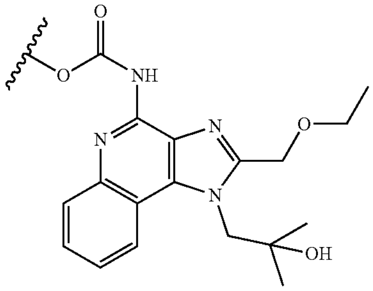

,

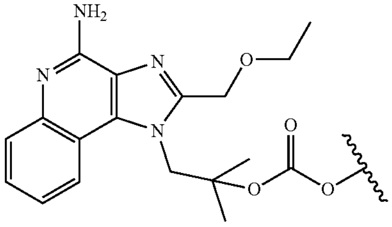

, or

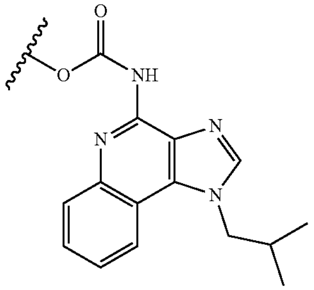

.

In E46.24, p is 0 and L is —OC(O)—.

E.46.25. The method of E46.18, the compound, or pharmaceutically acceptable salt of E46.18, or the compound, or pharmaceutically acceptable salt, for use in the method of E46.18, wherein t is 1; L is

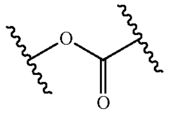

;

and D is doxorubicin.

According to the definition of "payload moiety," the payload moiety D' refers to a payload D or D' minus its nucleophilic group such as NH, $NC_{1-4}$alkyl, O, or S that attaches to a linker or minus its electrophilic group such as C(O) that attaches to a linker, i.e., the remainder of the payload. For example, a compound of formula

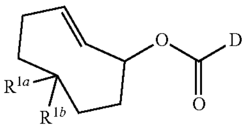

includes a compound such as

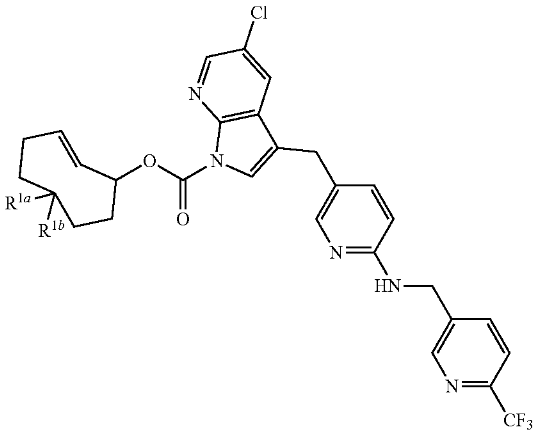

or

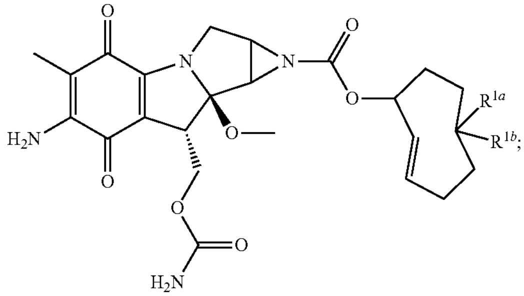

a compound

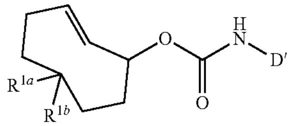

includes a compound such as

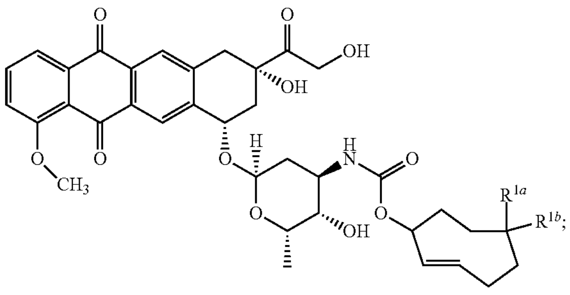

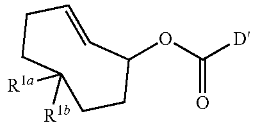

includes a compound such as

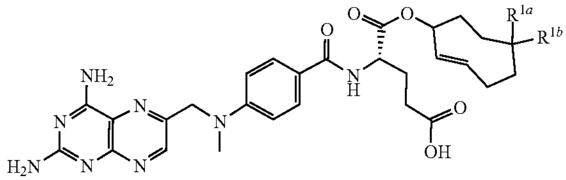

a compound of formula

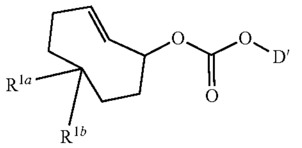

includes a compound such as

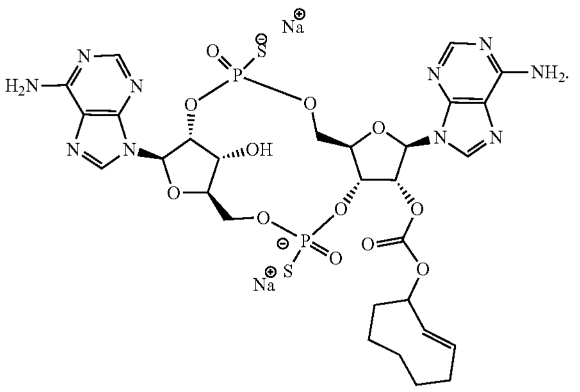 [SMILES: [Na+] ; Nc1ncnc2c1ncn2[C@@H]1O[C@@H]2COP(=O)(S)O[C@H]3[C@@H](OC(=O)OC4/C=C/CCCCC4)[C@H](n4cnc5c(N)ncnc54)O[C@@H]3COP(=O)([S-])O[C@@H]1[C@@H]2O ; [Na+]]

Release of DH, $NH_2$-D', HOOC-D', or HO-D' releases the payload molecule per se. In accordance with the foregoing definition of a payload moiety, a "cyclic dinucleotide payload moiety" is a cyclic dinucleotide payload minus its nucleophilic group (typically O) that attaches to a linker. For example, when

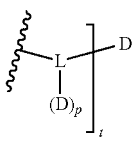 is 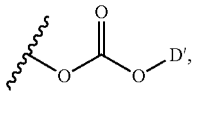

a cyclic dinucleotide payload moiety may be

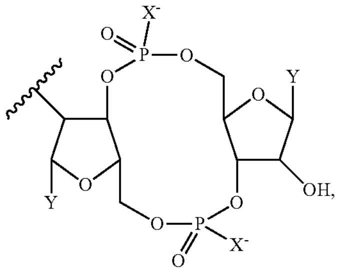

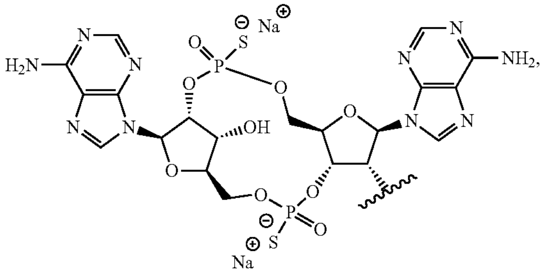 or

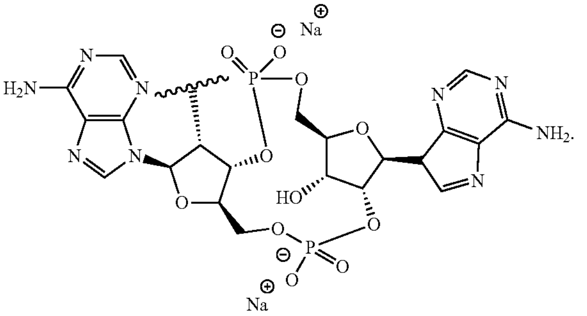

In the compounds described herein,

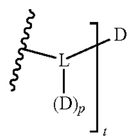

may be

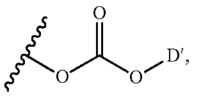

wherein D' is a cyclic dinucleotide payload moiety. In accordance with the foregoing definition of a payload moiety, an "imidazo[4,5-c]quinolin-4-amine payload moiety" is an imidazo[4,5-c]quinolin-4-amine minus its nucleophilic group (typically O or N) that attaches to a linker. For example, when

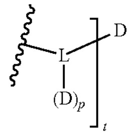 is

-continued
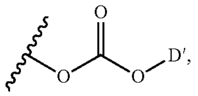
an imidazo[4,5-c]quinolin-4-amine payload moiety D' may be
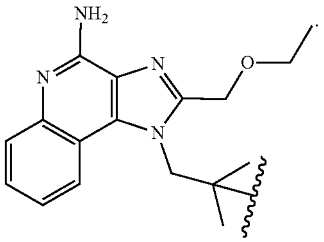 [SMILES: *C(C)(C)Cn1c(COCC)nc2c(N)nc3ccccc3c21]
For example, when
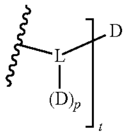
is
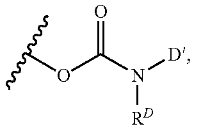
an imidazo[4,5-c]quinolin-4-amine payload moiety D' may be.
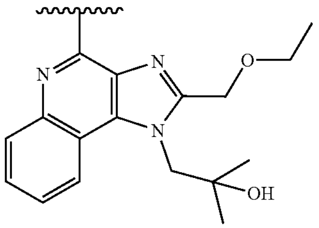
or
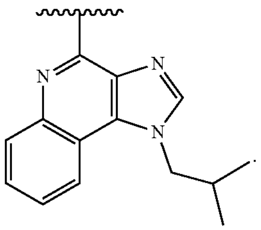
Preferred compounds of formula (III) include compounds of formula
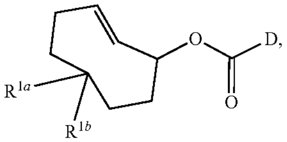
such as
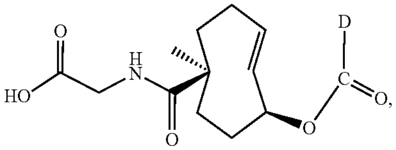
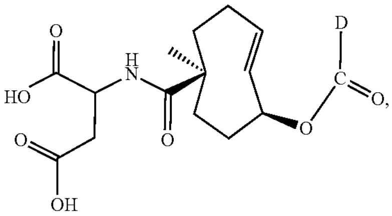
and
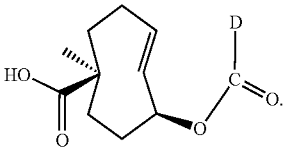
Preferred compounds of formula (III) include compounds of formula
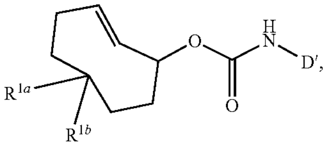
such as
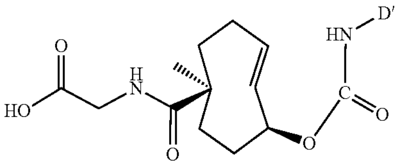
and
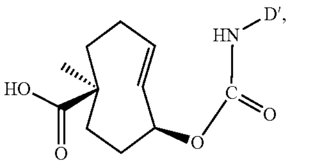

such as
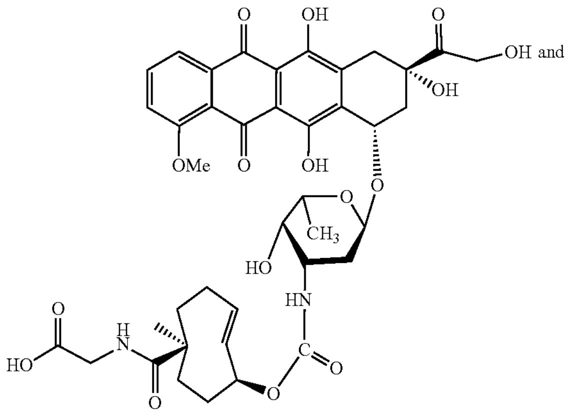
and
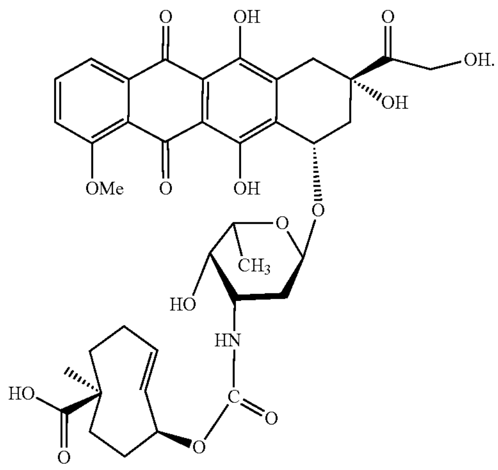
Compounds of formula (III) include
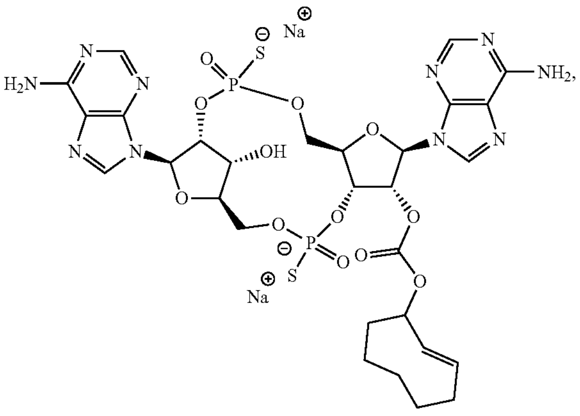
TCO-ADU-S100
-continued
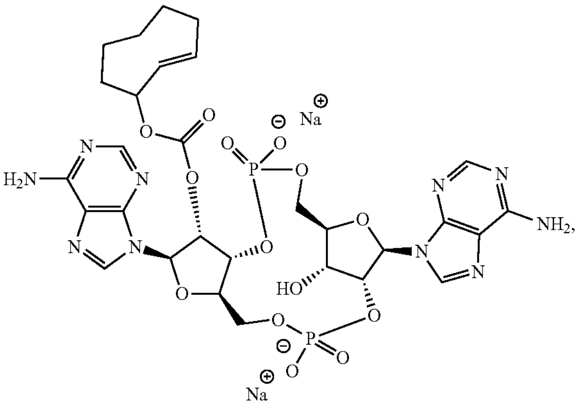
TCO-2′3′-cGAMP
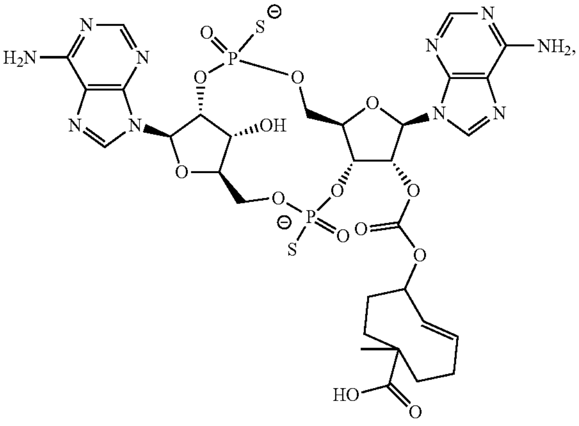
ADU-S100-TCO-Acid
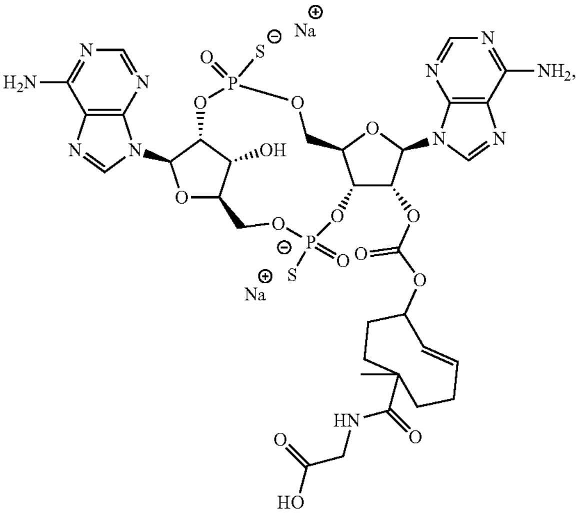
ADU-S100-TCO-Glycine -continued
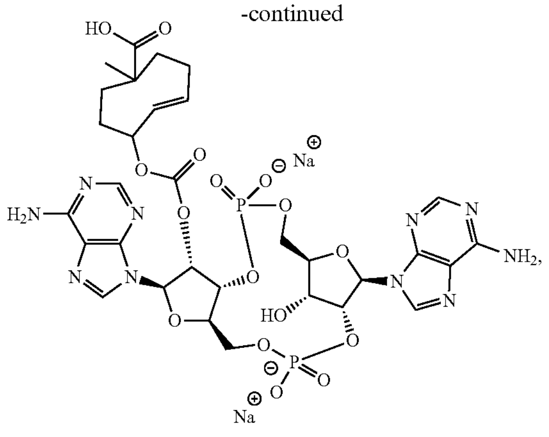
or
2′3′-cGAMP-TCO-Acid
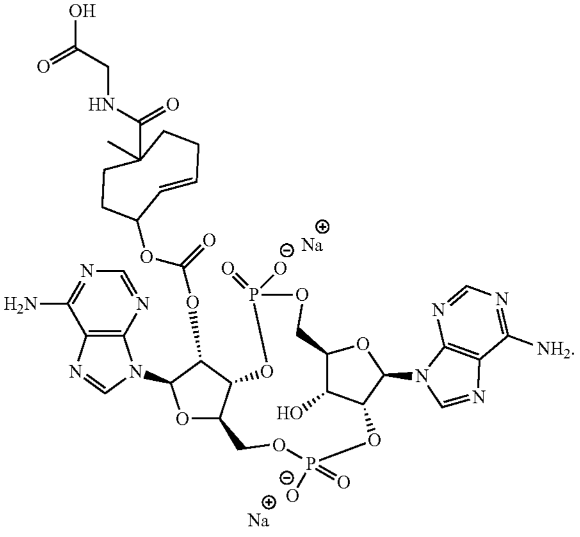
2′3′-cGAMP-TCO-Glycine
Compounds of formula (III) include
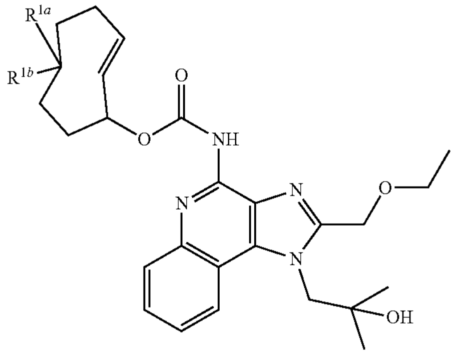
,
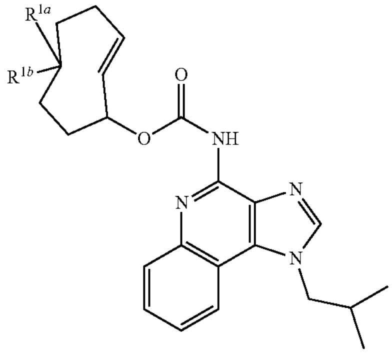
,
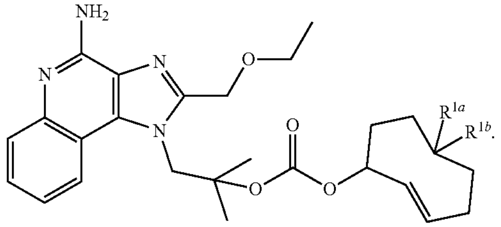
Compounds of formula (III) include
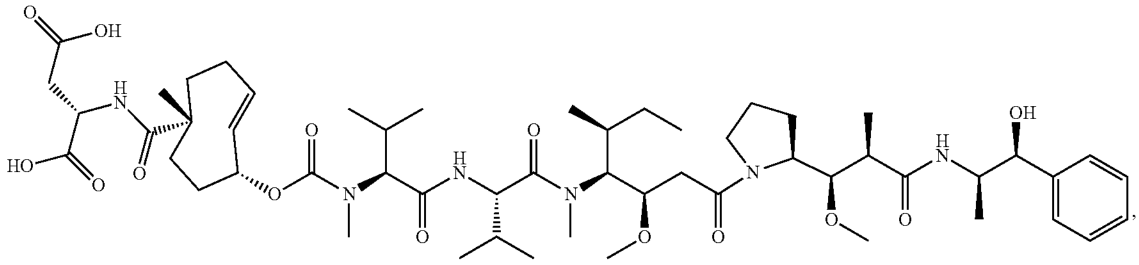
,
TCO(asp)-MMAE
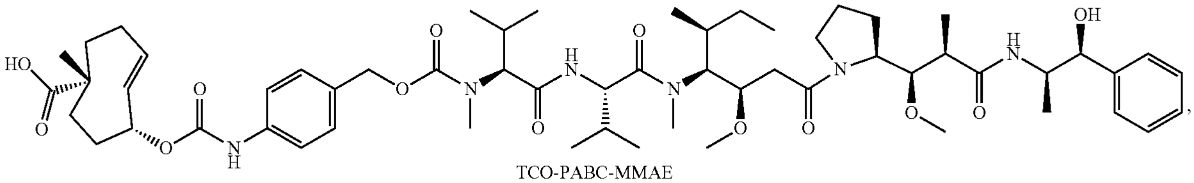
,
TCO-PABC-MMAE -continued
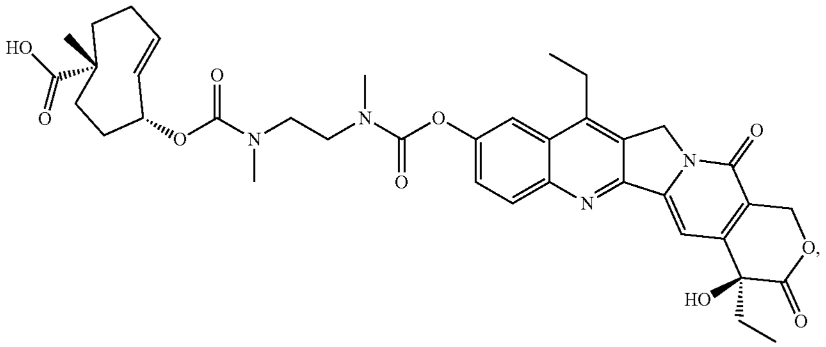
TCO-spacelink-SN-38
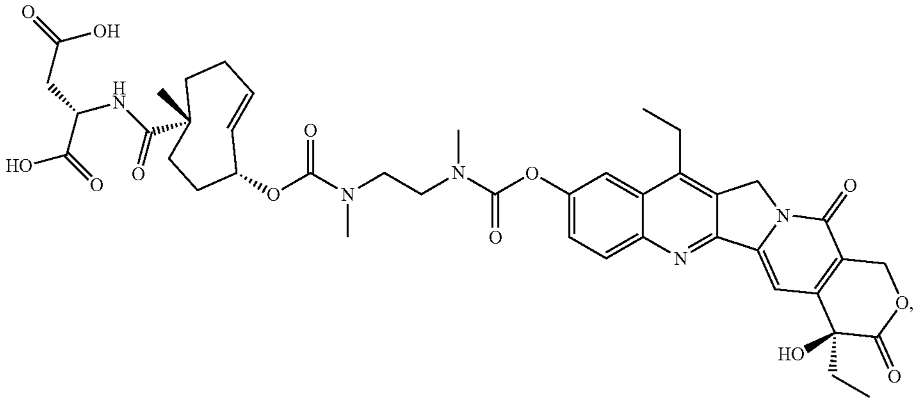
TCO(asp)-spacelink-SN-38
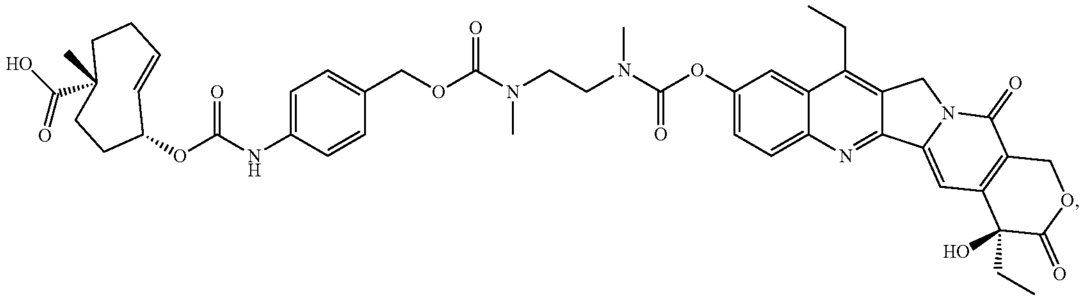
TCO-PABC-spacelink-SN-38
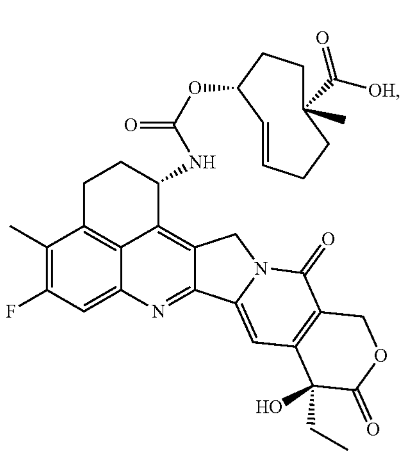
TCO-Exatecan
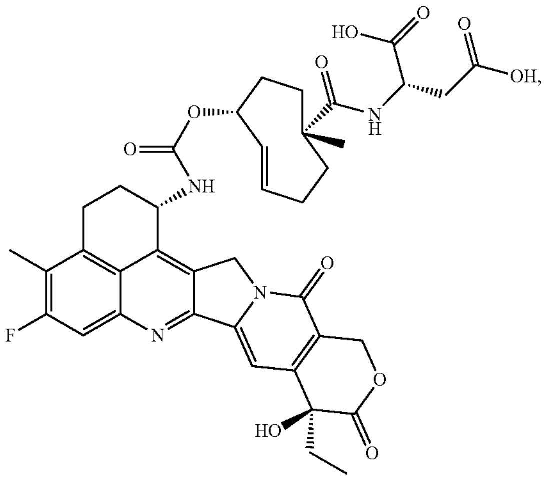
TCO(asp)-Exatecan -continued
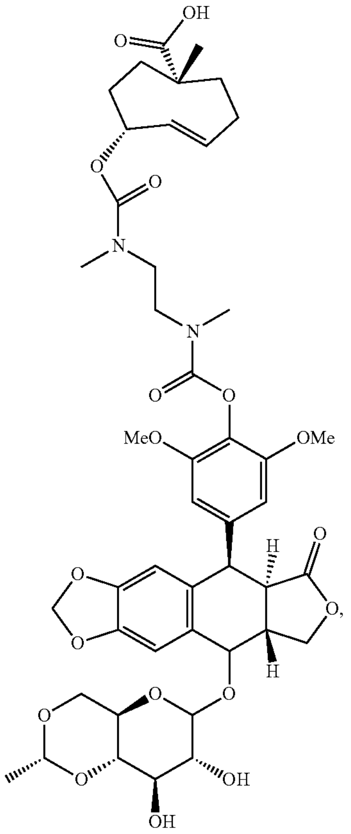
TCO-spacelink-Etoposide
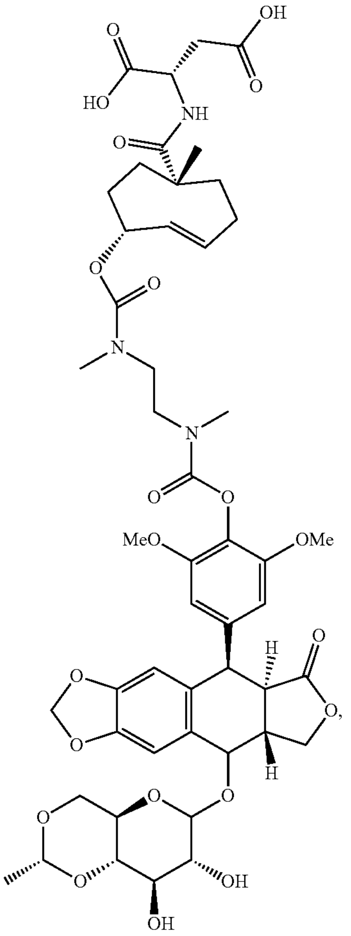
TCO(asp)-spacelink-Etoposide
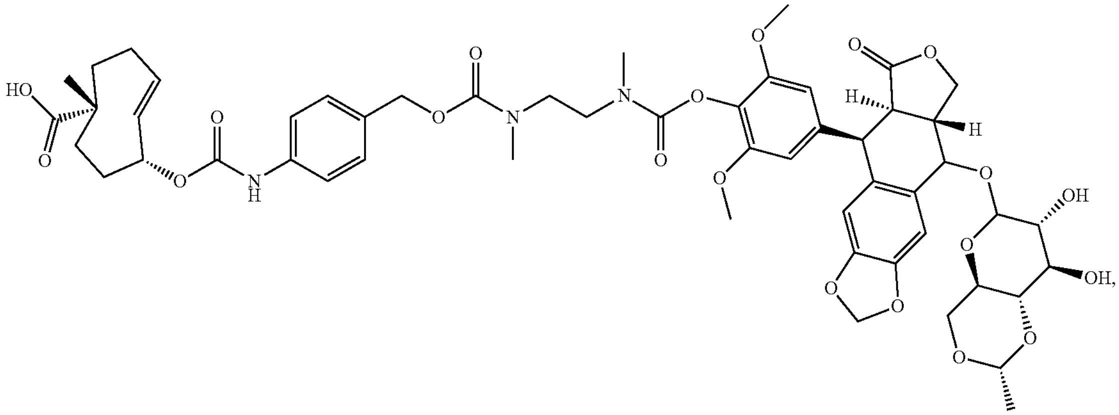
TCO-PABC-spacelink-Etoposide
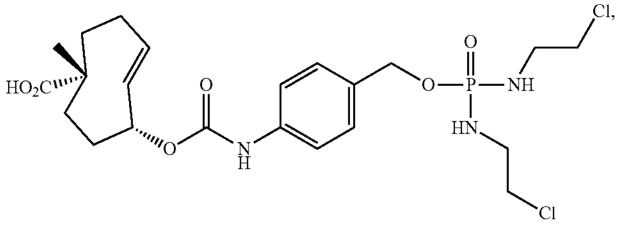
TCO-PABC-Cl-phosphamide -continued
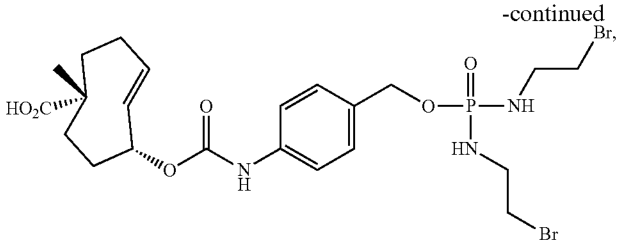
TCO-PABC-Br-phosphamide
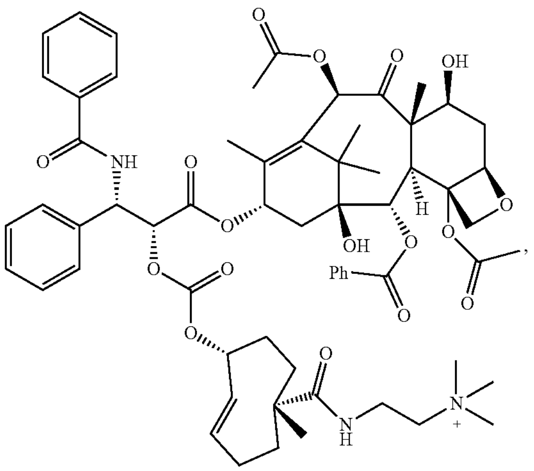
TCO-ammonium-Ptx
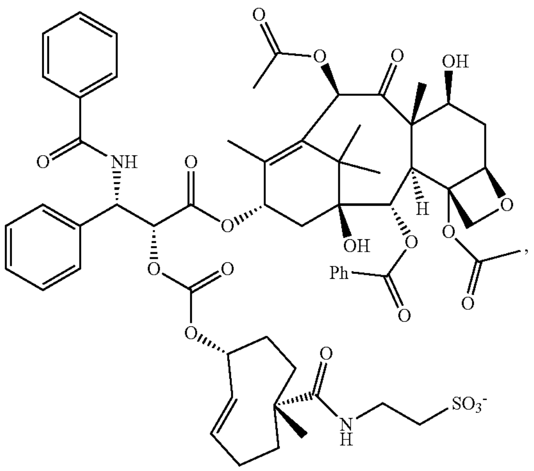
TCO-taurine-Ptx
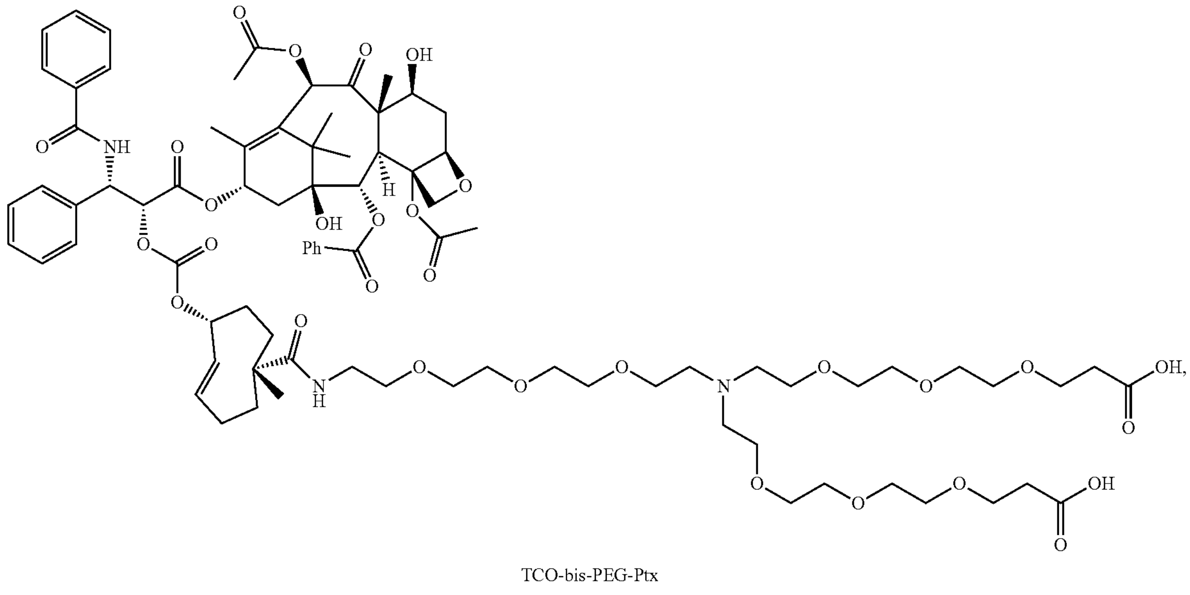
TCO-bis-PEG-Ptx -continued
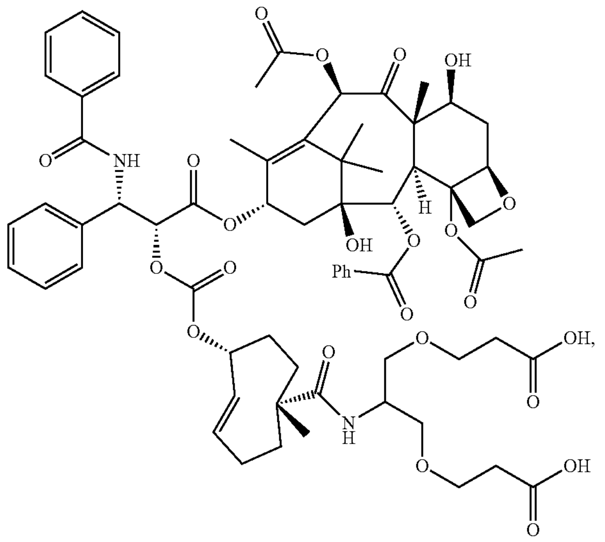
TCO-bis-acid-Ptx
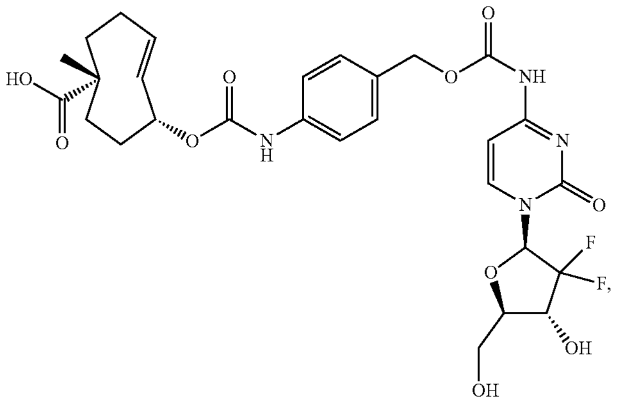
TCO-PABC-gemcitabine
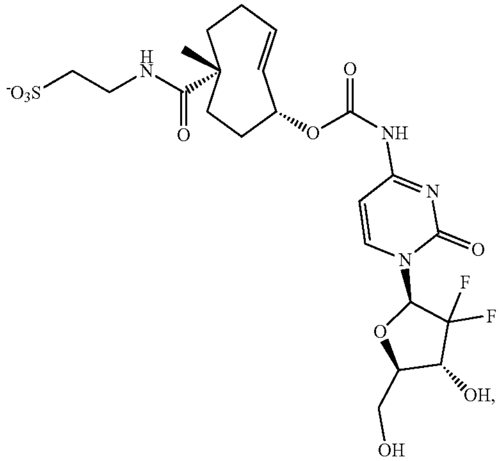
TCO(taurine)-gemitabine
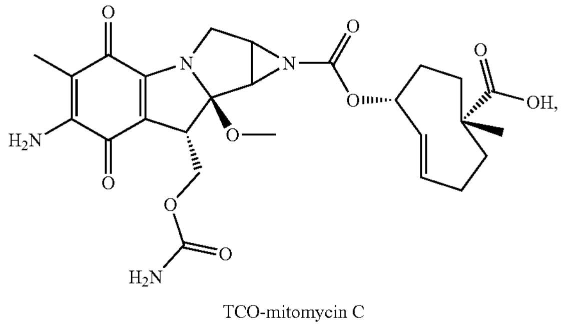
TCO-mitomycin C -continued

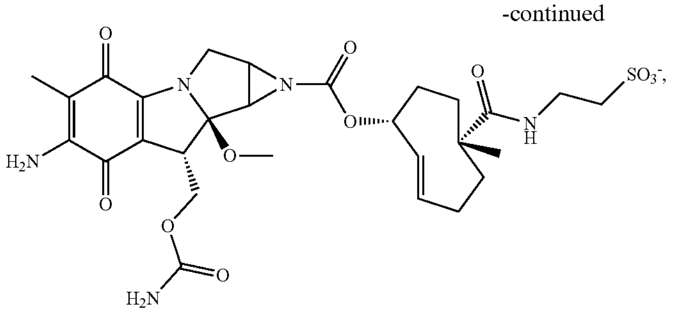

TCO(taurine)-mitomycin C

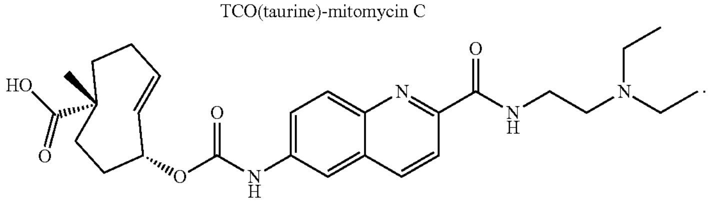

E. SYNTHETIC METHODS

The compounds and conjugates of the present disclosure can be better understood in connection with the following synthetic schemes and methods, which illustrate means by which the compounds may be prepared.

Conjugates of formula (I) or compounds of formula (III) may be prepared by reacting a primary amine, secondary amine, or a hydroxyl group with a suitably activated linker. It is to be understood that a reactive group on a linker (e.g., ester, carbonate, acyl chloride, carboxylic acid) can be located on any selected position of the linker group. Conversely, the linker may have a nucleophilic amine or hydroxyl group that may be reacted with a suitable group such as an aldehyde, ketone, ester, carbonate, carboxylic acid, or acyl chloride.

In certain embodiments, as shown below, a trans-cyclooctene activated for nucleophilic addition can be reacted with a suitable payload ($D/D^1$), or a payload attached to a linker, in the presence of a base to provide a functionalized payload. The payload or linker can include a primary amine, secondary amine, or hydroxyl group that reacts with the activated TCO. In certain embodiments, the leaving group (LG) is a chloro leaving group, a p-nitrophenol leaving group, or an N-hydroxysuccinimide leaving group. Exemplary bases for use in the reaction include organic and inorganic bases, such as for example, triethylamine, pyridine, sodium hydroxide, and sodium bicarbonate.

Scheme 1A

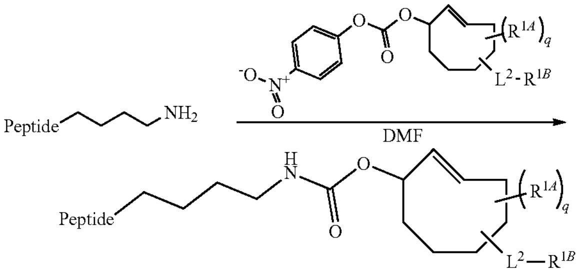

Scheme 1A illustrates a general method of conjugating a trans-cyclooctene to a lysine side chain of a (poly) peptide, including a protein (e.g., a monoclonal antibody). The nitrophenol carbonate may react with the amino group under basic conditions to provide a trans-cyclooctene-conjugated (poly) peptide. More specifically, a solution of an antibody in aqueous buffer may be incubated with a molar excess of carbonate reagent. The reaction mixture can be quenched by addition of excess amine (such as ethanolamine, taurine, etc.). The trans-cyclooctene-antibody conjugate may then be purified by gel filtration. The number of trans-cyclooctene molecules bound per antibody molecule can be determined by measuring spectrophotometrically.

Scheme 1B

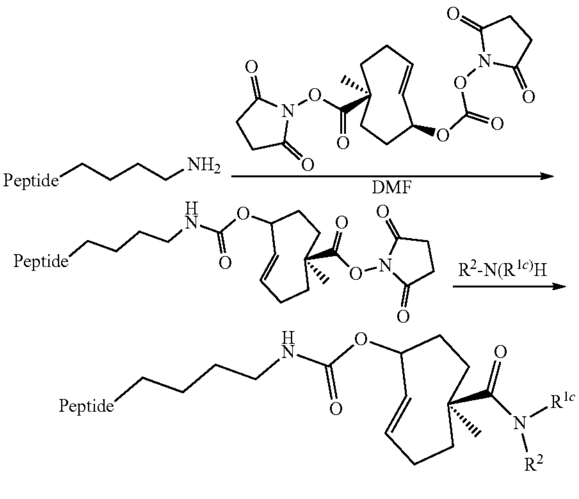

Scheme 1B illustrates a two-step method for conjugating a trans-cyclooctene to a protein or peptide. Reaction between a carbonate ester and the lysine side chain followed by further coupling with an amino-containing group $R^2$—N ($R^{1c}$) H under basic conditions may provide the trans-cyclooctene functionalized protein/peptide wherein $R^{1c}$ is as defined herein and $R^2$ is —$C_{1-6}$alkylene-$CO_2H$, —$CHR^{1e}CO_2H$, —$C_{1-6}$alkylene-C(O)O$C_{1-4}$alkyl, C(O)O$C_{1-4}$alkyl, or —$CHR^{1e}$C(O)O$C_{1-4}$alkyl.

Alcohol-containing side chains and a (poly)peptide N-terminal amino group may react analogously to Schemes 1A and 1B to provide trans-cyclooctene conjugates.
Scheme 2
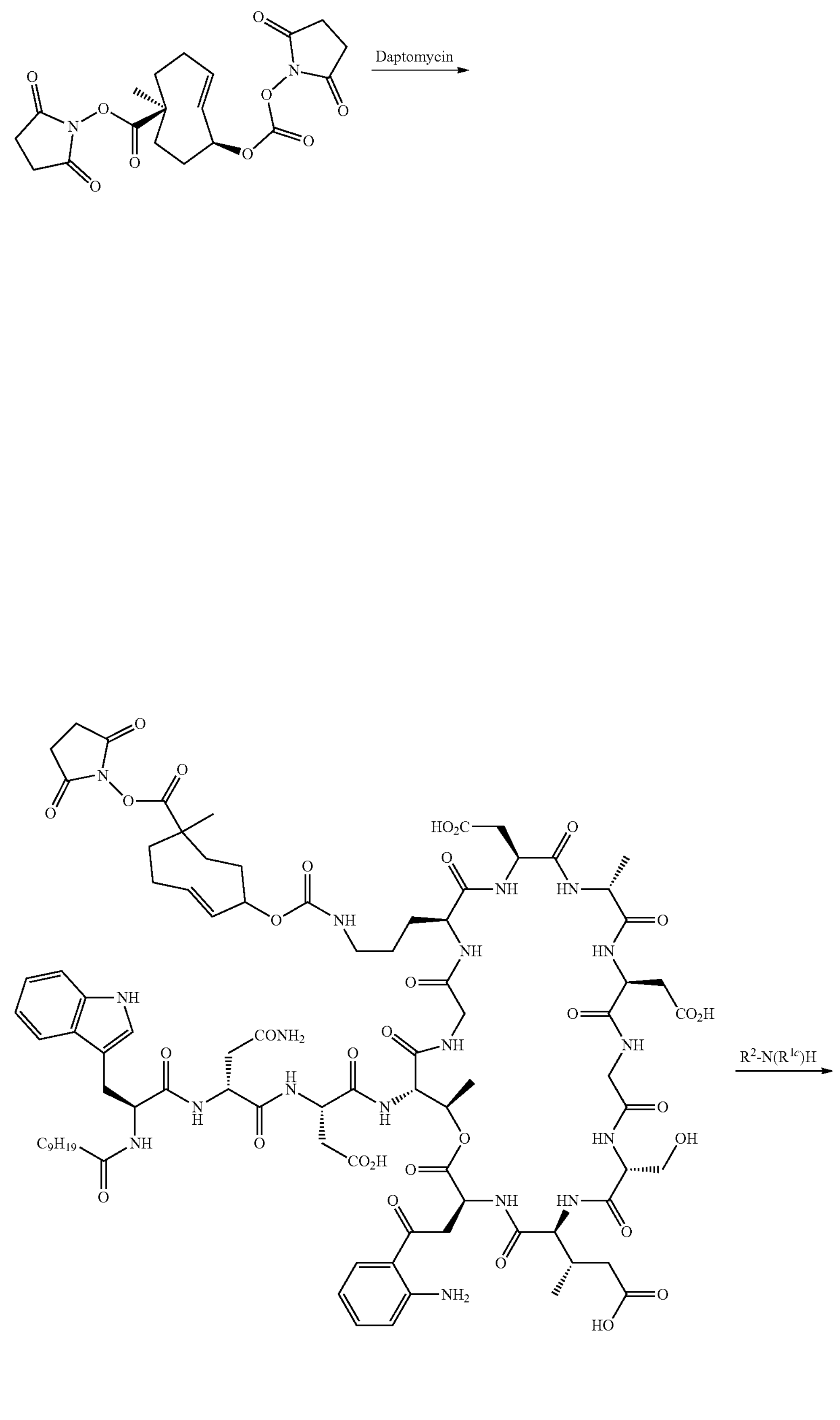

-continued
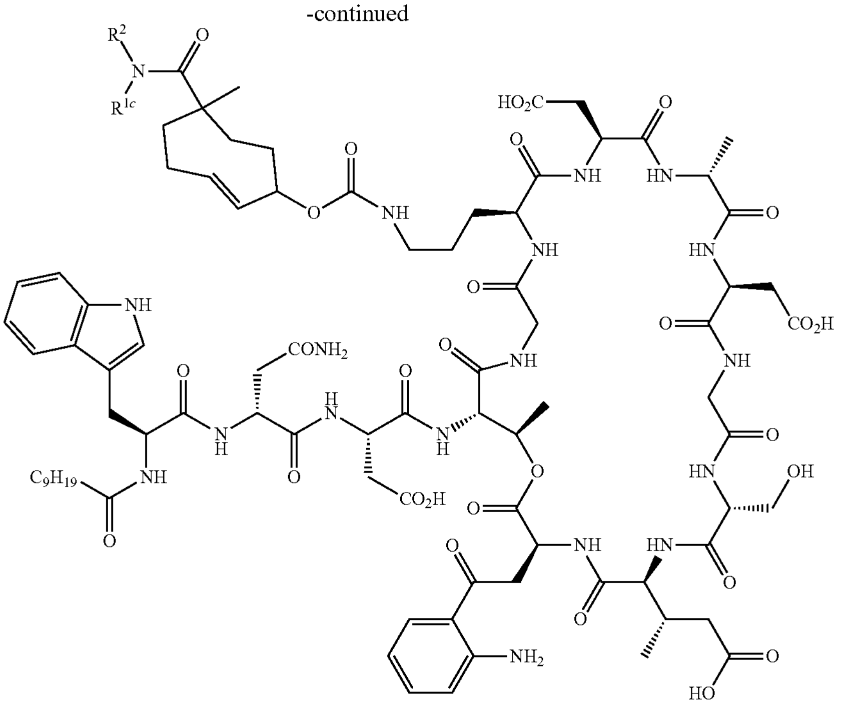
Scheme 2 illustrates a similar reaction between a carbonate ester and the ornithine side chain of daptomycin followed by further coupling with an amino-containing group $R^2$—N($R^{1c}$)H under basic conditions (e.g., $R^2$ is —$C_{1-6}$ alkylene-$CO_2H$, —$CHR^{1e}CO_2H$, —$C_{1-6}$alkylene-C(O)$OC_{1-4}$ alkyl, C(O)$OC_{1-4}$alkyl, or —$CHR^{1c}C(O)OC_{1-4}$alkyl).
Scheme 3
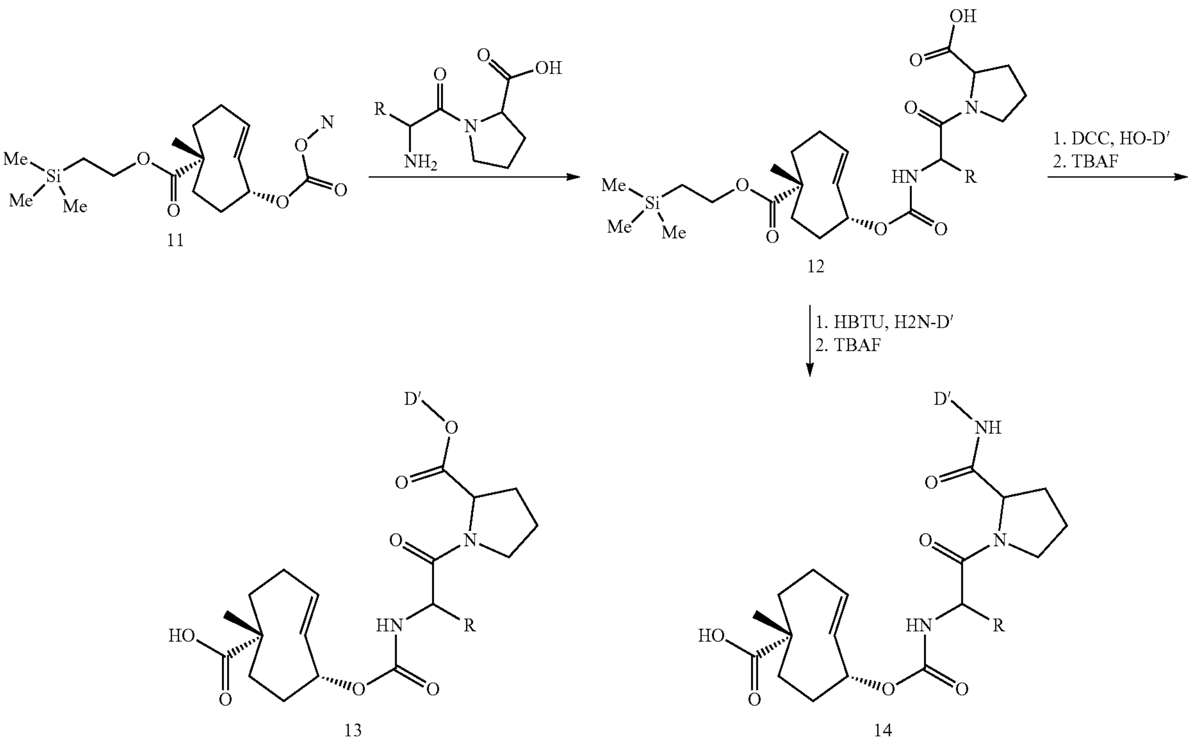

Scheme 3 illustrates conversion of 11 to a carboxylic acid intermediate that may be further converted to payload-bearing products 13 and 14. In Scheme 3, D' represents a payload moiety (e.g., immunomodulatory payload moiety, anticancer agent payload moiety, TLR agonist payload moiety).

-continued

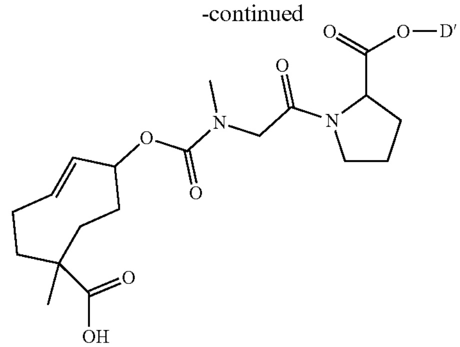

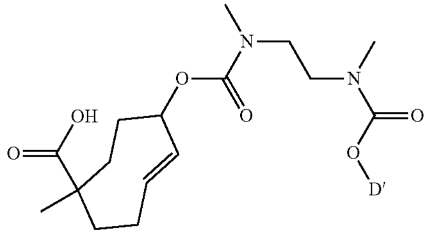

Scheme 4

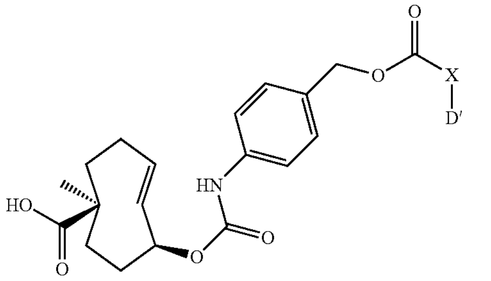

Other carboxylic acids that may be prepared using 11 include those shown in Scheme 4.

Scheme 5

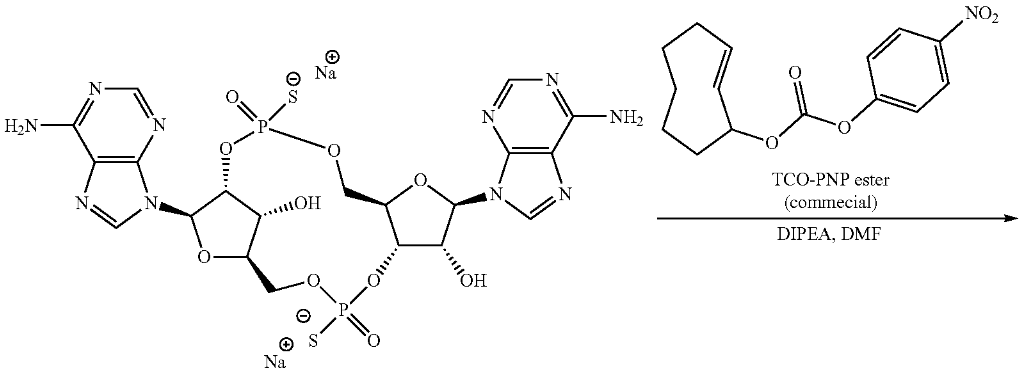

ADU-S100
(commercial)

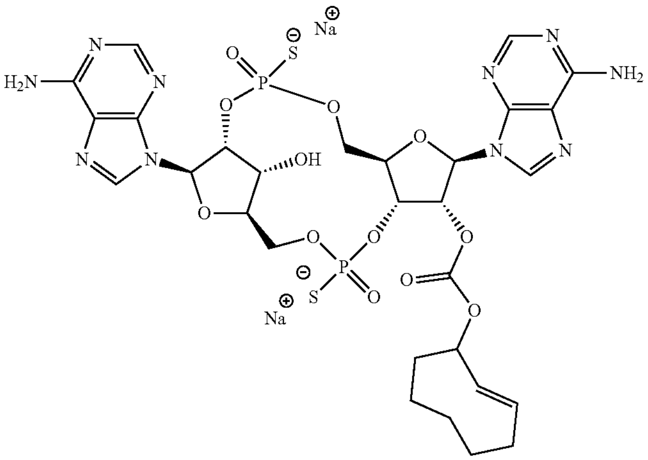

TCO-ADU-S100

-continued
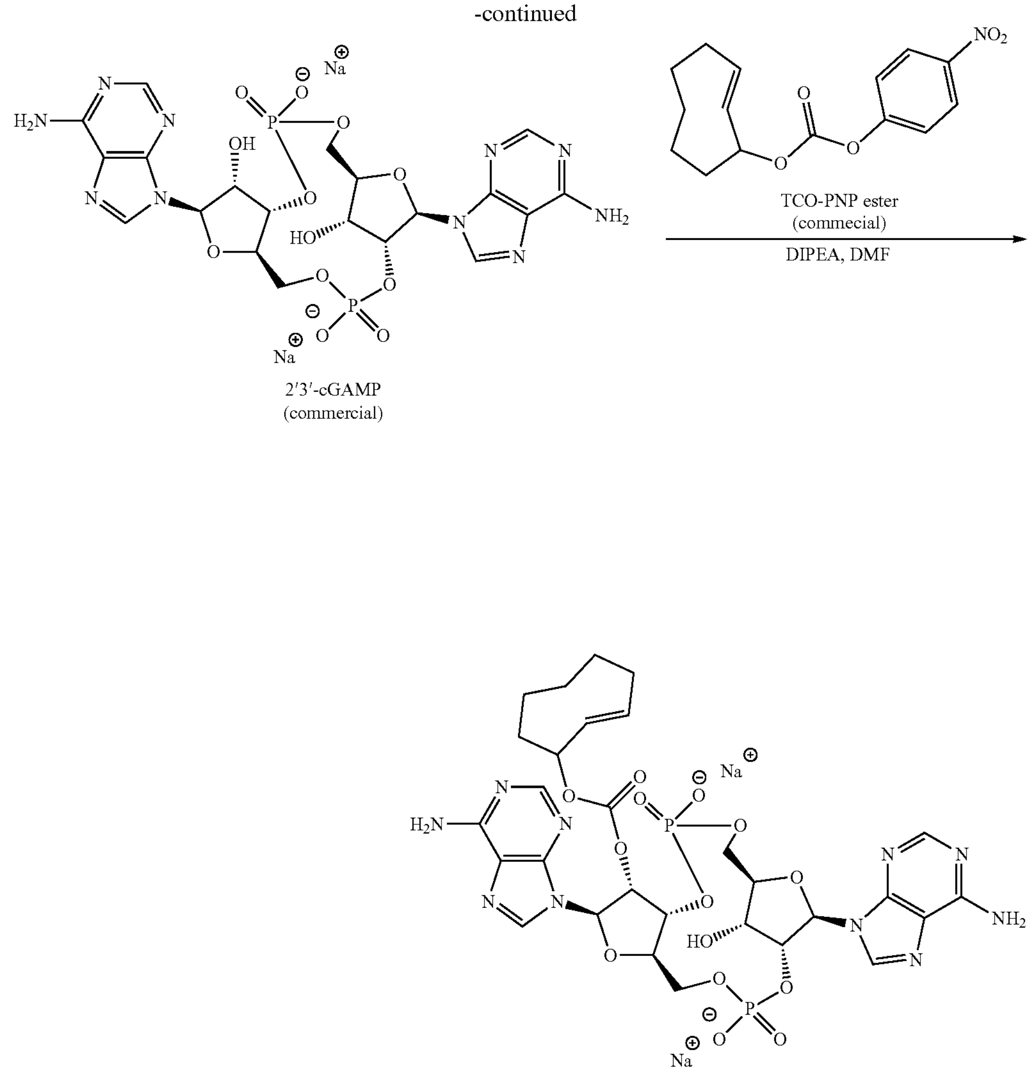
2′3′-cGAMP
(commercial)
TCO-2′3′-cGAMP
Synthetic methods to prepare representative STING agonist TCO conjugates are shown in Scheme 5.
Scheme 6
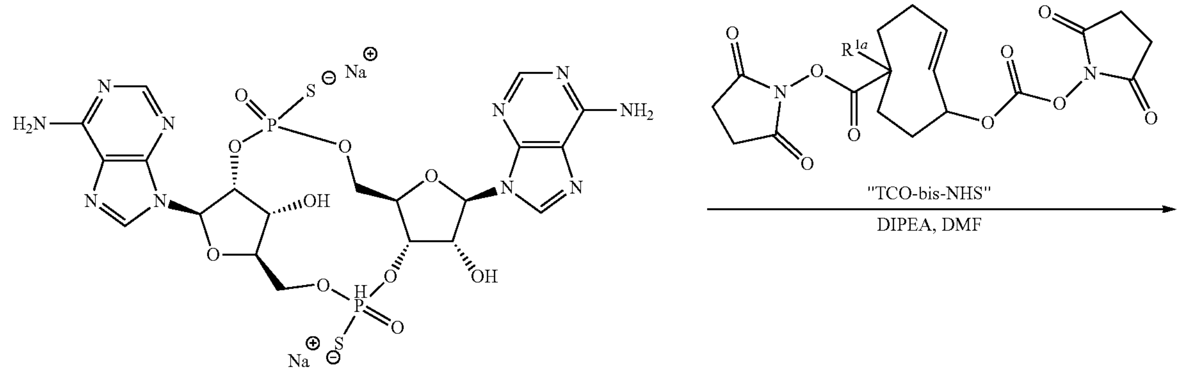
ADU-S100
(commercial)

-continued
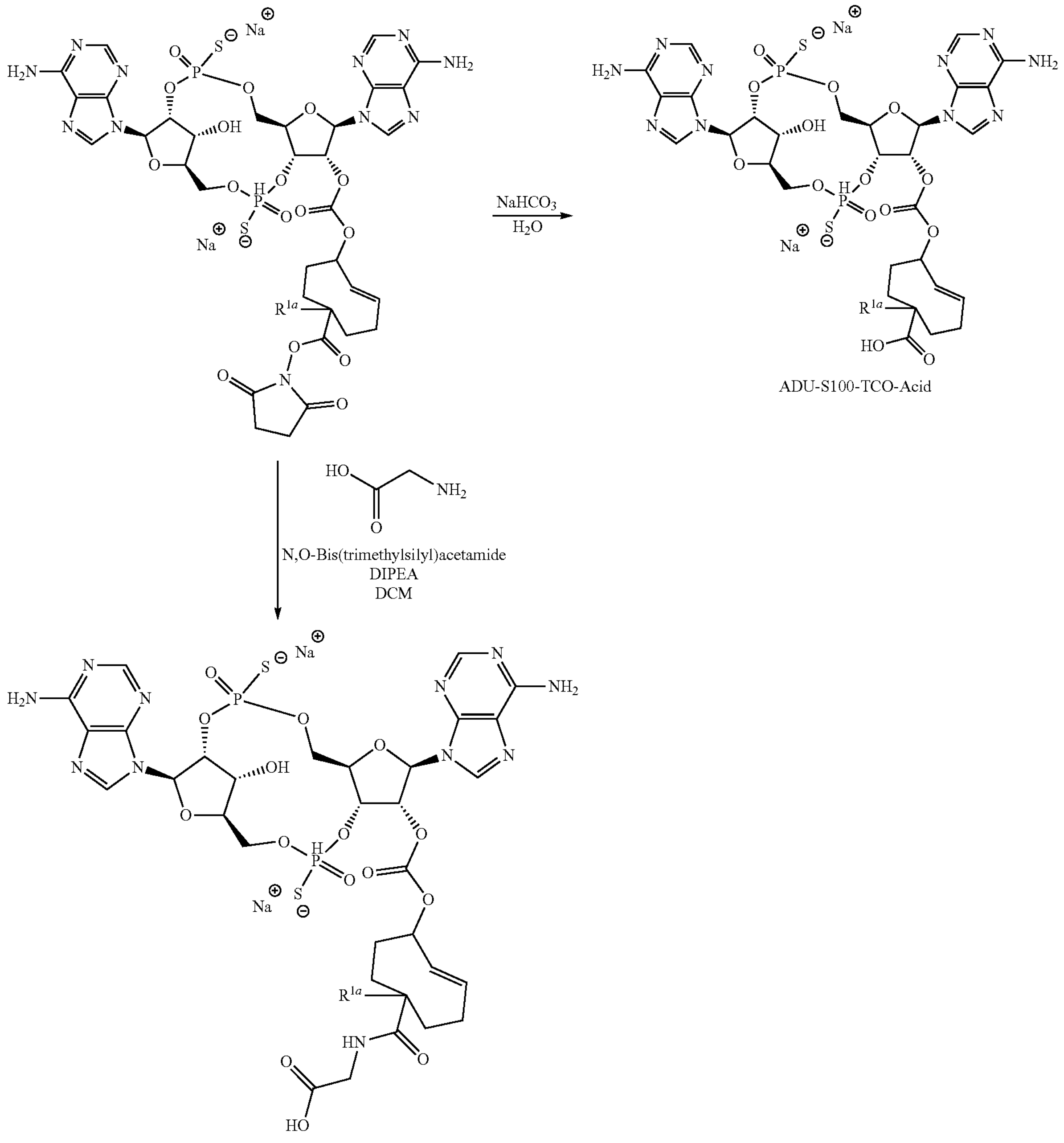
ADU-S100-TCO-Acid
ADU-S100-TCO-Glycine
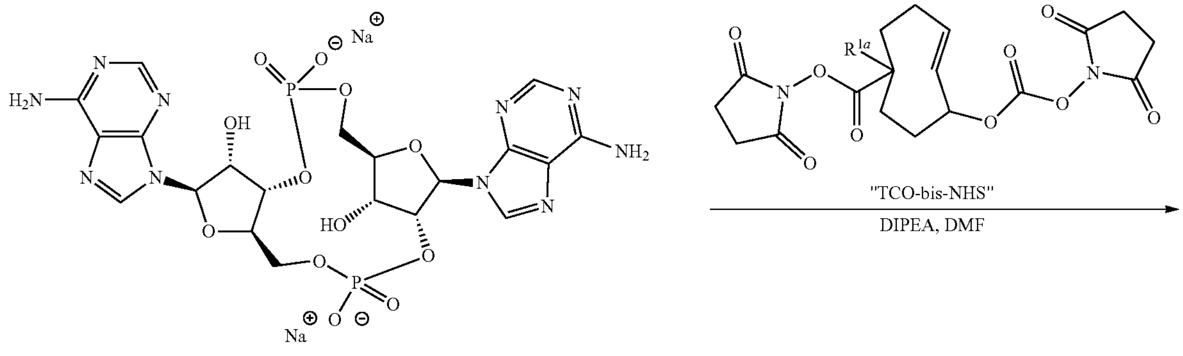
2′3′-cGAMP
(commerical)

-continued
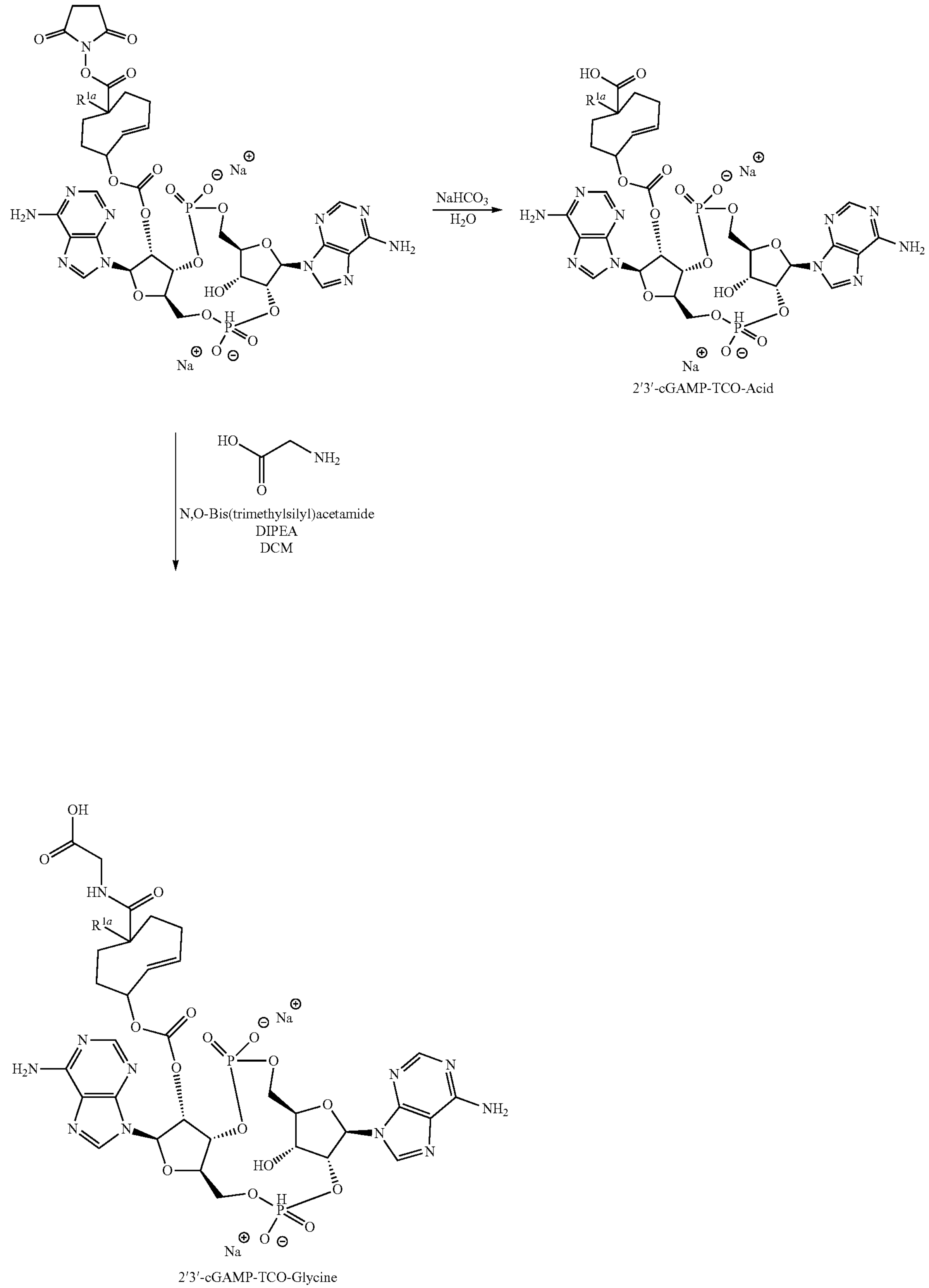
2'3'-cGAMP-TCO-Acid
2'3'-cGAMP-TCO-Glycine

Synthetic methods to prepare representative STING agonist TCO conjugates are shown in Scheme 6.

Scheme 7

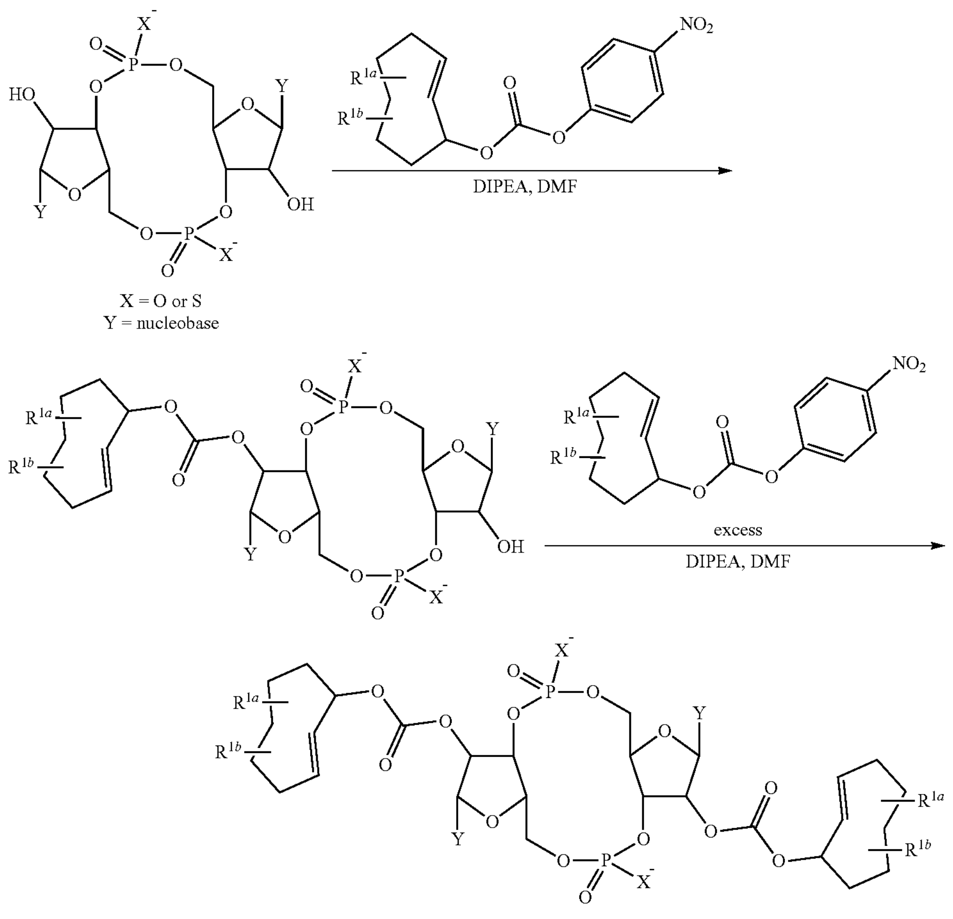

Scheme 7 illustrates a general method of conjugating a cyclic dinucleotide to a trans-cyclooctene, as in formula (I). The illustrated method proceeds by reaction of a cyclic dinucleotide molecule with a nitrophenyl carbonate substituted trans-cyclooctene in the presence of a base to form a mono- or bis-substituted cyclic dinucleotide, depending on the amount of trans-cyclooctene reagent.

Scheme 8

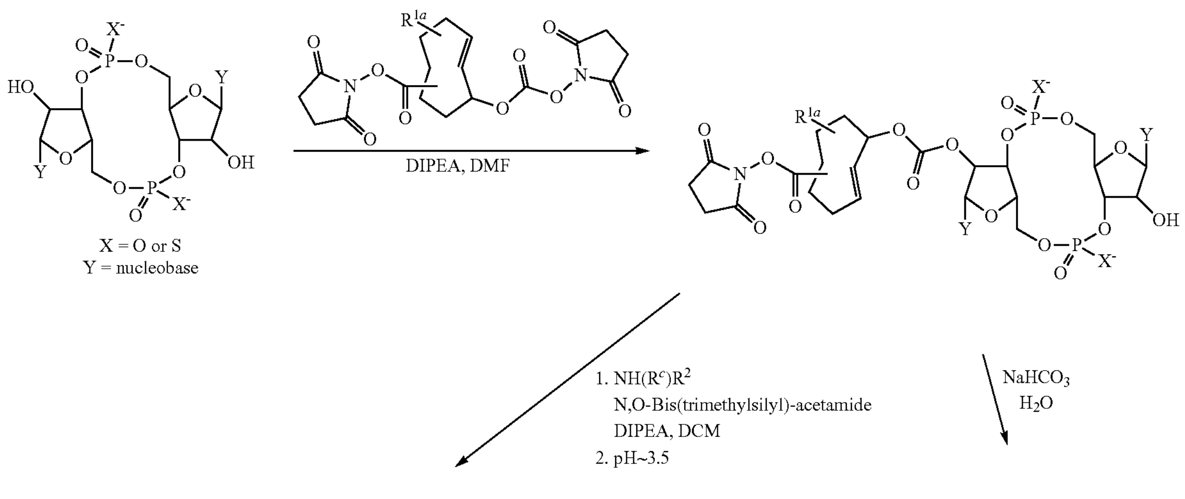

-continued

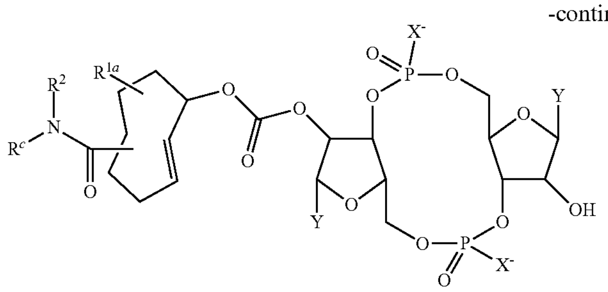

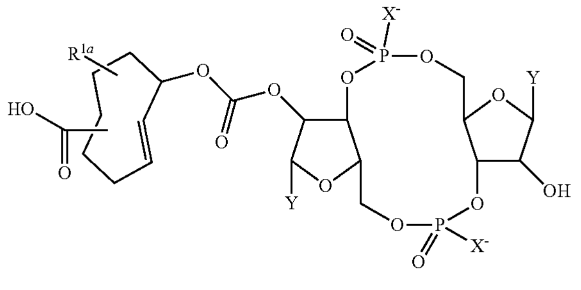

Scheme 8 illustrates a general method of conjugating a cyclic dinucleotide to a transcyclooctene wherein $R^2$ is —$C_{1-6}$alkylene-$CO_2H$, —$CHR^{1e}CO_2H$, —$C_{1-6}$alkylene-C(O)$OC_{1-4}$alkyl, C(O)$OC_{1-4}$alkyl, or —$CHR^{1e}C(O)OC_{1-4}$alkyl, which corresponds with $R^{1b}$ in formula (I) being one of C(O)N($R^{1c}$)—$C_{1-6}$alkylene-$CO_2H$, C(O)OH, C(O)N($R^{1e}$)$CHR^{1e}CO_2H$, C(O)N($R^{1e}$)—$C_{1-6}$alkylene-C(O)$OC_{1-4}$alkyl, C(O)$OC_{1-4}$alkyl, or C(O)N($R^{1e}$)$CHR^{1e}C(O)OC_{1-4}$alkyl. The processes illustrated in Scheme 8 may be modified to provide bis-conjugated cyclic dinucleotides using excess trans-cyclooctene reagent, analogous to Scheme 7.

Scheme 9

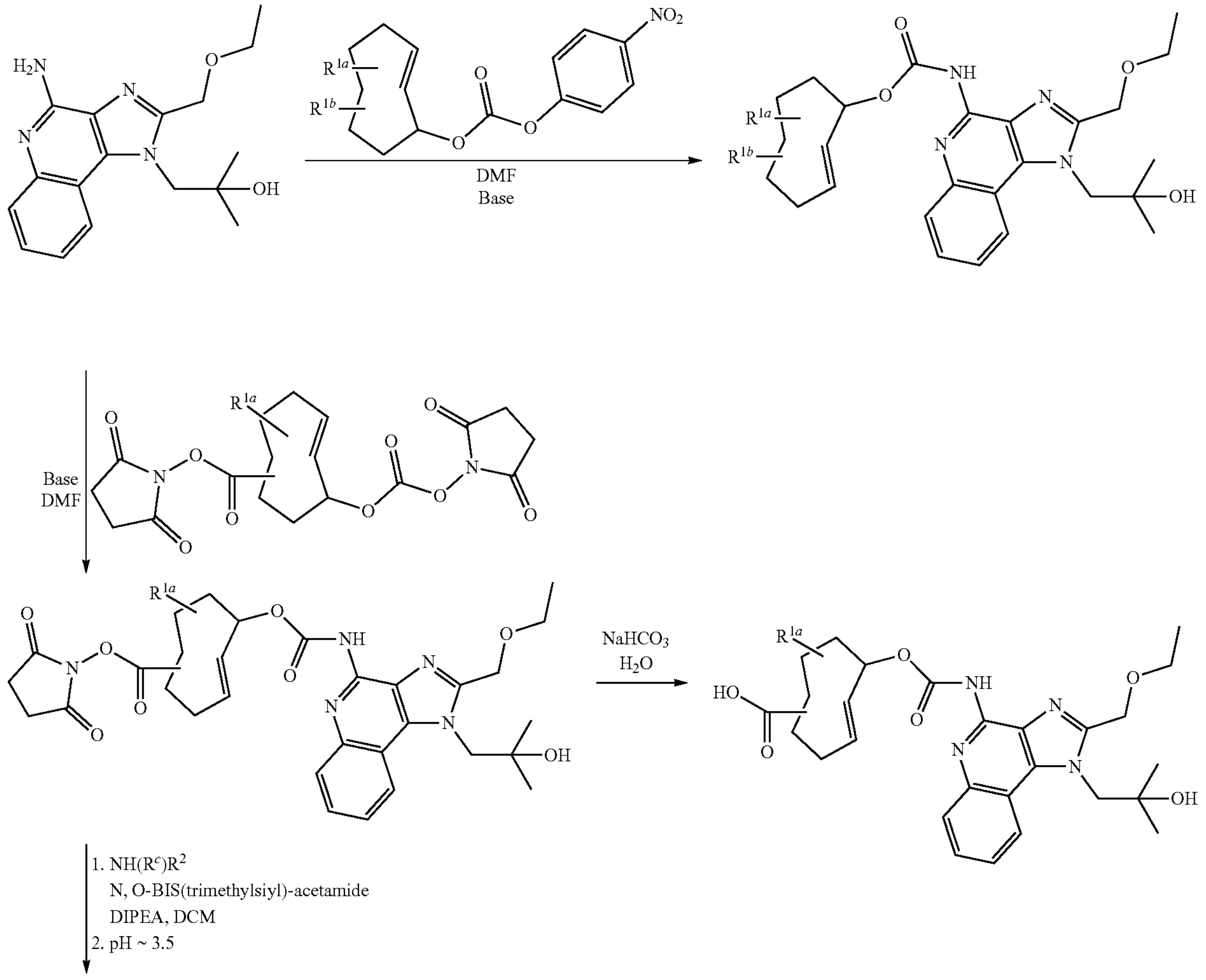

-continued
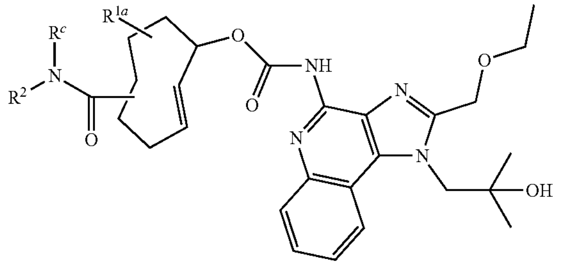
Schemes 9 and 10 illustrate representave synthetic methods of conjugating an imidazo[4,5-c]quinolin-4-amine to a trans-cyclooctene, as in formula (I), following analogous procedures to Schemes 7 and 8.
Scheme 10
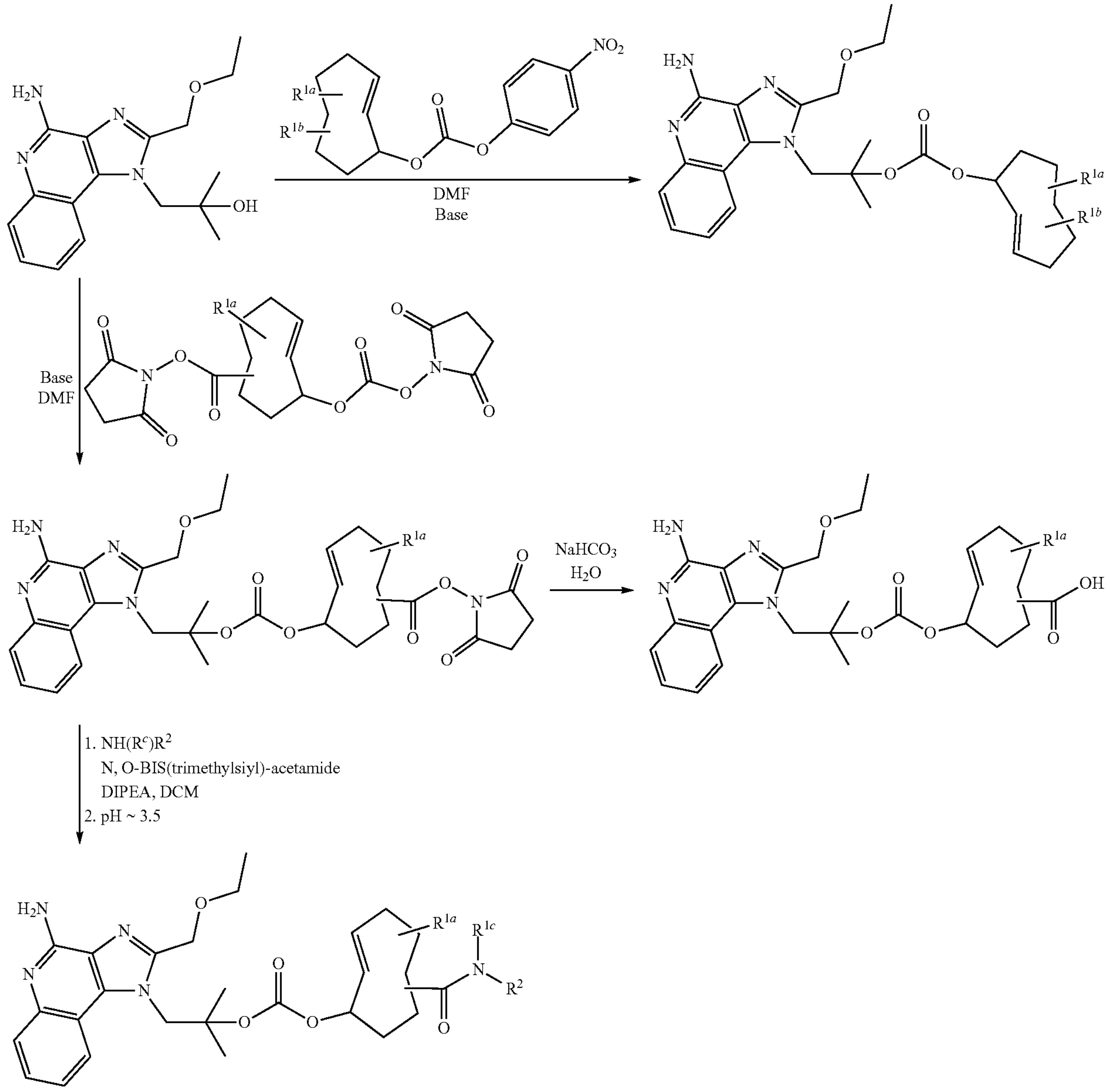

The disclosed compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts," J. Pharm. Sci. Vol. 66, pp. 1-19.

For example, if the compound is anionic, or has a functional group which may be anionic (e.g., —COOH may be —COO—), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., $—NH_2$ may be $—NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999); J. F. W. McOmie, "Protective Groups in Organic Chemistry," Plenum Press, London and New York 1973; "The Peptides"; Volume 3 (editors: E. Gross and J. Meienhofer), Academic Press, London and New York 1981; "Methoden der organischen Chemie," Houben-Weyl, 4th edition, Vol. 15/1, Georg Thieme Verlag, Stuttgart 1974; H.-D. Jakubke and H. Jescheit, "Aminosauren, Peptide, Proteine," Verlag Chemie, Weinheim, Deerfield Beach, and Basel 1982; in Jochen Lehmann, "Chemie der Kohlenhydrate: Monosaccharide and Derivate," Georg Thieme Verlag, Stuttgart 1974.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester ($—OC(O)CH_3$, —OAc).

An aldehyde or ketone group may be protected as an acetal ($RCH(OR)_2$) or ketal ($R_2C(OR)_2$), respectively, in which the carbonyl group ($R_2C{=}O$) is converted to a diether ($R_2C(OR)_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide ($—NHC(O)CH_3$); a benzyloxy amide ($—NHC(O)OCH_2C_6H_5$, —NH—Cbz); as a t-butoxy amide ($—NHC(O)OC(CH_3)_3$, —NH-Boc); a 2-biphenyl-2-propoxy amide ($—NHCO(O)C(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N-0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether ($—S—CH_2NHC(O)CH_3$).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

F. FORMULATIONS

Compositions (e.g., support composition, conjugates, trans-cyclooctene prodrugs) can be provided in any suitable form, e.g., in the form of a pharmaceutically acceptable formulation, and can be formulated for any suitable route of administration, e.g., oral, topical or parenteral administration. Where the composition is provided as a liquid injectable (such as in those embodiments where they are administered intravenously or directly into a tissue), the composition can be provided as a ready-to-use dosage form, or as a reconstitutable storage-stable powder or liquid that may include pharmaceutically acceptable carriers and excipients.

A “pharmaceutically acceptable excipient,” “pharmaceutically acceptable diluent,” “pharmaceutically acceptable carrier,” or “pharmaceutically acceptable adjuvant” means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. “A pharmaceutically acceptable excipient, diluent, carrier and/or adjuvant” as used herein includes one or more such excipients, diluents, carriers, and adjuvants.

Methods for formulating compositions can be adapted from those readily available. For example, compositions can be provided in a pharmaceutical formulation that includes a therapeutically effective amount of a composition and a pharmaceutically acceptable carrier (e.g., saline). The pharmaceutical formulation may optionally include other additives (e.g., buffers, stabilizers, preservatives, and the like). In some embodiments, the formulations are suitable for administration to a mammal, such as those that are suitable for administration to a human.

The compositions of the present disclosure can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the subject.

The compositions of the present disclosure can also be administered by injection, that is, intravenously, intramuscularly, intracutaneously, subcutaneously, intraduodenally, or intraperitoneally. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

In some instances, the compositions described herein can be administered by inhalation, for example, intranasally.

In some instances, the compositions of the present disclosure can be administered transdermally.

In some instances, the compositions can be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

Accordingly, the present disclosure also provides pharmaceutical formulations including a composition as described herein and a pharmaceutically acceptable carrier or excipient.

For preparing pharmaceutical formulations from the compositions of the present disclosure, pharmaceutically acceptable carriers can be solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are found, for example in Remington's Pharmaceutical Sciences, Maack Publishing Co, Easton PA (“Remington's”).

In some embodiments, the pharmaceutical composition of the invention is a vaccine that comprises a conjugate, or a pharmaceutically acceptable salt thereof, a pharmaceutically acceptable carrier, and optionally an antigen. Antigens for use in the immunogenic compositions provided herein may be provided in an effective amount (e.g., an amount effective for use in therapeutic or prophylactic methods). For example, immunogenic compositions of the invention may be used to treat or prevent diseases or conditions such as infections and cancer. Exemplary antigens include, but are not limited to, tumor antigens and infectious disease antigens. Antigens for use in the immunogenic compositions provided herein are typically macromolecules (e.g., polypeptides, polysaccharides, polynucleotides) that are foreign to the host. An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen may refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

In certain embodiments, a tumor antigen or cancer antigen is used in conjunction with the immunogenic compositions provided herein. In certain embodiments, the tumor antigen is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA. In certain embodiments, the tumor antigen is a whole, live or dead or permeabilized cancer cell. Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including polysaccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NYESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-R1 701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolaseA (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanomamelanocyte differentiation antigens such as MART-1/Melan A, gp 100, MC1 R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSHP1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/MeI-40, H-Ras, E2A-PRL, H4-RET, IGH-IGK, MYL-RAR, Epstein Barr virus antigens, EBNA, human papillomavirus (HPV) antigens, including E6 and E7, hepatitis Band C virus antigens, human T-cell lymphotropic virus antigens, TSP-180, p185erbB2, p180erbB-3, c-met, nm-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, C0-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

G. KITS

Aspects of the present disclosure include kits that have a composition as described herein.

A kit may include a compound of formula (I), or a pharmaceutically acceptable salt or composition thereof, and a therapeutic support composition. A kit may include a compound of formula (I), or a pharmaceutically acceptable salt or composition thereof, and a compound of formula (II), or formula (III), or a pharmaceutically acceptable salt or composition thereof.

A kit may include a compound of formula (II) or formula (III), or a pharmaceutically acceptable salt or composition thereof, and one or more immunomodulatory agents, or a pharmaceutically acceptable salt or composition thereof, and optionally a therapeutic support composition. A kit may include a therapeutic support composition, as described herein, and one or more immunomodulatory agents, or a pharmaceutically acceptable salt or composition thereof.

The therapeutic support composition, one or more immunomodulatory agents, and the compound of formula (I), (II), and/or (III) may be in separate containers in the packaging. One or more therapeutic support compositions may be provided in a kit.

The kits described herein may include a packaging configured to contain the composition (e.g., therapeutic support composition and/or one or more immunomodulatory agents). Similarly, one or more compounds of formula (I), (II), and/or (III) may be provided in a kit. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

In certain embodiments, the kit includes a reagent that may be used as the releasing agent for a releasable linker as described herein. The releasing reagent may be any one of the releasing agents described herein, such as, but not limited to, a chemical releasing agent (e.g., an acid, a base, an oxidizing agent, a reducing agent, etc.), a solvent, and the like. The releasing reagent in the kit may be provided in any convenient form, such as, but not limited to, a gas, a solution, a solid, granules, a powder, a suspension, and the like. The releasing reagent may be packaged in a separate container from the composition(s) in the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form for the instructions would be a computer readable medium, e.g., CD, DVD, Blu-Ray, computer-readable memory (e.g., flash memory), etc., on which the information has been recorded or stored. Yet another form for the instructions that may be present is a website address which may be used via the Internet to access the information at a removed site. Any convenient means may be present in the kits.

H. EXAMPLES

The present disclosure has multiple aspects, illustrated by the following non-limiting examples. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Abbreviations:

ACN acetonitrile
dapto daptomycin
DCM dichloromethane
DIPEA diisopropylethylamine
DMF N,N-dimethylformamide
DMSO dimethylsulfoxide
doxo doxorubicin
Et ethyl
EtOAc ethyl acetate
FCC flash column chromatography
h or hr hour
HA hyaluronic acid
HAT hyaluronic acid modified with tetrazine 1
HMT hydrogel modified tetrazine
HOAt 1-hydroxy-7-azabenzotriazole
LCMS liquid chromatography-mass spectrometry
Me methyl
MeCN acetonitrile
MeOH methanol
MeTz methyltetrazine
min minutes
MTD maximum tolerated dose
NHS N-hydroxysuccinimide
PBS phosphate buffered saline
Ph phenyl
ppm parts per million
rt/RT room temperature
SEM standard error of the mean
TAG tetrazine-modified activating gel
TCO trans-cyclooctene
TEA triethylamine
THF tetrahydrofuran
TFA trifluoroacetic acid

Example 1

Trans-Cyclooctene-Antibody Conjugate (Prophetic Example)

A solution of antibody (2.5 mg/mL) in aqueous buffer (50 mM potassium phosphate, 50 mM sodium chloride, 2 mM ethylenediaminetetraacetic acid disodium salt), pH 6.5, is incubated with a molar excess of trans-cyclooctene derivatized carbonate in dimethylacetamide (DMA). The reaction is allowed to proceed at ambient temperature and, upon completion, purified by gel filtration colum. The concentration of the conjugate is determine spectrophotometrically using the known extinction coefficients for the antibody.

Example 2
Synthesis of TCO-Monomethyl Auristatin E (TCO-MMAE) Conjugate
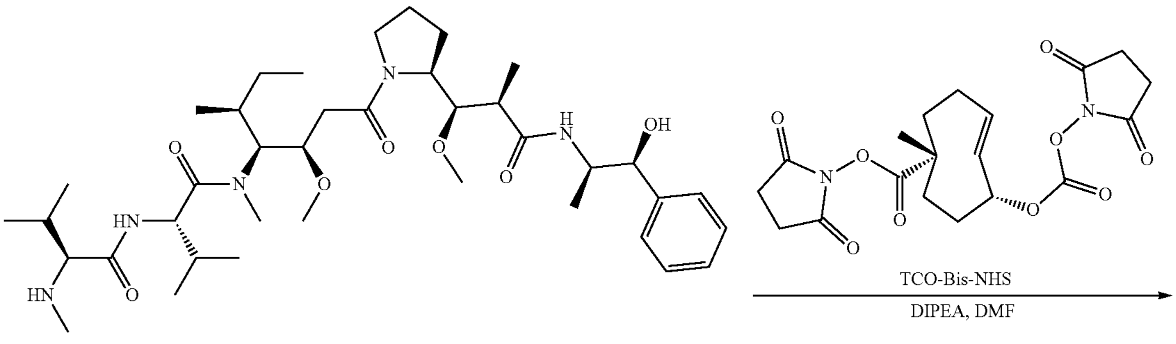
Monomethyl auristatin E (MMAE)
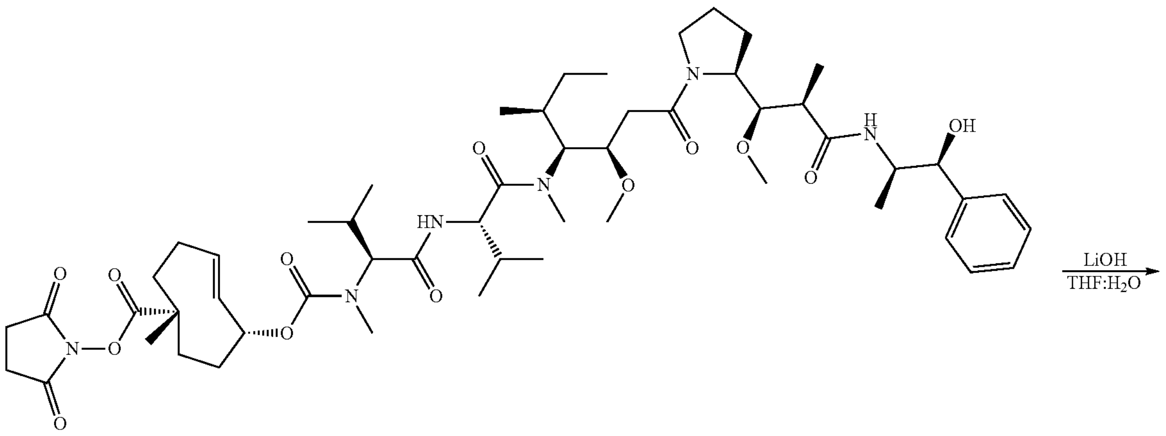
TCO-NHS-MMAE
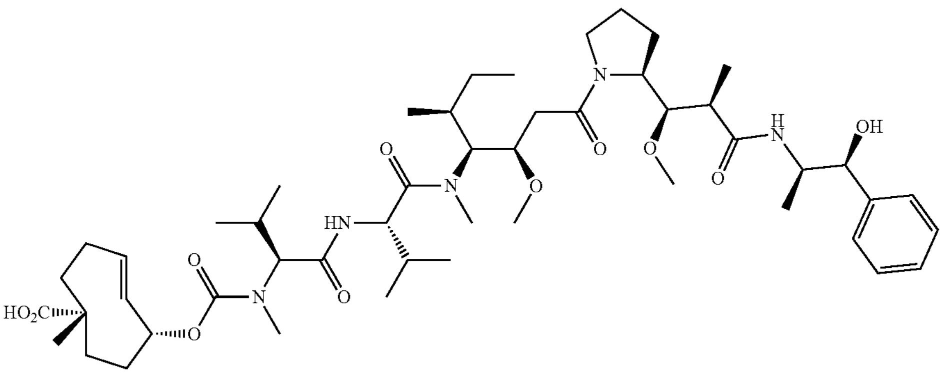
TCO-Acid-MMAE Preparation of TCO-MMAE conjugate. To monomethyl auristatin E (170 mg, 0.24 mmol) in DMF (2 mL) at rt, TCO-Bis-NHS (100 mg, 0.24 mmol) and DIPEA (93 mg, 0.72 mmol) were added. The solution was stirred at rt for 20 h, acetonitrile (ACN, 8 mL) was added and the mixture was purified by prep-HPLC (ACN/water from 0 to 100%, formic acid 0.1%) to give TCO-NHS-MMAE (88 mg, 36%). To TCO-NHS-MMAE (78 mg, 0.076 mmol) in THF (2 mL) and $H_2O$ (2 mL) at rt was added LiOH (9.2 mg, 0.38 mmol). The solution was stirred at rt for 20 h. After removal of solvent, HCl (aq, 0.5 N) was added to pH~3. The mixture was purified by prep-HPLC (ACN/water from 0 to 100%, formic acid 0.1%) to give TCO-Acid-MMAE (54 mg, 76%, two isomers). LCMS: (ESI+) 928 [M+H].

The synthesis of TCO-Acid-MMAE is representative of functionalization of an N-terminal amino group of a polypeptide.

Example 3

Dapto-TCO-Amino Acid Synthesis

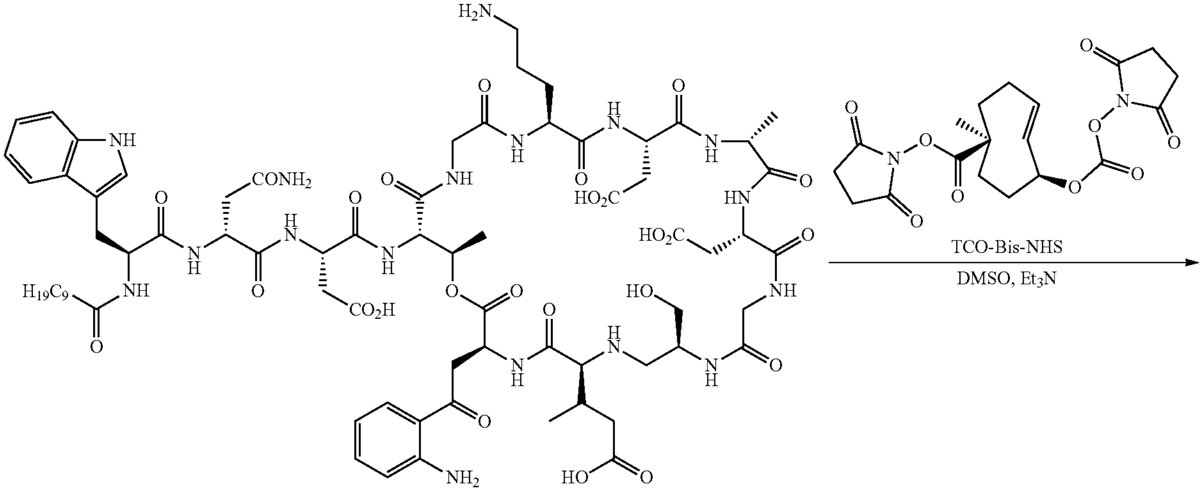

Daptomycin

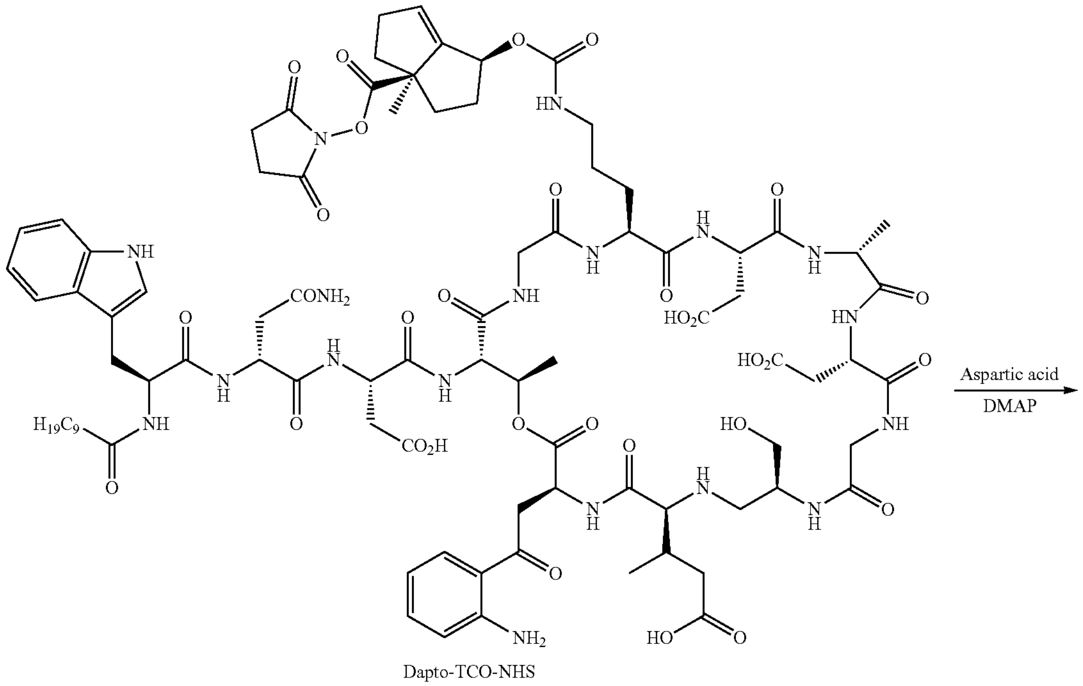

Dapto-TCO-NHS

-continued

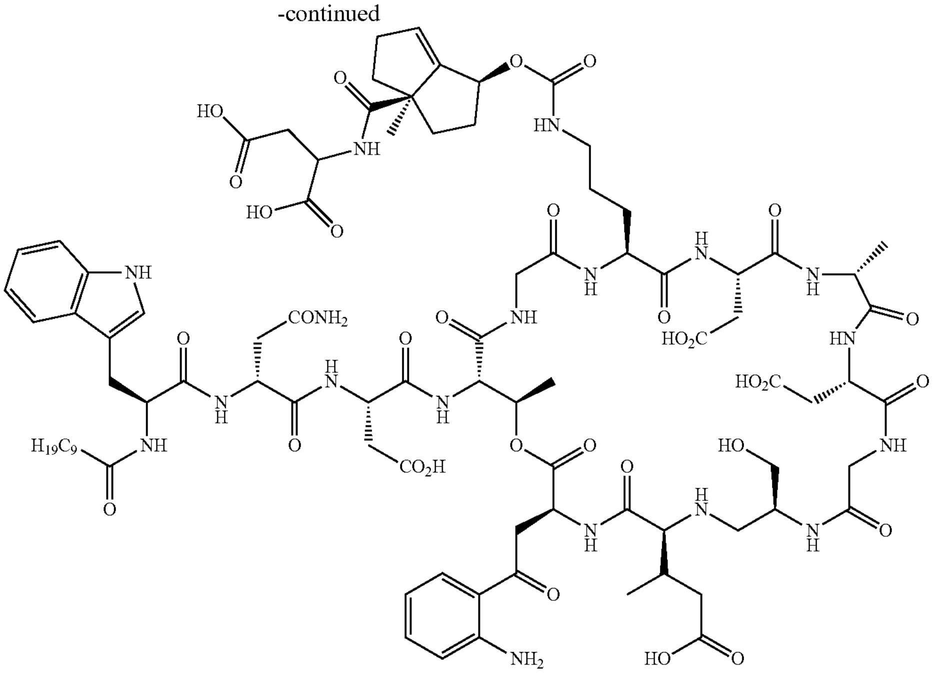

Dapto-TCO-Aspartic Acid

Example protocol: Add daptomycin (100 mg, 0.062 mmol), TCO-Bis-NHS (62.5 mg, 0.149 mmol), and triethylamine (62.5 µL, 45.3 mg, 0.448 mmol) to DMSO and stir at RT overnight to produce Dapto-TCO-NHS. LCMS: (ESI−) 1926.8 [M−H]. To Dapto-TCO-NHS (126.1 mg, 0.0654 mmol), add aspartic acid (104.5 mg, 0.785 mmol) and 4-dimethylaminopyridine (150.9 mg, 1.235 mmol), and stir for 18 h at 37° C. Purify by HPLC to obtain Dapto-TCO-Aspartic Acid. Yield: 100 mg, 0.0514 mmol. LCMS: (ESI−) 1944.8 [M−H].

This approach has been used to produce glycine and aspartic acid-modified TCO-prodrugs, and can be generally applied to for the incorporation of other amino acid cargos as well.

Example 4

Daptomycin-TCO-Glycine Conjugate

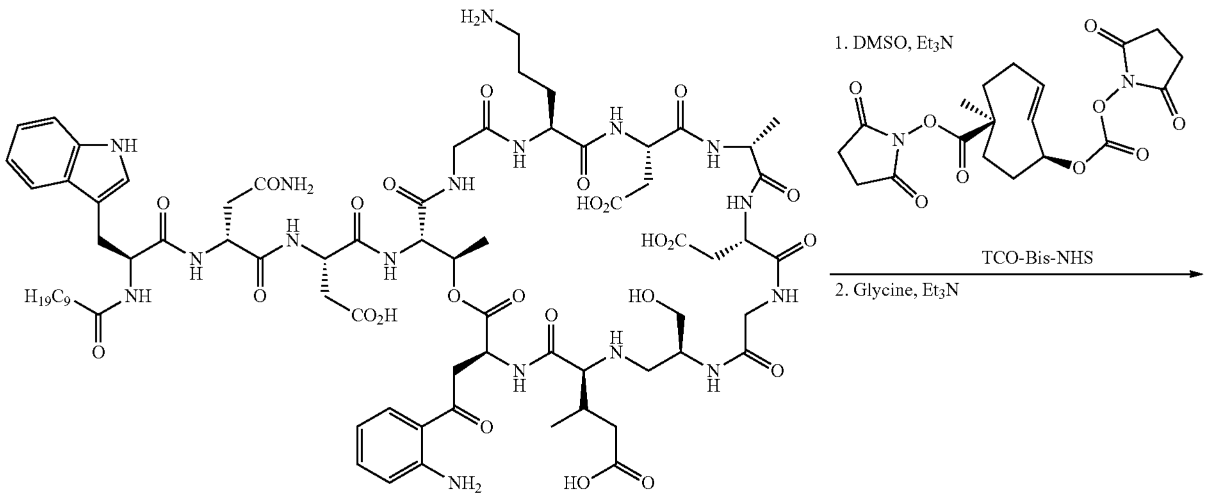

Daptomycin

-continued

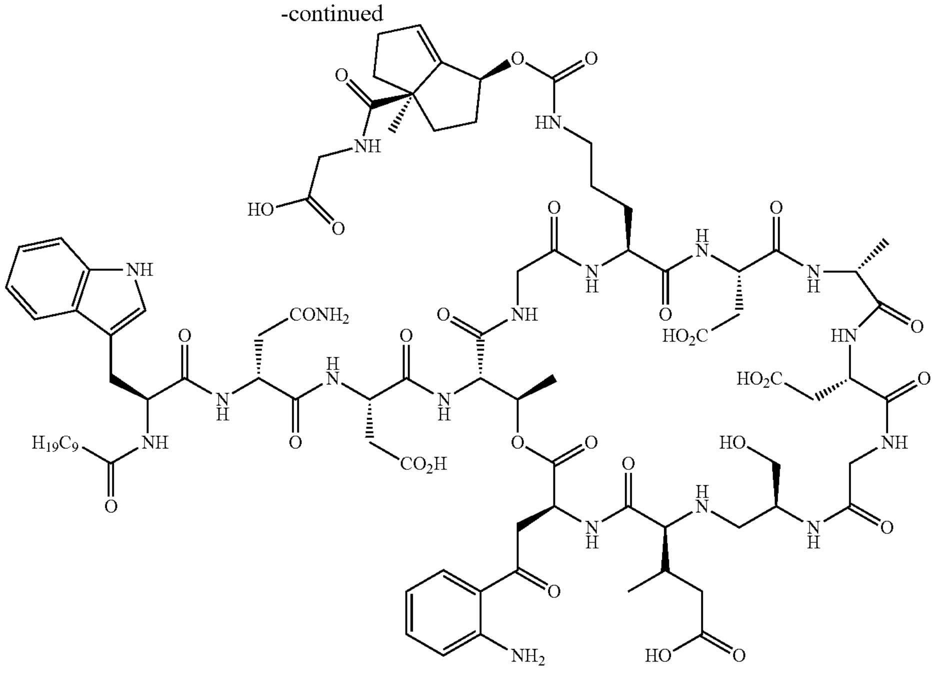

Dapto-TCO-Glycine

Daptomycin (537 mg, 0.33 mmol), TCO-Bis-NHS (350 mg, 0.83 mmol), and triethylamine (0.350 mL, 2.51 mmol) in DMSO (11 mL). Stir at RT overnight. Then heat to 37° C. Add glycine (300 mg, 4.00 mmol) and triethylamine (1.8 mL, 13 mmol), and stir for 18 h. Add 8 mL water and purify by HPLC. Yield: Dapto-TCO-Glycine-373 mg, 0.20 mmol, 59.6%.

The syntheses of Dapto-TCO-glycine and Dapto-TCO-aspartic acid are representative of derivatization of a lysine side chain of a polypeptide.

Example 5

MMAE-TCO-Asp Conjugate

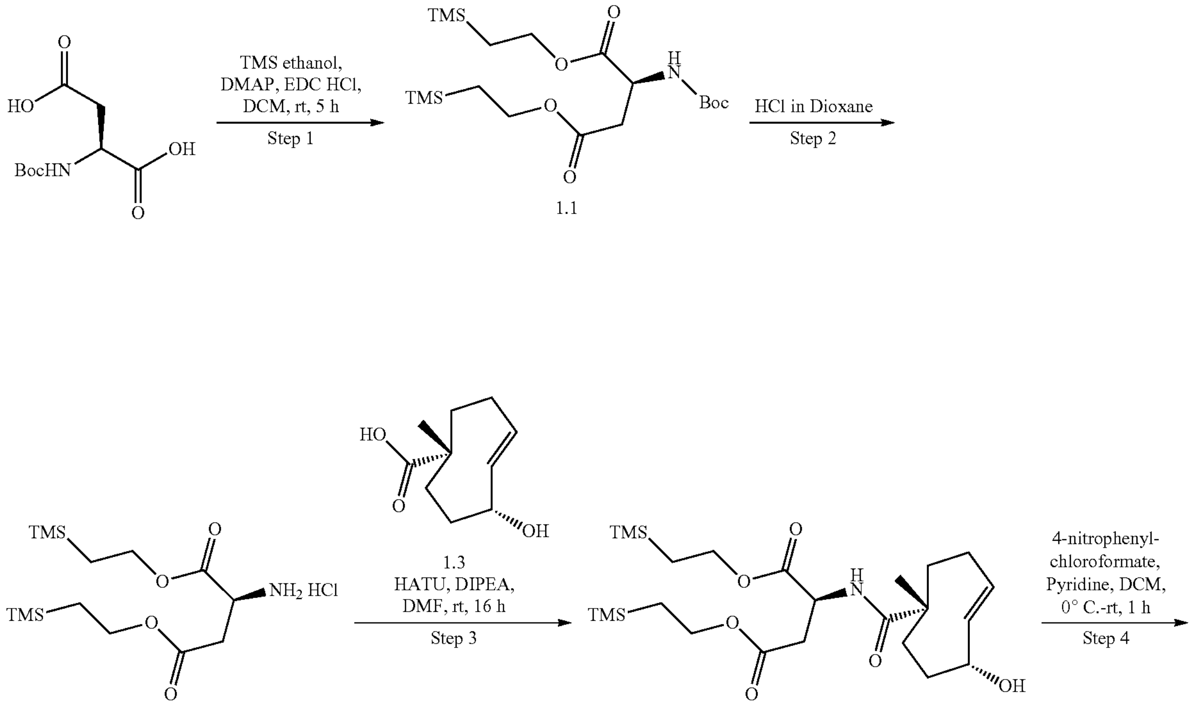

1.2 1.4

-continued

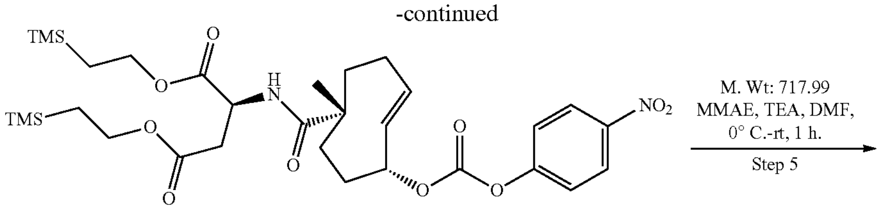

1.5

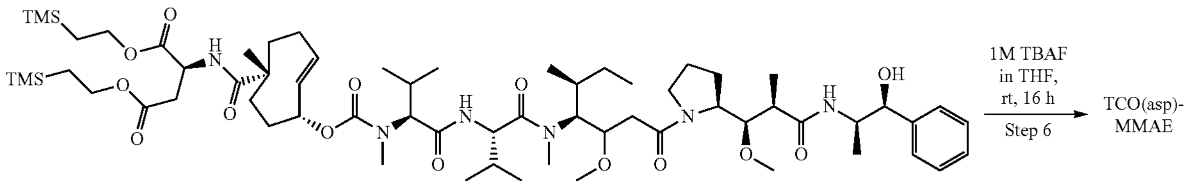

1.6

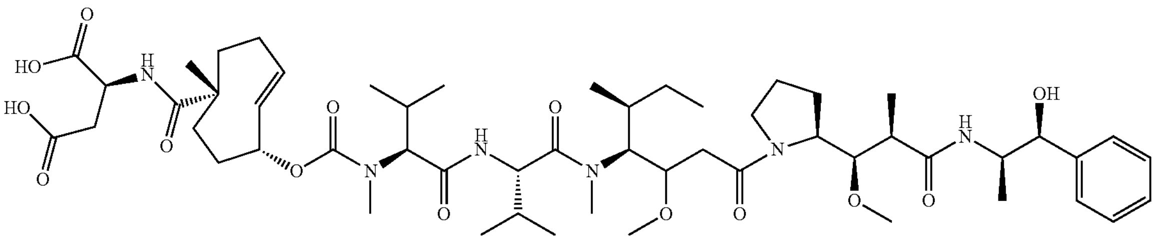

bis(2-(trimethylsilyl)ethyl) (tert-butoxycarbonyl)-L-aspartate (1.1). Step-1: To a mixture of Boc-Asp-OH (10.0 g, 42.9 mmol, 1.0 eq., Combi-blocks QA-1348), DIEA (37.3 mL, 214.0 mmol, 5.0 eq.), 2-(trimethylsilyl)ethan-1-ol (12.2 g, 103.0 mmol, 2.4 eq.), and DMAP (1.1 g, 8.6 mmol, 0.2 eq.) in DCM (200.0 mL) cooled in ice bath was added EDC (23.0 g, 120.0 mmol, 2.8 eq.). The mixture was stirred at rt overnight, diluted with DCM (100.0 mL), and washed with aq HCl (0.5 M) until pH in organic layer turned neutral. The organic layer was further washed with saturated $NaHCO_3$ solution, dried with $Na_2SO_4$, and filtered. The filtrate was concentrated and purified by flash chromatography (ISCO column, 220 g) using a gradient of EtOAc in hexanes (0-30%) to afford 13.0 g (70%) of bis(2-(trimethylsilyl) ethyl) (tert-butoxycarbonyl)-L-aspartate as a colorless oil. $^1$H-NMR (300 MHz, $CDCl_3$): 5.50 (br d, J=8.79 Hz, 1H), 4.61-4.48 (m, 1H), 4.30-4.14 (m, 4H), 3.04-2.93 (m, 1H), 2.83-2.73 (m, 1H), 1.45 (s, 9H), 1.06-0.94 (m, 4H), 0.004 (s, 9H), 0.03 (s, 9H).

bis(2-(trimethylsilyl)ethyl) L-aspartate hydrochloride (1.2). Step-2: To a solution of compound-1.1 (10.4 g, 24.0 mmol) in dry DCM (30 mL) cooled in an ice-bath was added HCl (100 mL, 2.0 M HCl in ether). To this mixture after stirring at rt for 90 min was added more HCl (100 mL, 4.0 M HCl in dioxane). Upon completion the reaction monitored by LCMS, the mixture was concentrated to dryness. Suspended in EtOAc and reconcentrated. Obtained 11.4 g (~20 wt % solvent) of 2-(trimethylsilyl)ethan-1-ol as a tarry residue. (+esi) $[M+H]^+$=334.

bis(2-(trimethylsilyl)ethyl) ((1R,6R,E)-6-hydroxy-1-methylcyclooct-4-ene-1-carbonyl)-L-aspartate (1.4). Step-3: To a solution of compound-1.2 (11.0 g, 80% pure, 23.9 mmol, 2.0 eq.) in DMF (100.0 mL) were added DIPEA (11.0 mL, 62.7 mmol, 5.3 eq.), (1R,6R,E)-6-hydroxy-1-methylcyclooct-4-ene-1-carboxylic acid (1.3), (2.2 g, 11.9 mmol, 1.0 eq), and HATU (9.1 g, 23.9 mmol, 2.0 eq.) sequentially. The mixture was stirred at RT overnight, diluted with EtOAc (400 mL) and water (400 mL). The aqueous layer was extracted with EtOAc (400 mL) once. The combined organic layer was dried with $Na_2SO_4$ and filtered. The filtrate was concentrated and purified on flash chromatography (220 g, ISCO column) eluting with a gradient of EtOAc in hexanes (0-70%) and isocratic at 70% EtOAc in hexane to afford 3.96 g (75% pure, 50% yield) of bis(2-(trimethylsilyl)ethyl) ((1R,6R,E)-6-hydroxy-1-methylcyclooct-4-ene-1-carbonyl)-L-aspartate as a sticky oil. (+esi)$[M+H]^+$=500.4.

bis(2-(trimethylsilyl)ethyl) ((1R,6R,E)-1-methyl-6-(((4-nitrophenoxy)carbonyl)oxy)cyclooct-4-ene-1-carbonyl)-L-aspartate (1.5). Step-4: To a solution of compound 1.4 (4.0 g, 7.9 mmol, 1.0 eq.) in anhydrous DCM (113 mL) was added pyridine (1.88 g, 23.8 mmol, 3.0 eq.). To this mixture cooled in an ice-bath was slowly added a solution of p-nitrophenyl chloroformate (2.1 g, 10.3 mmol, 1.3 eq.) in DCM (28 mL). The mixture was stirred at RT for 12 h and partitioned with EtOAc and water. The organic phase was washed with aq sodium bicarbonate, water and then dried with sodium sulfate, filtered and concentrated. The residue was dissolved in a minimal amount of DCM and purified by flash chromatography on a 220 g silica gel column (ISCO) a step-wise gradient of EtOAc in hexane (0-40%) as eluent to afford 2.91 g (44% yield, desired product eluted around 30% EtOAc, coelutes with p-nitrophenol) of as a viscous oil.

bis(2-(trimethylsilyl)ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl) amino)-3-methyl-1-oxobutan-2-yl)(methyl)carbamoyl) oxy)-1-methylcyclooct-4-ene-1-carbonyl)-L-aspartate (1.6). Step 5: To bis(2-(trimethylsilyl)ethyl) ((1R,6R,E)-1-methyl-6-(((4-nitrophenoxy)carbonyl)oxy)cyclooct-4-ene-1-carbonyl)-L-aspartate (1.5, 296 mg, 0.45 mmol, 1.0 eq.) cooled to 0° C. were added (2S)—N-((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-

3-methyl-2-(methylamino)butanamido)butanamide (352 mg, 0.49 mmol, 1.1 eq., Monomethyl Auristatin E, Advanced ChemBlock,), DIPEA (173 mg, 1.34 mmol, 3.0 eq.), and HOBt (173 mg, 0.89 mmol, 2.0 eq.). The mixture was stirred at RT overnight and diluted with EtOAc. The mixture was washed with water twice and aq. $NH_4Cl$ solution, dried with $Na_2SO_4$, and filtered. The filtrate was concentrated under reduced pressure and purified by C18 Flash chromatography (100 g, ISCO gold capped C18 flash column) using a gradient of acetonitrile and water (0 to 100%) to afford 499 mg (90%) of bis(2-(trimethylsilyl) ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl) amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamoyl)oxy)-1-methylcyclooct-4-ene-1-carbonyl)-L-aspartate as an oil. (+esi)$[M+H]^+$=1244.3.

((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamoyl)oxy)-1-methylcyclooct-4-ene-1-carbonyl)-L-aspartic acid (TCO(asp)-MMAE). Step 6: To bis(2-(trimethylsilyl)ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl) pyrrolidin-1-yl)-3-methoxy-5-methyl-1-oxoheptan-4-yl) (methyl)amino)-3-methyl-1-oxobutan-2-yl)amino)-3-methyl-1-oxobutan-2-yl)(methyl)carbamoyl)oxy)-1-methylcyclooct-4-ene-1-carbonyl)-L-aspartate (1.6, 500 mg, 0.4 mmol, 1.0 eq.) in THF (10.0 mL) was added TBAF (1.0 M in THF). The mixture was stirred at RT overnight and purified directly by C18 Flash chromatography (100 g, ISCO gold capped C18 flash column) using a gradient of acetonitrile and water (0 to 100%) to afford 300 mg of solid which contained ~4 molar equivalents of tetrabutyl ammonium species. The mixture was dissolved in EtOAc (20 mL), washed with water (adjusted the pH to 3-5 with dilute HCl) six times, dried with $Na_2SO_4$, and filtered. The filtrate was concentrated to afford a glassy solid, which was treated with ether and concentrated to give a powdery solid free of the tetrabutyl ammonium by-product. (−esi)$[M-H]^-$=1042.1.

Example 6

TCO(asp)-Spacelink-Etoposide

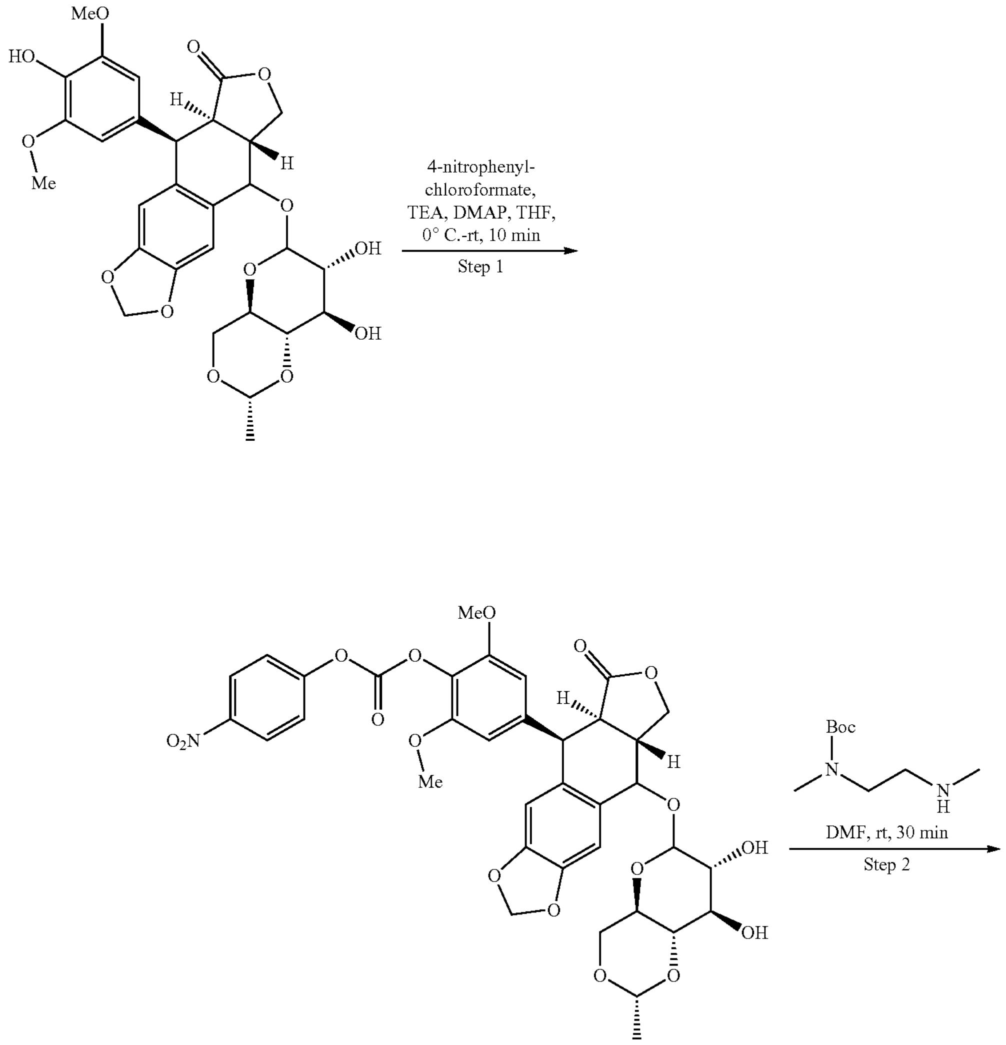

3.1

-continued
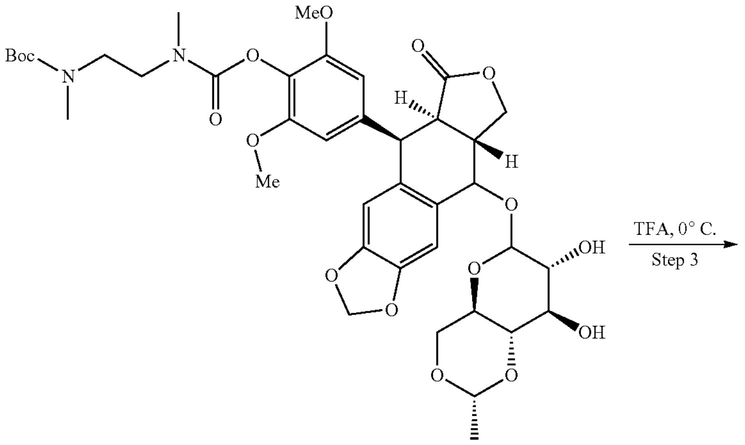
3.2
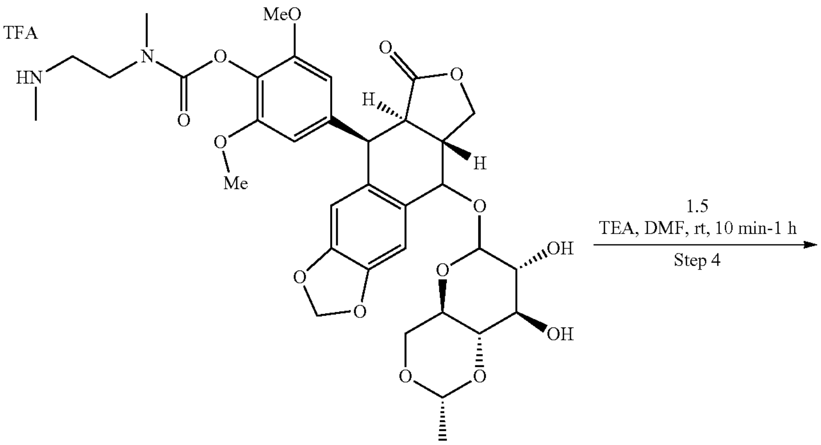
3.3
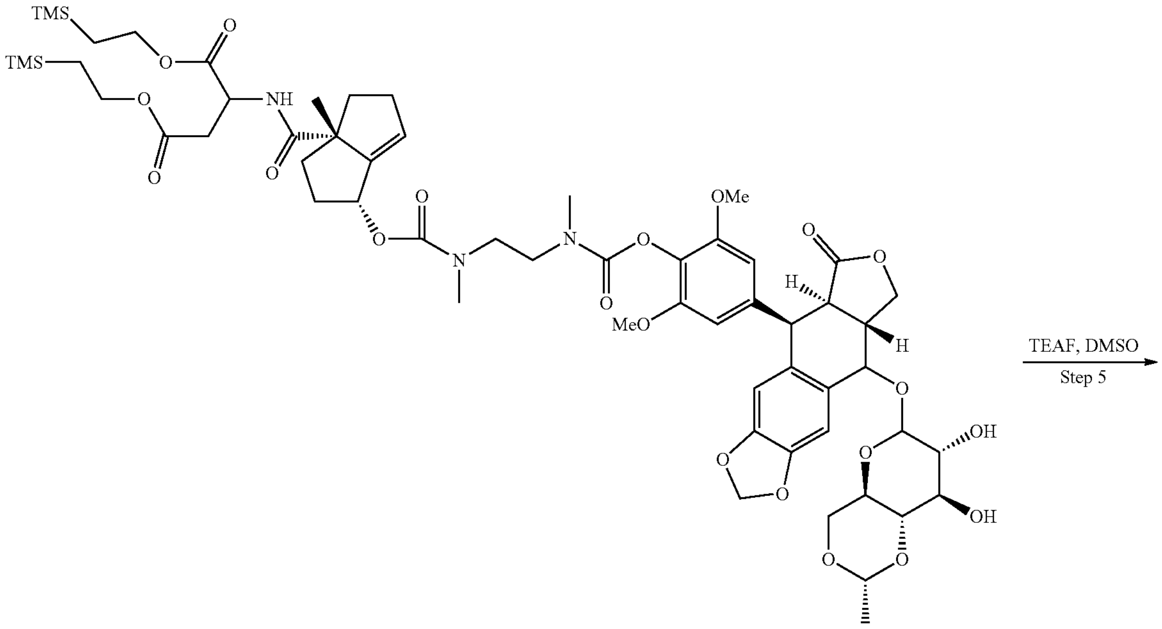
3.4
TCO(asp)-spacelink-Etoposide 4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl (4-nitrophenyl) carbonate (3.1). Step 1: Etoposide (1.5 g, 2.5 mmol, 1.0 eq., Etoposide, Combi-blocks QA-7668) was dissolved in dried THF. Triethylamine (1.1 mL, 7.6 mmol, 3.0 eq.) and DMAP (31 mg, 0.25 mmol, 0.1 eq.) were added. The reaction was cooled to 0° C. PNP-chloroformate (0.62 g, 3.1 mmol, 1.2 eq.) was dissolved in THF and added dropwise. The reaction was stirred at room temp. Upon completion as assessed by TLC, 1 mL of acetic acid was added and the reaction was stirred for 2 min. The precipitate was filtered, and the filtrate was concentrated under reduced pressure. The crude product was purified by column chromatography on silica gel using a gradient of 0-100% EtOAC in hexane to afford the desired product (2.25 g, 82% yield, 70% pure) that was still contaminated with unreacted Etoposide (~30% as assessed by $^1$H NMR).

tert-butyl (4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl) ethane-1,2-diylbis(methylcarbamate) (3.2). Step 2: Compound 3.1 was dissolved in DMF (10 mL) and mono-Boc protected N,N-dimethylethylene-diamine (532 mg, 2.82 mmol, 1.1 eq) was added. The reaction was stirred for 30 minutes. After completion the DMF was removed under reduced pressure and the crude product was purified by flash chromatography using a gradient of 0-100% EtOAC in hexanes to give the desired product (1.1 g, 53% yield). (+esi)M+$NH_3$+$H^+$=820.8.

4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl methyl(2-(methylamino)ethyl)carbamate 2,2,2-trifluoroacetate (3.3). Step 2: Compound 3.2 (460 mg, 0.573 mmol) from above step, was dissolved in DCM (10 mL) and cooled to 0° C. TFA (3 mL) was added and the reaction mixture was stirred for 1 hour and concentrated to dryness. The material was used directly in the next step without further purification.

bis(2-(trimethylsilyl)ethyl) ((1R,6R,E)-6-(((2-(((4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenoxy)carbonyl)(methyl)amino)ethyl)(methyl)carbamoyl)oxy)-1-methylcyclooct-4-ene-1-carbonyl)-L-aspartate (3.4). Step 4: Compound 3.3 (464 mg, 0.579 mmol, 1.1 eq) was dissolved in DMF (3.0 mL). HOBT (202 mg, 1.05 mmol, 2 eq) and DIPEA (0.275 mL, 1.58 mmol, 3 eq) were added. Compound 1.5 (350 mg, 0.526 mmol, 1.0 eq) was dissolved in DCM (2.0 ml) and added to the above solution. The reaction mixture was allowed to stir overnight at room temperature. The reaction was partitioned with EtOAc and aq ammonium chloride. The organic layer was washed with water, dried with sodium sulfate, filtered, and concentrated. The material was chromatographed 4×, first with a hexane: acetone gradient, then a hexane:EtOAc gradient, next with a DCM:EtOAC gradient and finally with DCM:ACN gradient. The final chromatography purged a close eluting impurity and the desired compound eluted around 70% ACN: 30% DCM. The fractions were pooled and concentrated to yield the desired target (94 mg, 17% yield). (+esi)M+$H^+$=1228.1.

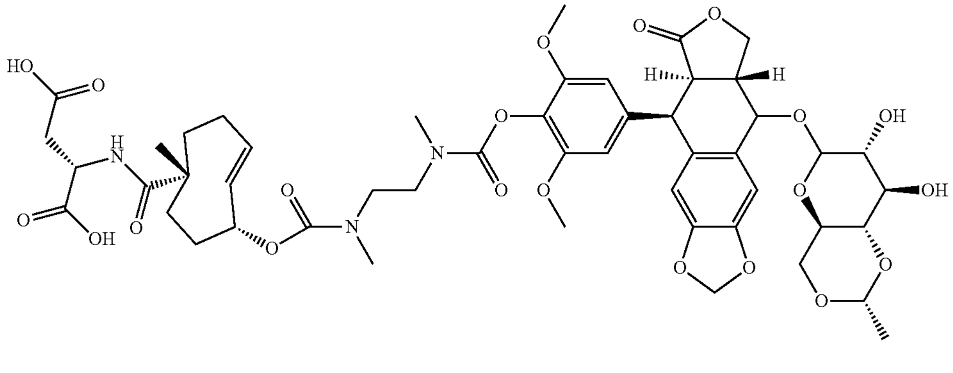

((1R,6R,E)-6-(((2-(((4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenoxy)carbonyl)(methyl)amino)ethyl)(methyl)carbamoyl)oxy)-1-methylcyclooct-4-ene-1-carbonyl)-L-aspartic acid (TCO (asp)-spacelink-Etoposide). Step 5: Compound 3.4 was dissolved in DMSO (1.0 ml). Tetraethyl ammonium fluoride×$H_2O$ (78.2 mg, 0.524 mmol) was added in one portion. The reaction was stirred for 105 minutes and worked-up based on the favorable LC-MS profile. The reaction was partitioned with EtOAc and water acidified to pH 4 with dilute HCl. The organic phase was washed with water 2× and then dried with sodium sulfate, filtered and concentrated. The residue was purified by prepHPLC (gradient of ACN in $H_2O$ with 0.1% formic acid). The fractions containing pure compound were pooled and lyophilized to obtain a white lyophilizate (42 mg, 55% yield). (−esi)[M−H]$^-$=1026.2.

Example 7

Ranibizumab—Cy5.5-TCO Conjugate

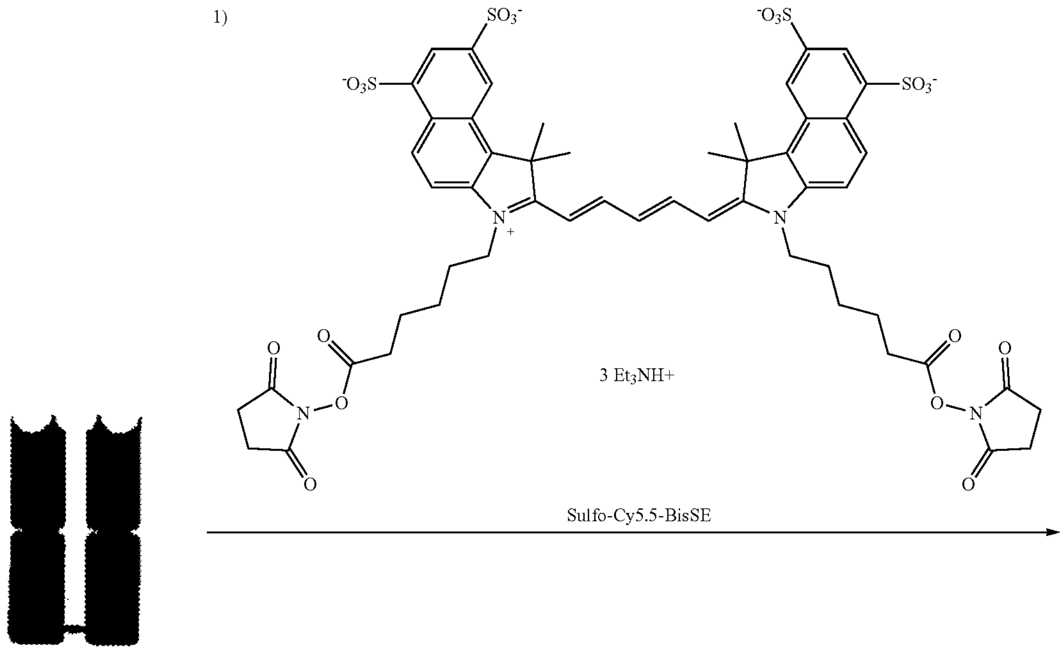

Ranibizumab

-continued
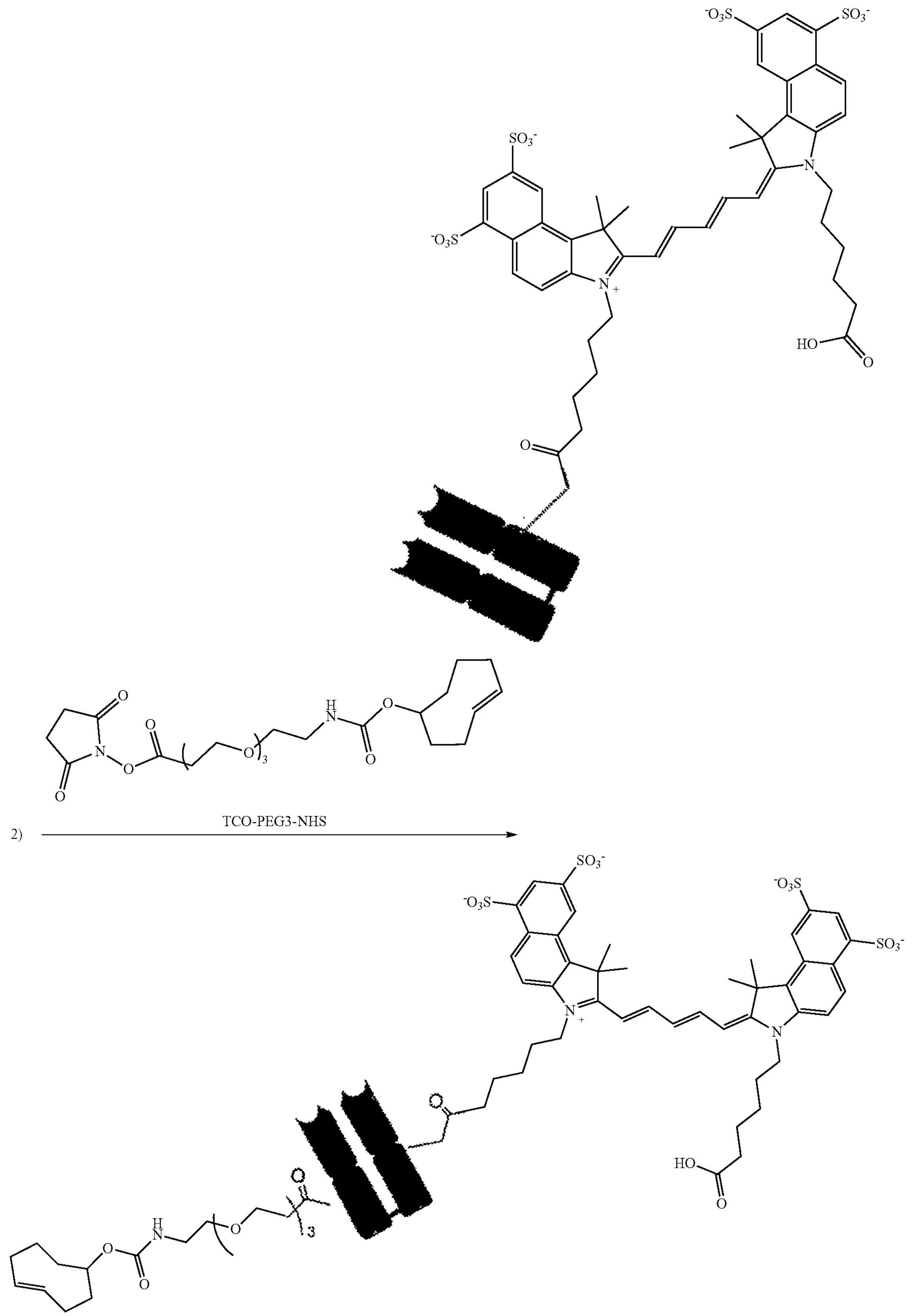

Ranibizumab solution in PBS, was pH adjusted with bicarbonate buffer (1 M) to pH 8.5. The fluorescent dye sulfonated-Cy5.5-bissuccinimidal ester (BisSE) (AAT Bio-Quest Cat #158) was dissolved in DMSO to 10 mM and added to the protein solution (75 μg dye per mg protein, 750 μg total, ~2.5 equiv). The reaction mixture was rotated at room temperature for 1 hour. The product was purified by buffer exchange with a PD-10 Desalting column, equilibrated with PBS, per the manufacturer's instructions. The product was collected and the protein concentration and labeling ratio calculated by measuring the UV absorbance and using the Degree of Labeling Calculator (https://www.aatbio.com/tools/degree-of-labeling-calculator). The ratio of labeling was 1.5. 1 mg was retained and diluted to 3.1 mg/mL with PBS, followed by filtration with 0.22 μm syringe filter to sterilize the product. The endotoxin was measured at 3.8 EU/mL. The remaining material was used for preparing the TCO conjugate.

Ranibizumab-Cy5.5 conjugate solution in PBS (0.71 mL at 8.5 mg/mL), was pH adjusted with bicarbonate buffer (1 M) to pH 8.5. The trans-cyclooctene-PEG3-NHS (SiChem #SC-8406) (10 mM in DMSO) was added to the solution (~38 μg reagent per mg protein, ~225 μg total, ~3.8 equiv). The reaction mixture was rotated at room temperature for 1 hour. The product was purified by buffer exchange with a PD-10 Desalting column, equilibrated with PBS, per the manufacturer's instructions. The product was collected. A sample of the conjugate was treated with a Cy3-tetrazine (AAT Bioquest Cat #910) and the protein concentration and labeling ratio calculated by measuring the UV absorbance and using the Degree of Labeling Calculator (https://www.aatbio.com/tools/degree-of-labeling-calculator). The ratio of labeling was 1.8. The solution was sterilized by filtration with 0.22 μm syringe filter. The final product yielded 0.71 mL of solution with protein concentration of 5.4 mg/mL. The endotoxin was measured at 6.5 EU/mL.

Cy3-tetrazine

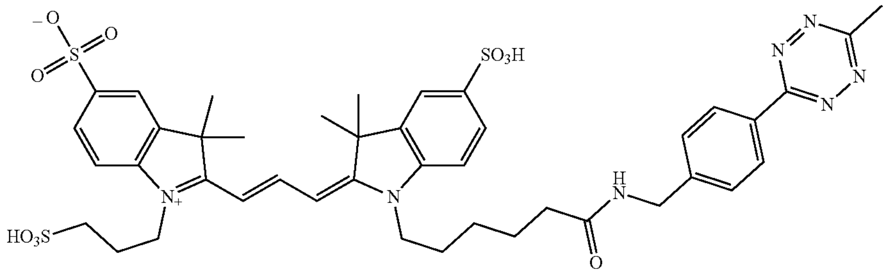

Example 8

Trans-Cyclooctene-Trastuzumab Conjugate

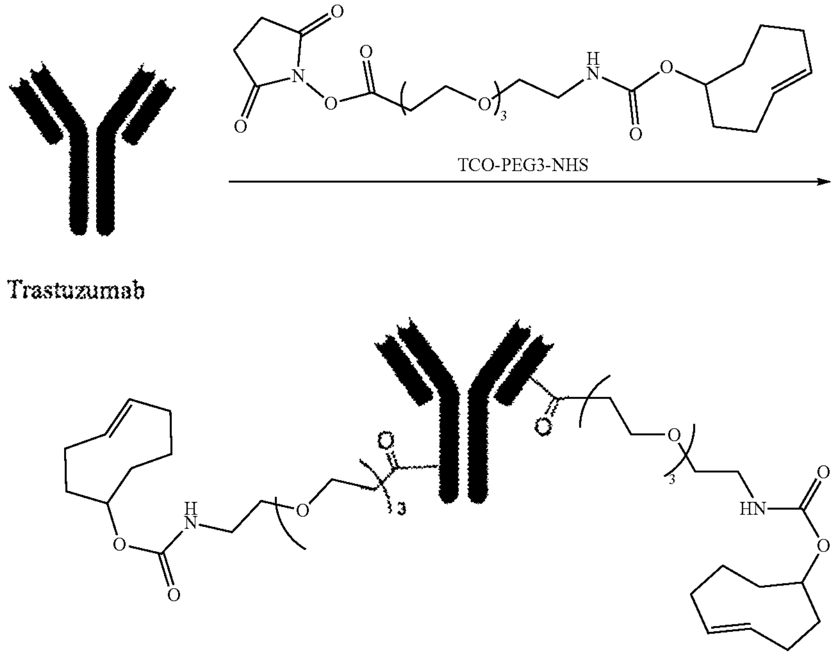

A solution of antibody, such as trastuzumab, (2.51 mg/mL) in aqueous buffer (50 mM potassium phosphate, 50 mM sodium chloride, 2 mM ethylenediaminetetraacetic acid disodium saltPBS), pH 7.46.5, is incubated with a 5-fold molar excess of trans-cyclooctene-NHS ester derivatized carbonate in dimethylacetamide (DMA). The reaction is allowed to proceed at ambient temperature for 1 hour. The reaction mixture was then applied to a NAP-10 column, equilibrated with PBS, and then eluted with fresh PBS, pH 7.4, upon completion, purified by gel filtration column. The concentration of the conjugate is determined spectrophotometrically using the known extinction coefficients for the antibody. Quantification of the effective concentration of TCO can be measured by treatment of a sample of the conjugate with an appropriate tetrazine-functionalized fluorescent dye, followed by separation by SDS-PAGE and measurement of the fluorescent signal associated with the protein band.

Example 9

TCO-Spacelink-SN-38

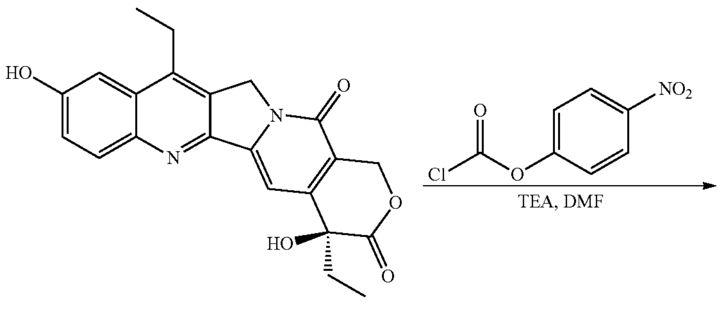

1

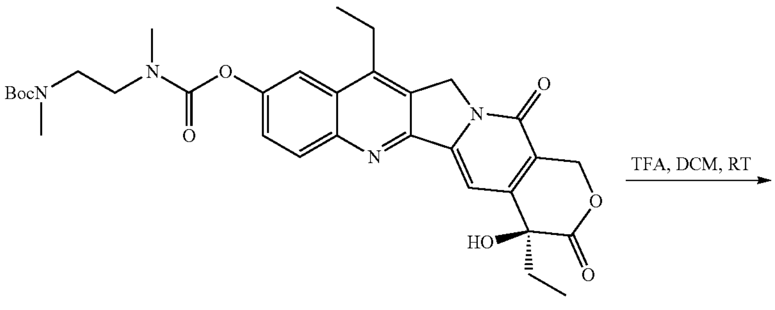

2

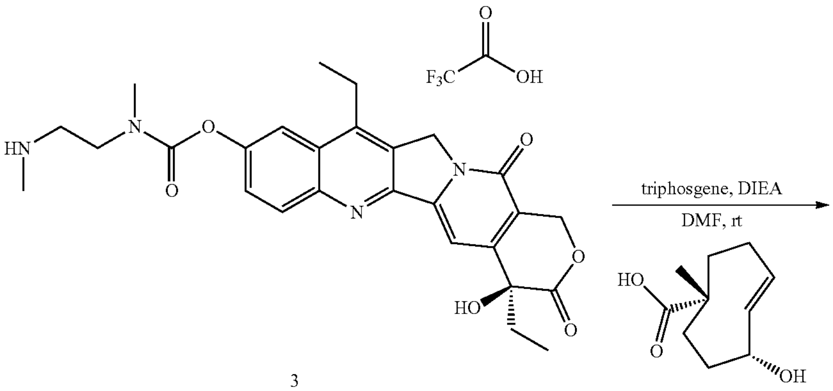

3

-continued
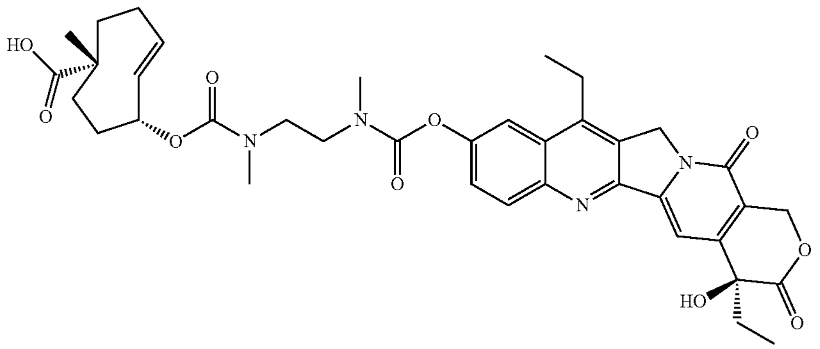
4
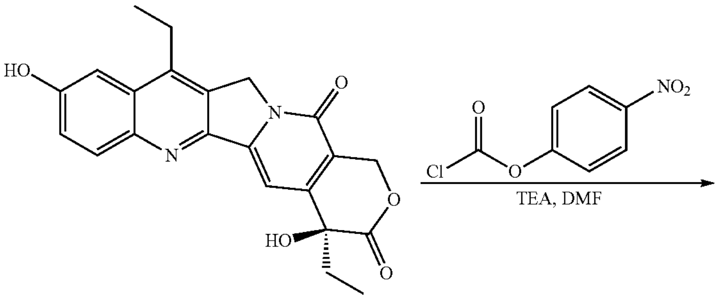
1
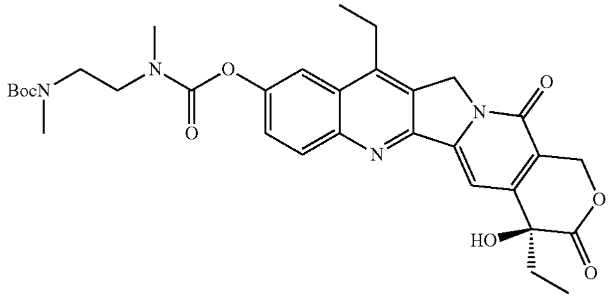
2

(S)-tert-butyl (4,11-diethyl-4-hydroxy-3,14-dioxo-3,4,12,14-tetrahydro-1H-pyrano[3',4':6,7]indolizino[1,2-b]quinolin-9-yl) ethane-1,2-diylbis(methylcarbamate). To a solution of 7-ethyl-10-hydroxycamptothecin (SN-38, 660 mg, 1.68 mmol) in DMF (30 mL) was added 4-nitrophenyl chloroformate (336 mg, 1.68 mmol) and $Et_3N$ (708 µL, 504 mg, 5.04 mmol). The mixture was stirred at room temperature for 1.5 hrs. To the mixture was added $Et_3N$ (708 µL, 504 mg, 5.04 mmol) and 4-nitrophenyl chloroformate (336 mg, 1.68 mmol). The mixture was stirred for another 20 mins and added a solution of tert-butyl methyl[2-(methylamino)ethyl]carbamate (948 mg, 5.04 mmol) in DMF (10.68 mL). The mixture was stirred at room temperature for 1 h and added water (20 mL). The reaction mixture was extracted with EtOAc (4*50 ml). The organic phase was washed with water (3*20 mL), dried ($Na_2SO_4$) and concentrated. The residue was purified with silica gel chromatography (DCM to 10% MeOH in DCM) to give desired product (343 mg, yield: 41%) as a slightly yellow solid. LCMS: (m/z, $C_4H_9N_4O_8$)=607.2 $[M+H]^+$.

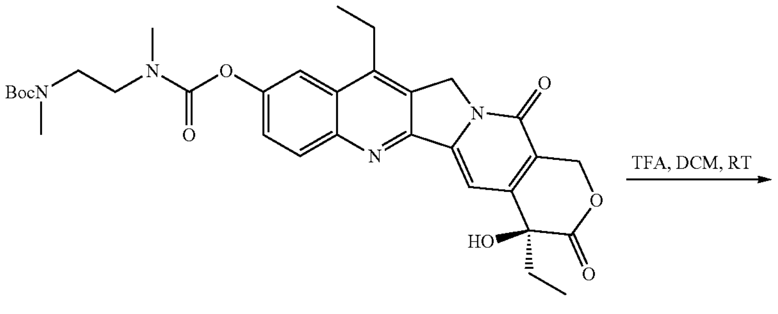

2

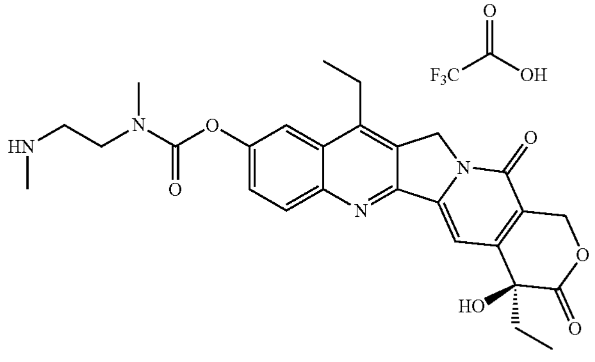

3

(S)-4,11-diethyl-4-hydroxy-3,14-dioxo-3,4,12,14-tetrahydro-1H-pyrano[3',4':6,7]indolizino[1,2-b]quinolin-9-yl methyl(2-(methylamino)ethyl)carbamate 2,2,2-trifluoroacetate. To a stirred mixture of compound 2 (343 mg, 0.57 mmol) in DCM (3 mL) was added TFA (0.5 mL). The mixture was stirred at room temperature for 2 hrs. The resulting mixture was concentrated and dried in the vacuum to give crude compound 3 (280 mg) as a white solid. The residue was used in next step without further purification. LCMS: (m/z, $C_{29}H_{31}N_4F_3O_8$)=507.1 $[M+H]^+$.

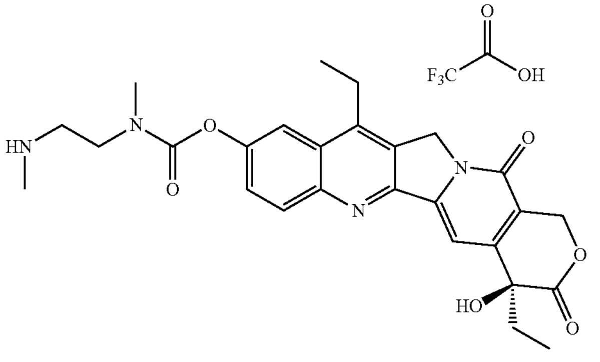

3

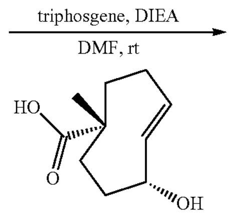

-continued

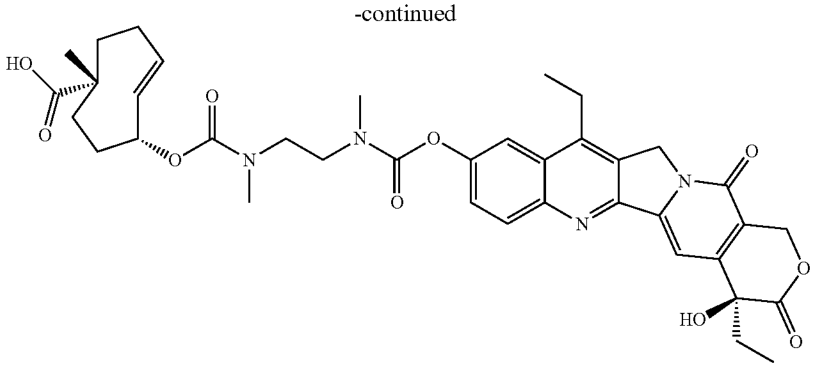

4

TCO-spacelink-SN-38. To a stirred mixture of triphosgene (47.5 mg, 0.16 mmol) in DMF (4 mL) was added (1R,6R,E)-6-hydroxy-1-methylcyclooct-4-ene-1-carboxylic acid (82.8 mg, 0.45 mmol) and DIPEA (116.0 mg, 0.9 mmol). The mixture was stirred at room temperature for 30 mins. The mixture was added to a mixture of compound 3 (280.0 mg, 0.45 mmol) and DIPEA (116.0 mg, 0.9 mmol) in DMF (3 mL). The resulting mixture was stirred at room temperature for 12 hours. The mixture was purified by PREP-HPLC (($CH_3CN/H_2O$(FA)) 0% to 70%) to give the desired product (105 mg, yield 32%). LCMS: (m/z, $C_{39}H_{46}N_4O_{12}$)=717.4 $[M+H]^+$.

Example 10

TCO(asp)-Spacelink-SN-38

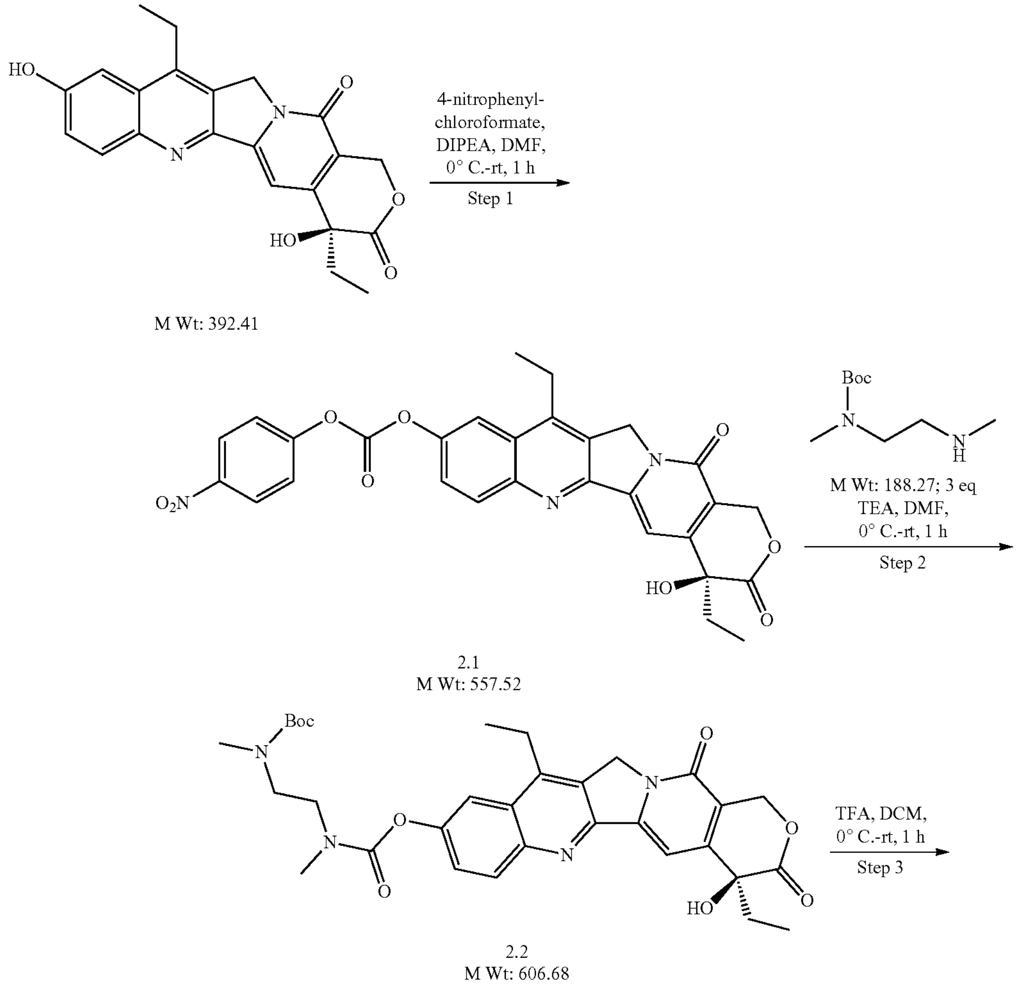

-continued

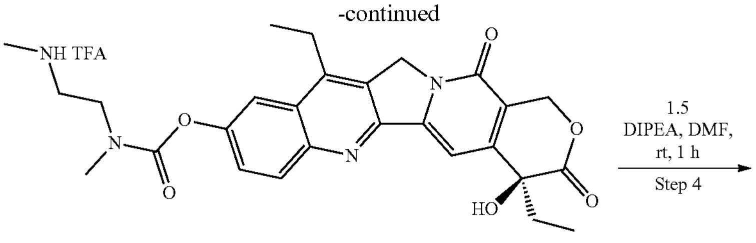

2.3
M Wt: 603.58

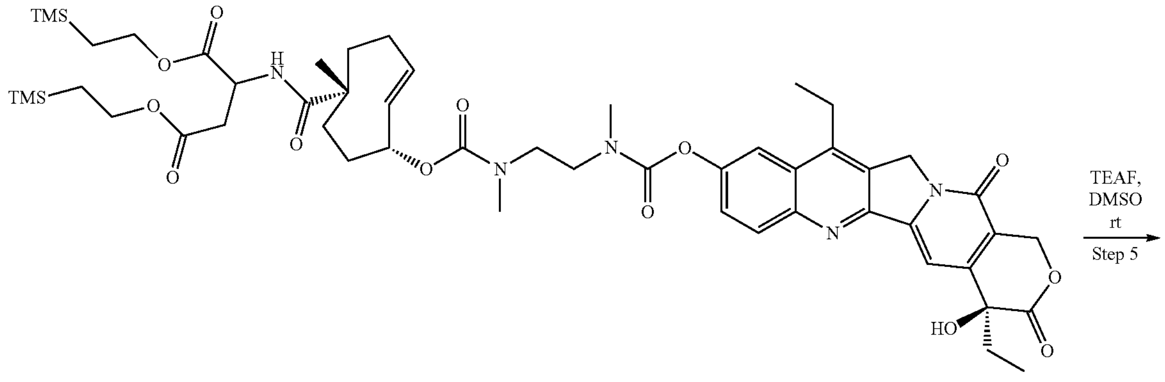

2.4
M Wt: 1032.35

TCO(asp)-spacelink-SN-38

(S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (2.1). Step-1: 4-Nitrophenyl chloroformate (771 mg, 3.82 mmol) was added into a mixture of SN-38 (1.25 g, 3.19 mmol, Advanced ChemBlocks Cat #10250, Lot 10602) and DIPEA (1.25 mL, 7.50 mmol) in DMF (20 mL) at 0° C. The mixture was stirred at room temperature for 1 h. Upon completion of reaction by TLC, the mixture was diluted with EtOAc, washed with water, brine, and dried over $Na_2SO_4$, concentrated, and purified by silica gel using a gradient 0-100% EtOAC in hexanes to afford the desired product.

(S)-tert-butyl (4,11-diethyl-4-hydroxy-3,14-dioxo-3,4,12,14-tetrahydro-1H-pyrano[3',4':6,7]indolizino[1,2-b]quinolin-9-yl) ethane-1,2-diylbis(methylcarbamate) (2.2). Step-2: The compound from above (2.1) was dissolved in DMF (10 mL) and mono-Boc protected N,N-dimethylethylene-diamine (1.76 g, 9.37 mmol, 2.5 eq) was added. The reaction was stirred for 30 minutes. After completion, the DMF was removed under reduced pressure and the crude product was purified by flash chromatography (ethyl acetate 100%) to give desired product (1.3 g, 57% yield over 2 steps). (+esi)$[M+H]^+$=607.5.

(S)-4,11-diethyl-4-hydroxy-3,14-dioxo-3,4,12,14-tetrahydro-1H-pyrano[3',4':6,7]indolizino[1,2-b]quinolin-9-yl methyl(2-(methylamino)ethyl)carbamate 2,2,2-trifluoroacetate (2.3). Step 3: Compound 2.2 (514 mg, 0.847 mmol) from above was dissolved in DCM (10 mL) and cooled to 0° C. TFA (2.0 mL) was added and the mixture was stirred for 20 minutes and then brought to room temperature for 1 hour. The reaction mixture was concentrated to dryness, redissolved in dichloroethane and reconcentrated. The crude material was used in the subsequent step without further purification.

bis(2-(trimethylsilyl)ethyl) ((1R,6R,E)-6-(((2-(((((S)-4,11-diethyl-4-hydroxy-3,14-dioxo-3,4,12,14-tetrahydro-1H-pyrano[3',4':6,7]indolizino[1,2-b]quinolin-9-yl)oxy)carbonyl)(methyl)amino)ethyl)(methyl)carbamoyl)oxy)-1-methylcyclooct-4-ene-1-carbonyl)-L-aspartate (2.4). Step 4: Compound 2.3 (513 mg, 0.827 mmol, 1.1 eq) was dissolved in DMF (5.0 mL). DIPEA (0.393 μL, 2.26 mmol, 3 eq) and HOBT (288 mg, 1.50 mmol, 2 eq) were added. Then intermediate 1.5 (500 mg, 0.752 mmol, 1.0 equivalent) was added as a solution in a minimal amount of DCM. The reaction mixture was stirred overnight at room temperature and then partitioned with EtOAc and aq ammonium chloride. The organic phase was washed with water, dried with sodium sulfate, filtered and concentrated. The residue was dissolved in a minimal amount of DCM and loaded onto a 40 g silica gel column (ISCO) for purification by flash chromatography using a gradient of 0-100% EtOAc in hexanes. The desired fraction eluted at 100% EtOAc, just after a close eluting impurity (M+H+=918.5, 156 mg, 23% yield) that lacked the diamine spacer. The fractions containing of the latest eluting peak and target compound were combined and concentrated to yield the product (406 mg, 52.3% yield). (+esi)$[M+H]^+$=1032.4.

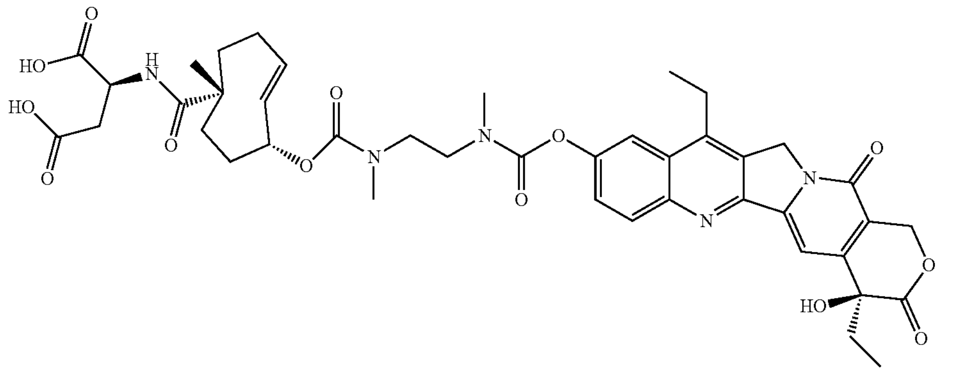

((1R,6R,E)-6-(((2-(((((S)-4,11-diethyl-4-hydroxy-3,14-dioxo-3,4,12,14-tetrahydro-1H-pyrano[3',4':6,7]indolizino[1,2-b]quinolin-9-yl)oxy)carbonyl)(methyl)amino)ethyl)(methyl)carbamoyl)oxy)-1-methylcyclooct-4-ene-1-carbonyl)-L-aspartic acid (TCO(asp)-spacelink-SN-38). Step 5: Compound 2.4 (272 mg, 0.263 mmol) was dissolved in DMSO (3.0 mL) in a 40 mL vial equipped with a septum lined capped. Tetraethylammonium fluoride×$H_2O$ (393 mg, 2.63 mmol) was added. The reaction immediately turned dark green. After 2 hours, the reaction was diluted with acetonitrile containing 0.1% TFA and then loaded onto an equilibrated C18 flash gold column (ISCO, 15.5 g) and eluted with a gradient of 10-100% ACN (w/0.1% TFA) in water (w/0.1% TFA). The desired product eluted around 45% ACN. The two fractions containing the product were lyophilized over two days and characterized by HPLC, which indicated some other close eluting impurities. The product was further purified by preparative HPLC using the same mobile phase conditions. The pure fractions were combined and concentrated to obtain the desired product as an orange lyophilisate. $^1$H NMR indicated excess water was present, so the sample was suspended in acetonitrile and concentrated to dryness, yielding a readily transferrable orange powder (62 mg, 25% yield as the monotrifluoroacetate salt). $^1$H NMR indicated the presence of TFA. (−esi) $[M-H]^-$=830.5.

Example 11

AB25409

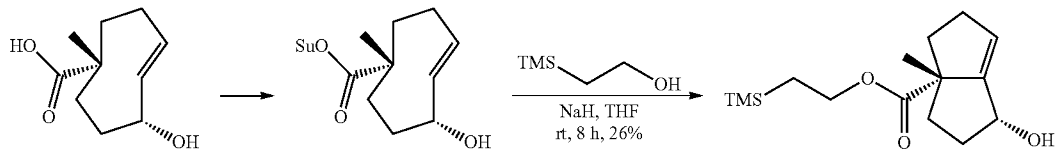

1 2 3

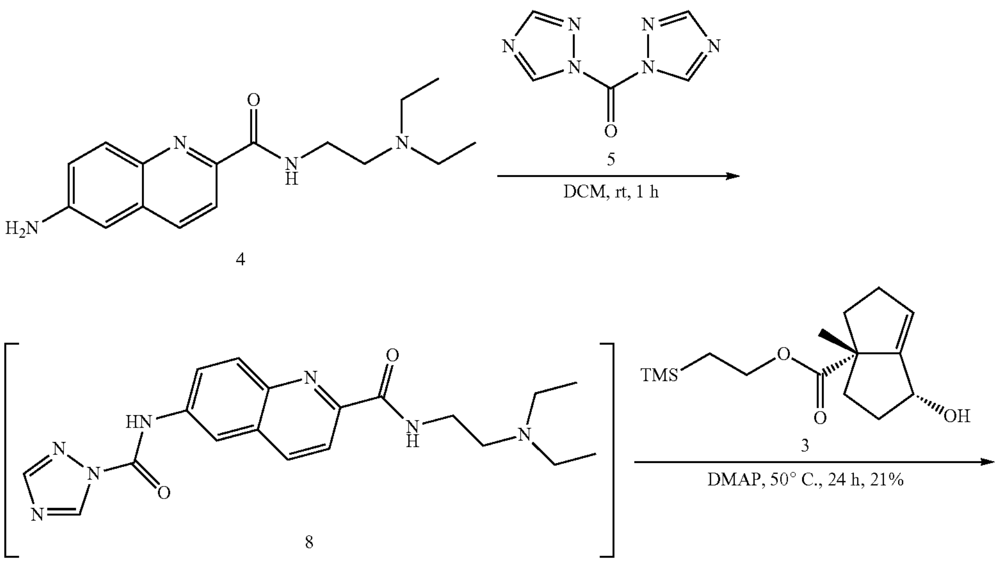

4 5 8 3

-continued

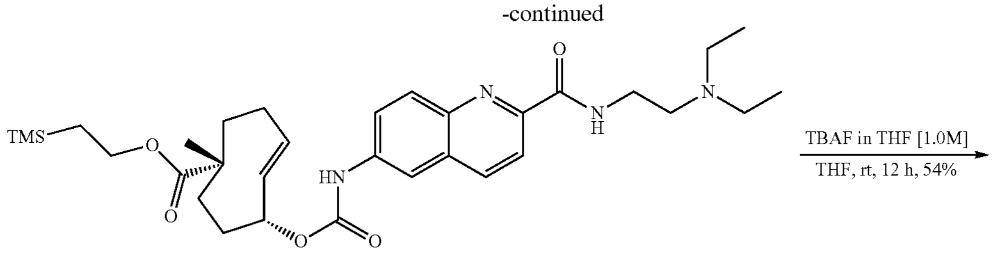

7

AB25409

General Procedure for the Preparation of Compound 2. Compound 2 was prepared according to the literature procedure (Chem. Sci., 2021, 12, 1259).

General Procedure for the Preparation of Compound 3. To a flame dried round bottom flask was charged sodium hydride (60%, 399 mg, 9.96 mmol, 3.0 eq.) and dry THF (10 mL). The mixture was cooled to 0° C. and TMS-ethanol (3.33 mL, 23.2 mmol, 7.0 eq) was added dropwise at 0° C. The mixture was stirred for 30 min and a solution of compound 2 (934 mg, 3.32 mmol, 1 eq.) in anhydrous THF (3 mL) was added slowly via a syringe at 0° C. under nitrogen atmosphere. The reaction was warmed to rt and the stirring was continued for 8 h. The reaction was monitored by TLC for consumption of starting material. The reaction was quenched by pouring the reaction mixture into ice water (20 mL) and extracted with ethyl acetate (3×50 mL). The combined extracts were washed with sat. $NH_4Cl$ and dried over $Na_2SO_4$. After concentration, the residue was purified by flash chromatography using a gradient of ethyl acetate in hexanes (0-20%) to give compound 3 mixed with TMS-ethanol. The compound was then kept on high vacuum at 40° C. for 30 min to give compound 3 (405 mg, 26%). TLC: PE/EA=¼. Rf (compound 2)=0.2. Rf (product, 3)=0.5

General Procedure for the Preparation of Compound 7. To a solution of compound 4 (109 mg, 0.38 mmol, 1.0 eq) in dry DCM (2 mL) was added compound 5 (63 mg, 0.38 mmol, 1.0 eq). The reaction mixture was stirred for 1 h. The LCMS analysis of reaction mixture showed a peak at m/z=381.90 which confirms the formation of intermediate compound 6. To the above reaction mixture was added DMAP (93 mg, 0.76 mmol, 2.0 eq) followed with a solution of compound 3 (108 mg, 0.38 mmol, 1.0 eq.) in THF (1 mL). The resulting reaction mixture was heated at 50° C. for 24 h. The reaction was monitored by HPLC and LCMS. The reaction mixture was concentrated to give a crude, which was purified by silica gel flash chromatography using a gradient of MeOH in DCM (0-5%) to give compound 7 (47 mg, 21%). TLC: MeOH/DCM=0.05/1. Rf (compound 4)=0.2. Rf (compound 6)=0.3. Rf (product, 7)=0.4. LCMS of Compound 6: 381.90 [M+H]+. LCMS of Compound 7:596.90 [M+H]+

General Procedure for the Preparation of Compound AB25409. To a solution of compound 7 (47 mg, 0.079 mmol, 1.0 eq) in THF (3 mL) was added TBAF (1.0 M in THF, 1.2 mL, 1.2 mmol, 15 eq). The reaction mixture was stirred at rt for 15 h. The reaction was monitored by LCMS and HPLC. The solvent was removed. The crude mixture was purified by preparative HPLC using 5 to 100% ACN in water with 0.1% TFA. After lyophilization, the desired compound AB25409 (21 mg, 54%) was obtained as light yellow solid. LCMS: 497.0 [M+H]+; $^1$H NMR (400 MHz, CD3OD) δ 9.85 (s, 1H), 8.34 (d, J=8.2 Hz, 1H), 8.20 (s, 1H), 8.14 (d, J=8.4 Hz, 1H), 8.07 (d, J=9.0 Hz, 1H), 7.86 (d, J=8.4 Hz, 1H), 5.99-6.14 (m, 1H), 5.71-5.77 (m, 1H), 5.29 (s, 1H), 3.86 (br t, J=5.9 Hz, 2H), 3.45 (br t, J=5.4 Hz, 2H), 3.30-3.35 (m, 4H), 2.27-2.31 (m, 2H), 2.05-2.23 (m, 3H), 1.70-2.02 (m, 3H), 1.36 (t, J=7.3 Hz, 6H), 1.15 (s, 3H) ppm.

Example 12

TCO-Spacelink-Etoposide

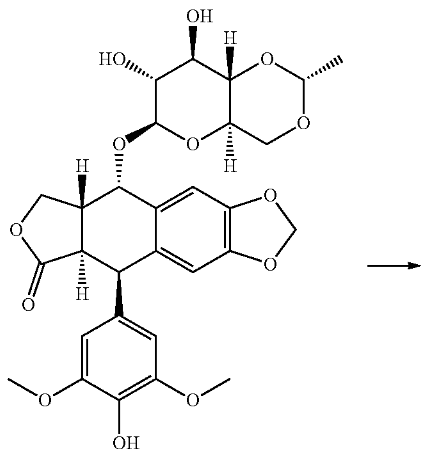

Etoposide

-continued
-continued
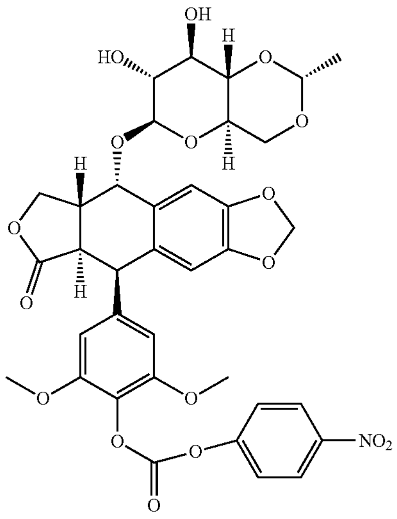
1
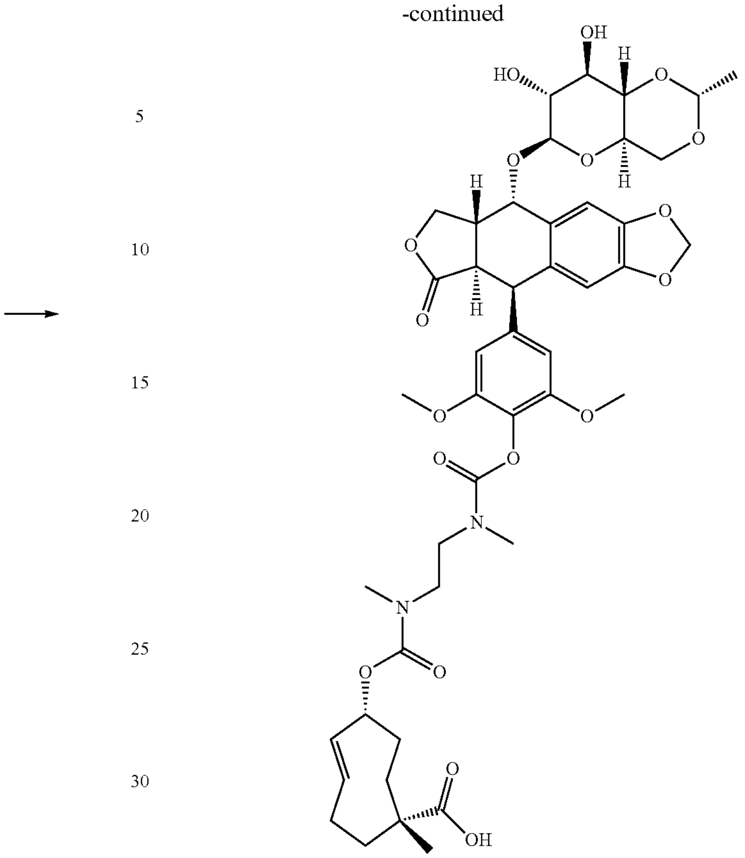
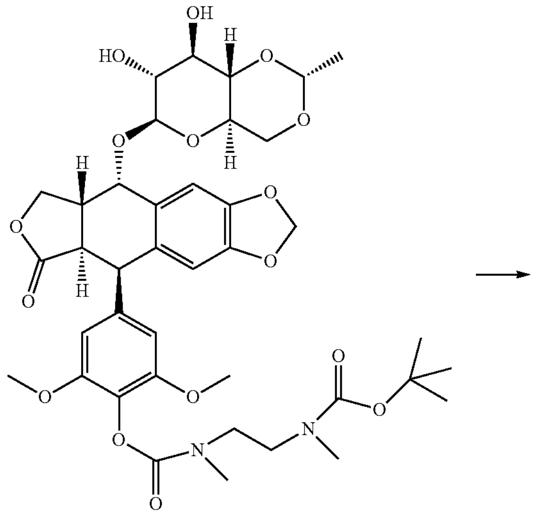
2
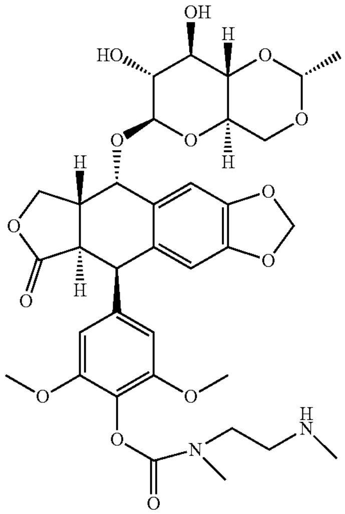
3
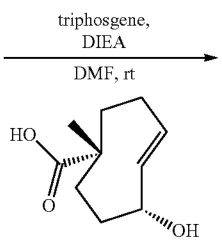
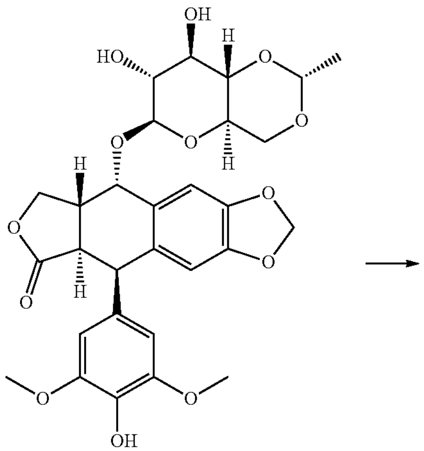
Etoposide -continued

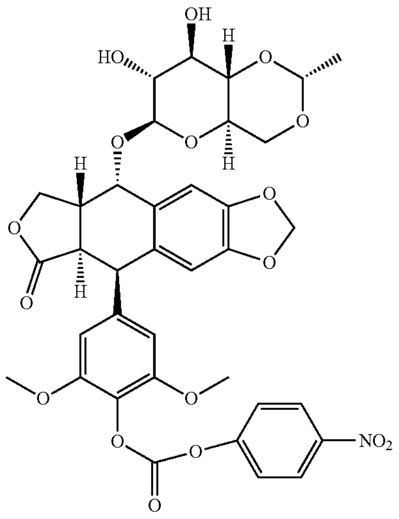

1

-continued

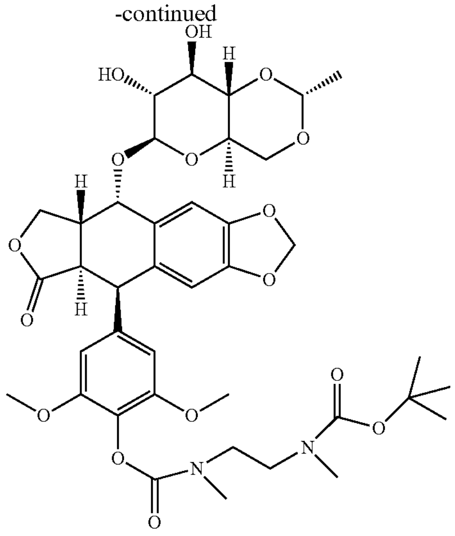

2

4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl (4-nitrophenyl) carbonate. To a solution of Etoposide (1.0 g, 1.7 mmol) and TEA (2.5 g, 25 mmol) in anhydrous THF (35 mL) was added a solution of, 4-nitrophenyl chloroformate (0.39 g, 1.95 mmol) in anhydrous THF (15 mL). The reaction mixture was stirred at room temperature overnight. The mixture was filtered and concentrated under reduced pressure. The residue was purified by flash column chromatography (silica gel, DCM/$CH_3CN$ 2/1) to give compound 1 (0.78 g, 60% yield). LCMS: (m/z, C36H35NO17)=754.2 $[M+H]^+$; observe 754.1.

tert-butyl (4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl) ethane-1,2-diylbis(methylcarbamate). To a solution of etoposide carbonate compound 1 (1.2 g, 1.6 mmol) in DMF (10 mL) was added N-Boc, N,N'-dimethyl-ethylenediamine (450 mg, 2.37 mmol), DIPEA (0.68 mL, 3.98 mmol), and DMAP (250 mg, 2.04 mmol) and the reaction mixture was stirred at 60° C. for 3 hrs. The mixture was purified by reverse phase chromatography (C18, ACN/$H_2O$ (FA) 0%-100%) to give compound 2 (650 mg, yield 51%). LCMS: (m/z, C39H50N2O16)=825.3 $[M+Na]^+$; observe 826.1.

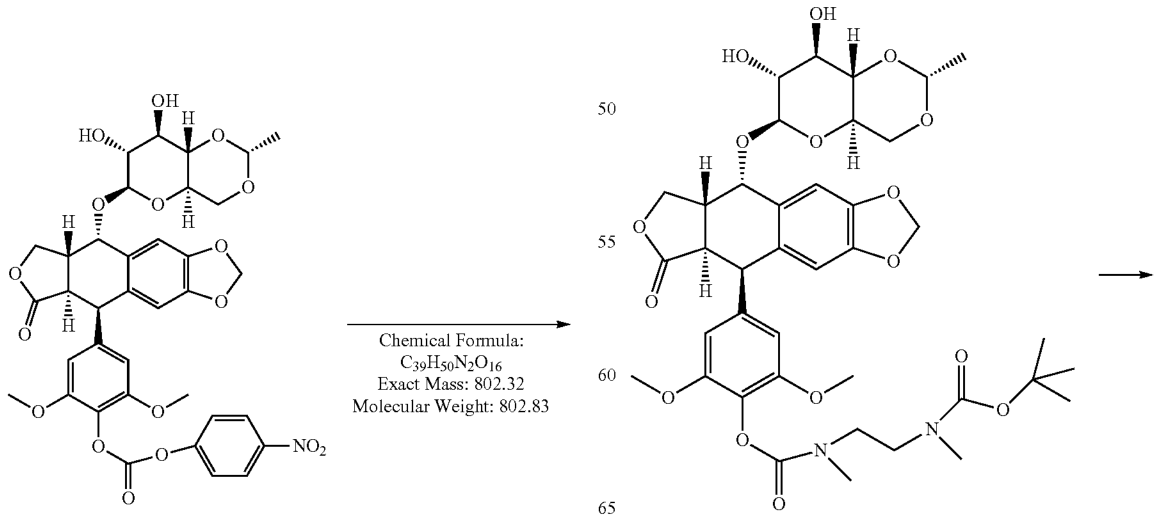

1

2

-continued

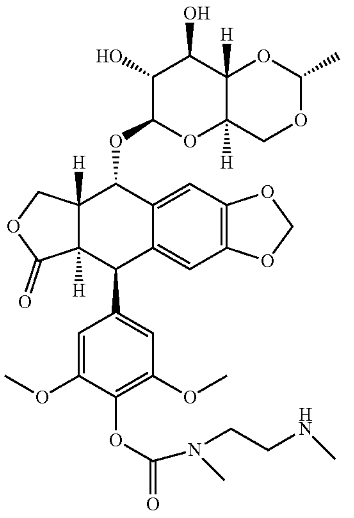

3

4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl methyl(2-(methylamino)ethyl)carbamate. To a solution of compound 2 (650 mg, 0.81 mmol) in DCM (10 mL) cooled in an ice-water bath was added TFA (1 mL). The mixture was stirred at 0° C. for 6 hrs. The reaction mixture was concentrated under vacuum. The residue was purified by reverse phase chromatography (C18, ACN/$H_2O$ (FA) 0%-100%) to give compound 3 (350 mg, yield 61%). LCMS: (m/z, C34H42N2O14)=703.3 [M+H]$^+$; observe 703.1.

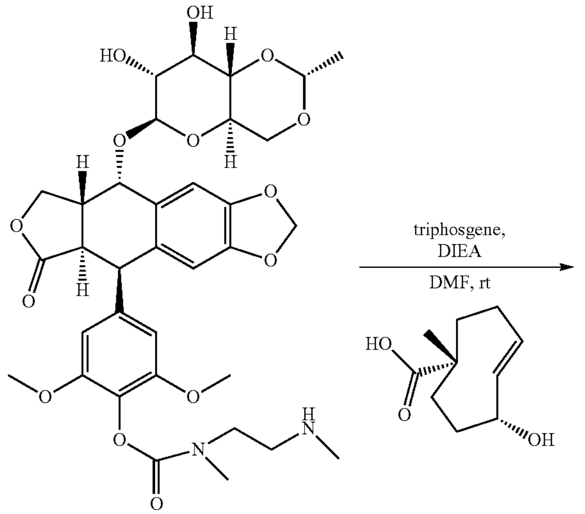

3

-continued

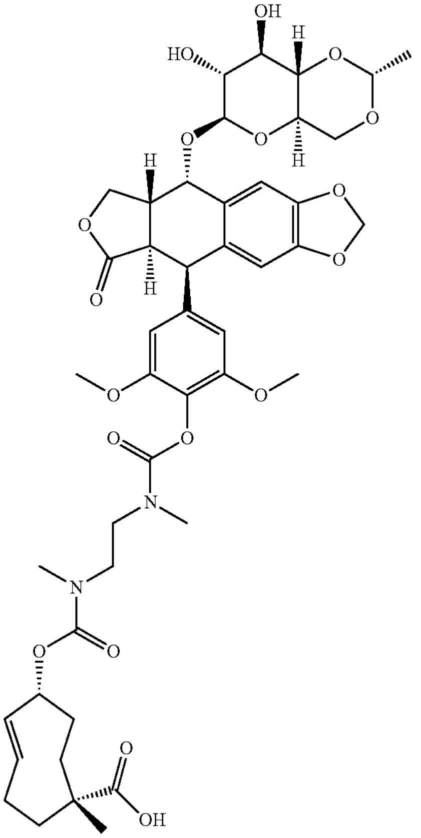

TCO-spacelink-Etoposide. To a solution of TCO (80 mg, 0.434 mmoL) in THF (5 mL) was added Triphosgene (52.5 mg, 0.177 mmoL) and DMAP (130 mg, 1.07 mmoL). The mixture was stirred at room temperature for 30 mins. The mixture was added to a solution of compound 3 (300 mg, 0.427 mmol) and DIPEA (117 mg, 0.9 mmol) in DMF (2 mL) and stirred at room temperature for 5 mins. The mixture was warmed to 50° C. and stirred for another 2 hrs. To the mixture was added EtOAc (20 mL) and HCl (10 mL, 1N in H2O). The organic phase was separated and concentrated. The residue was purified by reverse phase chromatography (C18, ACN/$H_2O$ (FA) 0%-100%) to give TCO-spacelink-Etoposide (105 mg, yield 26.9%). LCMS: (m/z, C45H56N2O18)=911.4 [M−H]$^-$; observe 911.3.

Example 13

TCO(asp)-Exatecan

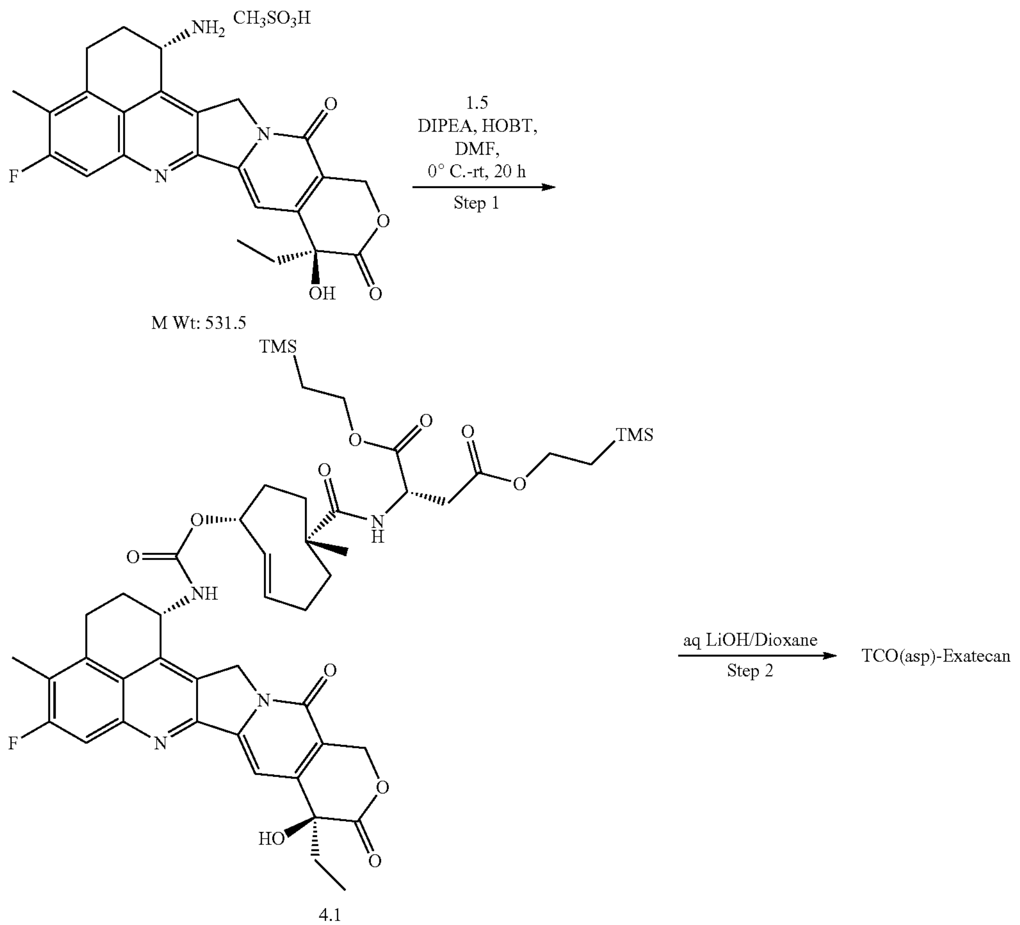

M Wt: 531.5

4.1
M Wt: 961.24

TCO(asp)-Exatecan bis(2-(trimethylsilyl)ethyl) ((6R,E)-6-((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl) carbamoyl)oxy)-1-methylcyclooct-4-ene-1-carbonyl)-L-aspartate (4.1). Step 1: Compound 1.5 (250 mg, 0.376 mmol, 1.0 eq) was dissolved in DMF (~5 mL) and cooled to 0° C. in an ice-water bath. To the solution was added Exetecan mesylate (220 mg, 0.414 mmol, 1.1 eq, Advanced Chemblocks Cat #10484, Lot 100981), DIPEA (200 μL, 1.1 mmol, 3 eq), and wetted HOBt (144 mg, 0.752 mmol, 2 eq, ~80% purity). The resulting slurry was allowed to warm to room temperature under ambient conditions. After 20 hours, analysis of the reaction by LCMS indicated near complete consumption of the starting materials. The reaction was partitioned with EtOAc and water. The organic phase was washed with water (2×), aq ammonium chloride (1×) and brine. There was some insoluble solid that was removed by filtration. The organic phase was dried with sodium sulfate, filtered and concentrated. The resulting dark brown/black oily residue was dissolved in a minimal amount of DCM and loaded onto a hexane flushed silca gel column (24 g, gold-capped ISCO) and eluted with 0-100% EtOAc in hexanes to afford the desired compound as a sticky grey/green solid (240 mg, 66% yield). (+ESI)[M+H]$^{-}$=962.2.

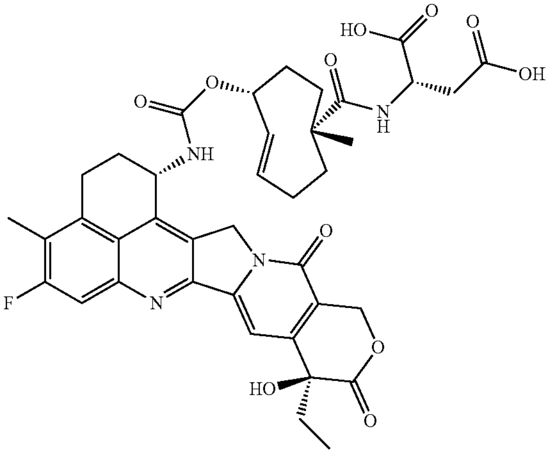

((6R,E)-6-((((1S,9S)-5-fluoro-9-hydroxy-4,9-dimethyl-10,13-dioxo-2,3,9,10,13,15-hexahydro-1H,12H-benzo[de]pyrano[3',4':6,7]indolizino[1,2-b]quinolin-1-yl)carbamoyl)oxy)-1-methylcyclooct-4-ene-1-carbonyl)-L-aspartic acid (TCO(asp)-Exetecan). Step 2: Compound 4.1 (150 mg, 0.156 mmol, 1.0 eq) was dissolved in 1,4-dioxane (~5 mL). To the solution was added 2.0 M aq LiOH (500 μL, 1.00 mmol, 6.4 eq). Analysis after 1 hour by LCMS indicates the presence of starting material, monoester intermediate, product and by-product. An additional 500 μL of the same LiOH solution was added. After another 30 minutes, LCMS indicated the starting material was consumed and the reaction was an approximate equal ratio of desired compound and side-product. The reaction mixture was acidified first with acetic acid and then with dilute HCl to adjust the pH to 1-2. The product was extracted with EtOAc (5×). The organic extracts were combined, dried with sodium sulfate, filtered and concentrated. The off-white solid was subject to purification by prepHPLC which yielded two separate compounds with identical mass spectra and similar $^1$H NMR spectra. The early eluting peak was labeled as peak 2 (16 mg, 13% yield). (−ESI)[M−H]−=759.4. HPLC (tr=8.73 min). The late eluting peak was labeled as peak 1 (20 mg, 17% yield). (−ESI)[M−H]−=759.4. HPLC (tr=8.96 min).

Example 14

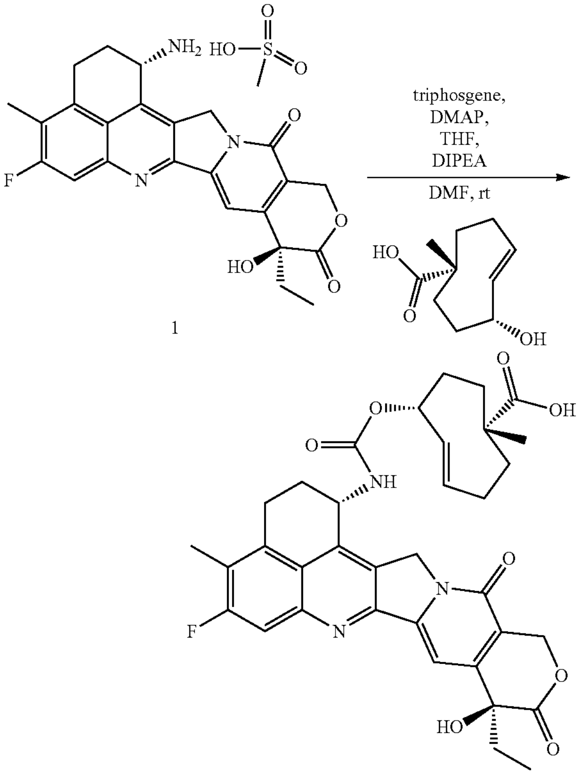

1

TCO-Exatecan. To a mixture of triphosgene (177 mg, 0.6 mmol) in THF (10 mL) was added (1R,6R,E)-6-hydroxy-1-methylcyclooct-4-ene-1-carboxylic acid (220 mg, 1.20 mmol) and DMAP (292 mg, 2.40 mmol). The mixture was stirred at room temperature for 30 mins. The mixture was added to a mixture of compound 1 (700 mg, 1.32 mmol) and DIPEA (510 mg, 3.96 mmol) in DMF (10 mL). The resulting mixture was stirred at room temperature for 12 hours. The mixture was purified by PREP-HPLC($CH_3CN$/H2O (FA)) 0% to 70%) to give desired product (110 mg, yield 14%). LCMS: (m/z, C35H36FN3O8)=646.3 $[M+H]^+$.

Example C1

In-Vivo Imaging of SQL70-Targeted Fab-TCO Conjugate

Monoclonal antibodies and antibody drug conjugates are widely prescribed for treatment of different types of cancer. The therapeutic potential of these drugs is limited by their systemic toxicity. Here, we evaluate a targeted version of a biologic drug, termed TCO-Fab, that is intravenously (IV) administered and locally retained upon reacting with a subcutaneously (SC) injected targeting biopolymer.

Study Objective

The goal of this study is to provide a proof-of-concept for using a biopolymer-targeting agent in combination with an appropriately functionalized biologic drug. The biologic drug will be tracked to the injection site of the biopolymer using in vivo imaging.

Study Design

Six-week-old, female nu/nu mice were SC injected with 100 μL of SQL70 biopolymer (Group 1 and Group 2) or control biopolymer (Group 3, used as negative control) in the right flank.

One hour after the SQL70 biopolymer injection, animals were dosed IV via tail vein injections (TVI) with TCO-Fab-Cy5.5 at 10 mg/kg (Group 1), or Fab-Cy5.5 at 10 mg/kg (Group 2, as a negative control).

One hour after the control biopolymer, animals were dosed via TVI with TCO-Fab-Cy5.5 at 10 mg/kg (Group 3) as a negative control. The three treatment groups are detailed in Table 1.

TABLE 1

Treatment Groups

| Group | Subcutaneous Injection on Day 1 | IV Drug | Dose Level (mg/kg/dose) | Dosing Day |
|---|---|---|---|---|
| 1 | 100 μL SQL70 | TCO-Fab-Cy5.5 | 10 | 1 |
| 2 | 100 μL SQL70 | Fab-Cy5.5 | 10 | 1 |
| 3 | 100 μL Control biopolymer | TCO-Fab-Cy5.5 | 10 | 1 |

Test Articles a. TCO-Fab-Cy5.5—(Ranibizumab-Cy5.5-TCO Conjugate)

Supplier: |Storage: 4° C., protected from light

Description: clear solution with red color.

Formulation: Protein concentration as indicated in 25 mM sodium citrate, 100 mM sodium chloride, pH 5.5; sterile; ready for injection.

b. Fab-Cy5.5—(Ranibizumab-Cy5.5 Conjugate)

Supplier: |Storage: 4° C., protected from light

Description: clear solution with blue color.

Formulation: Protein concentration as indicated in 25 mM sodium citrate, 100 mM sodium chloride, pH 5.5; sterile; ready for injection.

c. SQL70 Biopolymer.

A tetrazine-modified sodium hyaluronate modified as in the formula

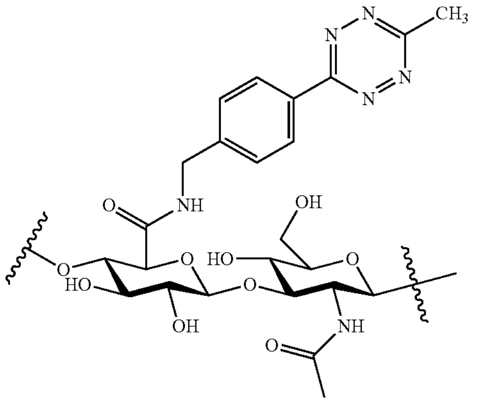

having ~10-15 kD MW and ~30% modification

Supplier: |Storage: 4° C., protected from light

Description: dark pink injectable liquid

Formulation: Sterile and already formulated in sodium chloride/sodium phosphate buffer a 63.2 mg/mL.

d. Control Biopolymer (Hyaluronic Acid)

Supplier: |Storage: 4° C.

Description: White hygroscopic solid.

Formulation: One time formulation in saline at pH 7.4 (63.2 mg/mL concentration) will be required. The product will be filtered through a 0.2-µm syringe filter inside a biohazard hood/under aseptic conditions. Once formulated, the control biopolymer is stable at 4° C. Please prepare fresh or up to 1 day ahead before use.

Dosing

Test articles and vehicle solution were administrated at indicated doses, routes and times, as described in Table 1. Dosing volumes were determined based on actual BWs of individual mice on the previous measurement day.

Live Imaging

Mice were imaged after biopolymer injection to determine baseline values. Mice were imaged at 1 h, 4 h, 24 h and 72 h post the IV injection. (NOTE: the timing is based on the IV injection of the different test articles and not the SC injection of the biopolymers.)

Fluorescent filters used were 680 nm excitation and 720 nm emission for Cy5.5.

At 72 hours post the IV injection (once the last live imaging time point has been completed), tissues were removed from the injection site for ex vivo imaging. The biopolymer injection site was defined as the region of interest for each animal.

Fluorescent filters used will be 680 nm excitation and 720 nm emission for Cy5.5.

Mice had no adverse reactions to the therapeutic. All were healthy and active throughout the study. One mouse in Group 1 (10 mg/kg TCO-Fab-Cy5.5) showed a signal at the site of the SQL70 injection versus the subjects of Group 2 and Group 3 (FIG. 1). Fluorescent signals can be seen in the liver, kidneys and bladder as the drug clears the body.

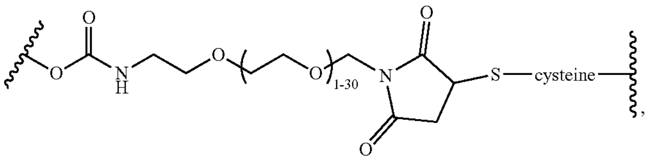

,

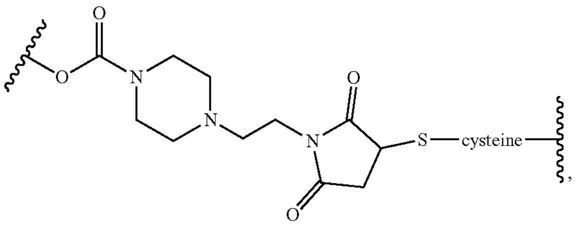

,

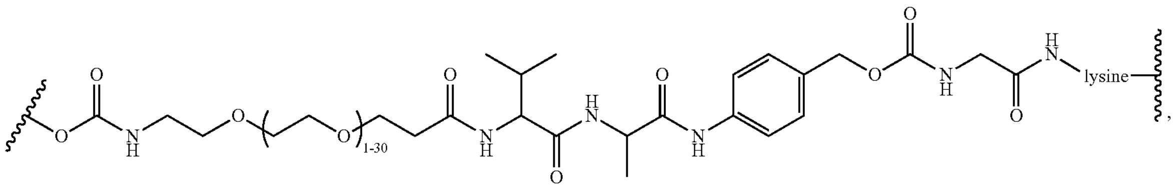

,

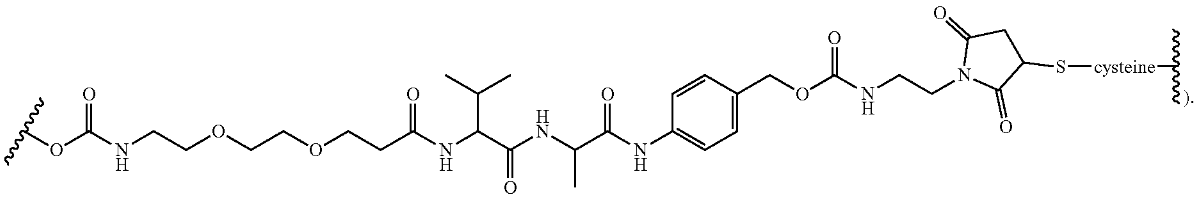

).

In some instances, the therapeutic agent is covalently attached to the linker through an amide bond; e.g., the therapeutic agent may be an amine-containing therapeutic agent for attachment of the therapeutic agent to a carbonyl group of the linker, or, in other cases, the therapeutic agent may be a carboxyl-containing therapeutic agent for attachment of the therapeutic agent to an amine group of the linker. In some instances, the therapeutic agent and linker, together form a carbamate group; e.g., the therapeutic agent may be an amine-containing therapeutic agent for attachment of the therapeutic agent to an acyloxy group of the linker. In some instances, the therapeutic agent and linker, together form a carbonate group; e.g., the therapeutic agent may be a hydroxy-containing therapeutic agent for attachment of the therapeutic agent to an acyloxy group of the linker.

E46.15A. The method of any of E46.1A, E46.2 to E46.6, or E46.7 to E46.14, the compound, or pharmaceutically acceptable salt, of any of E46.1B to E46.4 or E46.6B to E46.6F, or the compound, or pharmaceutically acceptable salt, for use in the method of any of E46.1B to E46.4 or E46.6B to E46.6F, wherein L is

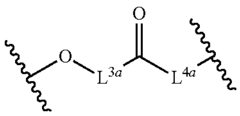

or —O—;

$L^{3a}$ is a bond or $C_{1-6}$alkylene;

$L^{4a}$ is a bond, —NHN, —$N(R^{10})$—$C_{2-6}$alkylene-N$(R^{11})$—, —$N(R^{12})$—$C_{2-3}$alkylene-$N(R^{13})C(O)$—, —$N(R^{10})$—$C_{1-6}$alkylene-C(O)NHN, —NHNHC(O)$C_{1-6}$alkylene-C(O)NHN, —$CH(NHC(O)R^{14})C_{1-4}$alkylene-S—S—$C_{1-4}$alkylene-OC(O)—, —NHNHC(O)$CH(NHC(O)R^{15})CH_2C(O)$—, —$C_{1-6}$alkylene-$CH(G^x)$OC(O)—,

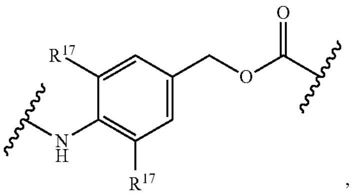

,

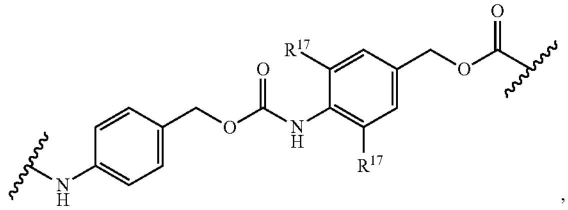

,

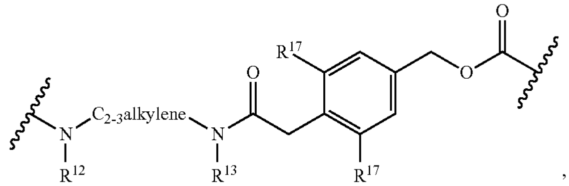

,

-continued

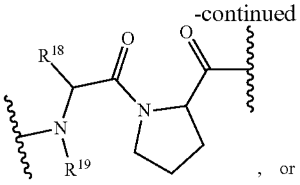

, or

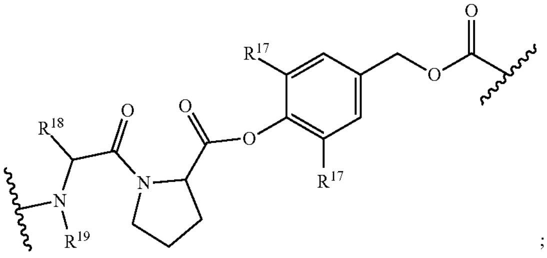

;

$R^{10}$, $R^{11}$, $R^{12}$, $R^{13}$, $R^{14}$, $R^{15}$, and $R^{19}$ are each independently hydrogen or $C_{1-4}$alkyl;

$R^{16}$ is hydrogen, $C_{1-4}$alkyl, —$C_{1-4}$alkylene-OH, —$C_{1-4}$alkylene-$OC_{1-4}$alkyl, —$C_{1-4}$alkylene-$CO_2H$, or —$C_{1-4}$alkylene-$CONH_2$;

$R^{17}$, at each occurrence, is independently hydrogen or —$CH_2OC(O)$—; and $G^x$ is phenyl optionally substituted with 1-5 substituents independently selected from the group consisting of halogen, $C_{1-4}$alkyl, $C_{1-4}$haloalkyl, $C_{1-4}$alkoxy, cyano, and nitro.

E46.15B. The method of any of E46.1A, E46.2 to E46.6, or E46.7 to E46.14, the compound, or pharmaceutically acceptable salt, of any of E46.1B to E46.4 or E46.6B to E46.6F, or the compound, or pharmaceutically acceptable salt, for use in the method of any of E46.1B to E46.4 or E46.6B to E46.6F, wherein L is

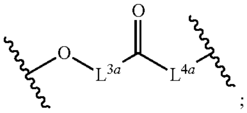

;

$L^{3a}$ is a bond;

$L^{4a}$ is

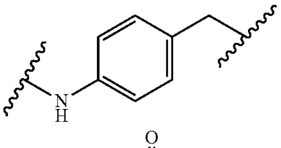

or

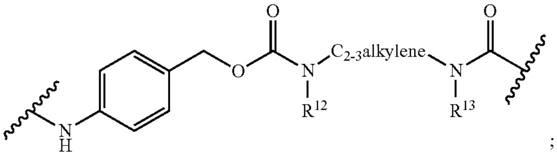

;

and $R^{12}$ and $R^{13}$ are each independently hydrogen or $C_{1-4}$alkyl.

E46.16. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein tis 1.
E46.17A. The method of E46.16, the compound, or pharmaceutically acceptable salt, of E46.16, or the compound, or pharmaceutically acceptable salt, for use in the method of E46.16, wherein
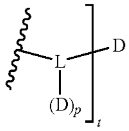 is 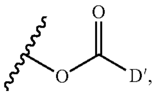 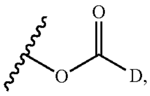
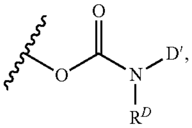 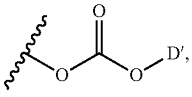
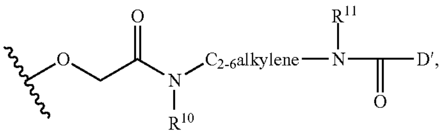
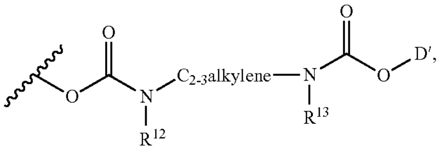
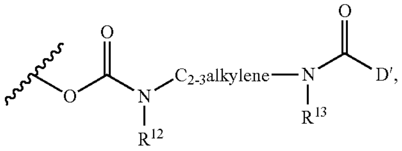
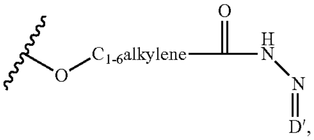
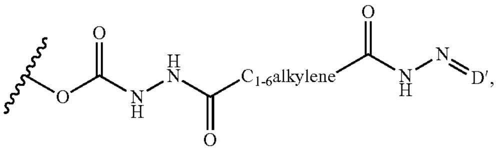
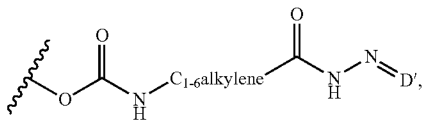
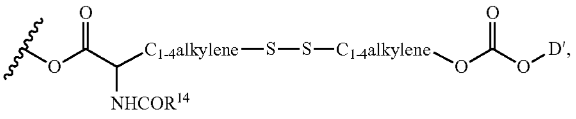
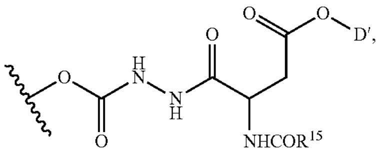
-continued
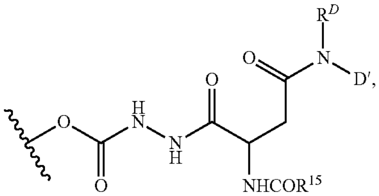
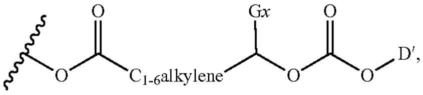
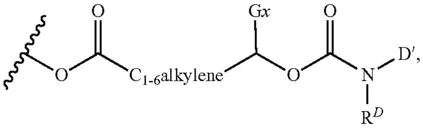
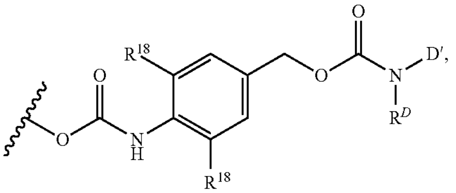
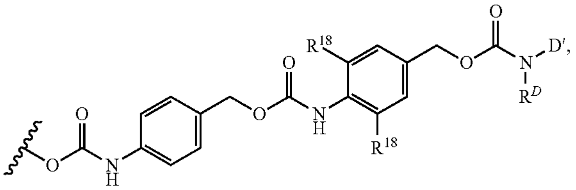
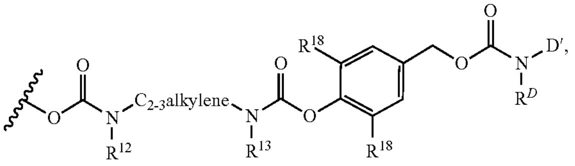
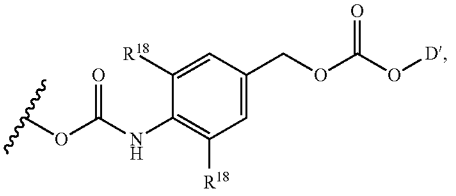
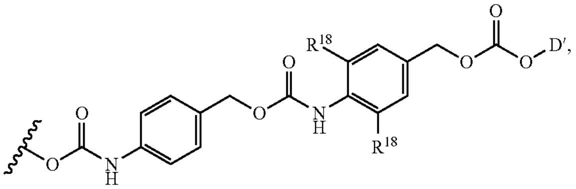
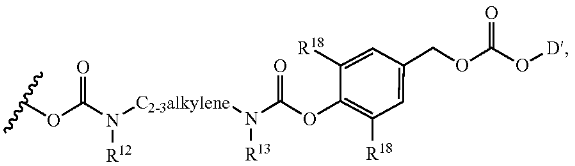
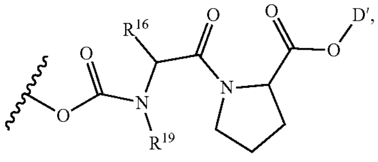

-continued

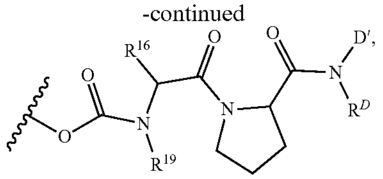

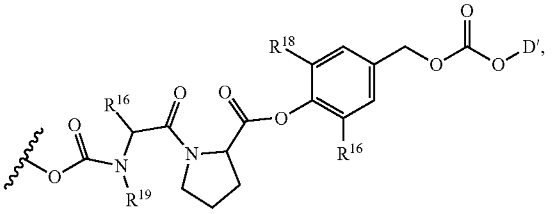

or

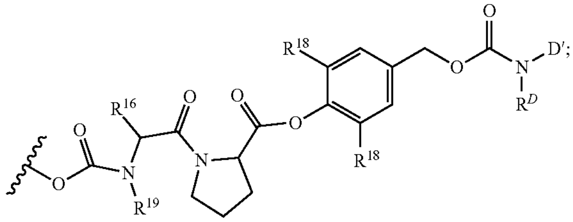

$R^{18}$, at each occurrence, is independently hydrogen or —CHOC(O)NHD';

$R^D$ is hydrogen or $C_{1-4}$alkyl on a nitrogen atom of the payload; and

D' is a payload moiety (e.g., cyclic dinucleotide payload moiety, imidazo[4,5-c]quinolin-4-amine payload moiety, TLR agonist payload moiety, STING agonist payload moiety, anticancer agent payload moiety).

E46.17B. The method of E46.16, the compound, or pharmaceutically acceptable salt, of E46.16, or the compound, or pharmaceutically acceptable salt, for use in the method of E46.16, wherein

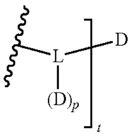

is

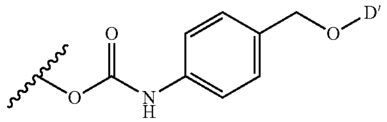

or

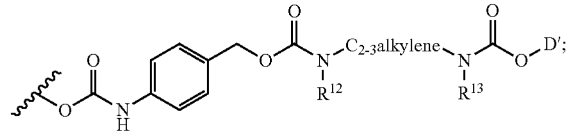

$R^{12}$ and $R^{13}$ are each independently hydrogen or $C_{1-4}$alkyl; and

D' is a payload moiety (e.g., anticancer agent payload moiety).

E46.18. The method of any of E46.1A, E46.2 to E46.6A, or E46.7 to E46.17B, the compound, or pharmaceutically acceptable salt of any of E46.1B to E46.4, E46.6B to E46.6F, or E46.15A to E46.17B, or the compound, or pharmaceutically acceptable salt, for use in the method of any of E46.1B to E46.4, E46.6B to E46.6F, or E46.15A to E46.17B, wherein p is 0.

E46.19. The method of E46.18, the compound, or pharmaceutically acceptable salt of E46.18, or the compound, or pharmaceutically acceptable salt, for use in the method of E46.18, wherein t is 2 or 3.

E46.20. The method of E46.19, the compound, or pharmaceutically acceptable salt of E46.19, or the compound, or pharmaceutically acceptable salt, for use in the method of E46.19, wherein t is 2 and

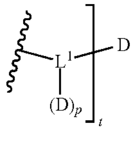

is

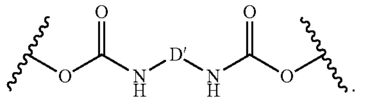

The person skilled in the art will recognize that a payload D bonded to a linker does not refer to a payload molecule per se, but refers to the portion of the payload molecule bonded to the linker. Release of the payload D from a prodrug, releases the payload per se.

D may be an anticancer agent payload of any of the anticancer agents described herein.

D may be a TLR agonist payload of any of the TLR agonists described herein. Preferably, D is an imidazo[4,5-c]quinolin-4-amine, such as

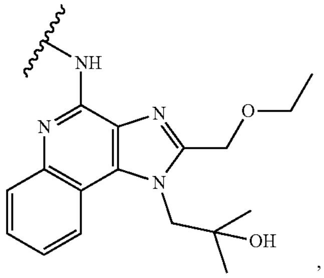

,

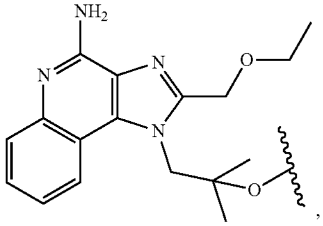

, and

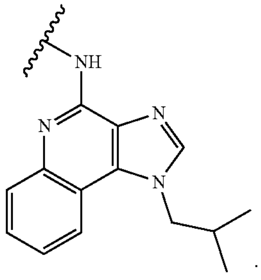

D may be a STING agonist payload of any of the STING agonists described herein. D may be a cyclic dinucleotide payload, such as

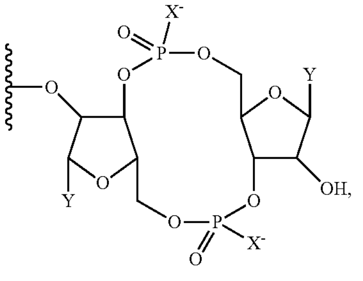

wherein Y is a nucleobase and X is O or S, and as illustrated below. A nucleobase includes naturally-occurring purine and pyrimidine bases, as well as modified purine and pyrimidine bases and other heterocyclic bases which have been modified. Such modifications include methylated purines or pyrimidines, acylated purines or pyrimidines, and the like. Nucleobase modifications may include, for example, deazapurines, N-1-methylguanosine, isoguanine, 2-aminopurine, 1,3-diaza-2-oxophenothiazine, 1,3-diaza-2-oxophenoxazine, 7-nitro-1,3-diaza-2-oxophenothiazine, 2,6-diaminopurine, purine, 6-thioguanine, hypoxanthine, 2-pyrimidinone, 2-pyridone, 4-thiouridine, imidazole-4-carboxamide, N-substituted 5-(carboxyamide) uridines such as 5-(N-benzylcarboxyamide)-uridine, or 5-fluoro-deoxyuridine. The payload D may be

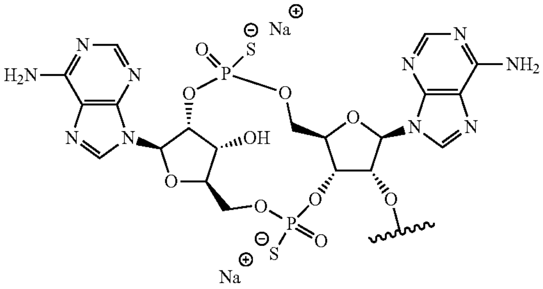

or

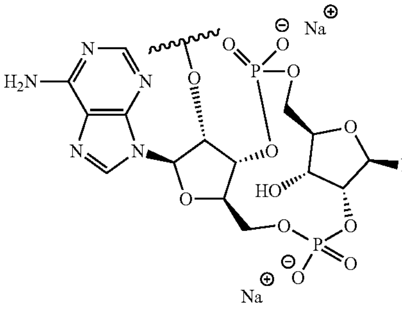

E46.21A. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

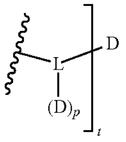

is

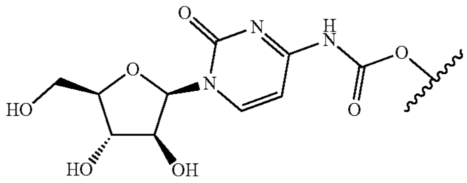

;

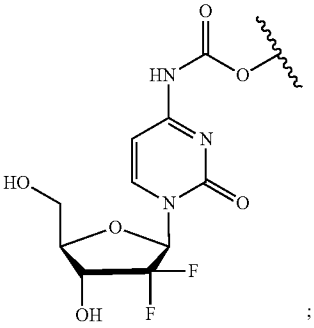

;

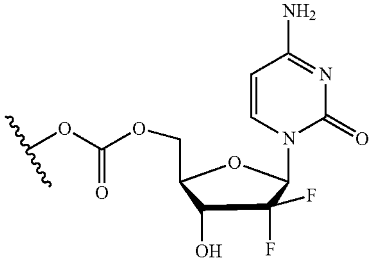

;

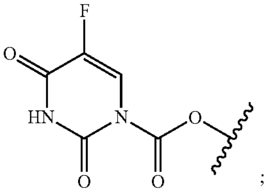

;

-continued
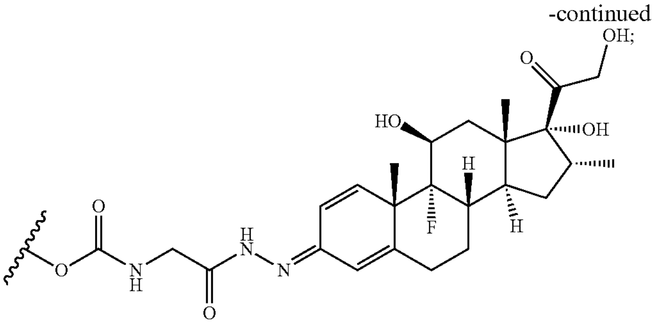
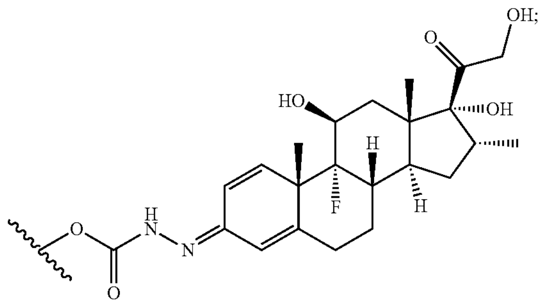
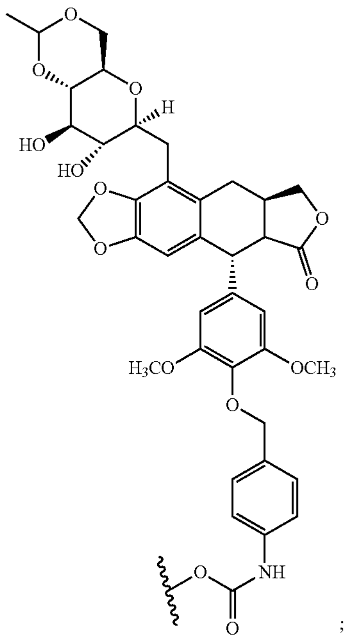
;
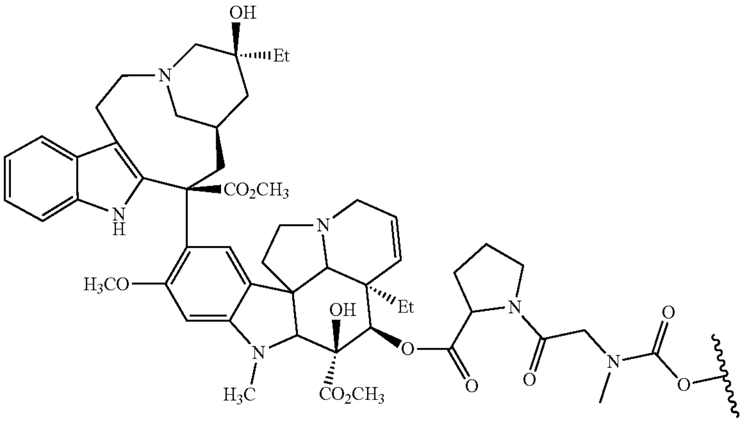
;
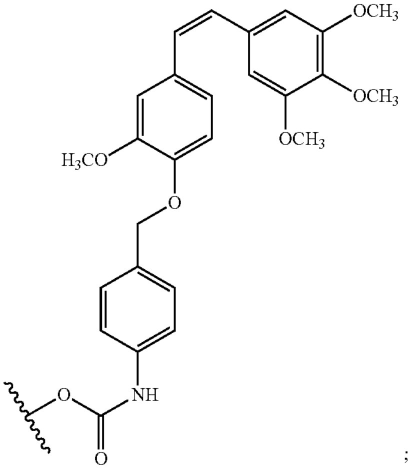
;
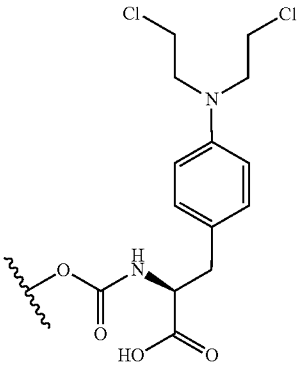
;
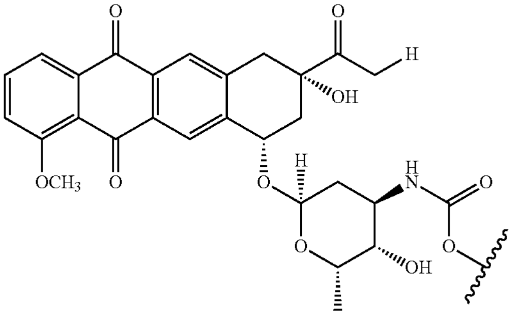
;
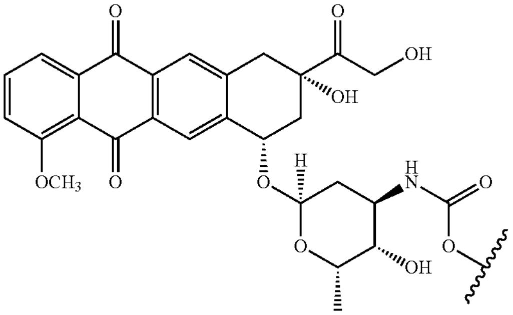
;

-continued
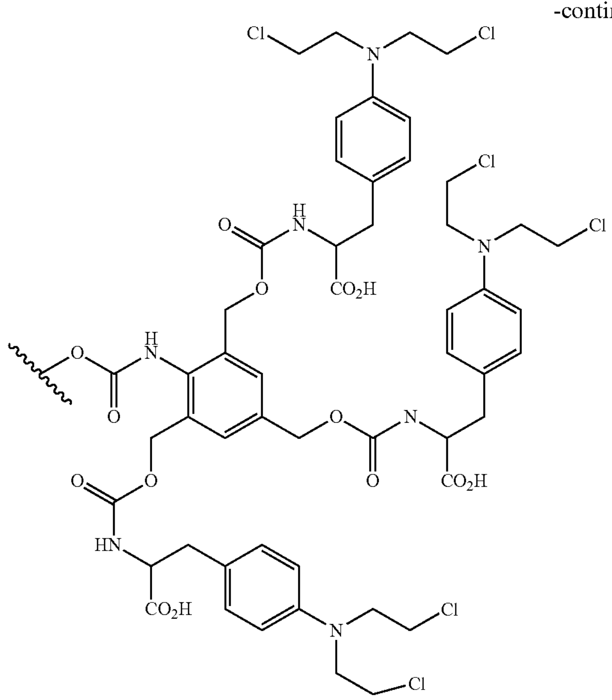
;
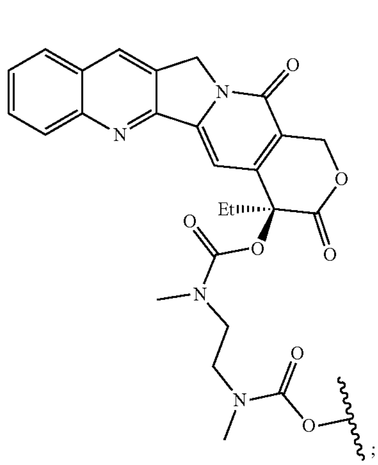
;
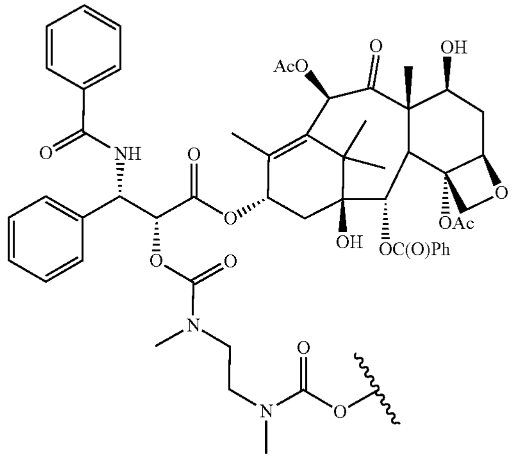
;
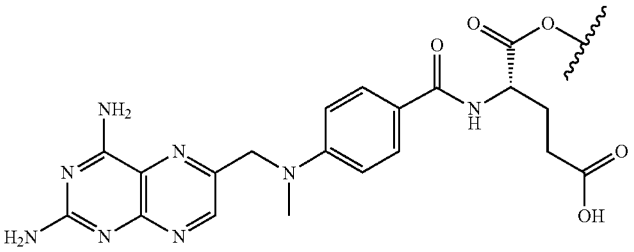
;
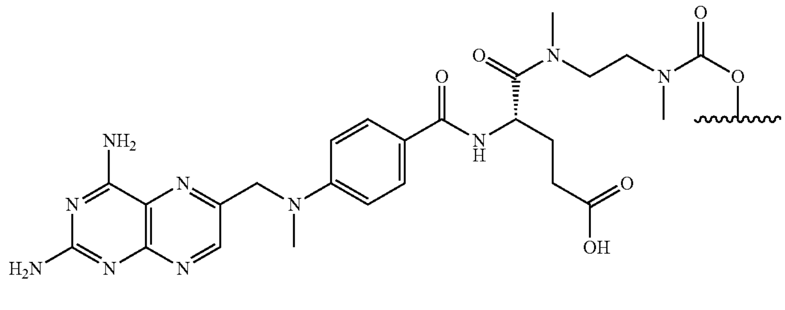
;

-continued
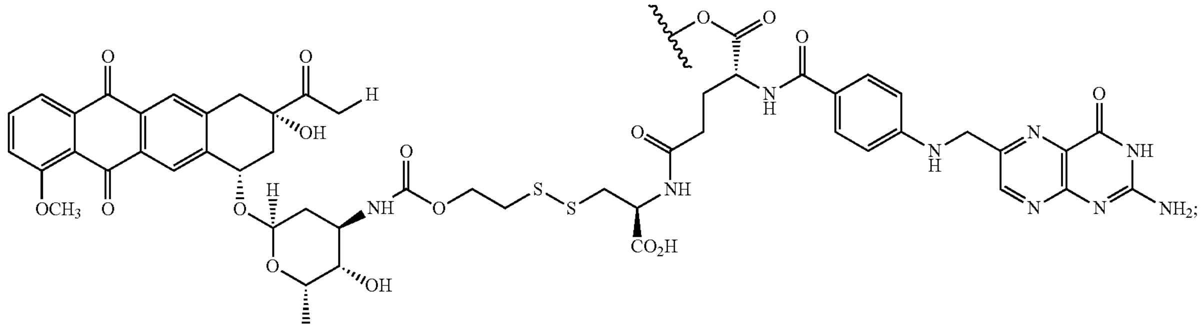
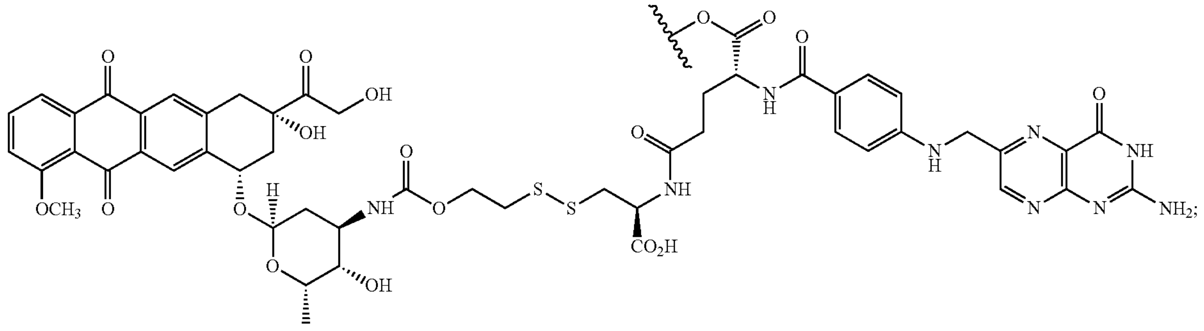
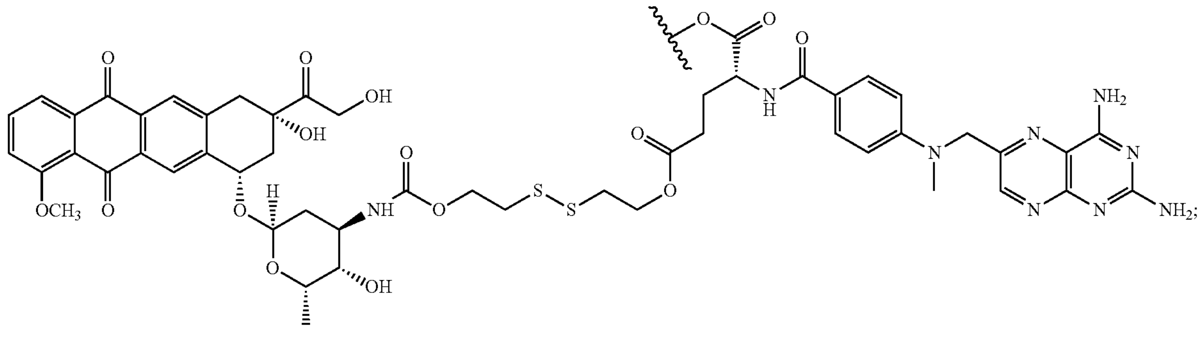
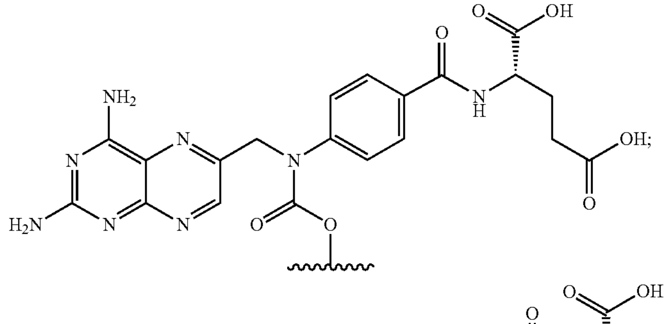
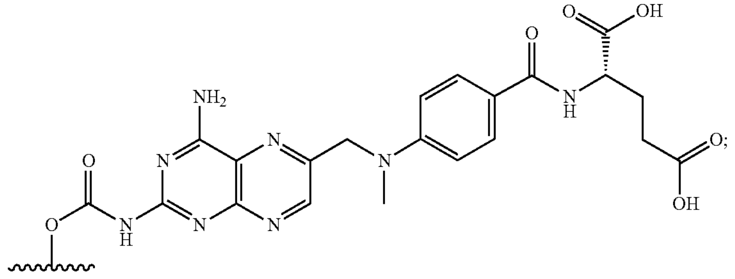

-continued
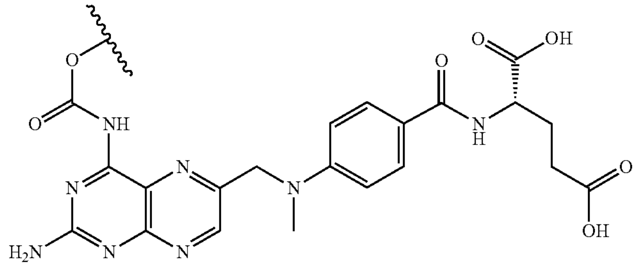
;
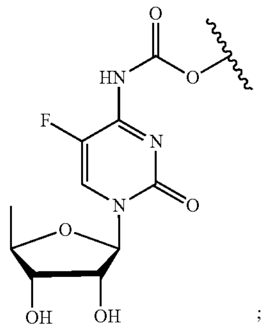
;
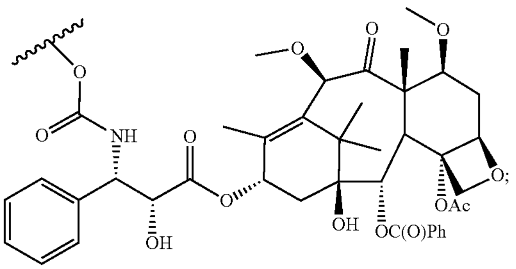
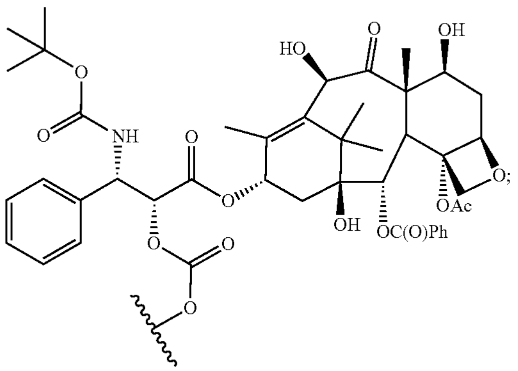
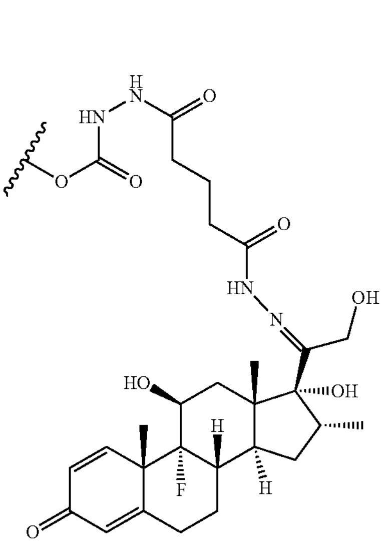
;
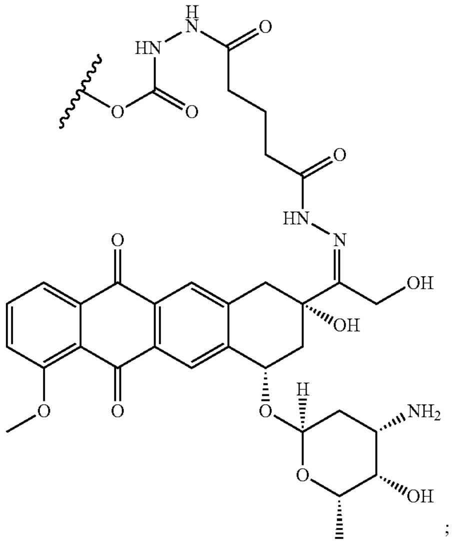
;
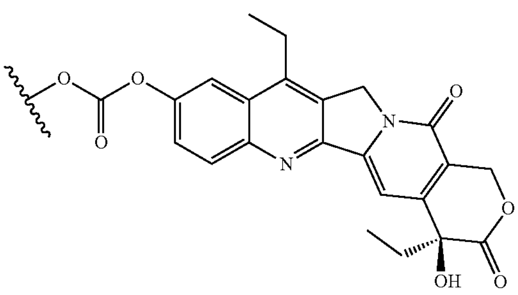
;
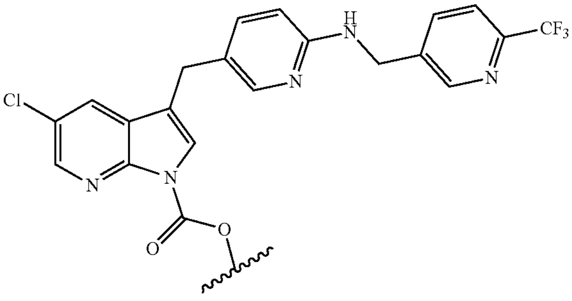
;

-continued
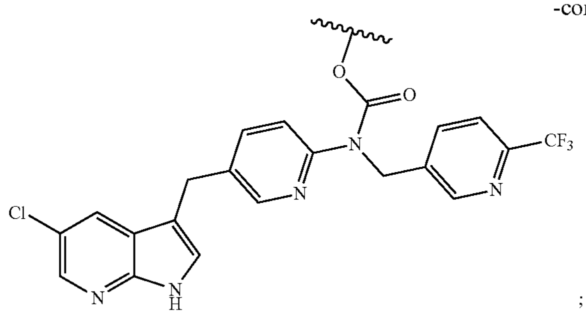
;
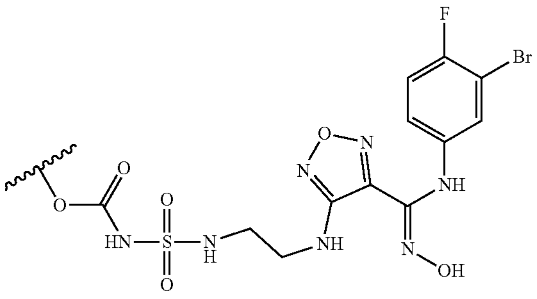
;
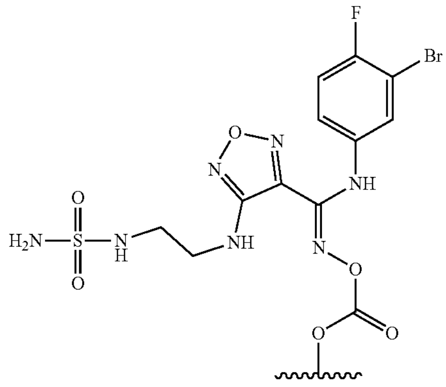
;
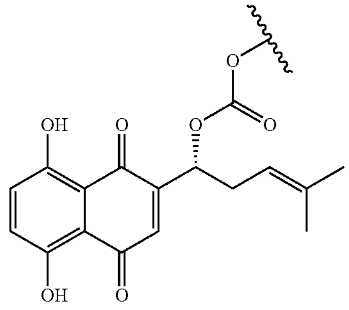
;
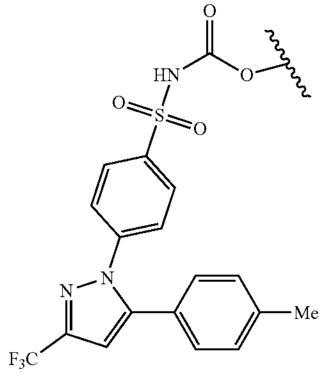
;
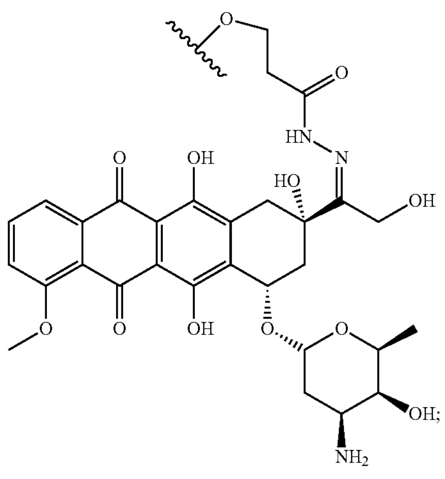

-continued
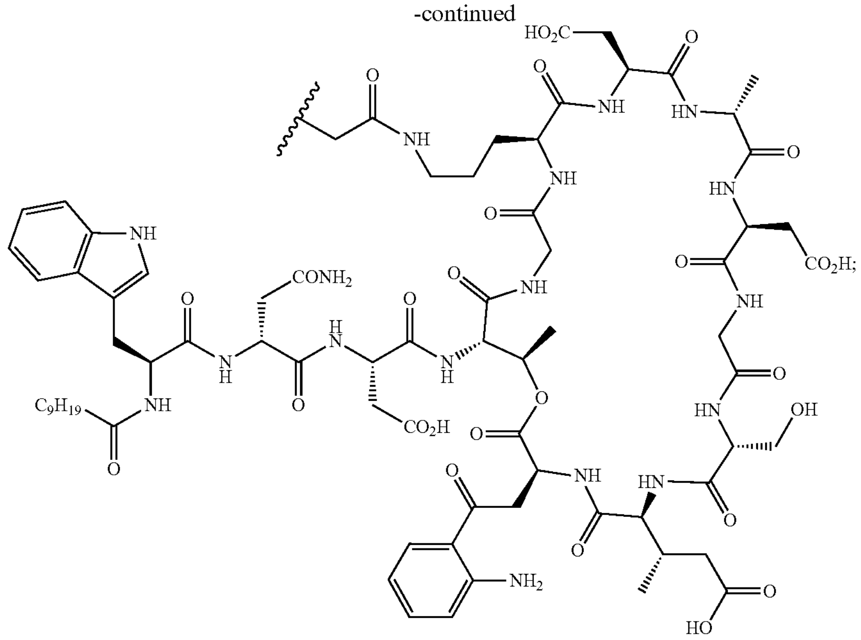
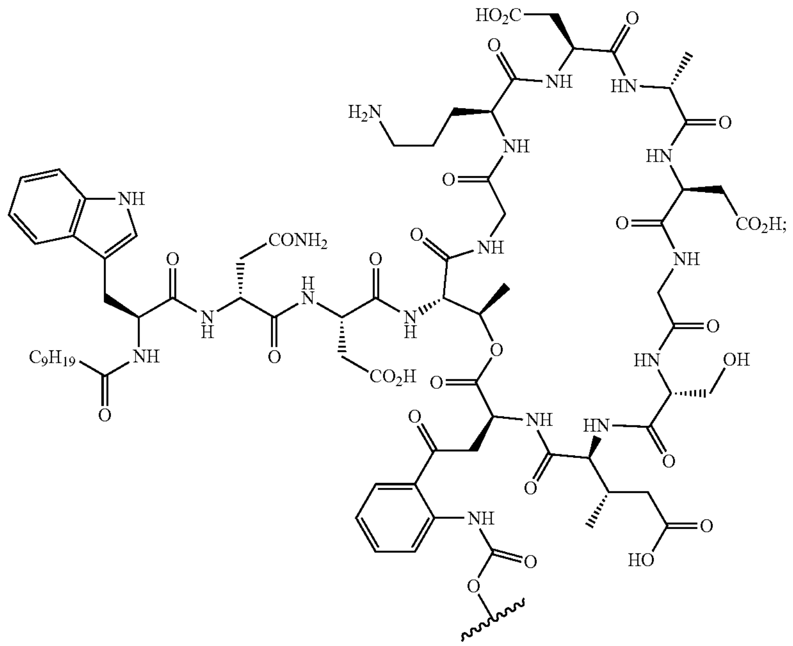

-continued
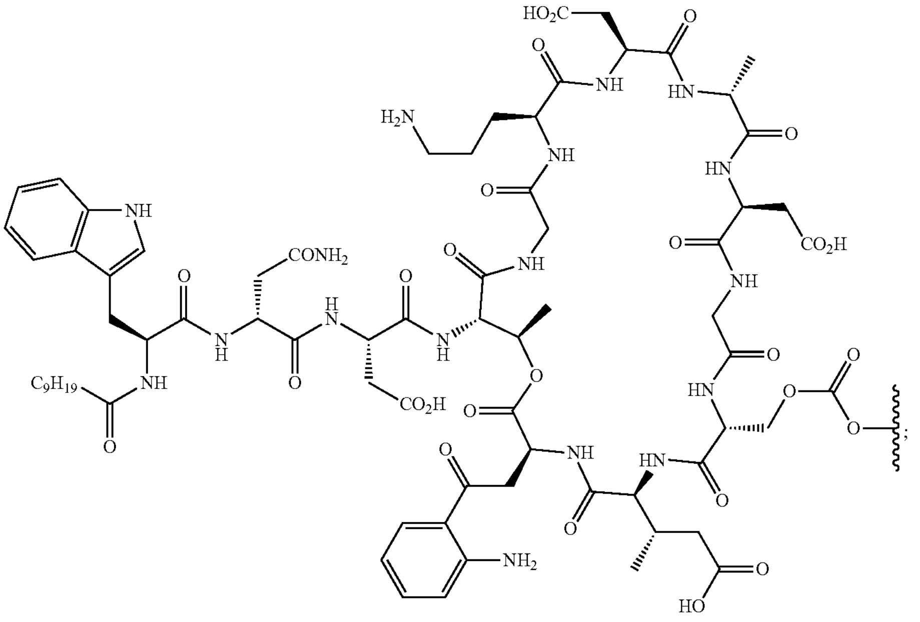
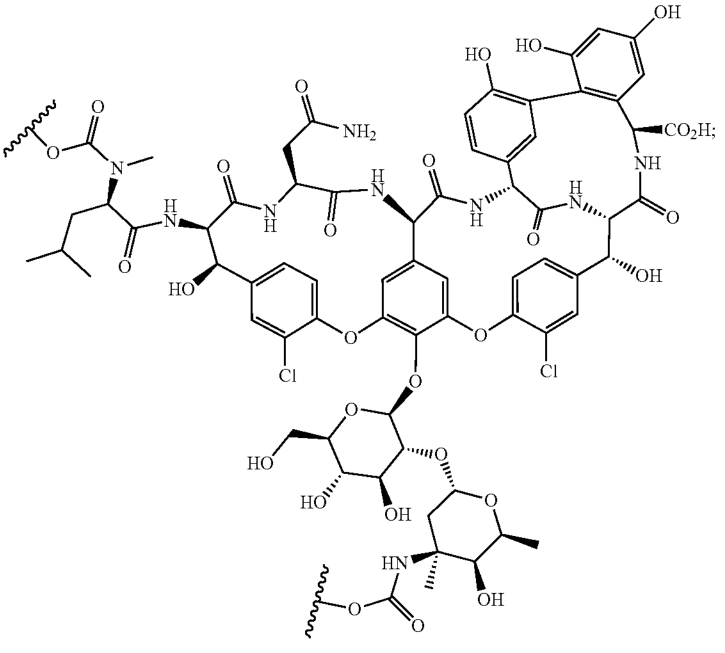

-continued
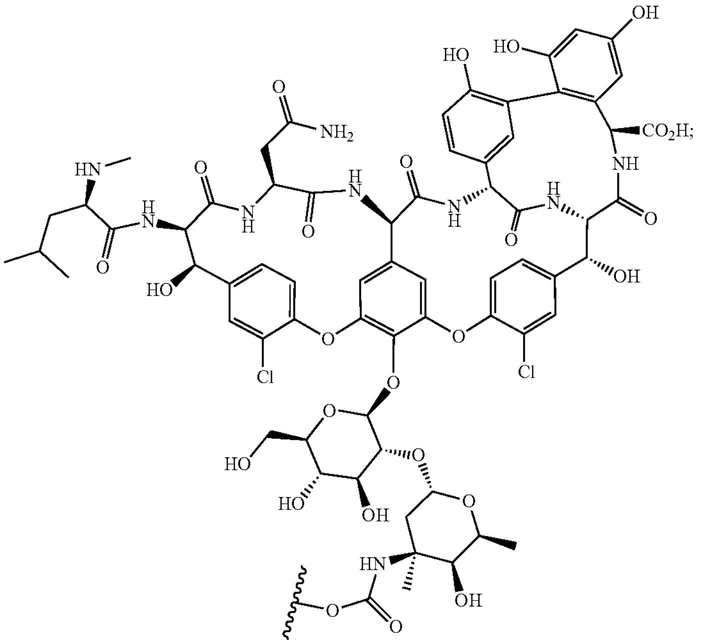
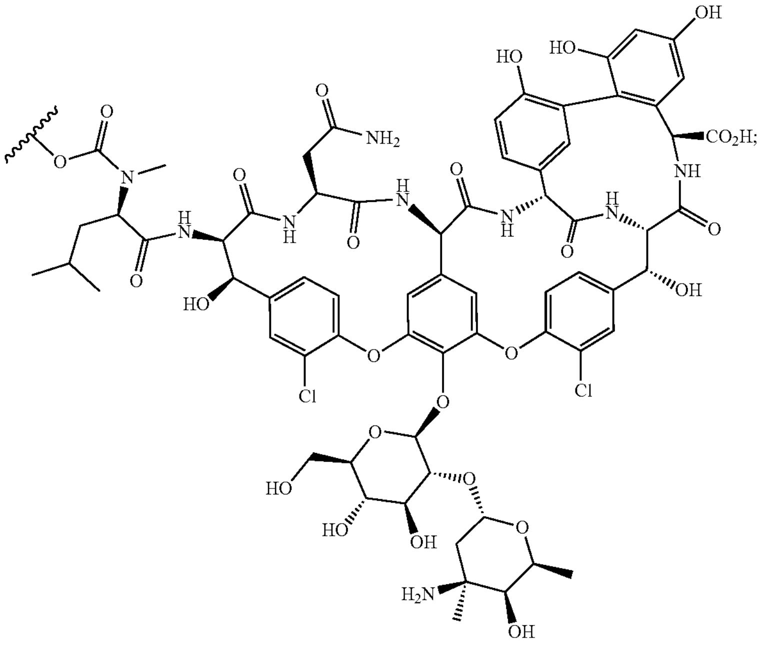
or
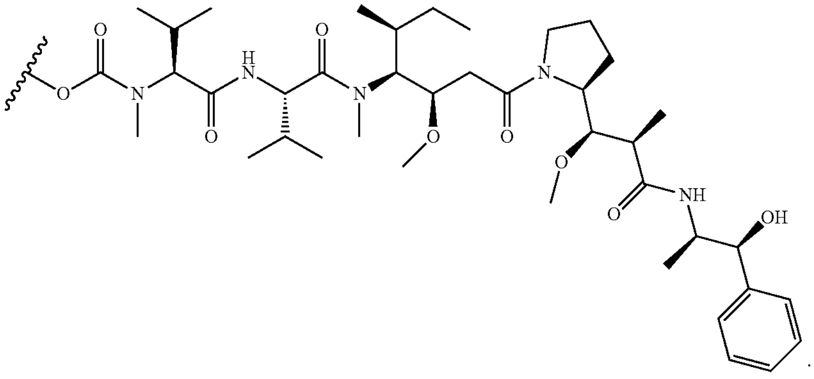

E46.21B. The method of any of B46.1A, E46.2 to B46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein
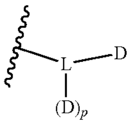 is
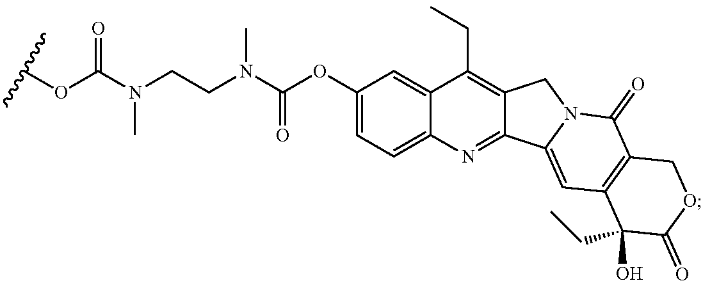
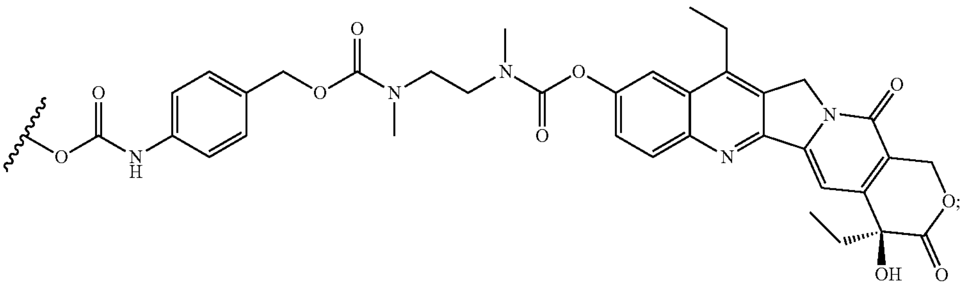
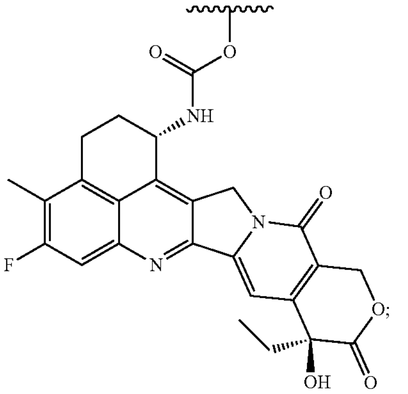
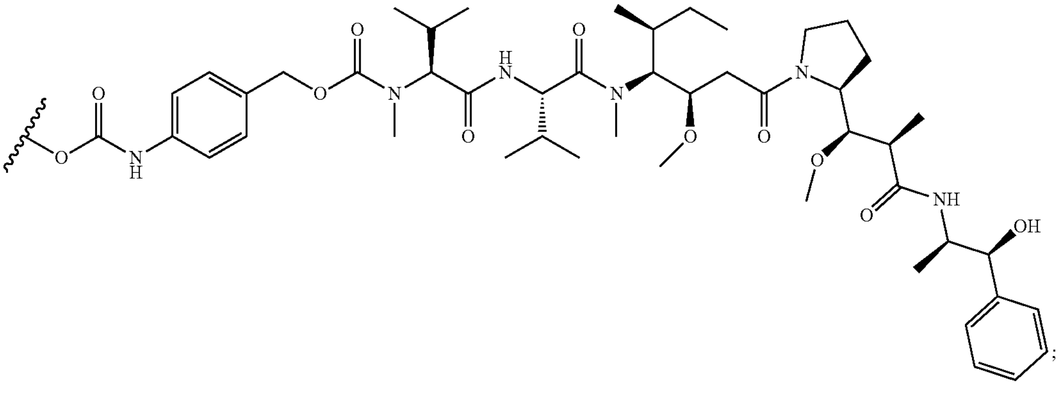

-continued
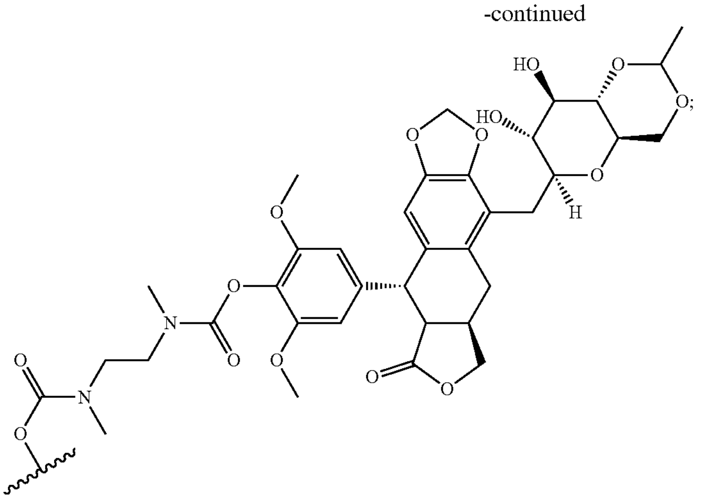
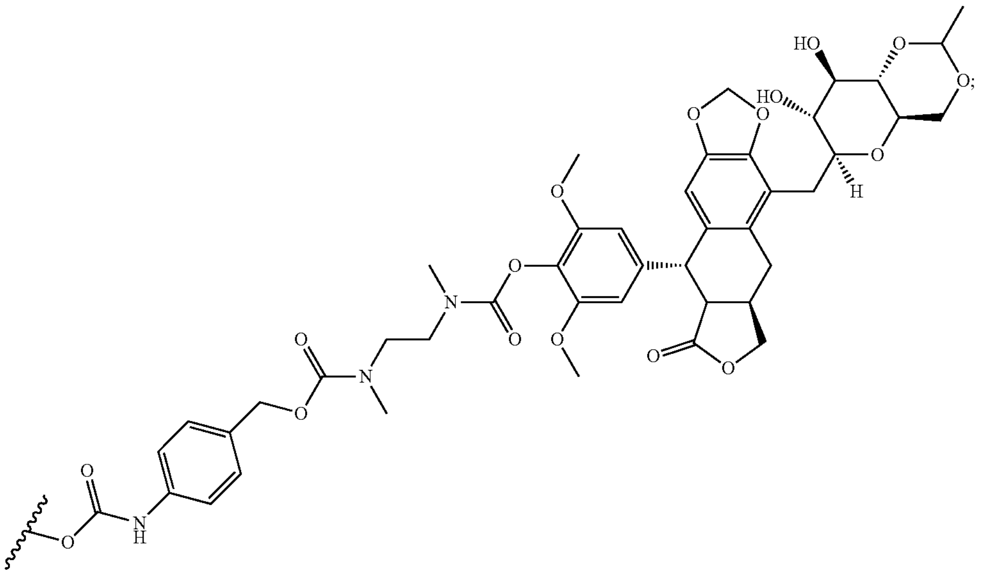
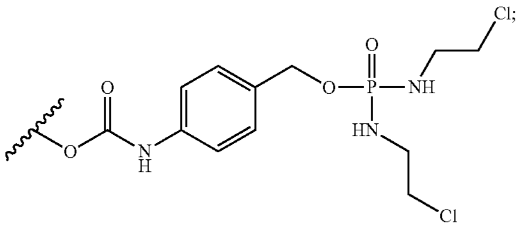
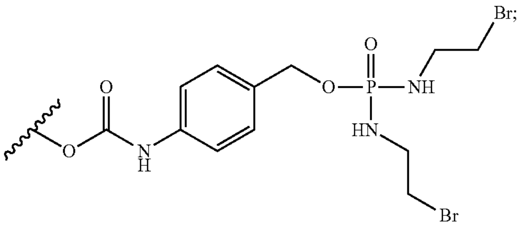

-continued
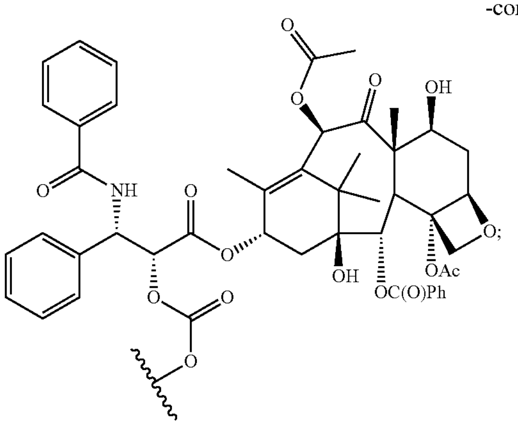
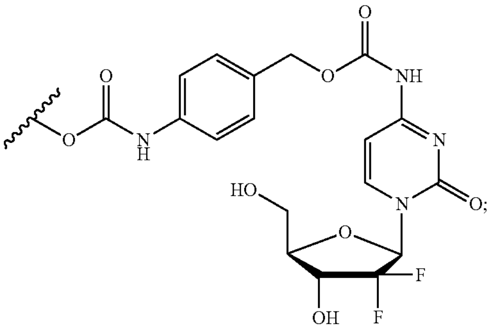
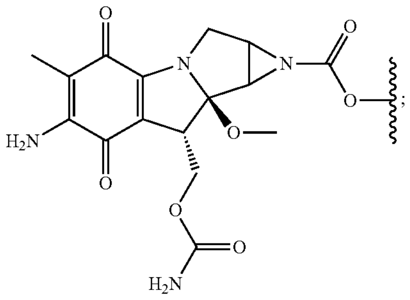
or
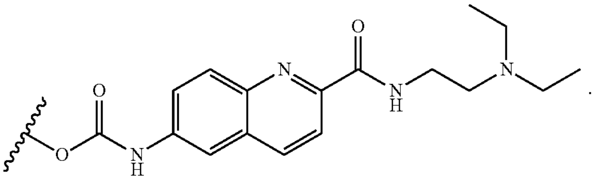
E46.22. The method of any of B46.1A, E46.2 to E46.6, or E46.7 to E46.15B, the compound, or pharmaceutically acceptable salt, of any of B46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein
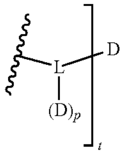
is
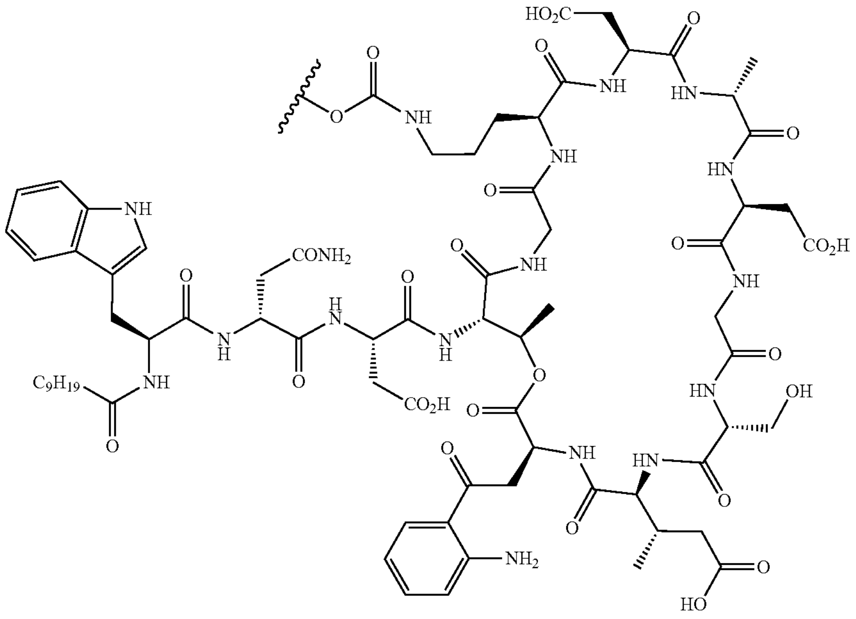
, -continued
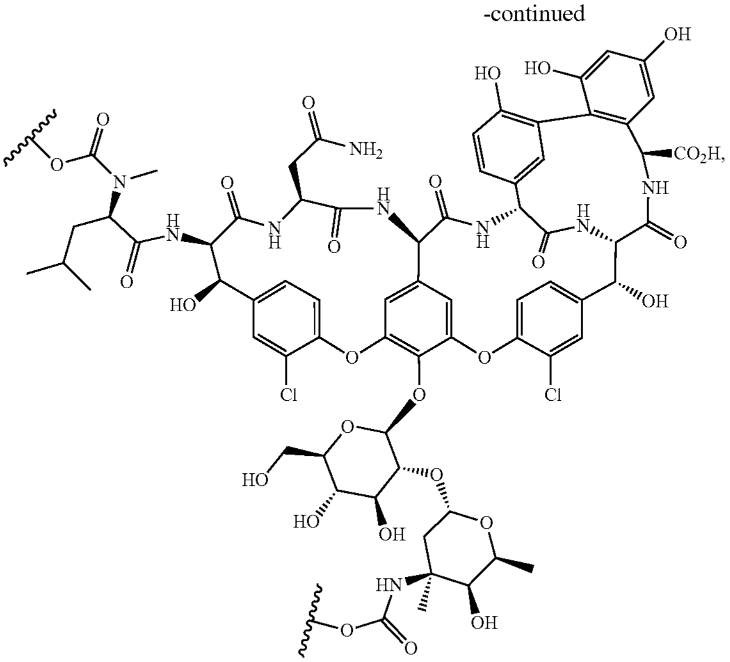
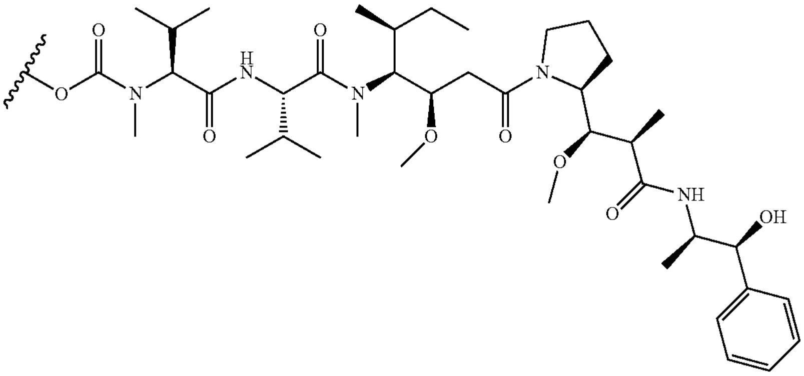
, or
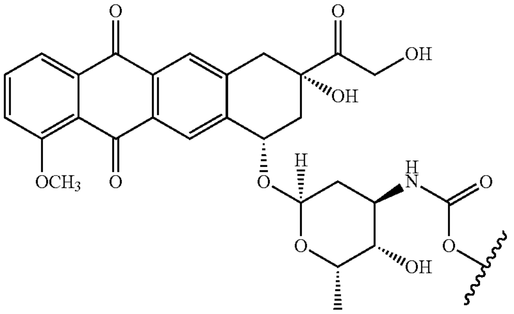
.

E46.23. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

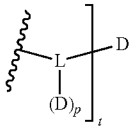

is

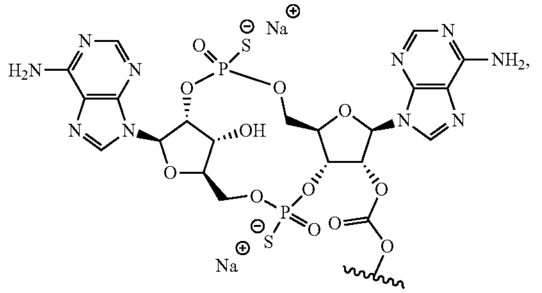

or

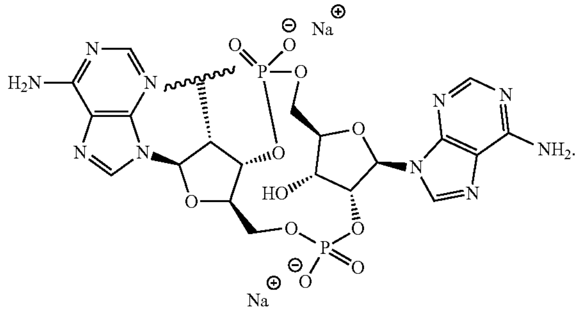

In E46.23, p is 0 and L is —OC(O)—.

E46.24. The method of any of E46.1A, E46.2 to E46.6, or E46.7 to E46.15B, the compound, or pharmaceutically acceptable salt, of any of E46.1B to E46.4, E46.6B to E46.6F, or E46.15A to E46.15B, or the compound, or pharmaceutically acceptable salt, for use in the method of any of E46.1B to E46.4, E46.6B to E46.6F, or E46.15A to E46.15B, wherein

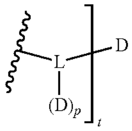

is

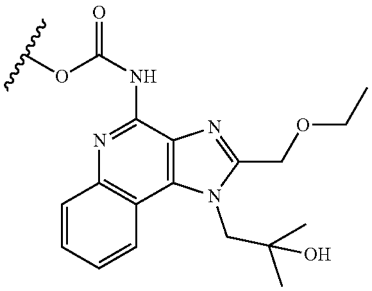

,

-continued

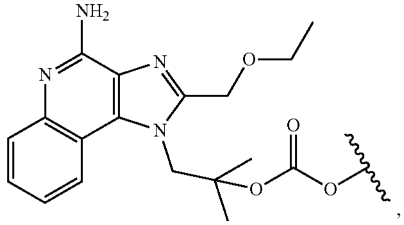

, or

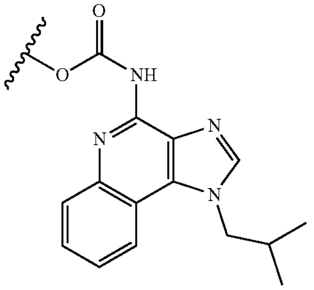

In E46.24, p is 0 and L is —OC(O)—.

E.46.25. The method of E46.18, the compound, or pharmaceutically acceptable salt of E46.18, or the compound, or pharmaceutically acceptable salt, for use in the method of E46.18, wherein tis 1; L is

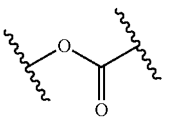

;

and D is doxorubicin.

According to the definition of “payload moiety,” the payload moiety D' refers to a payload D or $D^1$ minus its nucleophilic group such as NH, $NC_{1-4}$alkyl, O, or S that attaches to a linker or minus its electrophilic group such as C(O) that attaches to a linker, i.e., the remainder of the payload. For example, a compound of formula

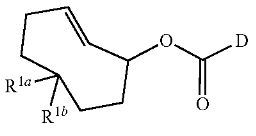

includes a compound such as

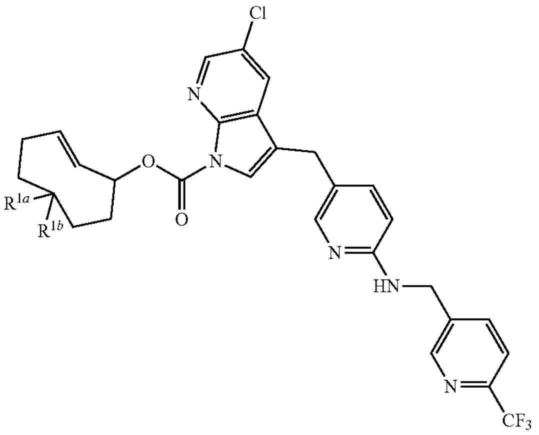

or

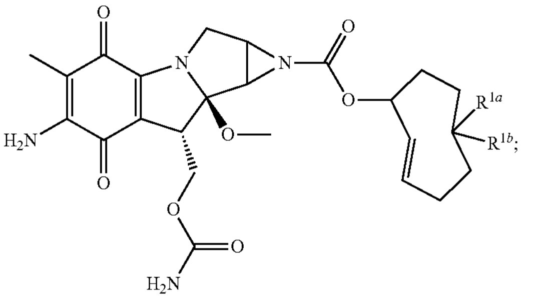

a compound

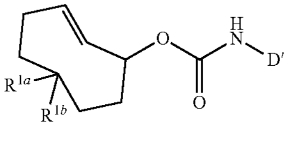

includes a compound such as

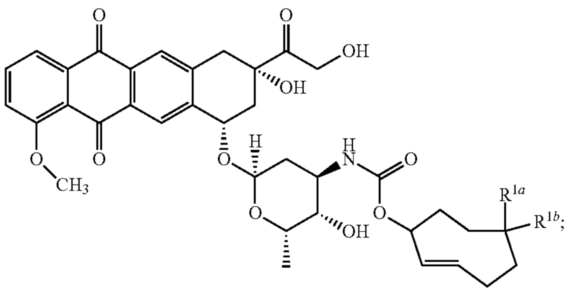

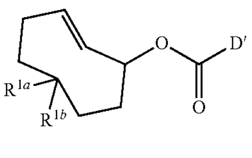

includes a compound such as

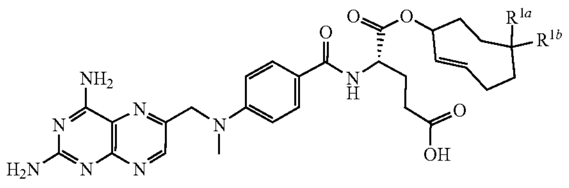

a compound of formula

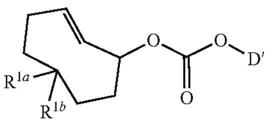

includes a compound such as

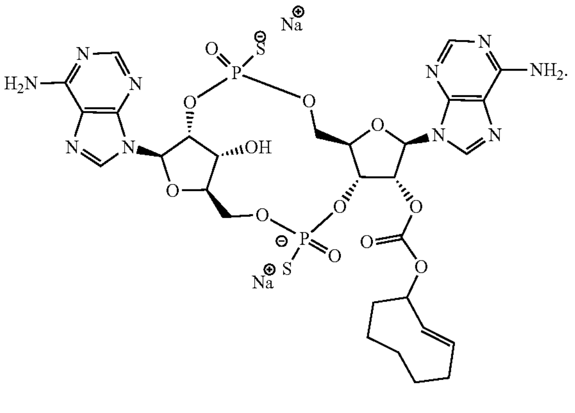

Release of DH, $NH_2$-D', HOOC-D', or HO-D' releases the payload molecule per se. In accordance with the foregoing definition of a payload moiety, a "cyclic dinucleotide payload moiety" is a cyclic dinucleotide payload minus its nucleophilic group (typically O) that attaches to a linker. For example, when

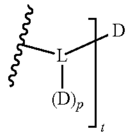

is

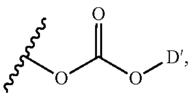

a cyclic dinucleotide payload moiety may be.

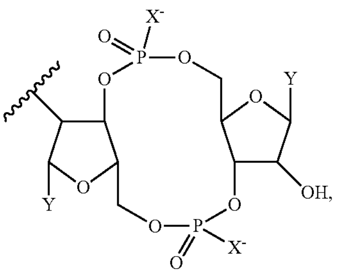

-continued

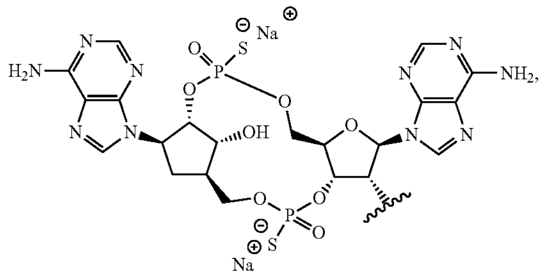

or

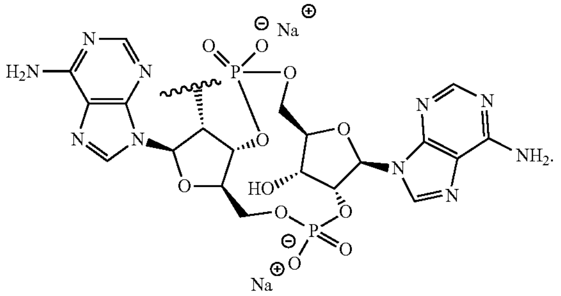

In the compounds described herein,

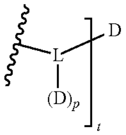

may be

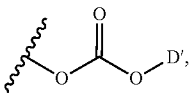

wherein D' is a cyclic dinucleotide payload moiety. In accordance with the foregoing definition of a payload moiety, an "imidazo[4,5-c]quinolin-4-amine payload moiety" is an imidazo[4,5-c]quinolin-4-amine minus its nucleophilic group (typically O or N) that attaches to a linker. For example, when

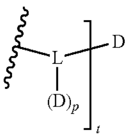

is

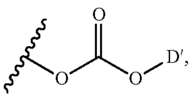

an imidazo[4,5-c]quinolin-4-amine payload moiety D' may be

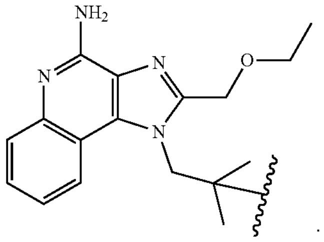 [SMILES: *C(C)(C)Cn1c(COCC)nc2c(N)nc3ccccc3c21]

For example, when

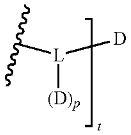

is

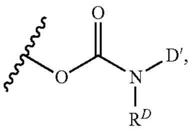

an imidazo[4,5-c]quinolin-4-amine payload moiety D' may be.

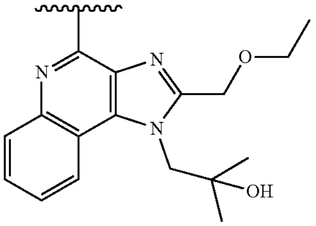

or

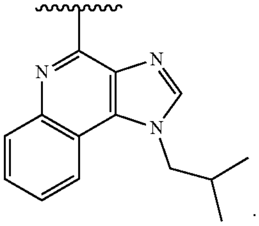

Preferred compounds of formula (II) include compounds of formula

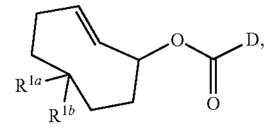

such as

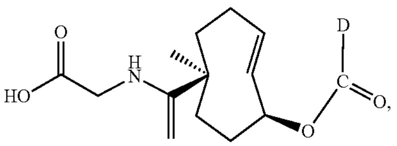

-continued
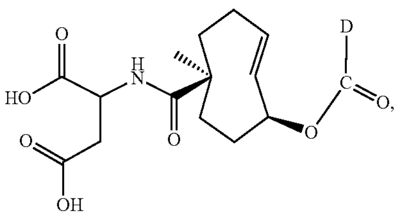
and
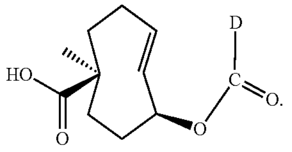
Preferred compounds of formula (III) include compounds of formula
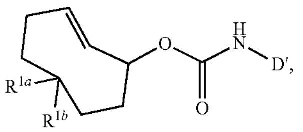
such as
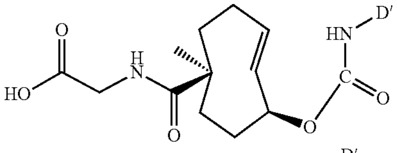
and
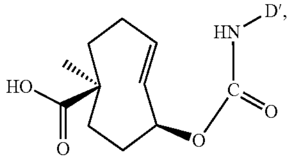
such as
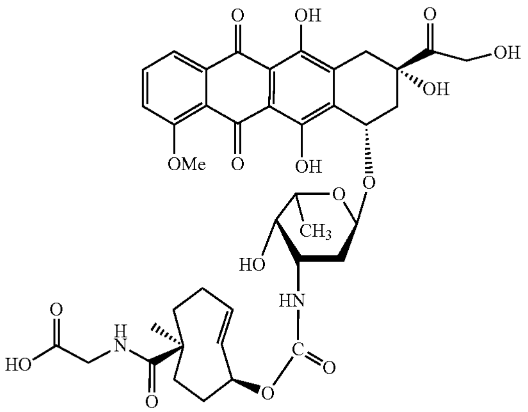
and
-continued
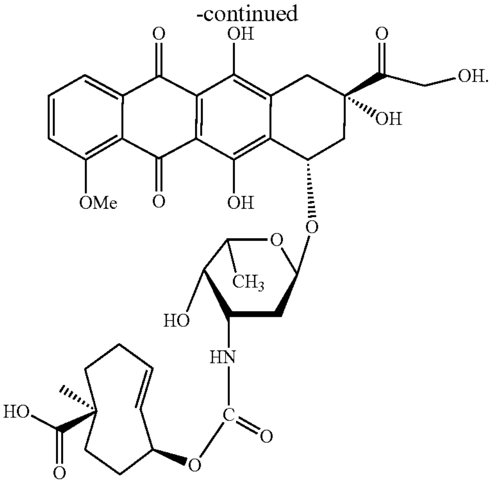
Compounds of formula (III) include
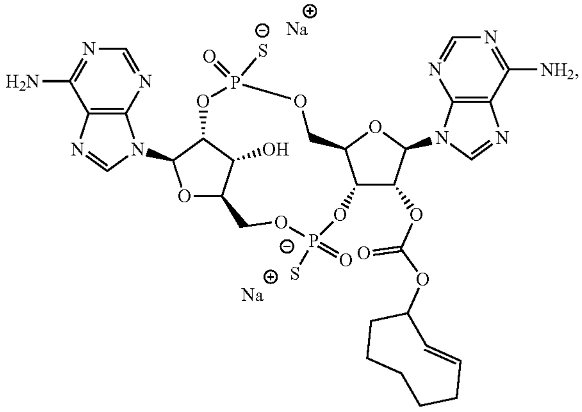
TCO-ADU-S100
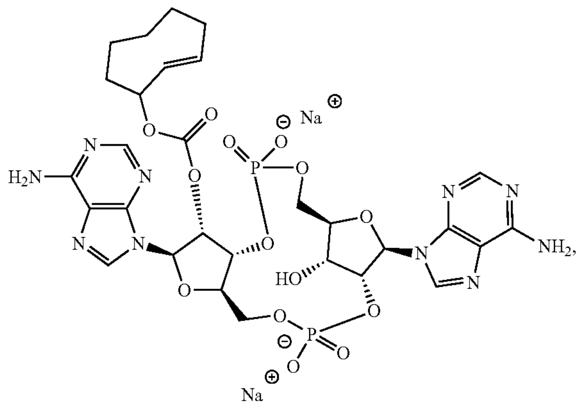
TCO-2′3′-cGAMP -continued
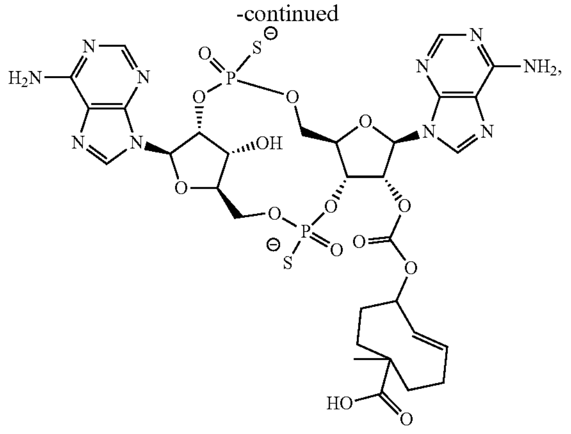
ADU-S100-TCO-Acid
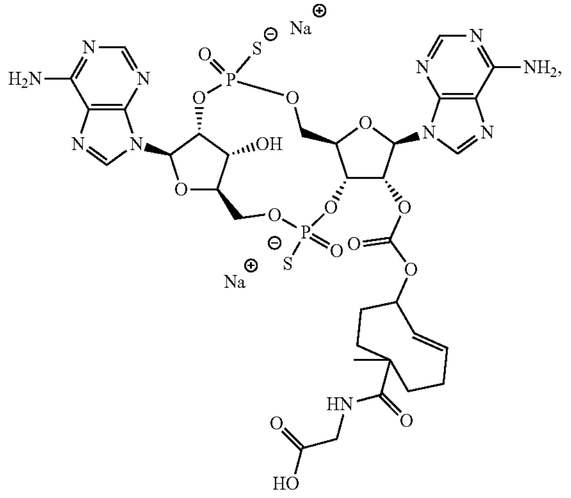
ADU-S100-TCO-Glycine
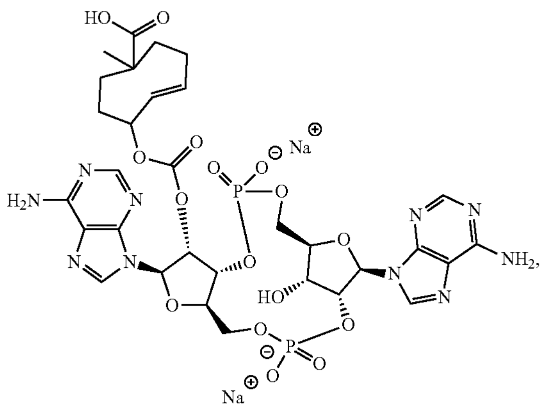
or
2'3'-cGAMP-TCO-Acid
-continued
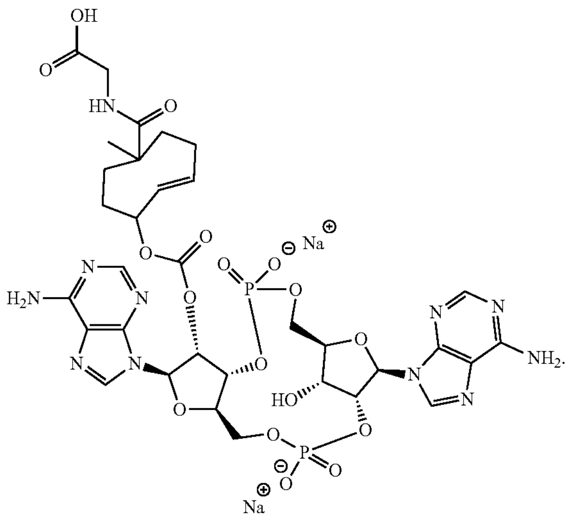
2'3'-cGAMP-TCO-Glycine
Compounds of formula (III) include
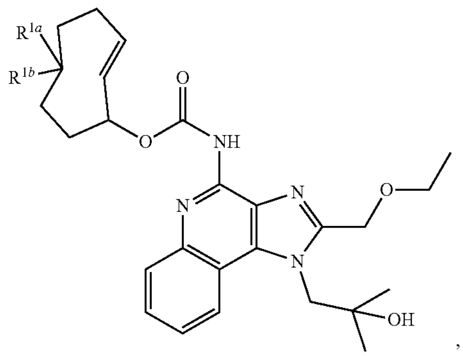
,
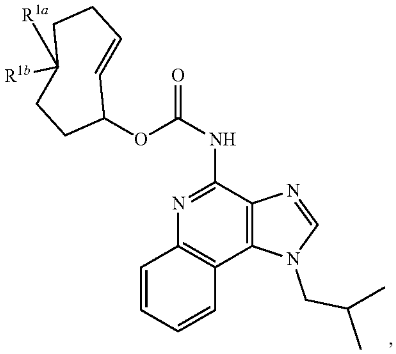
,
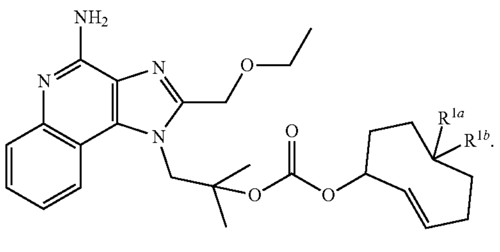

Compounds of formula (III) include
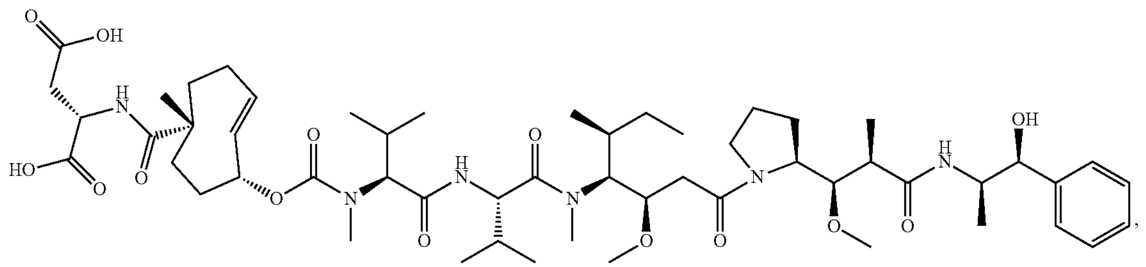
TCO(asp)-MMAE
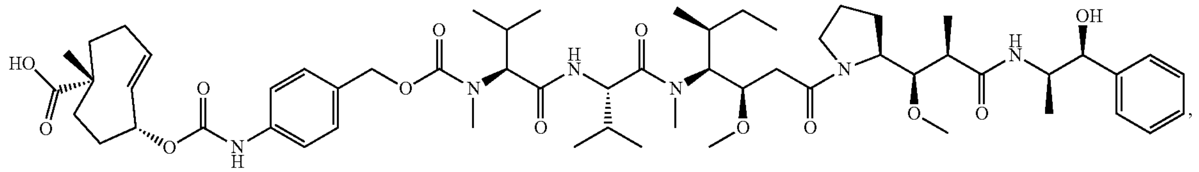
TCO-PABC-MMAE
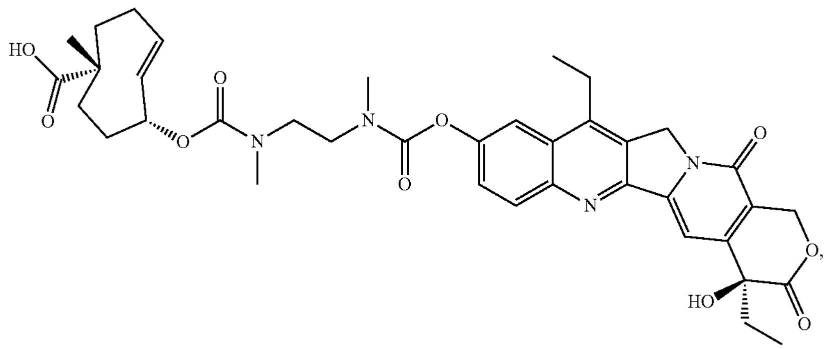
TCO-spacelink-SN-38
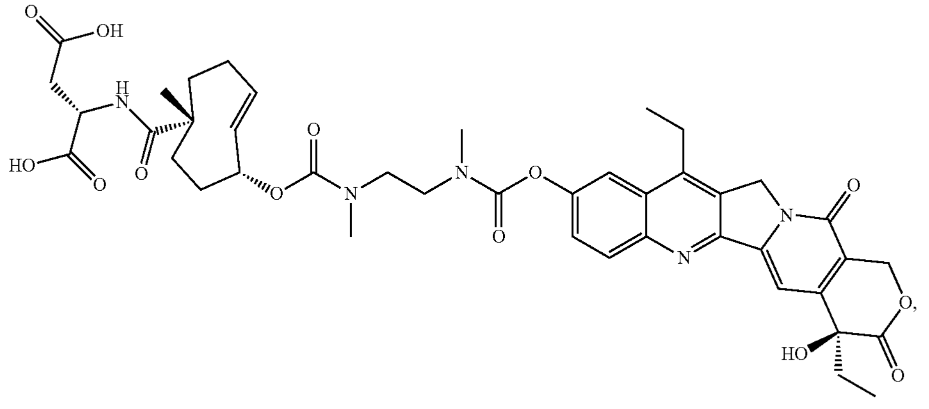
TCO(asp)-spacelink-SN-38
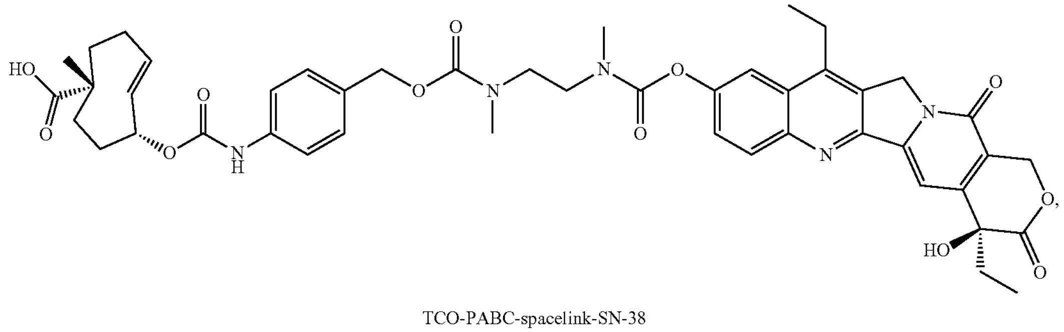
TCO-PABC-spacelink-SN-38

-continued
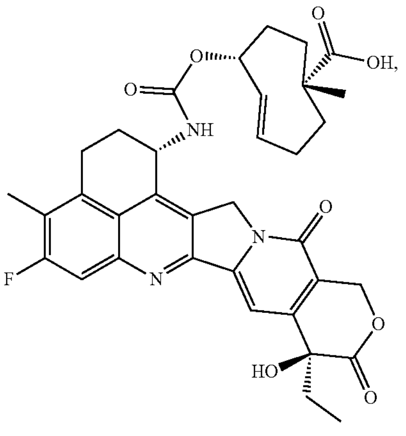
TCO-Exatecan
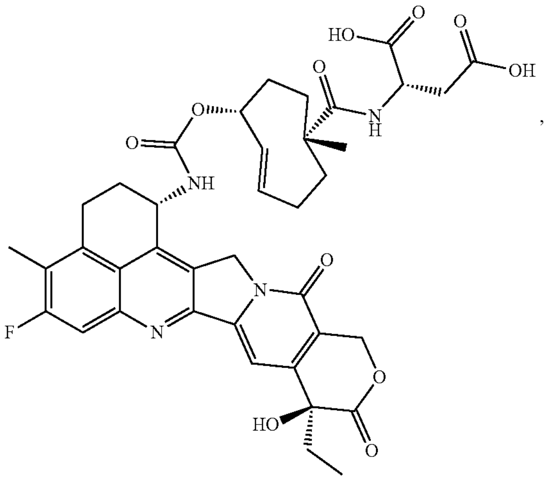
TCO(asp)-Exatecan
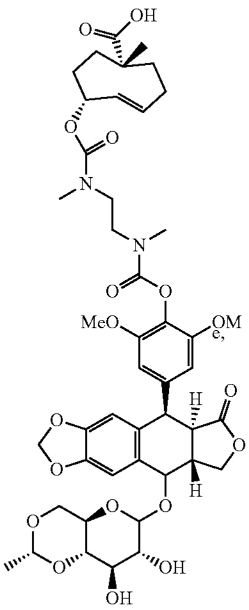
TCO-spacelink-Etoposide
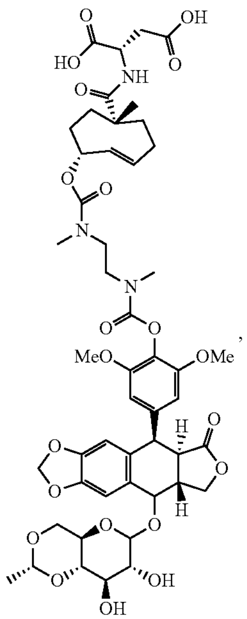
TCO(asp)-spacelink-Etoposide
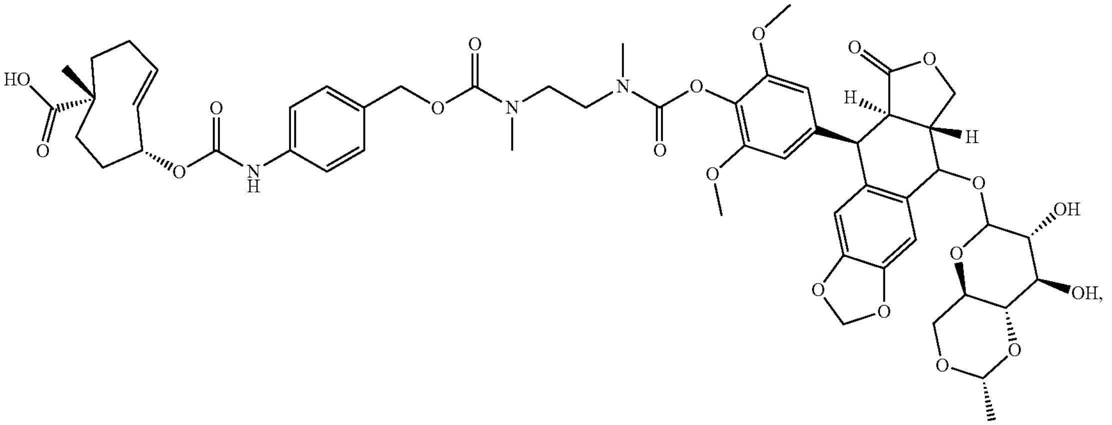
TCO-PABC-spacelink-Etoposide -continued
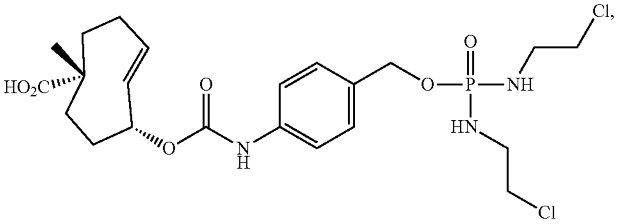
TCO-PABC-Cl-phosphamide
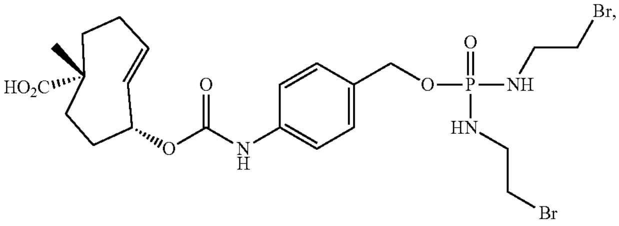
TCO-PABC-Br-phosphamide
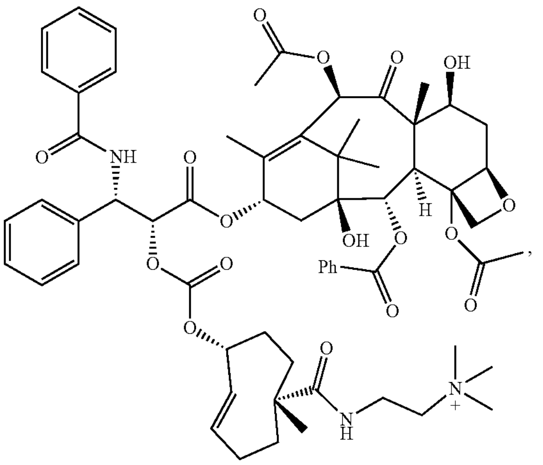
TCO-ammonium-Ptx
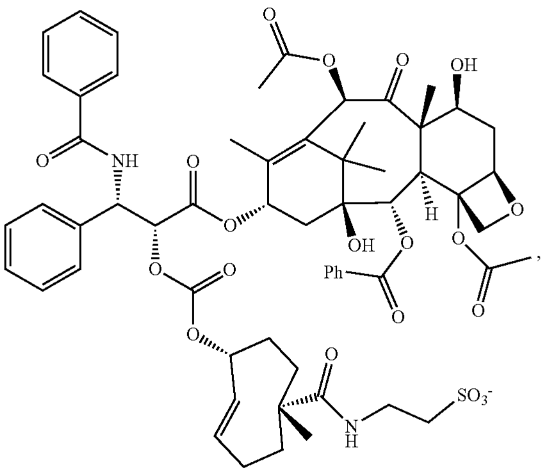
TCO-taurine-Ptx
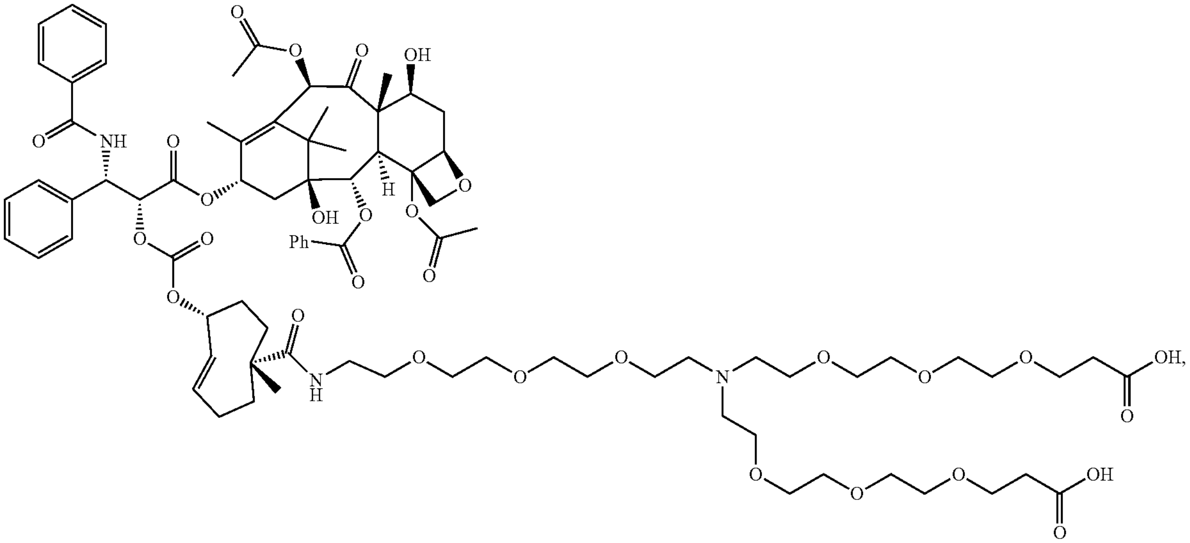
TCO-bis-PEG-Ptx -continued
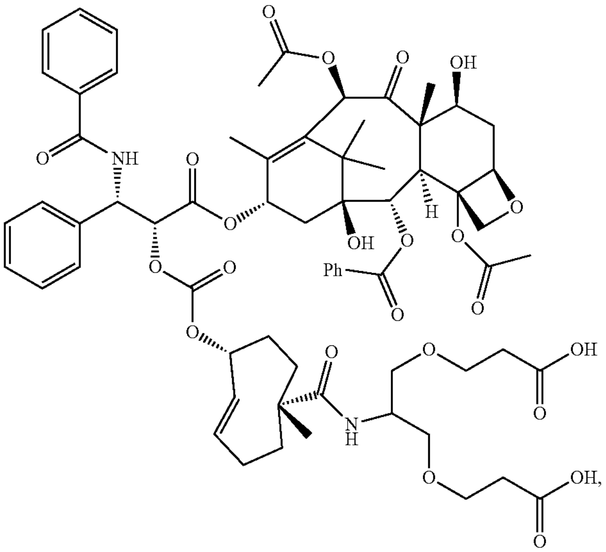
TCO-bis-acid-Ptx
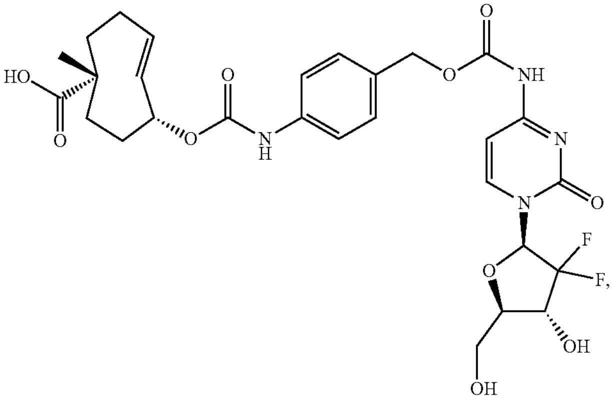
TCO-PABC-gemcitabine
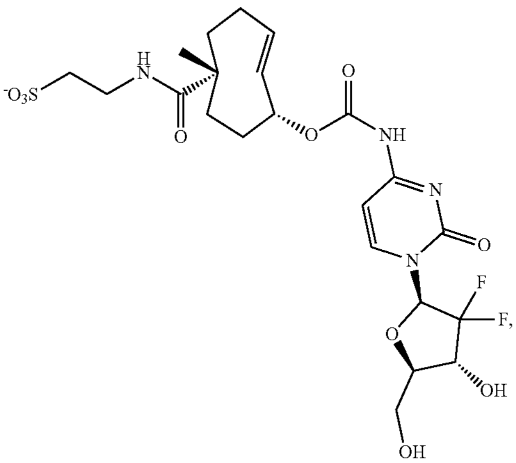
TCO(taurine)-gemcitabine
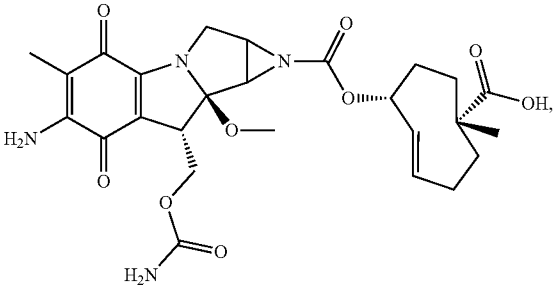
TCO-mitomycin C -continued

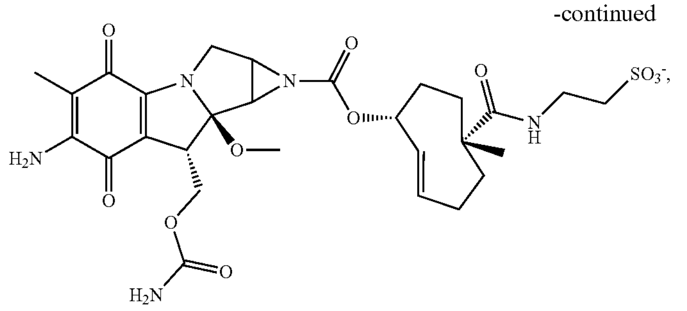

TCO(taurine)-mitomycin C

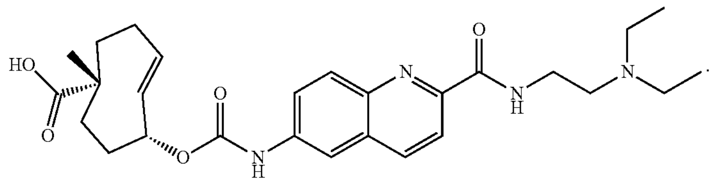

E. SYNTHETIC METHODS

The compounds and conjugates of the present disclosure can be better understood in connection with the following synthetic schemes and methods, which illustrate means by which the compounds may be prepared.

Conjugates of formula (I) or compounds of formula (III) may be prepared by reacting a primary amine, secondary amine, or a hydroxyl group with a suitably activated linker. It is to be understood that a reactive group on a linker (e.g., ester, carbonate, acyl chloride, carboxylic acid) can be located on any selected position of the linker group. Conversely, the linker may have a nucleophilic amine or hydroxyl group that may be reacted with a suitable group such as an aldehyde, ketone, ester, carbonate, carboxylic acid, or acyl chloride.

In certain embodiments, as shown below, a trans-cyclooctene activated for nucleophilic addition can be reacted with a suitable payload (D/D$^1$), or a payload attached to a linker, in the presence of a base to provide a functionalized payload. The payload or linker can include a primary amine, secondary amine, or hydroxyl group that reacts with the activated TCO. In certain embodiments, the leaving group (LG) is a chloro leaving group, a p-nitrophenol leaving group, or an N-hydroxysuccinimide leaving group. Exemplary bases for use in the reaction include organic and inorganic bases, such as for example, triethylamine, pyridine, sodium hydroxide, and sodium bicarbonate.

Scheme 1A

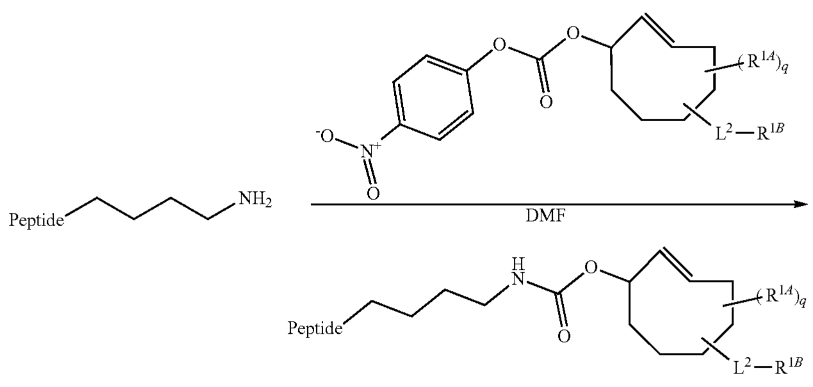

Scheme 1A illustrates a general method of conjugating a trans-cyclooctene to a lysine side chain of a (poly) peptide, including a protein (e.g., a monoclonal antibody). The nitrophenol carbonate may react with the amino group under basic conditions to provide a trans-cyclooctene-conjugated (poly) peptide. More specifically, a solution of an antibody in aqueous buffer may be incubated with a molar excess of carbonate reagent. The reaction mixture can be quenched by addition of excess amine (such as ethanolamine, taurine, etc.). The trans-cyclooctene-antibody conjugate may then be purified by gel filtration. The number of trans-cyclooctene molecules bound per antibody molecule can be determined by measuring spectrophotometrically.

Scheme 1B

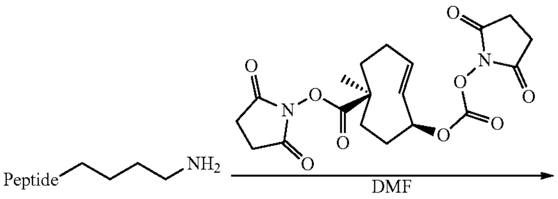

-continued

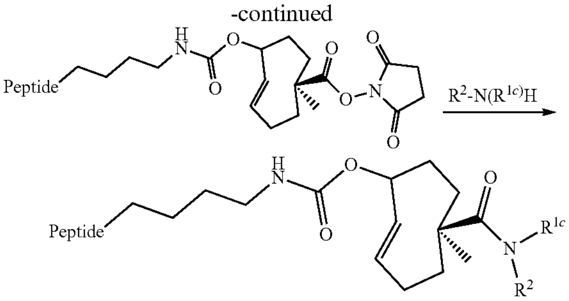

Scheme 1B illustrates a two-step method for conjugating a trans-cyclooctene to a protein or peptide. Reaction between a carbonate ester and the lysine side chain followed by further coupling with an amino-containing group $R^2$—N($R^{1c}$)H under basic conditions may provide the trans-cyclooctene functionalized protein/peptide wherein $R^{1c}$ is as defined herein and $R^2$ is —$C_{1-6}$alkylene-$CO_2$H, —$CHR^{1e}CO_2H$, —$C_{1-6}$alkylene-C(O)O$C_{1-4}$alkyl, C(O)O$C_{1-4}$alkyl, or —$CHR^{1e}$C(O)O$C_{1-4}$alkyl.

Alcohol-containing side chains and a (poly)peptide N-terminal amino group may react analogously to Schemes 1A and 1B to provide trans-cyclooctene conjugates.

Scheme 2

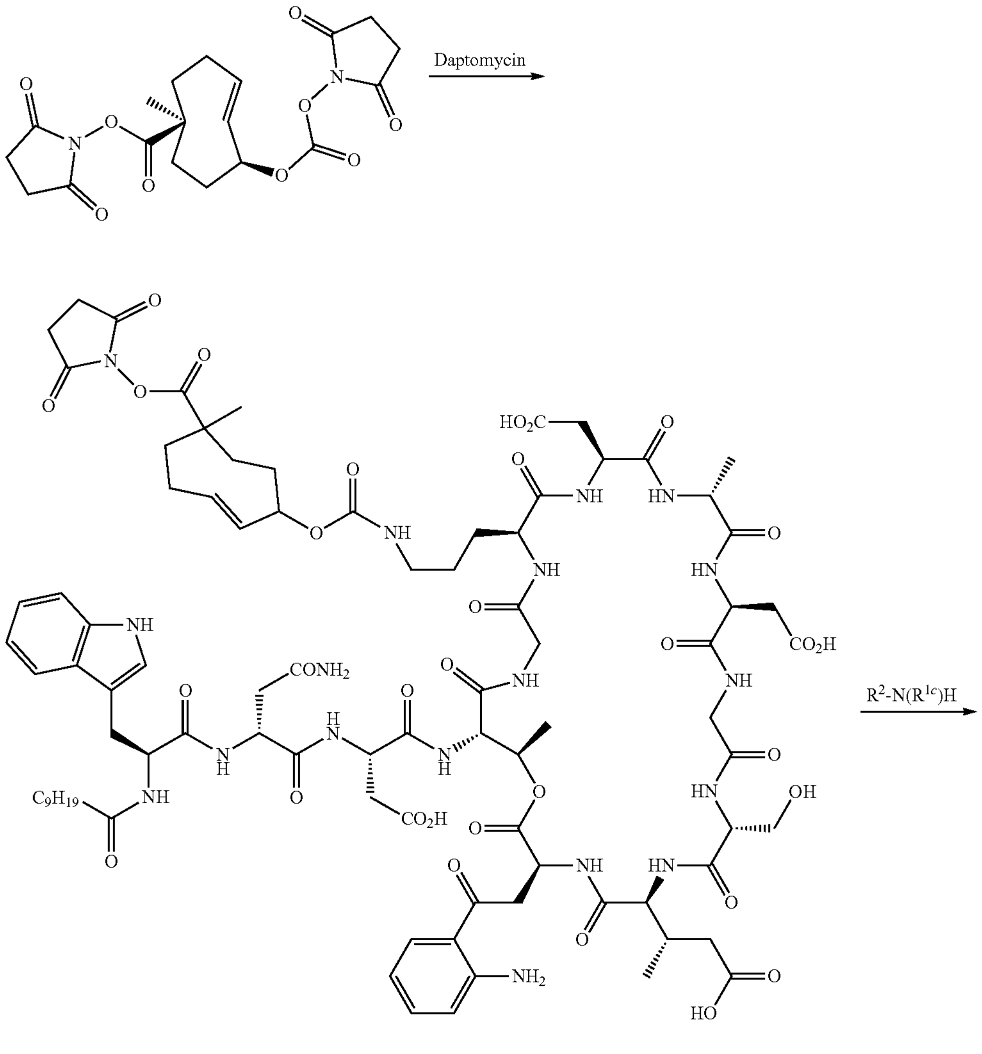

-continued
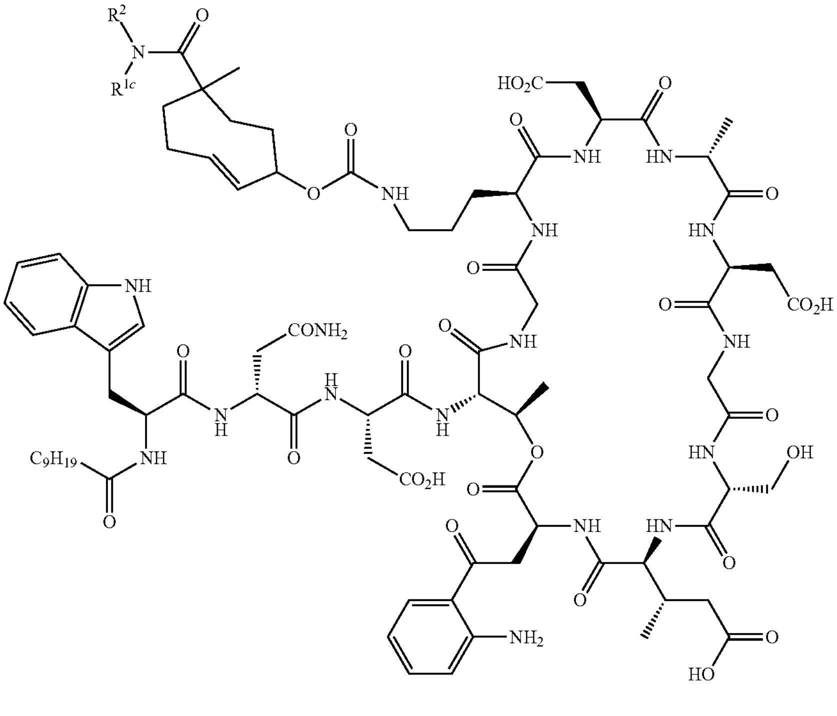
Scheme 2 illustrates a similar reaction between a carbonate ester and the ornithine side chain of daptomycin followed by further coupling with an amino-containing group $R^2$—N($R^{1e}$)H under basic conditions (e.g., $R^2$ is —$C_{1-6}$ alkylene-$CO_2H$, —$CHR^{1e}CO_2H$, —$C_{1-6}$alkylene-C(O)O$C_{1-4}$ alkyl, C(O)O$C_{1-4}$alkyl, or —$CHR^{1e}$C(O)O$C_{1-4}$alkyl).
Scheme 3
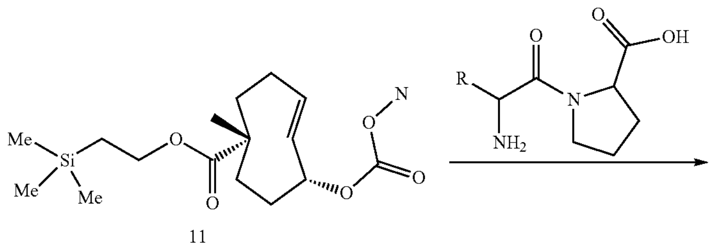
11

-continued
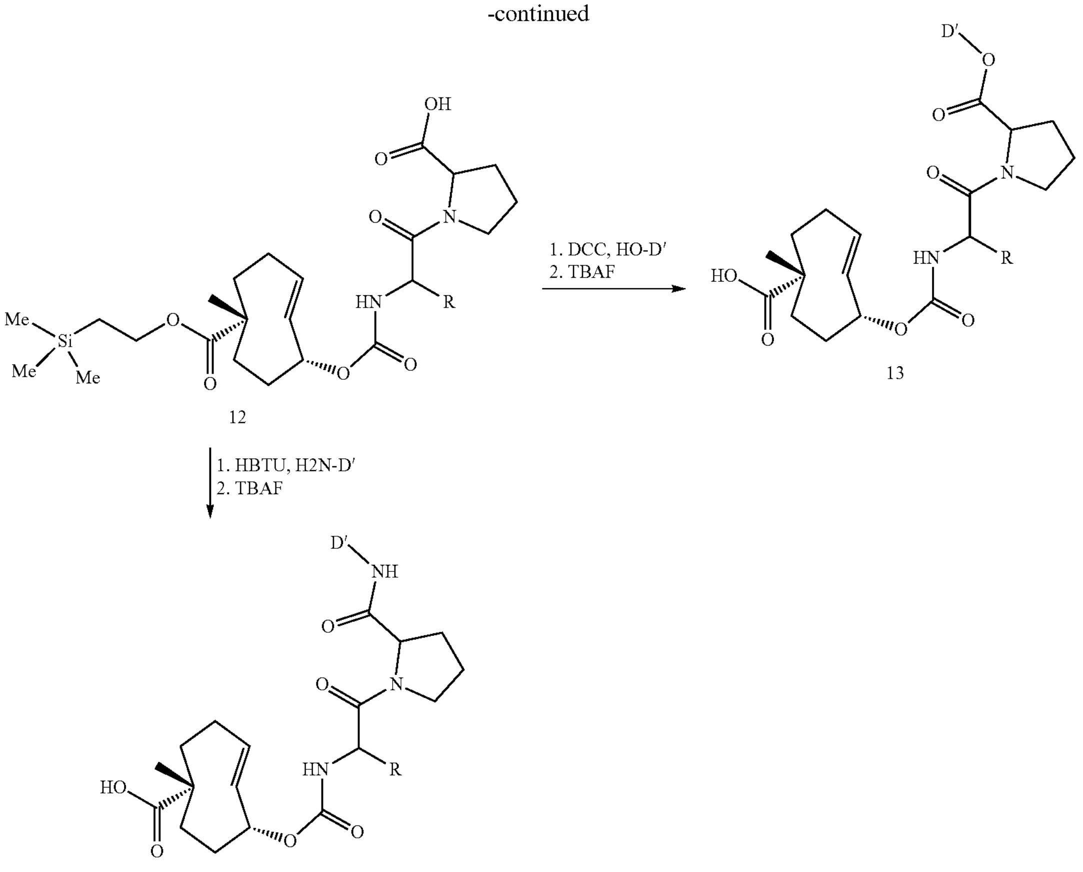
12
13
14
Scheme 3 illustrates conversion of 11 to a carboxylic acid intermediate that may be further converted to payload-bearing products 13 and 14. In Scheme 3, D' represents a payload moiety (e.g., immunomodulatory payload moiety, anticancer agent payload moiety, TLR agonist payload moiety).
Scheme 5
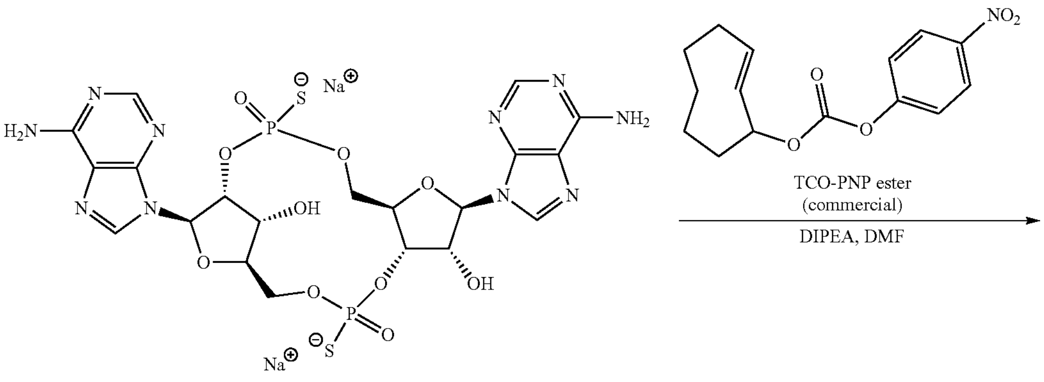
ADU-S100
(commercial)

-continued
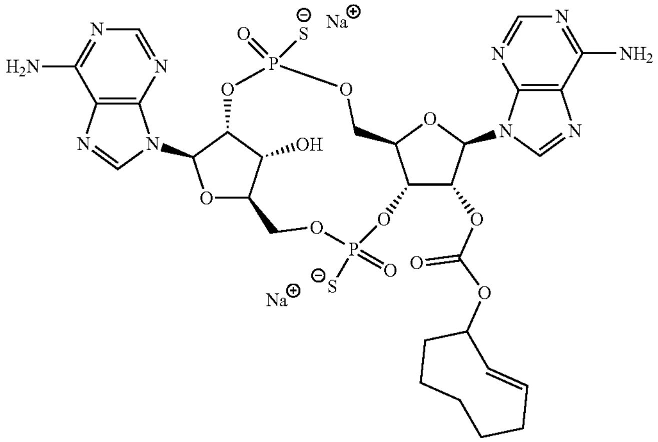
TCO-ADU-S100
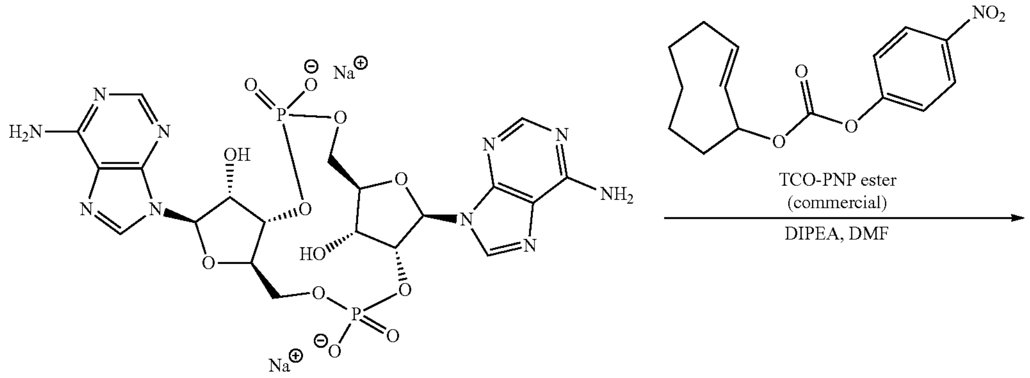
2'3'-cGAMP
(commercial)
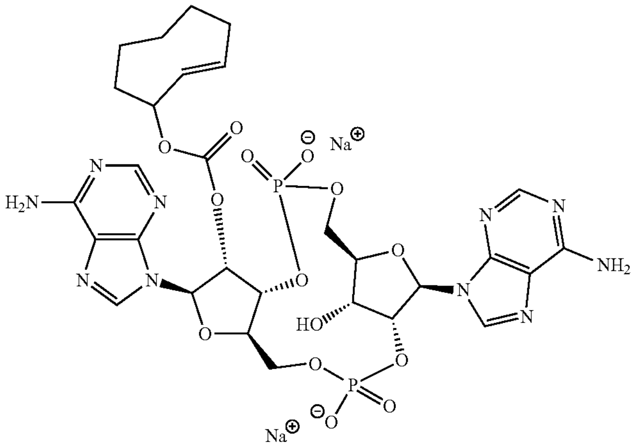
TCO-2'3'-cGAMP Other carboxylic acids that may be prepared using 11 include those shown in Scheme 4.
Scheme 5
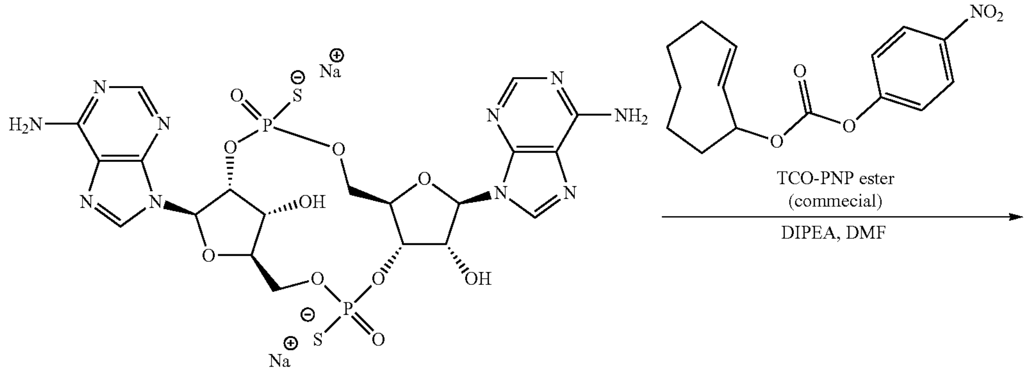
ADU-S100
(commercial)
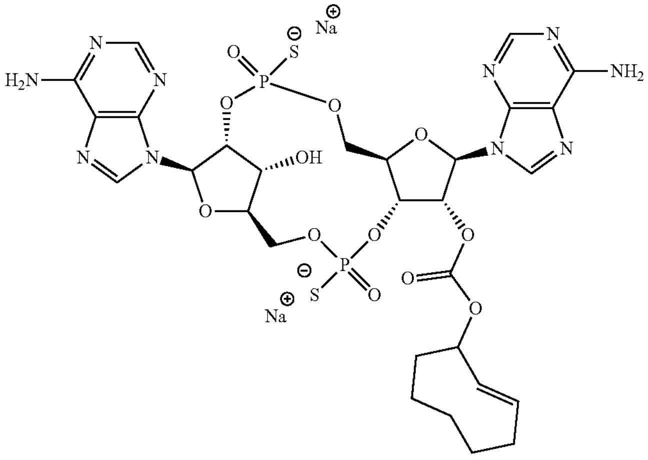
TCO-ADU-S100
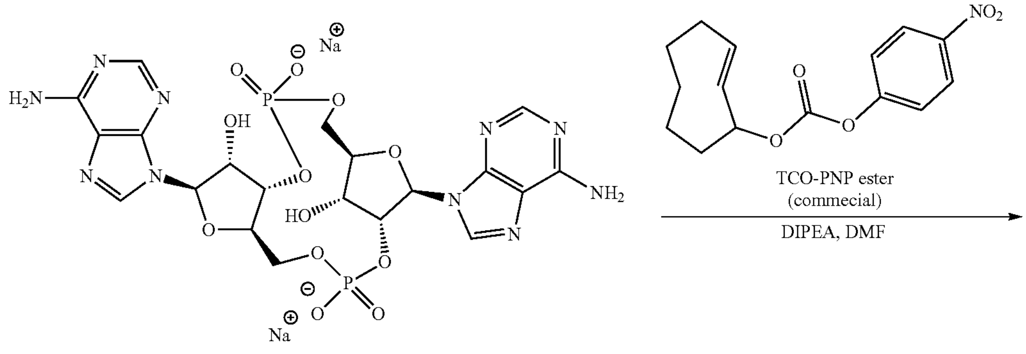
2'3'-cGAMP
(commercial)

-continued
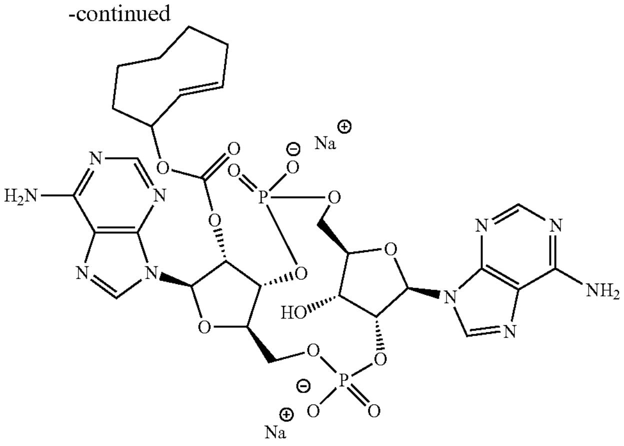
TCO-2′3′-cGAMP
Synthetic methods to prepare representative STING agonist TCO conjugates are shown in Scheme 5.
Scheme 6
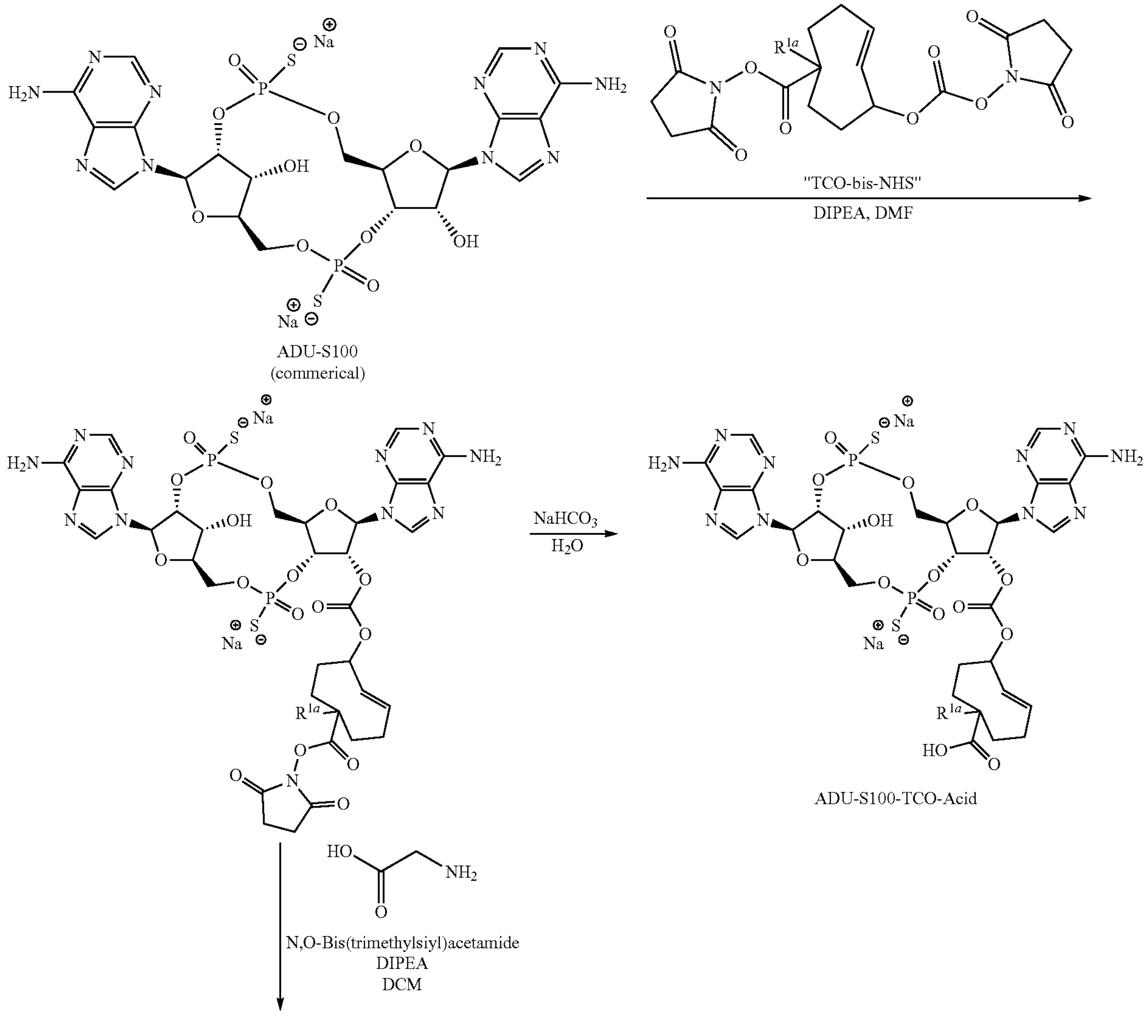

-continued
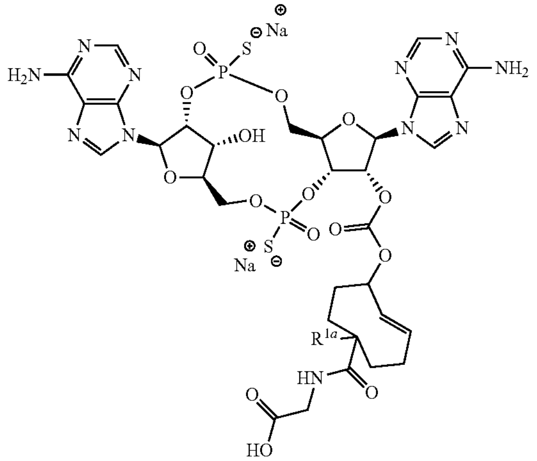
ADU-S100-TCO-Glycine
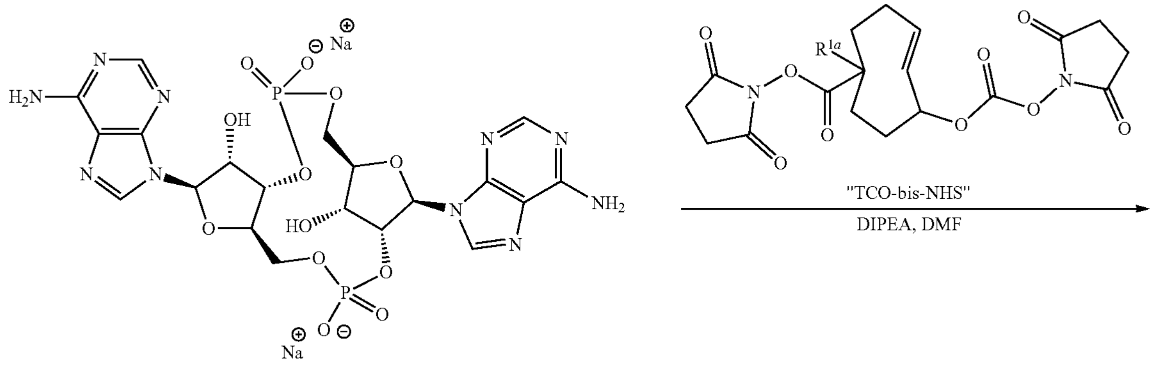
2′3′-cGAMP
(commerical)
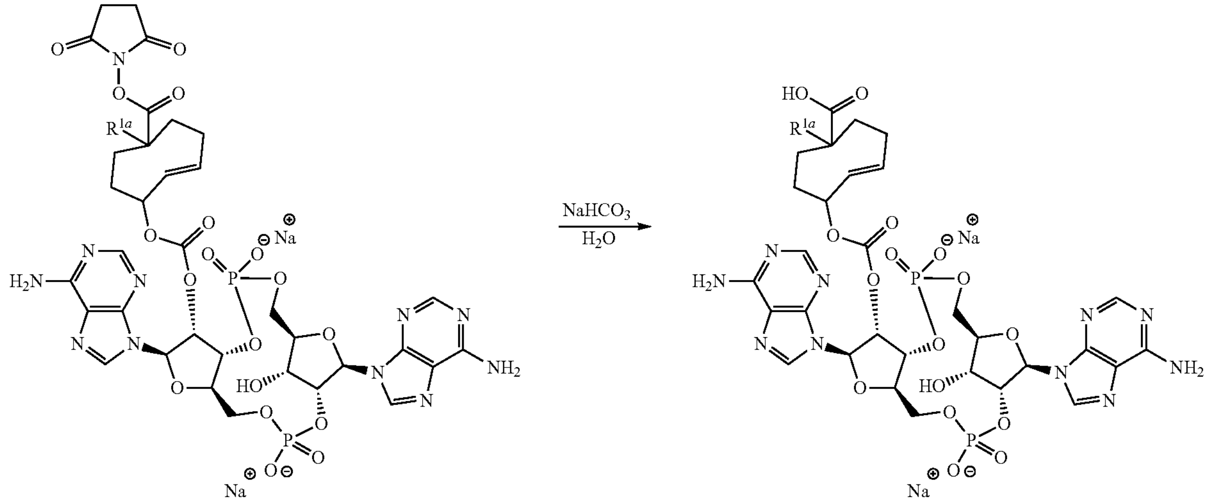
2′3′-cGAMP-TCO-Acid -continued
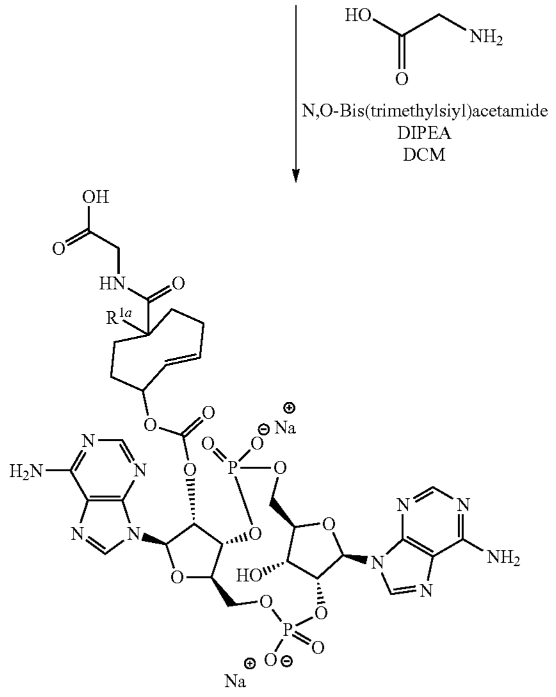
2′3′-cGAMP-TCO-Glycine
Synthetic methods to prepare representative STING agonist TCO conjugates are shown in Scheme 6.
Scheme 7
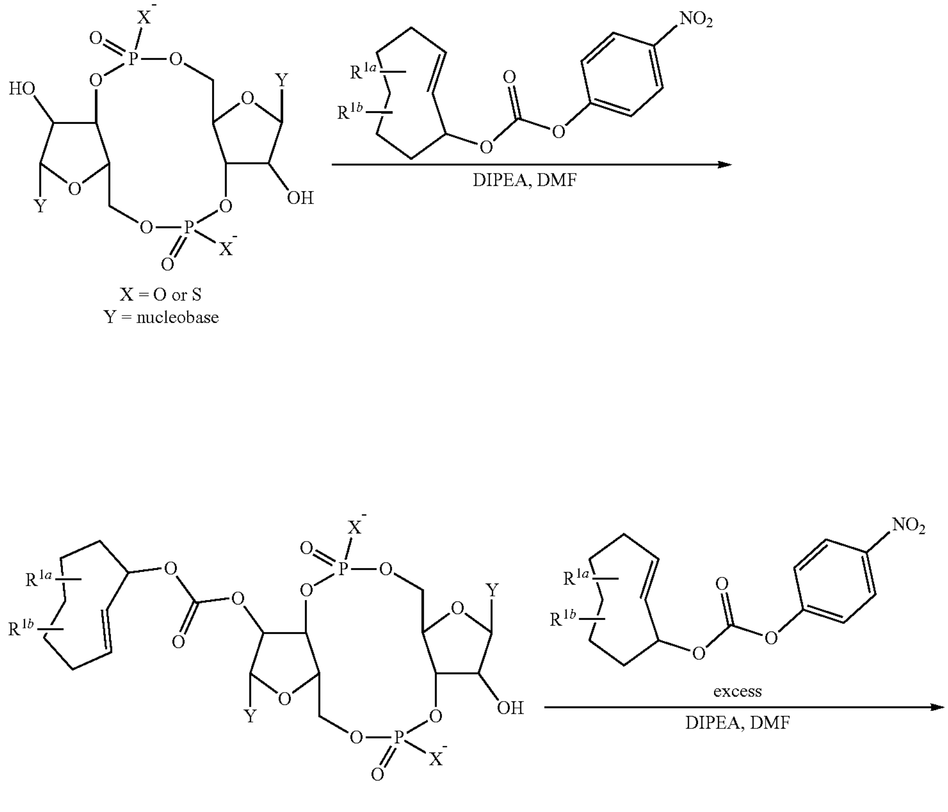

-continued

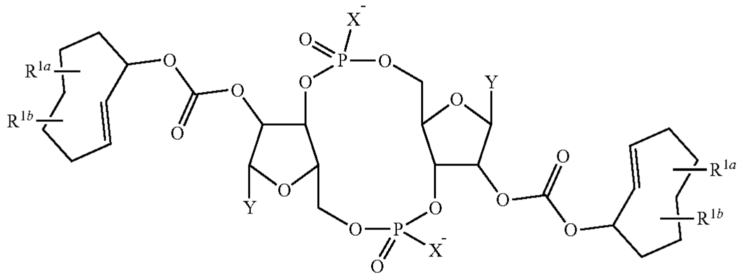

Scheme 7 illustrates a general method of conjugating a cyclic dinucleotide to a trans-cyclooctene, as in formula (I). The illustrated method proceeds by reaction of a cyclic dinucleotide molecule with a nitrophenyl carbonate substituted trans-cyclooctene in the presence of a base to form a mono- or bis-substituted cyclic dinucleotide, depending on the amount of trans-cyclooctene reagent.

Scheme 8

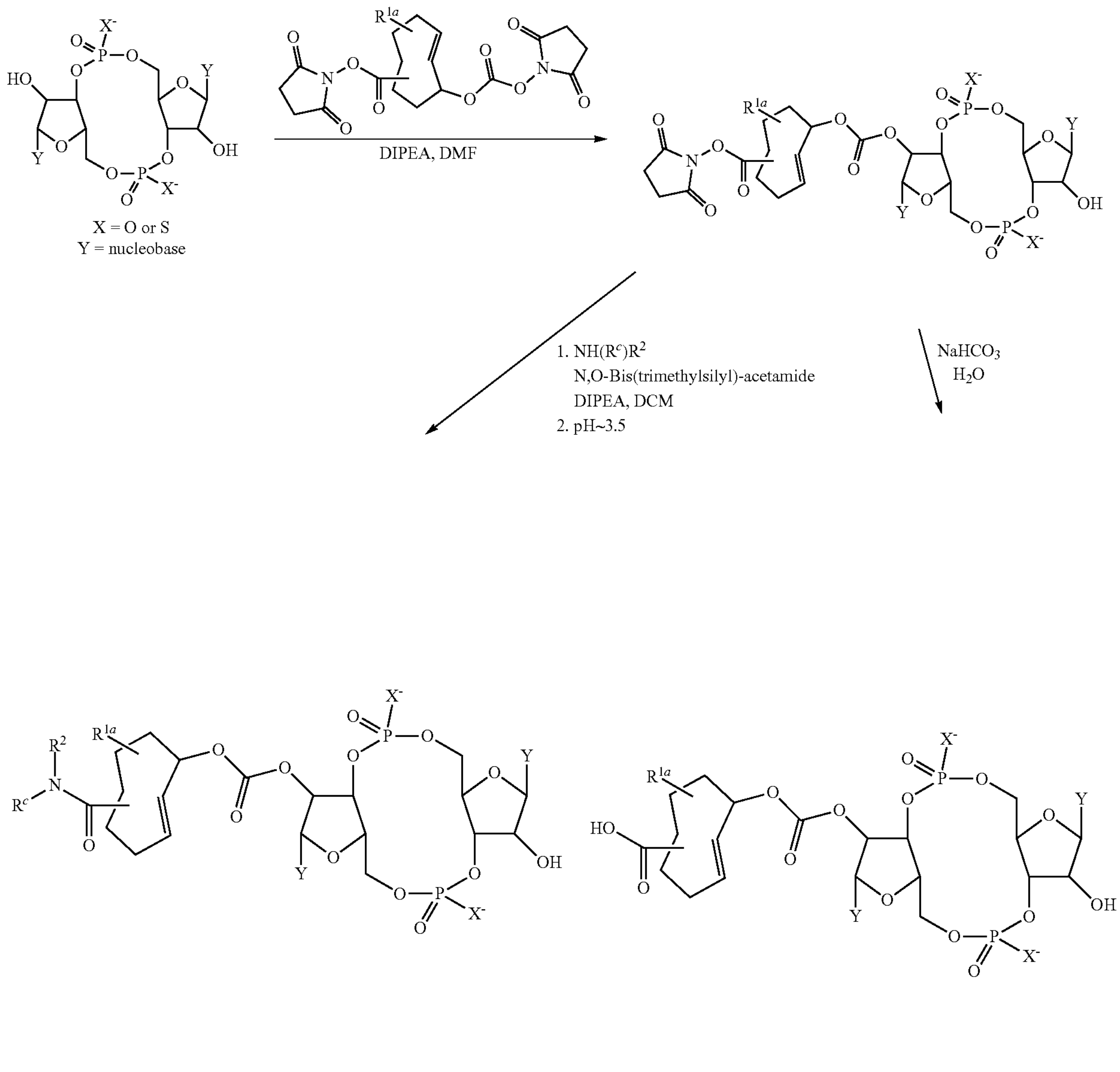

Scheme 8 illustrates a general method of conjugating a cyclic dinucleotide to a transcyclooctene wherein $R^2$ is —$C_{1-6}$alkylene-$CO_2H$, —$CHR^{1e}CO_2H$, —$C_{1-6}$alkylene-C(O)O$C_{1-4}$alkyl, C(O)O$C_{1-4}$alkyl, or —$CHR^{1e}$C(O)O$C_{1-4}$alkyl, which corresponds with $R^{1b}$ in formula (I) being one of C(O)N($R^{1c}$)—$C_{1-6}$alkylene-$CO_2H$, C(O)OH, C(O)N($R^{1c}$)$CHR^{1e}CO_2H$, C(O)N($R^{1c}$) $C_{1-6}$alkylene-C(O)O$C_{1-4}$alkyl, C(O)O$C_{1-4}$alkyl, or C(O)N($R^{1c}$)$CHR^{1e}$C(O)O$C_{1-4}$alkyl. The processes illustrated in Scheme 8 may be modified to provide bis-conjugated cyclic dinucleotides using excess trans-cyclooctene reagent, analogous to Scheme 7.

Scheme 9

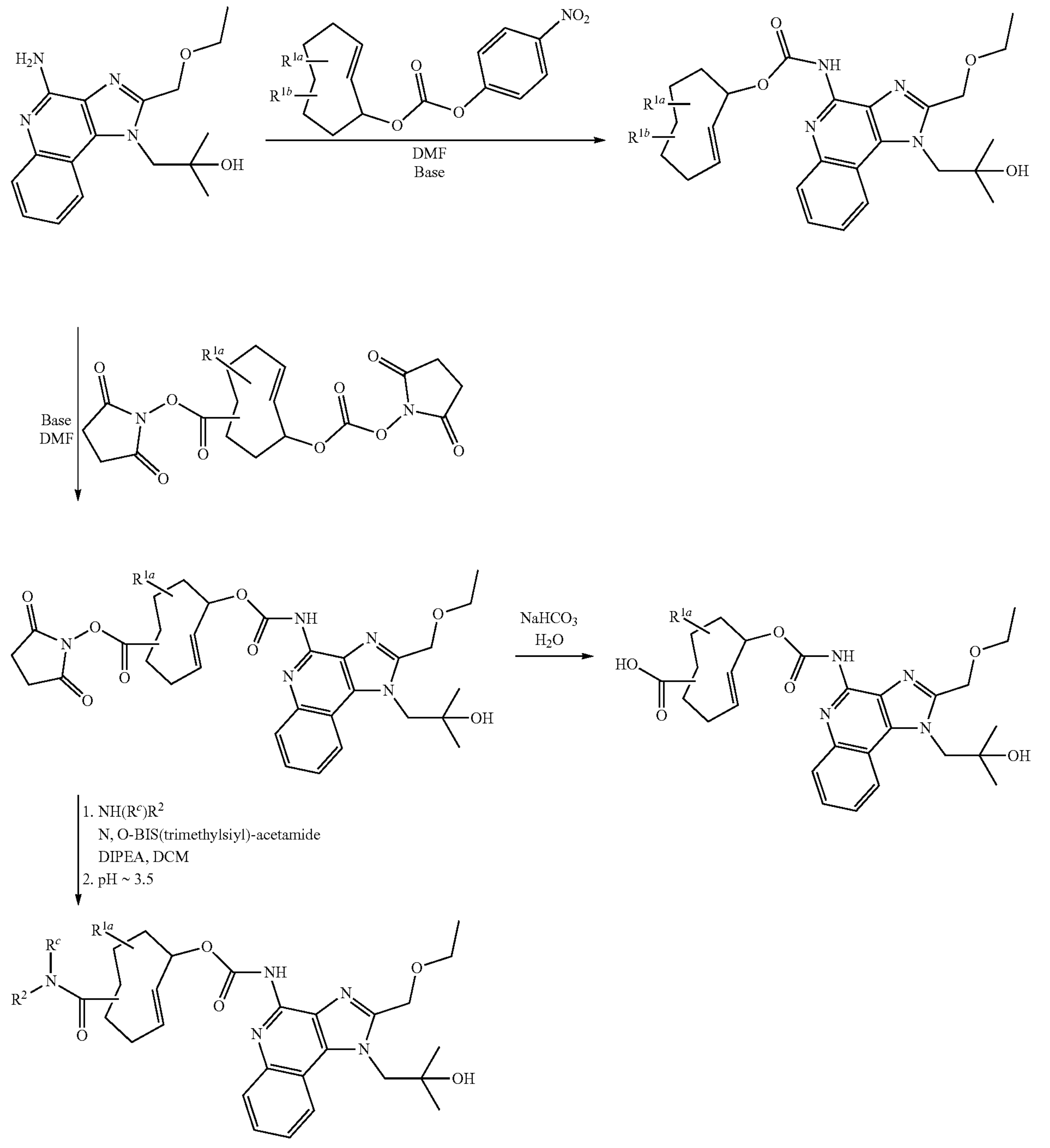

Schemes 9 and 10 illustrate representave synthetic methods of conjugating an imidazo[4,5-c]quinolin-4-amine to a trans-cyclooctene, as in formula (I), following analogous procedures to Schemes 7 and 8.

Scheme 10

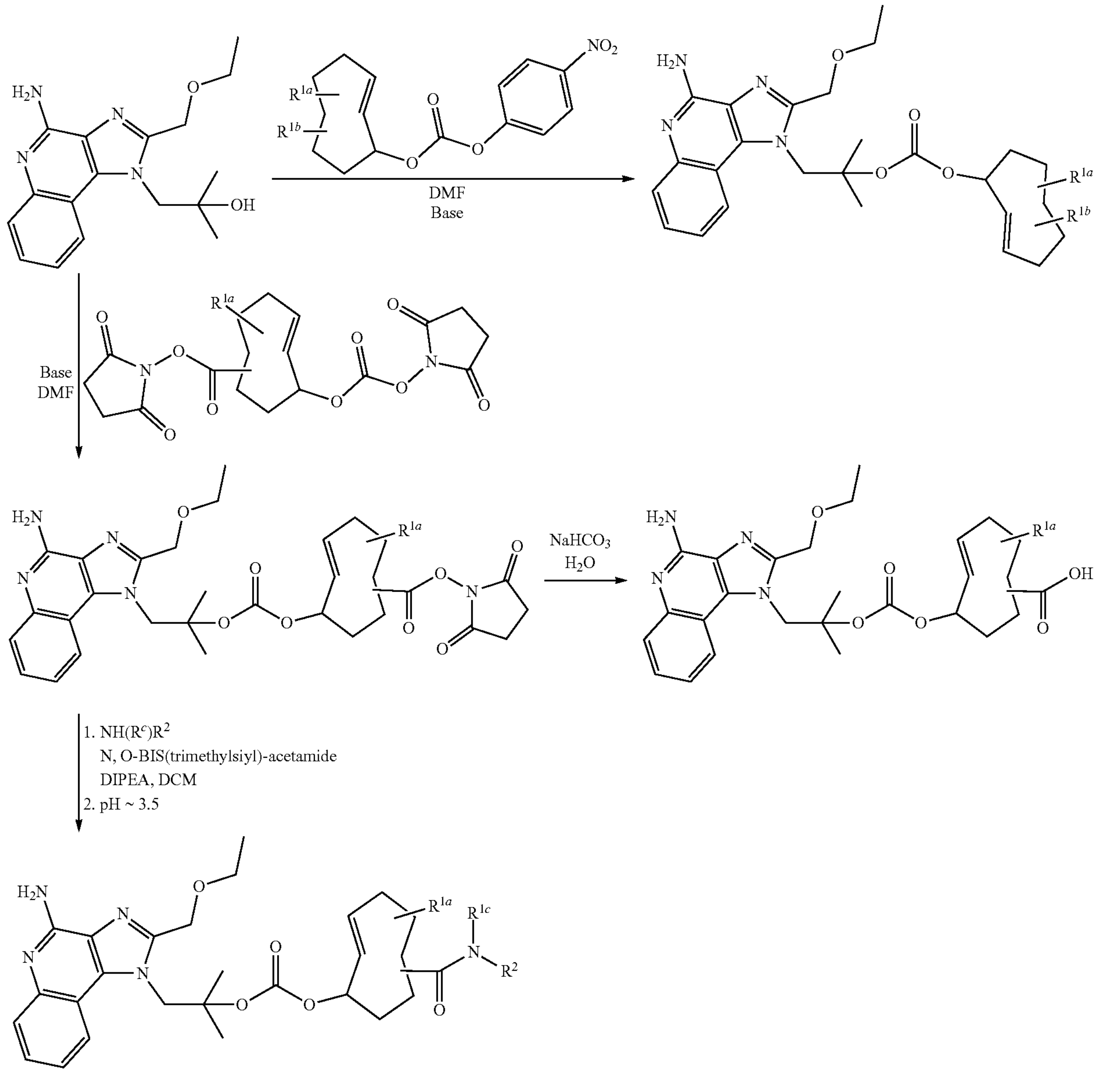

The disclosed compounds may be prepared in racemic form or as individual enantiomers or diastereomers by either stereospecific synthesis or by resolution. The compounds may, for example, be resolved into their component enantiomers or diastereomers by standard techniques, such as the formation of stereoisomeric pairs by salt formation with an optically active base, followed by fractional crystallization and regeneration of the free acid. The compounds may also be resolved by formation of stereoisomeric esters or amides, followed by chromatographic separation and removal of the chiral auxiliary. Alternatively, the compounds may be resolved using a chiral HPLC column. The enantiomers also may be obtained from kinetic resolution of the racemate of corresponding esters using lipase enzymes.

A compound described herein can be in the form of a salt, e.g., a pharmaceutically acceptable salt. The term "pharmaceutically acceptable salt" includes salts of the active compounds that are prepared with relatively nontoxic acids or bases, depending on the particular substituents found on the compounds described herein. Neutral forms of the compounds may be regenerated by contacting the salt with a base or acid and isolating the parent compound in a conventional manner. The parent form of the compound differs from the various salt forms in certain physical properties, such as solubility in polar solvents, but otherwise the salts are equivalent to the parent form of the compound for the purposes of this disclosure. Examples of pharmaceutically acceptable salts are discussed in Berge et al, 1977, "Pharmaceutically Acceptable Salts," J. Pharm. Sci. Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions (e.g., $NH_3R_1^+$, $NH_2R_2^+$, $NHR_3^+$, $NR_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, gluchep tonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle an active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999); J. F. W. McOmie, "Protective Groups in Organic Chemistry," Plenum Press, London and New York 1973; "The Peptides"; Volume 3 (editors: E. Gross and J. Meienhofer), Academic Press, London and New York 1981; "Methoden der organischen Chemie," Houben-Weyl, 4th edition, Vol. 15/1, Georg Thieme Verlag, Stuttgart 1974; H.-D. Jakubke and H. Jescheit, "Aminosauren, Peptide, Proteine," Verlag Chemie, Weinheim, Deerfield Beach, and Basel 1982; in Jochen Lehmann, "Chemie der Kohlenhydrate: Monosaccharide and Derivate," Georg Thieme Verlag, Stuttgart 1974.

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

A hydroxy group may be protected as an ether (—OR) or an ester (—OC(O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—$OC(O)CH_3$, —OAc).

An aldehyde or ketone group may be protected as an acetal ($RCH(OR)_2$) or ketal ($R_2C(OR)_2$), respectively, in which the carbonyl group ($R_2C{=}O$) is converted to a diether ($R_2C(OR)_2$), by reaction with, for example, a primary alcohol. The aldehyde or ketone group is readily regenerated by hydrolysis using a large excess of water in the presence of acid.

An amine group may be protected, for example, as an amide (—NRC(O)R) or a urethane (—NRC(O)OR), for example, as: a methyl amide (—$NHC(O)CH_3$); a benzyloxy amide (—$NHC(O)OCH_2C_6H_5$, —NH-Cbz); as a t-butoxy amide (—$NHC(O)OC(CH_3)_3$, —NH-Boc); a 2-biphenyl-2-propoxy amide (—$NHCO(O)C(CH_3)_2C_6H_4C_6H_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2(-phenylsulphonyl)ethyloxy amide (—NH-Psec); or, in suitable cases (e.g., cyclic amines), as a nitroxide radical (>N-0«).

A carboxylic acid group may be protected as an ester, for example, as: an alkyl ester (e.g., a methyl ester; a t-butyl ester); a haloalkyl ester (e.g., a haloalkyl ester); a trialkylsilylalkyl ester; or an arylalkyl ester (e.g., a benzyl ester; a nitrobenzyl ester); or as an amide, for example, as a methyl amide.

A thiol group may be protected as a thioether (—SR), for example, as: a benzyl thioether; an acetamidomethyl ether (—S—$CH_2NHC(O)CH_3$).

A compound described herein can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom substitution in aromatic rings.

In certain embodiments, the products may be further modified, for example, by manipulation of substituents. These manipulations may include, but are not limited to, reduction, oxidation, organometallic cross-coupling, alkylation, acylation, and hydrolysis reactions which are commonly known to those skilled in the art. In some cases, the order of carrying out the foregoing reaction schemes may be varied to facilitate the reaction or to avoid unwanted reaction products.

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

F. FORMULATIONS

Compositions (e.g., support composition, conjugates, trans-cyclooctene prodrugs) can be provided in any suitable form, e.g., in the form of a pharmaceutically acceptable formulation, and can be formulated for any suitable route of administration, e.g., oral, topical or parenteral administration. Where the composition is provided as a liquid injectable (such as in those embodiments where they are administered intravenously or directly into a tissue), the composition can be provided as a ready-to-use dosage form, or as a reconstitutable storage-stable powder or liquid that may include pharmaceutically acceptable carriers and excipients.

A "pharmaceutically acceptable excipient," "pharmaceutically acceptable diluent," "pharmaceutically acceptable carrier," or "pharmaceutically acceptable adjuvant" means an excipient, diluent, carrier, and/or adjuvant that are useful in preparing a pharmaceutical composition that are generally safe, non-toxic and neither biologically nor otherwise undesirable, and includes an excipient, diluent, carrier, and adjuvant that are acceptable for veterinary use and/or human pharmaceutical use. "A pharmaceutically acceptable excipient, diluent, carrier and/or adjuvant" as used herein includes one or more such excipients, diluents, carriers, and adjuvants.

Methods for formulating compositions can be adapted from those readily available. For example, compositions can be provided in a pharmaceutical formulation that includes a therapeutically effective amount of a composition and a pharmaceutically acceptable carrier (e.g., saline). The pharmaceutical formulation may optionally include other additives (e.g., buffers, stabilizers, preservatives, and the like). In some embodiments, the formulations are suitable for administration to a mammal, such as those that are suitable for administration to a human.

The compositions of the present disclosure can be prepared in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the subject.

The compositions of the present disclosure can also be administered by injection, that is, intravenously, intramuscularly, intracutaneously, subcutaneously, intraduodenally, or intraperitoneally. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances, which increase the viscosity of the suspension, such as sodium carboxymethyl cellulose, sorbitol, or dextran. Optionally, the suspension may also contain suitable stabilizers or agents, which increase the solubility of the compounds to allow for the preparation of highly, concentrated solutions. For injection, the agents of the invention may be formulated in aqueous solutions, preferably in physiologically compatible buffers such as Hanks's solution, Ringer's solution, or physiological saline buffer.

In some instances, the compositions described herein can be administered by inhalation, for example, intranasally.

In some instances, the compositions of the present disclosure can be administered transdermally.

In some instances, the compositions can be administered by intraocular, intravaginal, and intrarectal routes including suppositories, insufflation, powders and aerosol formulations (for examples of steroid inhalants, see Rohatagi, J. Clin. Pharmacol. 35:1187-1193, 1995; Tjwa, Ann. Allergy Asthma Immunol. 75:107-111, 1995).

Accordingly, the present disclosure also provides pharmaceutical formulations including a composition as described herein and a pharmaceutically acceptable carrier or excipient.

For preparing pharmaceutical formulations from the compositions of the present disclosure, pharmaceutically acceptable carriers can be solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are found, for example in Remington's Pharmaceutical Sciences, Maack Publishing Co, Easton PA ("Remington's").

In some embodiments, the pharmaceutical composition of the invention is a vaccine that comprises a conjugate, or a pharmaceutically acceptable salt thereof, a pharmaceutically acceptable carrier, and optionally an antigen. Antigens for use in the immunogenic compositions provided herein may be provided in an effective amount (e.g., an amount effective for use in therapeutic or prophylactic methods). For example, immunogenic compositions of the invention may be used to treat or prevent diseases or conditions such as infections and cancer. Exemplary antigens include, but are not limited to, tumor antigens and infectious disease antigens. Antigens for use in the immunogenic compositions provided herein are typically macromolecules (e.g., polypeptides, polysaccharides, polynucleotides) that are foreign to the host. An antigen may be any target epitope, molecule (including a biomolecule), molecular complex (including molecular complexes that contain biomolecules), subcellular assembly, cell or tissue against which elicitation or enhancement of immunoreactivity in a subject is desired. Frequently, the term antigen may refer to a polypeptide antigen of interest. However, antigen, as used herein, may also refer to a recombinant construct which encodes a polypeptide antigen of interest (e.g., an expression construct). In certain preferred embodiments the antigen may be, or may be derived from, or may be immunologically cross-reactive with, an infectious pathogen and/or an epitope, biomolecule, cell or tissue that is associated with infection, cancer, autoimmune disease, allergy, asthma, or any other condition where stimulation of an antigen-specific immune response would be desirable or beneficial.

In certain embodiments, a tumor antigen or cancer antigen is used in conjunction with the immunogenic compositions provided herein. In certain embodiments, the tumor antigen is a peptide-containing tumor antigens, such as a polypeptide tumor antigen or glycoprotein tumor antigens. In certain embodiments, the tumor antigen is a saccharide-containing tumor antigen, such as a glycolipid tumor antigen or a ganglioside tumor antigen. In certain embodiments, the tumor antigen is a polynucleotide-containing tumor antigen that expresses a polypeptide-containing tumor antigen, for instance, an RNA vector construct or a DNA vector construct, such as plasmid DNA. In certain embodiments, the tumor antigen is a whole, live or dead or permeabilized cancer cell. Tumor antigens appropriate for the use in conjunction with the immunogenic compositions provided herein encompass a wide variety of molecules, such as (a) polypeptide-containing tumor antigens, including polypeptides (which can range, for example, from 8-20 amino acids in length, although lengths outside this range are also common), lipopolypeptides and glycoproteins, (b) saccharide-containing tumor antigens, including polysaccharides, mucins, gangliosides, glycolipids and glycoproteins, and (c) polynucleotides that express antigenic polypeptides.

In certain embodiments, the tumor antigens are, for example, (a) full length molecules associated with cancer cells, (b) homologs and modified forms of the same, including molecules with deleted, added and/or substituted portions, and (c) fragments of the same. In certain embodiments, the tumor antigens are provided in recombinant form. In certain embodiments, the tumor antigens include, for example, class I-restricted antigens recognized by CD8+ lymphocytes or class II-restricted antigens recognized by CD4+ lymphocytes.

In certain embodiments, the tumor antigens include, but are not limited to, (a) cancer-testis antigens such as NYESO-1, SSX2, SCP1 as well as RAGE, BAGE, GAGE and MAGE family polypeptides, for example, GAGE-1, GAGE-2, MAGE-1, MAGE-2, MAGE-3, MAGE-4, MAGE-5, MAGE-6, and MAGE-12 (which can be used, for example, to address melanoma, lung, head and neck, NSCLC, breast, gastrointestinal, and bladder tumors), (b) mutated antigens, for example, p53 (associated with various solid tumors, e.g., colorectal, lung, head and neck cancer), p21/Ras (associated with, e.g., melanoma, pancreatic cancer and colorectal cancer), CDK4 (associated with, e.g., melanoma), MUM1 (associated with, e.g., melanoma), caspase-8 (associated with, e.g., head and neck cancer), CIA 0205 (associated with, e.g., bladder cancer), HLA-A2-RI 701, beta catenin (associated with, e.g., melanoma), TCR (associated with, e.g., T-cell non-Hodgkins lymphoma), BCR-abl (associated with, e.g., chronic myelogenous leukemia), triosephosphate isomerase, KIA 0205, CDC-27, and LDLR-FUT, (c) over-expressed antigens, for example, Galectin 4 (associated with, e.g., colorectal cancer), Galectin 9 (associated with, e.g., Hodgkin's disease), proteinase 3 (associated with, e.g., chronic myelogenous leukemia), WT 1 (associated with, e.g., various leukemias), carbonic anhydrase (associated with, e.g., renal cancer), aldolaseA (associated with, e.g., lung cancer), PRAME (associated with, e.g., melanoma), HER-2/neu (associated with, e.g., breast, colon, lung and ovarian cancer), alpha-fetoprotein (associated with, e.g., hepatoma), KSA (associated with, e.g., colorectal cancer), gastrin (associated with, e.g., pancreatic and gastric cancer), telomerase catalytic protein, MUC-1 (associated with, e.g., breast and ovarian cancer), G-250 (associated with, e.g., renal cell carcinoma), p53 (associated with, e.g., breast, colon cancer), and carcinoembryonic antigen (associated with, e.g., breast cancer, lung cancer, and cancers of the gastrointestinal tract such as colorectal cancer), (d) shared antigens, for example, melanomamelanocyte differentiation antigens such as MART-1/Melan A, gp 100, MC1 R, melanocyte-stimulating hormone receptor, tyrosinase, tyrosinase related protein-1/TRP1 and tyrosinase related protein-2/TRP2 (associated with, e.g., melanoma), (e) prostate associated antigens such as PAP, PSA, PSMA, PSHP1, PSM-P1, PSM-P2, associated with e.g., prostate cancer, (f) immunoglobulin idiotypes (associated with myeloma and B cell lymphomas, for example), and (g) other tumor antigens, such as polypeptide- and saccharide-containing antigens including (i) glycoproteins such as sialyl Tn and sialyl Lex (associated with, e.g., breast and colorectal cancer) as well as various mucins; glycoproteins are coupled to a carrier protein (e.g., MUC-1 are coupled to KLH); (ii) lipopolypeptides (e.g., MUC-1 linked to a lipid moiety); (iii) polysaccharides (e.g., Globo H synthetic hexasaccharide), which are coupled to a carrier proteins (e.g., to KLH), (iv) gangliosides such as GM2, GM12, GD2, GD3 (associated with, e.g., brain, lung cancer, melanoma), which also are coupled to carrier proteins (e.g., KLH).

In certain embodiments, the tumor antigens include, but are not limited to, p15, Hom/MeI-40, H-Ras, E2A-PRL, H4-RET, IGH-IGK, MYL-RAR, Epstein Barr virus antigens, EBNA, human papillomavirus (HPV) antigens, including E6 and E7, hepatitis Band C virus antigens, human T-cell lymphotropic virus antigens, TSP-180, p185erbB2, p180erbB-3, c-met, nm-23H1, TAG-72-4, CA 19-9, CA 72-4, CAM 17.1, NuMa, K-ras, p16, TAGE, PSCA, CT7, 43-9F, 5T4, 791 Tgp72, beta-HCG, BCA225, BTAA, CA 125, CA 15-3 (CA 27.29\BCAA), CA 195, CA 242, CA-50, CAM43, CD68\KP1, CO-029, FGF-5, Ga733 (EpCAM), HTgp-175, M344, MA-50, MG7-Ag, MOV18, NB/70K, NY-CO-1, RCAS1, SDCCAG16, TA-90 (Mac-2 binding protein\cyclophilin C-associated protein), TAAL6, TAG72, TLP, TPS, and the like.

G. KITS

Aspects of the present disclosure include kits that have a composition as described herein.

A kit may include a compound of formula (I), or a pharmaceutically acceptable salt or composition thereof, and a therapeutic support composition. A kit may include a compound of formula (I), or a pharmaceutically acceptable salt or composition thereof, and a compound of formula (II), or formula (III), or a pharmaceutically acceptable salt or composition thereof.

A kit may include a compound of formula (II) or formula (III), or a pharmaceutically acceptable salt or composition thereof, and one or more immunomodulatory agents, or a pharmaceutically acceptable salt or composition thereof, and optionally a therapeutic support composition. A kit may include a therapeutic support composition, as described herein, and one or more immunomodulatory agents, or a pharmaceutically acceptable salt or composition thereof.

The therapeutic support composition, one or more immunomodulatory agents, and the compound of formula (I), (II), and/or (III) may be in separate containers in the packaging. One or more therapeutic support compositions may be provided in a kit.

The kits described herein may include a packaging configured to contain the composition (e.g., therapeutic support composition and/or one or more immunomodulatory agents). Similarly, one or more compounds of formula (I), (II), and/or (III) may be provided in a kit. The packaging may be a sealed packaging, such as a sterile sealed packaging. By "sterile" is meant that there are substantially no microbes (such as fungi, bacteria, viruses, spore forms, etc.). In some instances, the packaging may be configured to be sealed, e.g., a water vapor-resistant packaging, optionally under an air-tight and/or vacuum seal.

In certain embodiments, the kit includes a reagent that may be used as the releasing agent for a releasable linker as described herein. The releasing reagent may be any one of the releasing agents described herein, such as, but not limited to, a chemical releasing agent (e.g., an acid, a base, an oxidizing agent, a reducing agent, etc.), a solvent, and the like. The releasing reagent in the kit may be provided in any convenient form, such as, but not limited to, a gas, a solution, a solid, granules, a powder, a suspension, and the like. The releasing reagent may be packaged in a separate container from the composition(s) in the kit.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Another form for the instructions would be a computer readable medium, e.g., CD, DVD, Blu-Ray, computer-readable memory (e.g., flash memory), etc., on which the information has been recorded or stored. Yet another form for the instructions that may be present is a website address which may be used via the Internet to access the information at a removed site. Any convenient means may be present in the kits.

H. EXAMPLES

The present disclosure has multiple aspects, illustrated by the following non-limiting examples. The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Abbreviations:

ACN acetonitrile
dapto daptomycin
DCM dichloromethane
DIPEA diisopropylethylamine
DMF N,N-dimethylformamide
DMSO dimethylsulfoxide
doxo doxorubicin
Et ethyl
EtOAc ethyl acetate
FCC flash column chromatography
h or hr hour
HA hyaluronic acid
HAT hyaluronic acid modified with tetrazine
HMT hydrogel modified tetrazine
HOAt 1-hydroxy-7-azabenzotriazole
LCMS liquid chromatography-mass spectrometry
Me methyl
MeCN acetonitrile
MeOH methanol
MeTz methyltetrazine
min minutes
MTD maximum tolerated dose
NHS N-hydroxysuccinimide
PBS phosphate buffered saline
Ph phenyl
ppm parts per million
rt/RT room temperature
SEM standard error of the mean
TAG tetrazine-modified activating gel
TCO trans-cyclooctene 1
TEA triethylamine
THF tetrahydrofuran
TFA trifluoroacetic acid

Example 1

Trans-Cyclooctene-Antibody Conjugate (Prophetic Example)

A solution of antibody (2.5 mg/mL) in aqueous buffer (50 mM potassium phosphate, 50 mM sodium chloride, 2 mM ethylenediaminetetraacetic acid disodium salt), pH 6.5, is incubated with a molar excess of trans-cyclooctene derivatized carbonate in dimethylacetamide (DMA). The reaction is allowed to proceed at ambient temperature and, upon completion, purified by gel filtration colum. The concentration of the conjugate is determine spectrophotometrically using the known extinction coefficients for the antibody.

Example 2

Synthesis of TCO-Monomethyl Auristatin E (TCO-MMAE) Conjugate

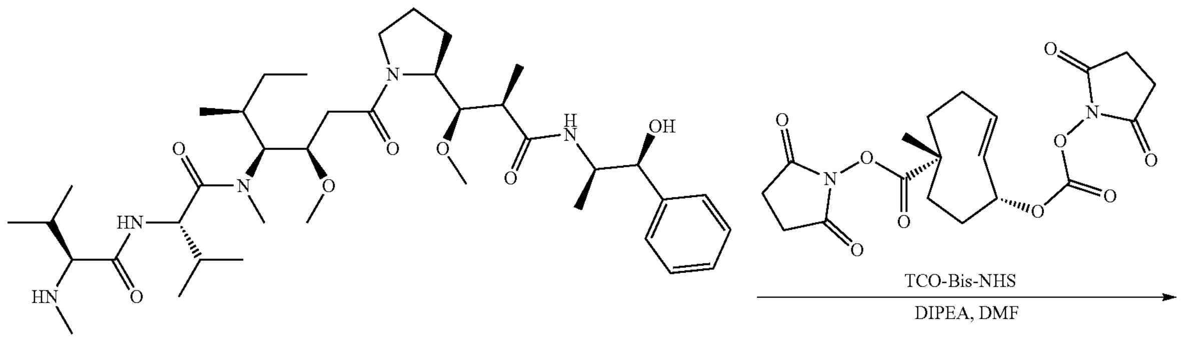

Monomethyl auristatin E (MMAE)

-continued

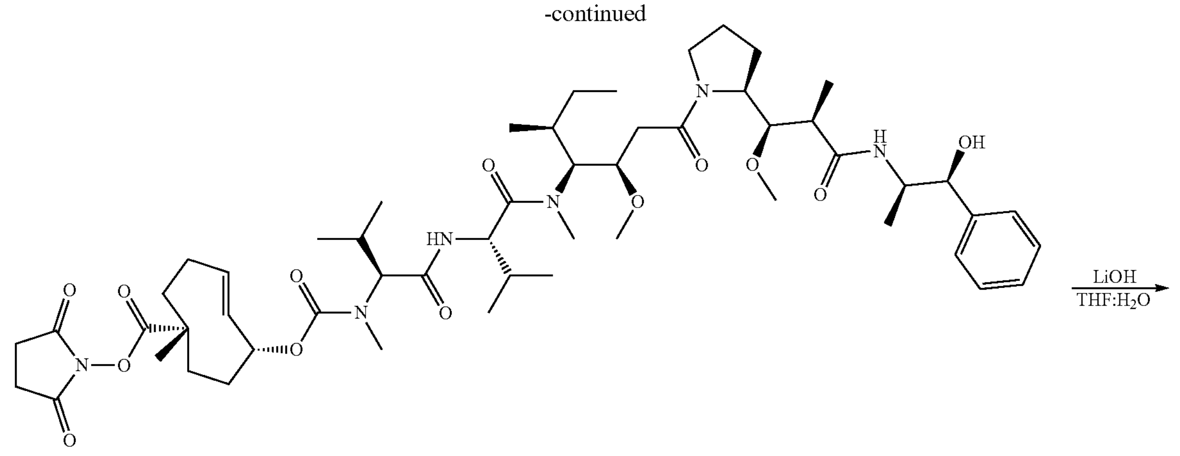

TCO-NHS-MMAE

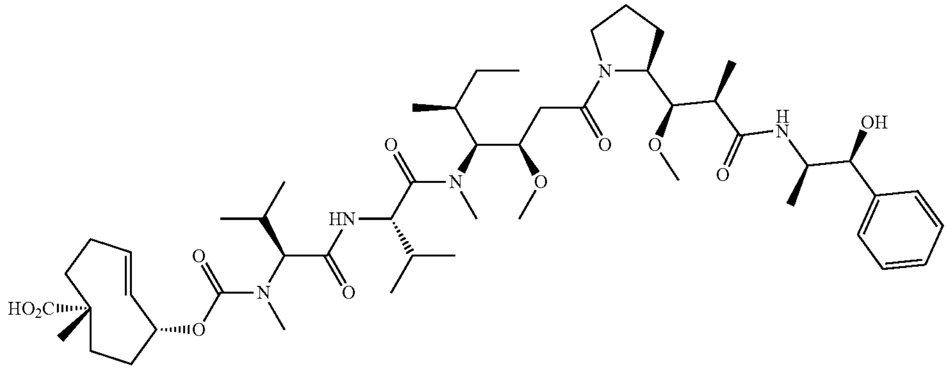

TCO-Acid-MMAE

Preparation of TCO-MMAE conjugate. To monomethyl auristatin E (170 mg, 0.24 mmol) in DMF (2 mL) at rt, TCO-Bis-NHS (100 mg, 0.24 mmol) and DIPEA (93 mg, 0.72 mmol) were added. The solution was stirred at rt for 20 h, acetonitrile (ACN, 8 mL) was added and the mixture was purified by prep-HPLC (ACN/water from 0 to 100%, formic acid 0.1%) to give TCO-NHS-MMAE (88 mg, 36%). To TCO-NHS-MMAE (78 mg, 0.076 mmol) in THF (2 mL) and $H_2O$ (2 mL) at rt was added LiOH (9.2 mg, 0.38 mmol). The solution was stirred at rt for 20 h. After removal of solvent, HCl (aq, 0.5 N) was added to pH~3. The mixture was purified by prep-HPLC (ACN/water from 0 to 100%, formic acid 0.1%) to give TCO-Acid-MMAE (54 mg, 76%, two isomers). LCMS: (ESI+) 928 [M+H].

The synthesis of TCO-Acid-MMAE is representative of functionalization of an N-terminal amino group of a polypeptide.

Example 3

Dapto-TCO-Amino Acid Synthesis

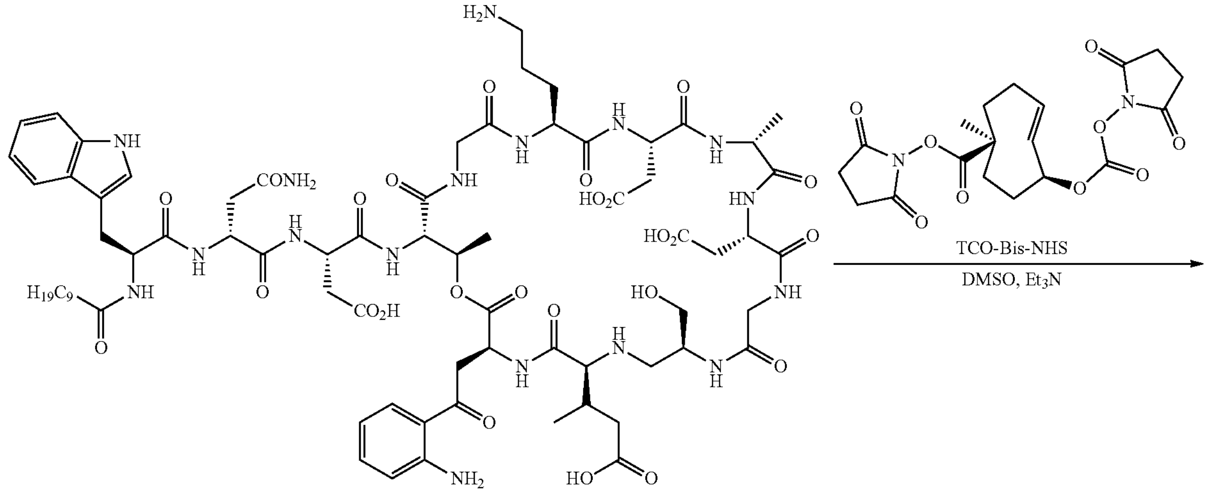

Daptomycin

-continued
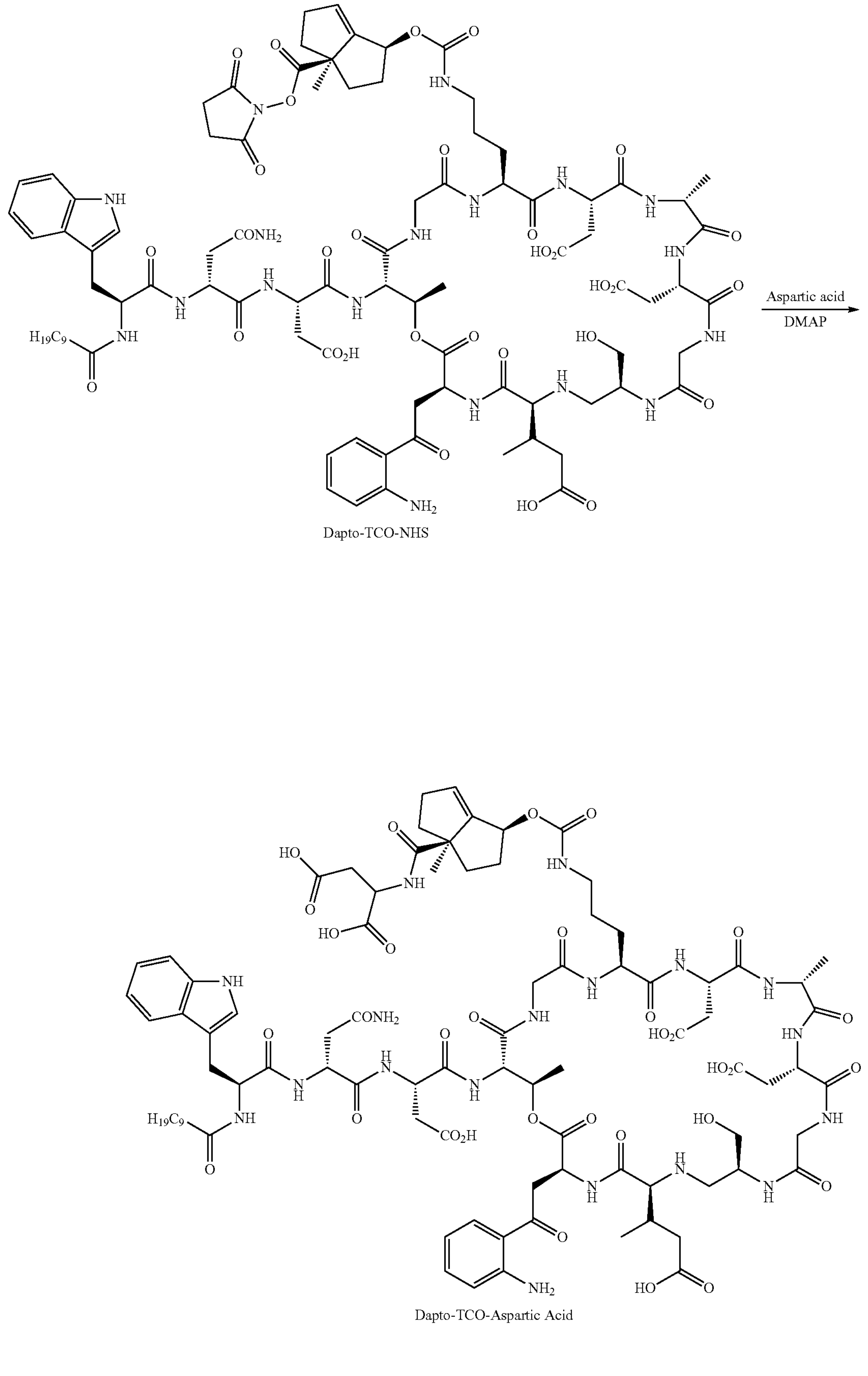
Dapto-TCO-NHS
Dapto-TCO-Aspartic Acid

Example protocol: Add daptomycin (100 mg, 0.062 mmol), TCO-Bis-NHS (62.5 mg, 0.149 mmol), and triethylamine (62.5 μL, 45.3 mg, 0.448 mmol) to DMSO and stir at RT overnight to produce Dapto-TCO-NHS. LCMS: (ESI−) 1926.8 [M−H]. To Dapto-TCO-NHS (126.1 mg, 0.0654 mmol), add aspartic acid (104.5 mg, 0.785 mmol) and 4-dimethylaminopyridine (150.9 mg, 1.235 mmol), and stir for 18 h at 37° C. Purify by HPLC to obtain Dapto-TCO-Aspartic Acid. Yield: 100 mg, 0.0514 mmol. LCMS: (ESI−) 1944.8 [M−H].

This approach has been used to produce glycine and aspartic acid-modified TCO-prodrugs, and can be generally applied to for the incorporation of other amino acid cargos as well.

Example 4

Daptomycin-TCO-Glycine Conjugate

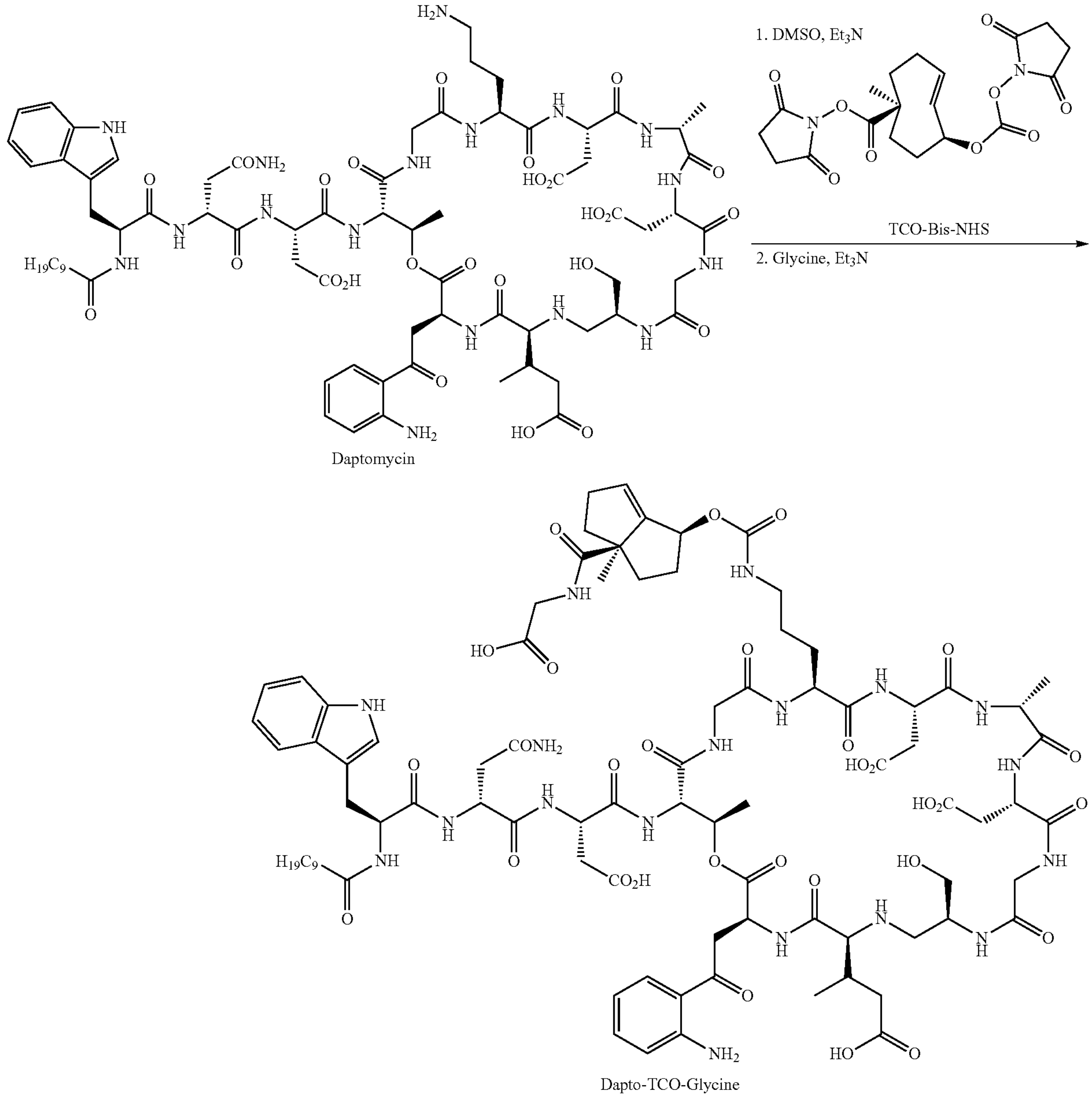

Daptomycin

Dapto-TCO-Glycine

Daptomycin (537 mg, 0.33 mmol), TCO-Bis-NHS (350 mg, 0.83 mmol), and triethylamine (0.350 mL, 2.51 mmol) in DMSO (11 mL). Stir at RT overnight. Then heat to 37° C. Add glycine (300 mg, 4.00 mmol) and triethylamine (1.8 mL, 13 mmol), and stir for 18 h. Add 8 mL water and purify by HPLC. Yield: Dapto-TCO-Glycine-373 mg, 0.20 mmol, 59.6%.

The syntheses of Dapto-TCO-glycine and Dapto-TCO-aspartic acid are representative of derivatization of a lysine side chain of a polypeptide.

Example 5

MMAE-TCO-Asp Conjugate

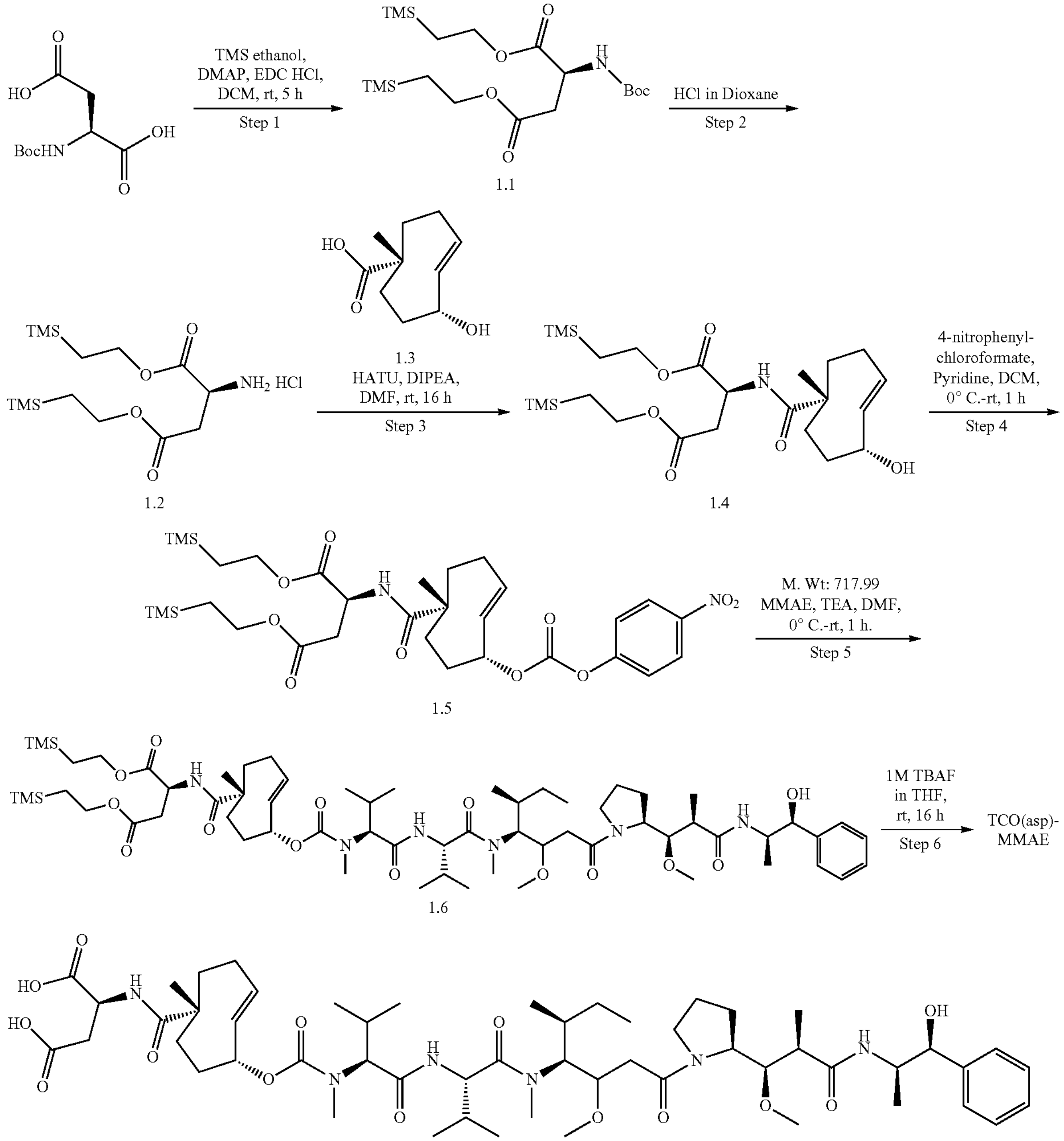

1.1

1.2

1.4

1.5

1.6 bis(2-(trimethylsilyl)ethyl) (tert-butoxycarbonyl)-L-aspartate (1.1). Step-1: To a mixture of Boc-Asp-OH (10.0 g, 42.9 mmol, 1.0 eq., Combi-blocks QA-1348), DIEA (37.3 mL, 214.0 mmol, 5.0 eq.), 2-(trimethylsilyl)ethan-1-ol (12.2 g, 103.0 mmol, 2.4 eq.), and DMAP (1.1 g, 8.6 mmol, 0.2 eq.) in DCM (200.0 mL) cooled in ice bath was added EDC (23.0 g, 120.0 mmol, 2.8 eq.). The mixture was stirred at rt overnight, diluted with DCM (100.0 mL), and washed with aq HCl (0.5 M) until pH in organic layer turned neutral. The organic layer was further washed with saturated $NaHCO_3$ solution, dried with $Na_2SO_4$, and filtered. The filtrate was concentrated and purified by flash chromatography (ISCO column, 220 g) using a gradient of EtOAc in hexanes (0-30%) to afford 13.0 g (70%) of bis(2-(trimethylsilyl) ethyl) (tert-butoxycarbonyl)-L-aspartate as a colorless oil. $^1$H-NMR (300 MHz, $CDCl_3$): 5.50 (br d, J=8.79 Hz, 1H), 4.61-4.48 (m, 1H), 4.30-4.14 (m, 4H), 3.04-2.93 (m, 1H), 2.83-2.73 (m, 1H), 1.45 (s, 9H), 1.06-0.94 (m, 4H), 0.004 (s, 9H), 0.03 (s, 9H).

bis(2-(trimethylsilyl)ethyl) L-aspartate hydrochloride (1.2). Step-2: To a solution of compound-1.1 (10.4 g, 24.0 mmol) in dry DCM (30 mL) cooled in an ice-bath was added HCl (100 mL, 2.0 M HCl in ether). To this mixture after stirring at rt for 90 min was added more HCl (100 mL, 4.0 M HCl in dioxane). Upon completion the reaction monitored by LCMS, the mixture was concentrated to dryness. Suspended in EtOAc and reconcentrated. Obtained 11.4 g (~20 wt % solvent) of 2-(trimethylsilyl)ethan-1-ol as a tarry residue. (+esi)$[M+H]^+$=334.

bis(2-(trimethylsilyl)ethyl) ((1R,6R,E)-6-hydroxy-1-methylcyclooct-4-ene-1-carbonyl)-L-aspartate (1.4). Step-3: To a solution of compound-1.2 (11.0 g, 80% pure, 23.9 mmol, 2.0 eq.) in DMF (100.0 mL) were added DIPEA (11.0 mL, 62.7 mmol, 5.3 eq.), (1R,6R,E)-6-hydroxy-1-methylcyclooct-4-ene-1-carboxylic acid (1.3), (2.2 g, 11.9 mmol, 1.0 eq), and HATU (9.1 g, 23.9 mmol, 2.0 eq.) sequentially. The mixture was stirred at RT overnight, diluted with EtOAc (400 mL) and water (400 mL). The aqueous layer was extracted with EtOAc (400 mL) once. The combined organic layer was dried with $Na_2SO_4$ and filtered. The filtrate was concentrated and purified on flash chromatography (220 g, ISCO column) eluting with a gradient of EtOAc in hexanes (0-70%) and isocratic at 70% EtOAc in hexane to afford 3.96 g (75% pure, 50% yield) of bis(2-(trimethylsilyl)ethyl) ((1R,6R,E)-6-hydroxy-1-methylcyclooct-4-ene-1-carbonyl)-L-aspartate as a sticky oil. (+esi)$[M+H]^+$=500.4.

bis(2-(trimethylsilyl)ethyl) ((1R,6R,E)-1-methyl-6-(((4-nitrophenoxy)carbonyl)oxy)cyclooct-4-ene-1-carbonyl)-L-aspartate (1.5). Step-4: To a solution of compound 1.4 (4.0 g, 7.9 mmol, 1.0 eq.) in anhydrous DCM (113 mL) was added pyridine (1.88 g, 23.8 mmol, 3.0 eq.). To this mixture cooled in an ice-bath was slowly added a solution of p-nitrophenyl chloroformate (2.1 g, 10.3 mmol, 1.3 eq.) in DCM (28 mL). The mixture was stirred at RT for 12 h and partitioned with EtOAc and water. The organic phase was washed with aq sodium bicarbonate, water and then dried with sodium sulfate, filtered and concentrated. The residue was dissolved in a minimal amount of DCM and purified by flash chromatography on a 220 g silica gel column (ISCO) a step-wise gradient of EtOAc in hexane (0-40%) as eluent to afford 2.91 g (44% yield, desired product eluted around 30% EtOAc, coelutes with p-nitrophenol) of as a viscous oil.

bis(2-(trimethylsilyl)ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamoyl)oxy)-1-methylcyclooct-4-ene-1-carbonyl)-L-aspartate (1.6). Step 5: To bis(2-(trimethylsilyl)ethyl) ((1R,6R,E)-1-methyl-6-(((4-nitrophenoxy)carbonyl)oxy)cyclooct-4-ene-1-carbonyl)-L-aspartate (1.5, 296 mg, 0.45 mmol, 1.0 eq.) cooled to 0° C. were added (2S)—N-((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide (352 mg, 0.49 mmol, 1.1 eq., Monomethyl Auristatin E, Advanced ChemBlock,), DIPEA (173 mg, 1.34 mmol, 3.0 eq.), and HOBt (173 mg, 0.89 mmol, 2.0 eq.). The mixture was stirred at RT overnight and diluted with EtOAc. The mixture was washed with water twice and aq. $NH_4Cl$ solution, dried with $Na_2SO_4$, and filtered. The filtrate was concentrated under reduced pressure and purified by C18 Flash chromatography (100 g, ISCO gold capped C18 flash column) using a gradient of acetonitrile and water (0 to 100%) to afford 499 mg (90%) of bis(2-(trimethylsilyl) ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl) amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamoyl)oxy)-1-methylcyclooct-4-ene-1-carbonyl)-L-aspartate as an oil. (+esi)$[M+H]^+$=1244.3.

((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)(methyl)amino)-3-methyl-1-oxobutan-2-yl)amino)-3-methyl-1-oxobutan-2-yl) (methyl)carbamoyl)oxy)-1-methylcyclooct-4-ene-1-carbonyl)-L-aspartic acid (TCO(asp)-MMAE). Step 6: To bis(2-(trimethylsilyl)ethyl) ((1R,6R,E)-6-((((2S)-1-(((2S)-1-(((4S,5S)-1-((S)-2-((1R,2R)-3-(((1S,2R)-1-hydroxy-1-phenylpropan-2-yl)amino)-1-methoxy-2-methyl-3-oxopropyl) pyrrolidin-1-yl)-3-methoxy-5-methyl-1-oxoheptan-4-yl) (methyl)amino)-3-methyl-1-oxobutan-2-yl)amino)-3-methyl-1-oxobutan-2-yl)(methyl)carbamoyl)oxy)-1-methylcyclooct-4-ene-1-carbonyl)-L-aspartate (1.6, 500 mg, 0.4 mmol, 1.0 eq.) in THF (10.0 mL) was added TBAF (1.0 M in THF). The mixture was stirred at RT overnight and purified directly by C18 Flash chromatography (100 g, ISCO gold capped C18 flash column) using a gradient of acetonitrile and water (0 to 100%) to afford 300 mg of solid which contained ~4 molar equivalents of tetrabutyl ammonium species. The mixture was dissolved in EtOAc (20 mL), washed with water (adjusted the pH to 3-5 with dilute HCl) six times, dried with $Na_2SO_4$, and filtered. The filtrate was concentrated to afford a glassy solid, which was treated with ether and concentrated to give a powdery solid free of the tetrabutyl ammonium by-product. (−esi)$[M-H]^-$=1042.1.

Example 6
TCO(asp)-Spacelink-Etoposide
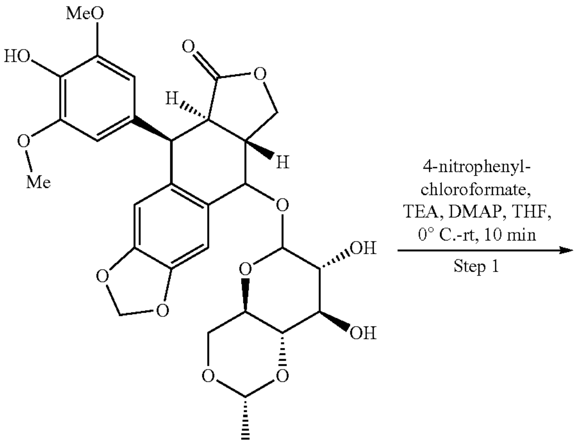
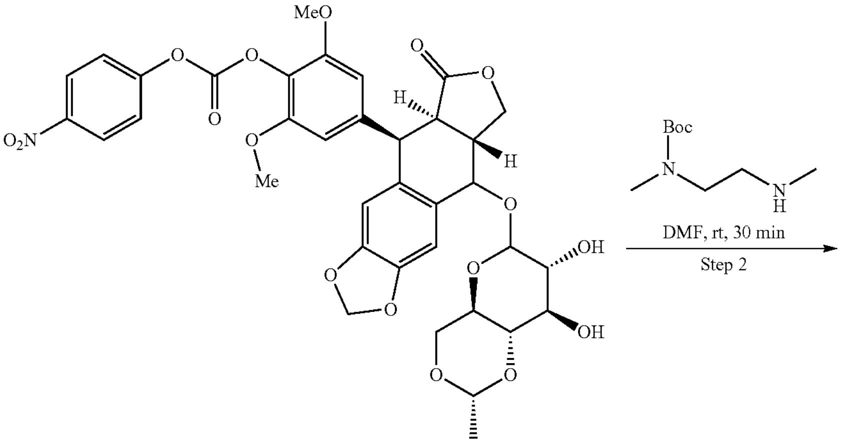
3.1
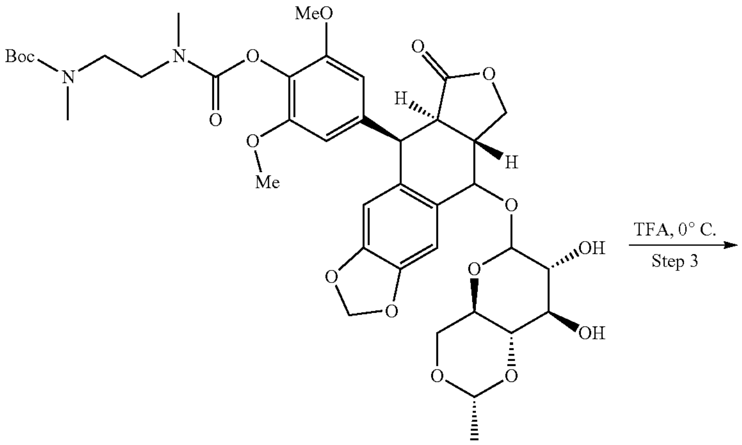
3.2

-continued

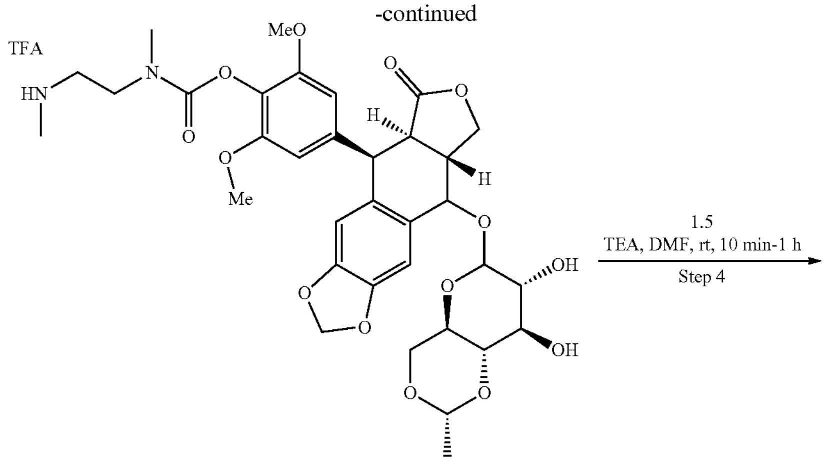

3.3

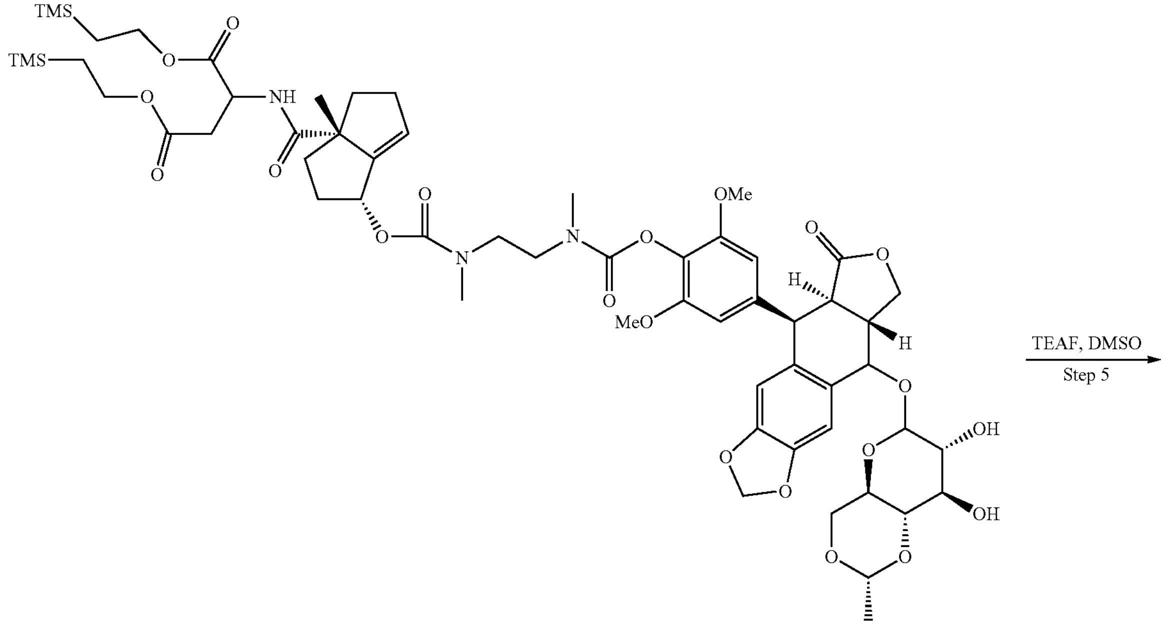

3.4

TCO(asp)-spacelink-Etoposide 4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl (4-nitrophenyl) carbonate (3.1). Step 1: Etoposide (1.5 g, 2.5 mmol, 1.0 eq., Etoposide, Combi-blocks QA-7668) was dissolved in dried THF. Triethylamine (1.1 mL, 7.6 mmol, 3.0 eq.) and DMAP (31 mg, 0.25 mmol, 0.1 eq:) were added. The reaction was cooled to 0° C. PNP-chloroformate (0.62 g, 3.1 mmol, 1.2 eq.) was dissolved in THF and added dropwise. The reaction was stirred at room temp. Upon completion as assessed by TLC, 1 mL of acetic acid was added and the reaction was stirred for 2 min. The precipitate was filtered, and the filtrate was concentrated under reduced pressure. The crude product was purified by column chromatography on silica gel using a gradient of 0-100% EtOAC in hexane to afford the desired product (2.25 g, 82% yield, 70% pure) that was still contaminated with unreacted Etoposide (~30% as assessed by $^{1}H$ NMR).

tert-butyl (4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl) ethane-1,2-diylbis(methylcarbamate) (3.2). Step 2: Compound 3.1 was dissolved in DMF (10 mL) and mono-Boc protected N,N-dimethylethylene-diamine (532 mg, 2.82 mmol, 1.1 eq) was added. The reaction was stirred for 30 minutes. After completion the DMF was removed under reduced pressure and the crude product was purified by flash chromatography using a gradient of 0-100% EtOAC in hexanes to give the desired product (1.1 g, 53% yield). (+esi)$M+NH_3+H^+$= 820.8.

4-((5R,5aR,8aR)-9-(((2R,4aR,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl methyl(2-(methylamino)ethyl)carbamate 2,2,2-trifluoroacetate (3.3). Step 2: Compound 3.2 (460 mg, 0.573 mmol) from above step, was dissolved in DCM (10 mL) and cooled to 0° C. TFA (3 mL) was added and the reaction mixture was stirred for 1 hour and concentrated to dryness. The material was used directly in the next step without further purification.

bis(2-(trimethylsilyl)ethyl) ((1R,6R,E)-6-(((2-(((4-((5R, 5aR,8aR)-9-(((2R,4aR,7R,8R,8aS)-7,8-dihydroxy-2-methylhexahydropyrano[3,2-d][1,3]dioxin-6-yl)oxy)-6-oxo-5, 5a,6,8,8a,9-hexahydrofuro[3',4':6,7]naphtho[2,3-d][1,3] dioxol-5-yl)-2,6-dimethoxyphenoxy)carbonyl)(methyl) amino)ethyl)(methyl)carbamoyl)oxy)-1-methylcyclooct-4-ene-1-carbonyl)-L-aspartate (3.4). Step 4: Compound 3.3 (464 mg, 0.579 mmol, 1.1 eq) was dissolved in DMF (3.0 mL). HOBT (202 mg, 1.05 mmol, 2 eq) and DIPEA (0.275 mL, 1.58 mmol, 3 eq) were added. Compound 1.5 (350 mg, 0.526 mmol, 1.0 eq) was dissolved in DCM (2.0 ml) and added to the above solution. The reaction mixture was allowed to stir overnight at room temperature. The reaction was partitioned with EtOAc and aq ammonium chloride. The organic layer was washed with water, dried with sodium sulfate, filtered, and concentrated. The material was chromatographed 4×, first with a hexane: acetone gradient, then a hexane:EtOAc gradient, next with a DCM:EtOAC gradient and finally with DCM:ACN gradient. The final chromatography purged a close eluting impurity and the desired compound eluted around 70% ACN:30% DCM. The fractions were pooled and concentrated to yield the desired target (94 mg, 17% yield). (+esi) $M+H^+=1228.1$.

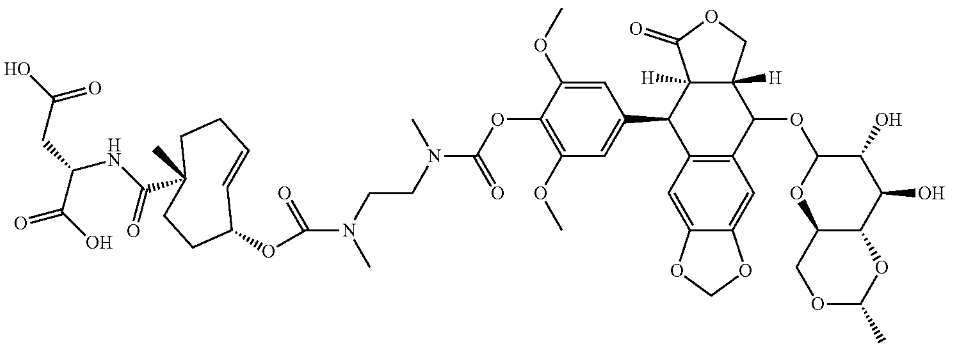

((1R,6R,E)-6-(((2-(((4-((5R,5aR,8aR)-9-(((2R,4aR,7R, 8R,8aS)-7,8-dihydroxy-2-methylhexahydropyrano[3,2-d] [1,3]dioxin-6-yl)oxy)-6-oxo-5,5a,6,8,8a,9-hexahydrofuro [3',4':6,7]naphtho[2,3-d][1,3]dioxol-5-yl)-2,6-dimethoxyphenoxy)carbonyl)(methyl)amino)ethyl)(methyl) carbamoyl)oxy)-1-methylcyclooct-4-ene-1-carbonyl)-L-aspartic acid (TCO(asp)-spacelink-Etoposide). Step 5: Compound 3.4 was dissolved in DMSO (1.0 ml). Tetraethyl ammonium fluoride×$H_2O$ (78.2 mg, 0.524 mmol) was added in one portion. The reaction was stirred for 105 minutes and worked-up based on the favorable LC-MS profile. The reaction was partitioned with EtOAc and water acidified to pH 4 with dilute HCl. The organic phase was washed with water 2× and then dried with sodium sulfate, filtered and concentrated. The residue was purified by prepHPLC (gradient of ACN in $H_2O$ with 0.1% formic acid). The fractions containing pure compound were pooled and lyophilized to obtain a white lyophilizate (42 mg, 55% yield). (−esi)$[M-H]^-=1026.2$.

Example 7
Ranibizumab—Cy5.5-TCO Conjugate
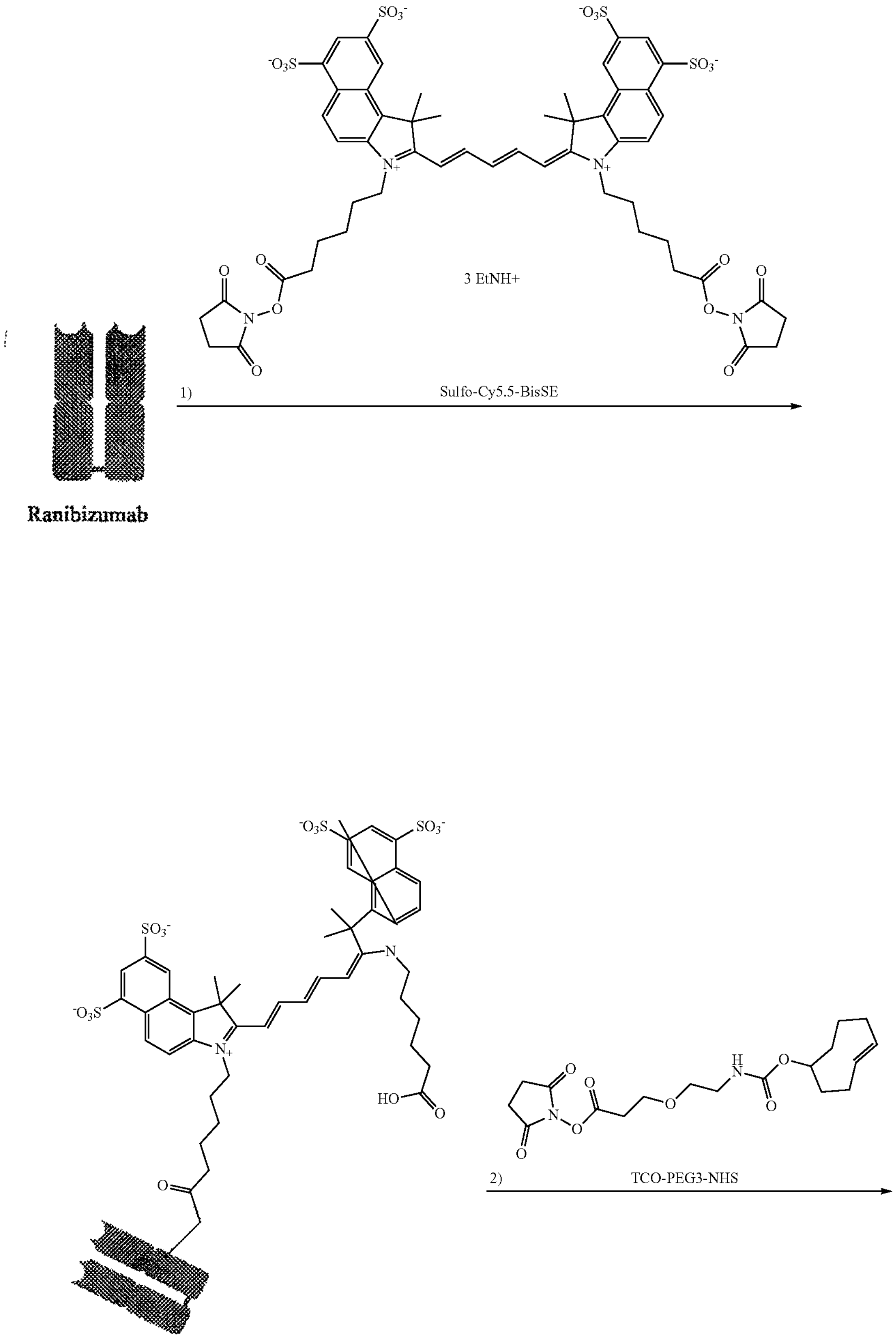

-continued

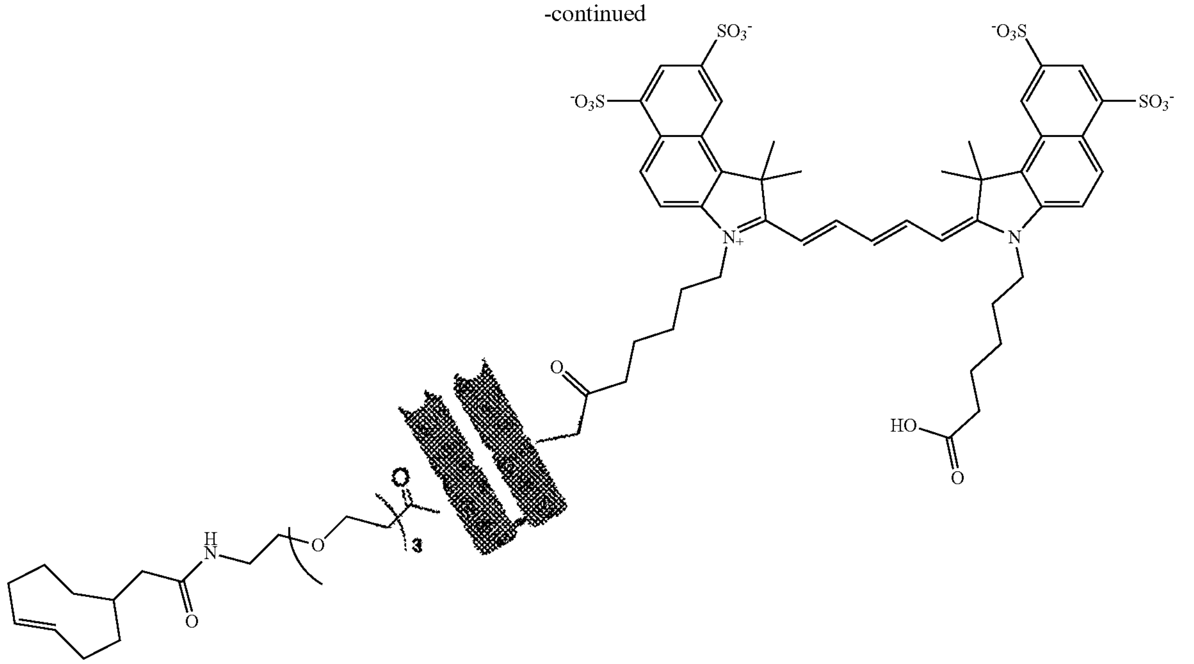

Ranibizumab solution in PBS, was pH adjusted with bicarbonate buffer (1 M) to pH 8.5. The fluorescent dye sulfonated-Cy5.5-bissuccinimidal ester (BisSE) (AAT Bio-Quest Cat #158) was dissolved in DMSO to 10 mM and added to the protein solution (75 μg dye per mg protein, 750 μg total, ~2.5 equiv). The reaction mixture was rotated at room temperature for 1 hour. The product was purified by buffer exchange with a PD-10 Desalting column, equilibrated with PBS, per the manufacturer's instructions. The product was collected and the protein concentration and labeling ratio calculated by measuring the UV absorbance and using the Degree of Labeling Calculator (https://www.aatbio.com/tools/degree-of-labeling-calculator). The ratio of labeling was 1.5. 1 mg was retained and diluted to 3.1 mg/mL with PBS, followed by filtration with 0.22 μm syringe filter to sterilize the product. The endotoxin was measured at 3.8 EU/mL. The remaining material was used for preparing the TCO conjugate.

Ranibizumab-Cy5.5 conjugate solution in PBS (0.71 mL at 8.5 mg/mL), was pH adjusted with bicarbonate buffer (1 M) to pH 8.5. The trans-cyclooctene-PEG3-NHS (SiChem #SC-8406) (10 mM in DMSO) was added to the solution (~38 μg reagent per mg protein, ~225 μg total, ~3.8 equiv). The reaction mixture was rotated at room temperature for 1 hour. The product was purified by buffer exchange with a PD-10 Desalting column, equilibrated with PBS, per the manufacturer's instructions. The product was collected. A sample of the conjugate was treated with a Cy3-tetrazine (AAT Bioquest Cat #910) and the protein concentration and labeling ratio calculated by measuring the UV absorbance and using the Degree of Labeling Calculator (https://www.aatbio.com/tools/degree-of-labeling-calculator). The ratio of labeling was 1.8. The solution was sterilized by filtration with 0.22 μm syringe filter. The final product yielded 0.71 mL of solution with protein concentration of 5.4 mg/mL. The endotoxin was measured at 6.5 EU/mL.

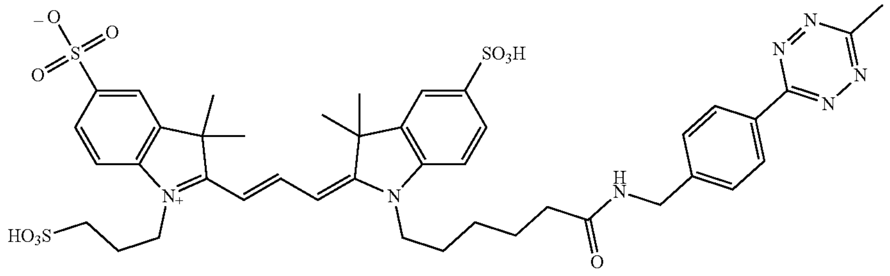 [SMILES: Cc1nnc(-c2ccc(CNC(=O)CCCCCN3/C(=C/C=C/C4=[N+](CCCS(=O)(=O)O)c5ccc(S(=O)(=O)O)cc5C4(C)C)C(C)(C)c4cc(S(=O)(=O)O)ccc43)cc2)nn1]

Cy3-Tetrazine

Example 8

Trans-cyclooctene-Trastuzumab conjugate

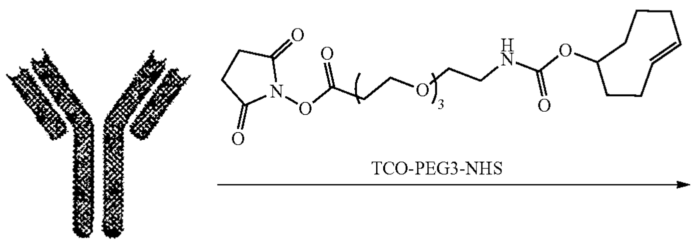

Trastuzumab

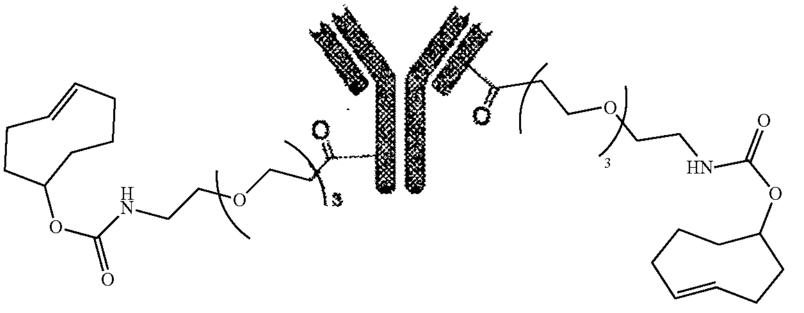

A solution of antibody, such as trastuzumab, (2.51 mg/mL) in aqueous buffer (50 mM potassium phosphate, 50 mM sodium chloride, 2 mM ethylenediaminetetraacetic acid disodium saltPBS), pH 7.46.5, is incubated with a 5-fold molar excess of trans-cyclooctene-NHS ester derivatized carbonate in dimethylacetamide (DMA). The reaction is allowed to proceed at ambient temperature for 1 hour. The reaction mixture was then applied to a NAP-10 column, equilibrated with PBS, and then eluted with fresh PBS, pH 7.4, upon completion, purified by gel filtration column. The concentration of the conjugate is determined spectrophotometrically using the known extinction coefficients for the antibody. Quantification of the effective concentration of TCO can be measured by treatment of a sample of the conjugate with an appropriate tetrazine-functionalized fluorescent dye, followed by separation by SDS-PAGE and measurement of the fluorescent signal associated with the protein band.

Example 9

TCO-Spacelink-SN-38

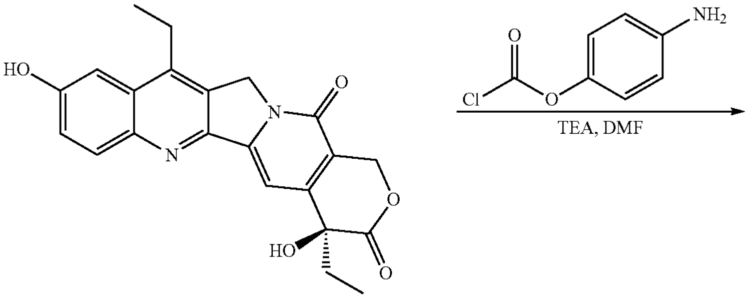

1

-continued
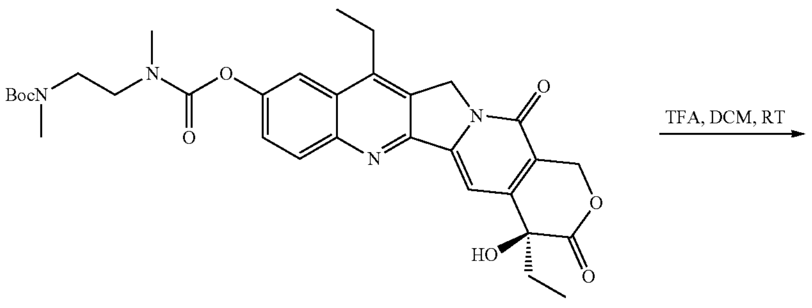
2
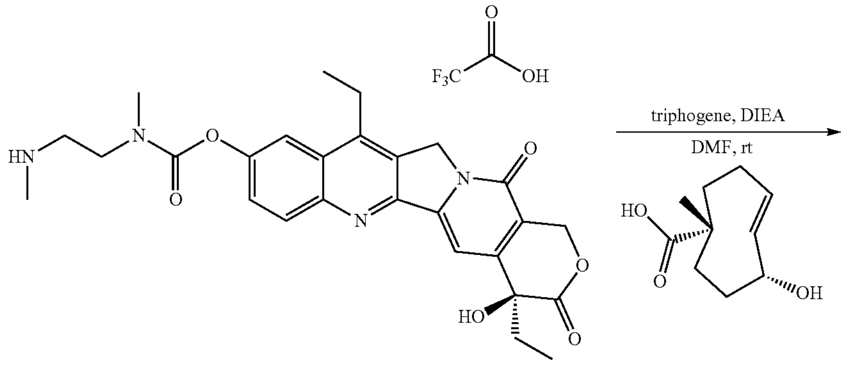
3
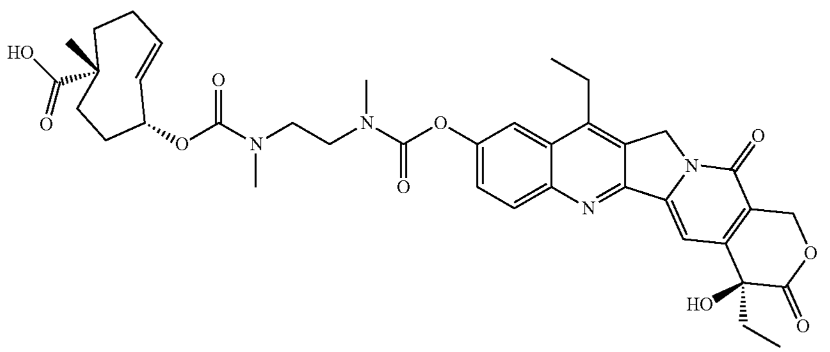
4
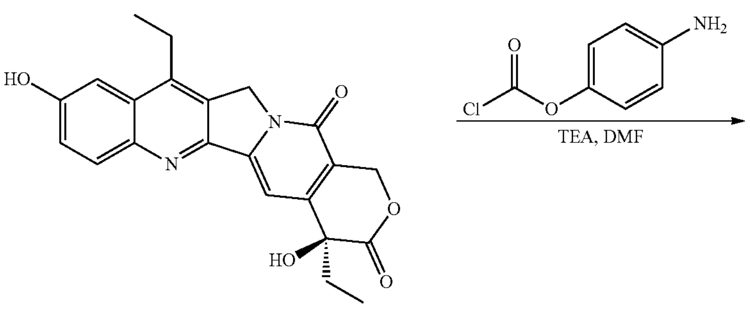
1

-continued

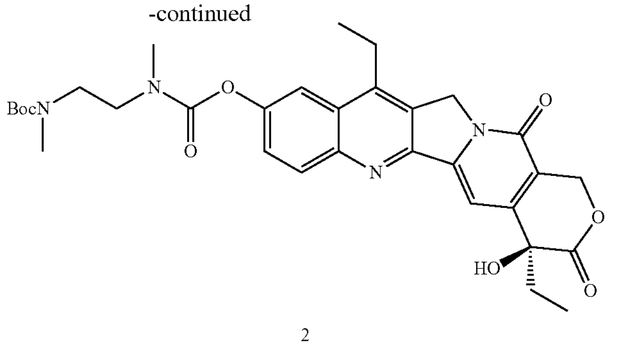

2

(S)-tert-butyl (4,11-diethyl-4-hydroxy-3,14-dioxo-3,4,12,14-tetrahydro-1H-pyrano[3',4':6,7]indolizino[1,2-b]quinolin-9-yl) ethane-1,2-diylbis(methylcarbamate). To a solution of 7-ethyl-10-hydroxycamptothecin (SN-38, 660 mg, 1.68 mmol) in DMF (30 mL) was added 4-nitrophenyl chloroformate (336 mg, 1.68 mmol) and $Et_3N$ (708 μL, 504 mg, 5.04 mmol). The mixture was stirred at room temperature for 1.5 hrs. To the mixture was added $Et_3N$ (708 μL, 504 mg, 5.04 mmol) and 4-nitrophenyl chloroformate (336 mg, 1.68 mmol). The mixture was stirred for another 20 mins and added a solution of tert-butyl methyl[2-(methylamino)ethyl] carbamate (948 mg, 5.04 mmol) in DMF (10.68 mL). The mixture was stirred at room temperature for 1 h and added water (20 mL). The reaction mixture was extracted with EtOAc (4*50 ml). The organic phase was washed with water (3*20 mL), dried ($Na_2SO_4$) and concentrated. The residue was purified with silica gel chromatography (DCM to 10% MeOH in DCM) to give desired product (343 mg, yield: 41%) as a slightly yellow solid. LCMS: (m/z, $C_4H_9N_4O_8$)= 607.2 $[M+H]^+$.

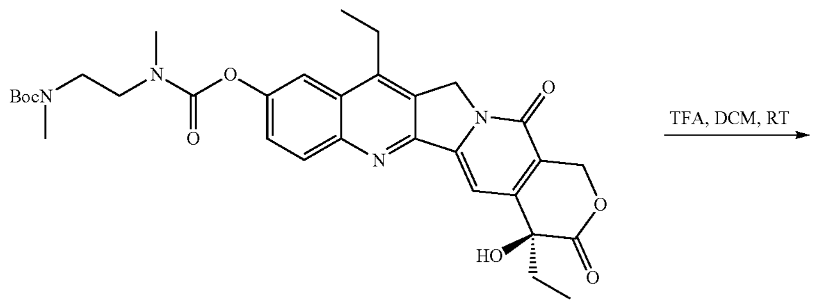

2

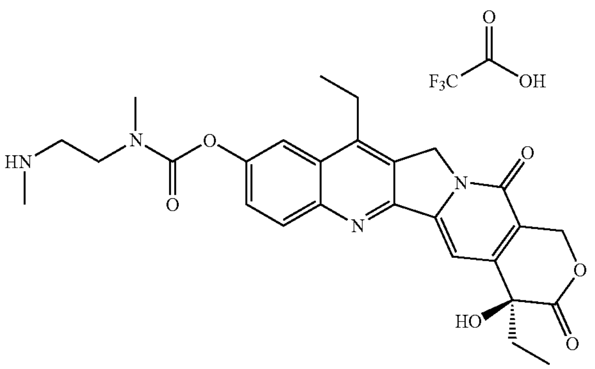

3

(S)-4,11-diethyl-4-hydroxy-3,14-dioxo-3,4,12,14-tetrahydro-1H-pyrano[3',4':6,7]indolizino[1,2-b]quinolin-9-yl methyl(2-(methylamino)ethyl)carbamate 2,2,2-trifluoroacetate. To a stirred mixture of compound 2 (343 mg, 0.57 mmol) in DCM (3 mL) was added TFA (0.5 mL). The mixture was stirred at room temperature for 2 hrs. The resulting mixture was concentrated and dried in the vacuum to give crude compound 3 (280 mg) as a white solid. The residue was used in next step without further purification. LCMS: (m/z, $C_{29}H_{31}N_4F_3O_8$)=507.1 [M+H]$^+$.

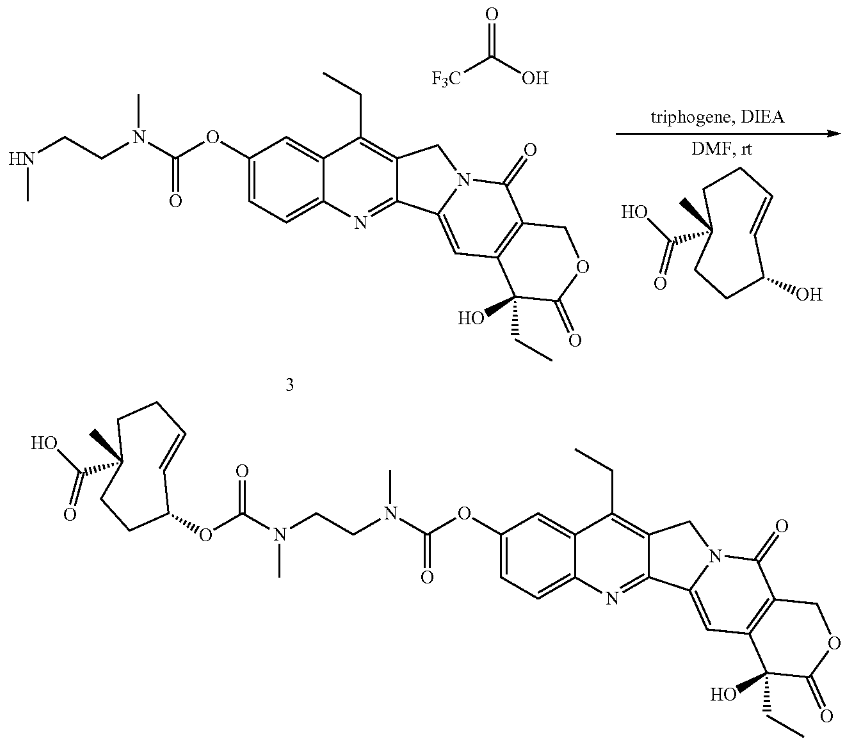

3

4

TCO-spacelink-SN-38. To a stirred mixture of triphosgene (47.5 mg, 0.16 mmol) in DMF (4 mL) was added (1R,6R,E)-6-hydroxy-1-methylcyclooct-4-ene-1-carboxylic acid (82.8 mg, 0.45 mmol) and DIPEA (116.0 mg, 0.9 mmol). The mixture was stirred at room temperature for 30 mins. The mixture was added to a mixture of compound 3 (280.0 mg, 0.45 mmol) and DIPEA (116.0 mg, 0.9 mmol) in DMF (3 mL). The resulting mixture was stirred at room temperature for 12 hours. The mixture was purified by PREP-HPLC (($CH_3CN/H_2O$(FA)) 0% to 70%) to give the desired product (105 mg, yield 32%). LCMS: (m/z, $C_{39}H_{46}N_4O_{12}$)=717.4 [M+H]$^+$.

Example 10

TCO(asp)-Spacelink-SN-38

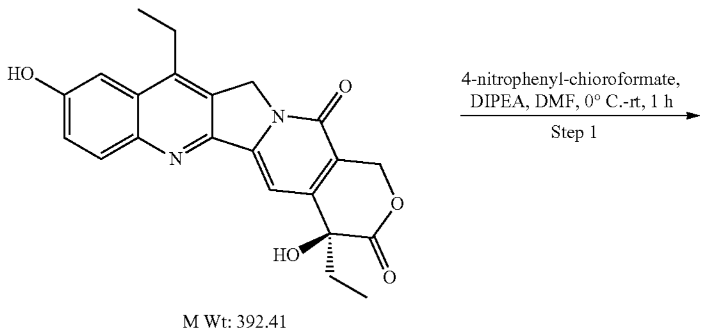

M Wt: 392.41

-continued

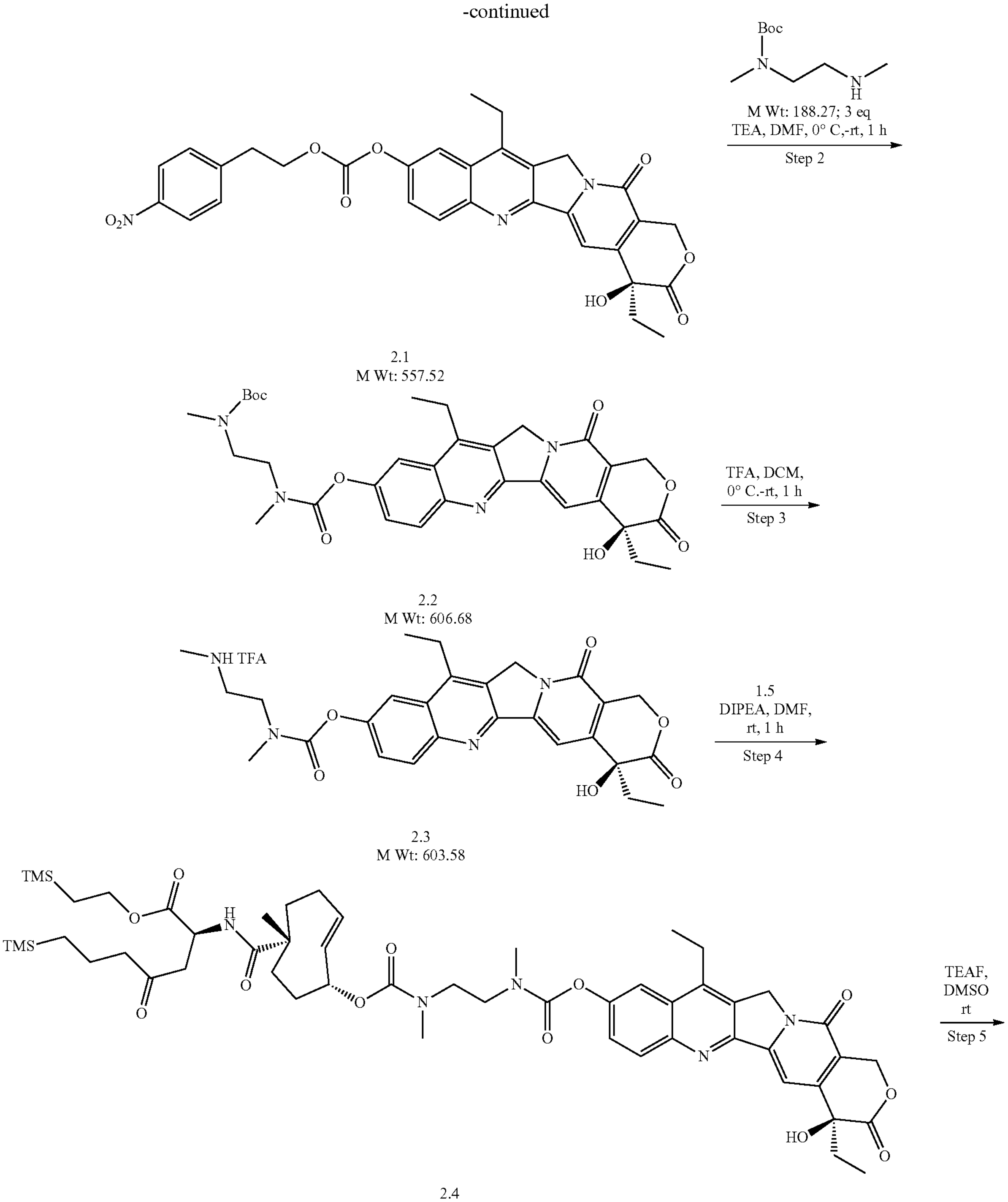

2.1
M Wt: 557.52

2.2
M Wt: 606.68

2.3
M Wt: 603.58

2.4
M Wt: 1032.35

TCO(asp)-spacelink-SN-38

(S)-4,11-diethyl-4-hydroxy-3,14-dioxo-3,4,12,14-tetrahydro-1H-pyrano[3',4':6,7]indolizino[1,2-b]quinolin-9-yl (4-nitrophenyl) carbonate (2.1). Step-1:4-Nitrophenyl chloroformate (771 mg, 3.82 mmol) was added into a mixture of SN-38 (1.25 g, 3.19 mmol, Advanced ChemBlocks Cat #10250, Lot 10602) and DIPEA (1.25 mL, 7.50 mmol) in DMF (20 mL) at 0° C. The mixture was stirred at room temperature for 1 h. Upon completion of reaction by TLC, the mixture was diluted with EtOAc, washed with water, brine, and dried over $Na_2SO_4$, concentrated, and purified by silica gel using a gradient 0-100% EtOAC in hexanes to afford the desired product.

(S)-tert-butyl (4,11-diethyl-4-hydroxy-3,14-dioxo-3,4,12,14-tetrahydro-1H-pyrano[3',4':6,7]indolizino[1,2-b]quinolin-9-yl) ethane-1,2-diylbis(methylcarbamate) (2.2). Step-2: The compound from above (2.1) was dissolved in DMF (10 mL) and mono-Boc protected N,N-dimethylethylene-diamine (1.76 g, 9.37 mmol, 2.5 eq) was added. The reaction was stirred for 30 minutes. After completion, the DMF was removed under reduced pressure and the crude product was purified by flash chromatography (ethyl acetate 100%) to give desired product (1.3 g, 57% yield over 2 steps). (+esi) $[M+H]^+$=607.5.

(S)-4,11-diethyl-4-hydroxy-3,14-dioxo-3,4,12,14-tetrahydro-1H-pyrano[3',4':6,7]indolizino[1,2-b]quinolin-9-yl methyl(2-(methylamino)ethyl)carbamate 2,2,2-trifluoroacetate (2.3). Step 3: Compound 2.2 (514 mg, 0.847 mmol) from above was dissolved in DCM (10 mL) and cooled to 0° C. TFA (2.0 mL) was added and the mixture was stirred for 20 minutes and then brought to room temperature for 1 hour. The reaction mixture was concentrated to dryness, redissolved in dichloroethane and reconcentrated. The crude material was used in the subsequent step without further purification.

bis(2-(trimethylsilyl)ethyl) ((1R,6R,E)-6-(((2-(((((S)-4,11-diethyl-4-hydroxy-3,14-dioxo-3,4,12,14-tetrahydro-1H-pyrano[3',4':6,7]indolizino[1,2-b]quinolin-9-yl)oxy)carbonyl)(methyl)amino)ethyl)(methyl)carbamoyl)oxy)-1-methylcyclooct-4-ene-1-carbonyl)-L-aspartate (2.4). Step 4: Compound 2.3 (513 mg, 0.827 mmol, 1.1 eq) was dissolved in DMF (5.0 mL). DIPEA (0.393 μL, 2.26 mmol, 3 eq) and HOBT (288 mg, 1.50 mmol, 2 eq) were added. Then intermediate 1.5 (500 mg, 0.752 mmol, 1.0 equivalent) was added as a solution in a minimal amount of DCM. The reaction mixture was stirred overnight at room temperature and then partitioned with EtOAc and aq ammonium chloride. The organic phase was washed with water, dried with sodium sulfate, filtered and concentrated. The residue was dissolved in a minimal amount of DCM and loaded onto a 40 g silica gel column (ISCO) for purification by flash chromatography using a gradient of 0-100% EtOAc in hexanes. The desired fraction eluted at 100% EtOAc, just after a close eluting impurity (M+H+=918.5, 156 mg, 23% yield) that lacked the diamine spacer. The fractions containing of the latest eluting peak and target compound were combined and concentrated to yield the product (406 mg, 52.3% yield). (+esi)$[M+H]^+$=1032.4.

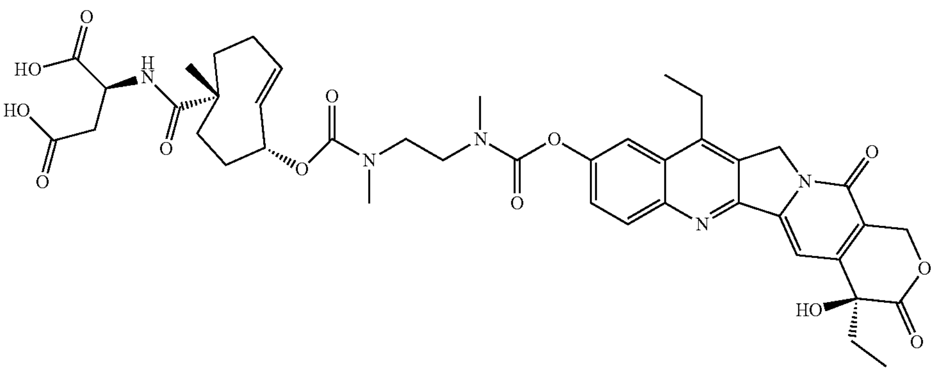

((1R,6R,E)-6-(((2-(((((S)-4,11-diethyl-4-hydroxy-3,14-dioxo-3,4,12,14-tetrahydro-1H-pyrano[3',4':6,7]indolizino[1,2-b]quinolin-9-yl)oxy)carbonyl)(methyl)amino)ethyl)(methyl)carbamoyl)oxy)-1-methylcyclooct-4-ene-1-carbonyl)-L-aspartic acid (TCO (asp)-spacelink-SN-38). Step 5: Compound 2.4 (272 mg, 0.263 mmol) was dissolved in DMSO (3.0 mL) in a 40 mL vial equipped with a septum lined capped. Tetraethylammonium fluoride×$H_2O$ (393 mg, 2.63 mmol) was added. The reaction immediately turned dark green. After 2 hours, the reaction was diluted with acetonitrile containing 0.1% TFA and then loaded onto an equilibrated $C_{18}$ flash gold column (ISCO, 15.5 g) and eluted with a gradient of 10-100% ACN (w/0.1% TFA) in water (w/0.1% TFA). The desired product eluted around 45% ACN. The two fractions containing the product were lyophilized over two days and characterized by HPLC, which indicated some other close eluting impurities. The product was further purified by preparative HPLC using the same mobile phase conditions. The pure fractions were combined and concentrated to obtain the desired product as an orange lyophilisate. $^1H$ NMR indicated excess water was present, so the sample was suspended in acetonitrile and concentrated to dryness, yielding a readily transferrable orange powder (62 mg, 25% yield as the monotrifluoroacetate salt). $^1H$ NMR indicated the presence of TFA. (−esi)[M−H]$^-$=830.5.

Example 11

AB25409

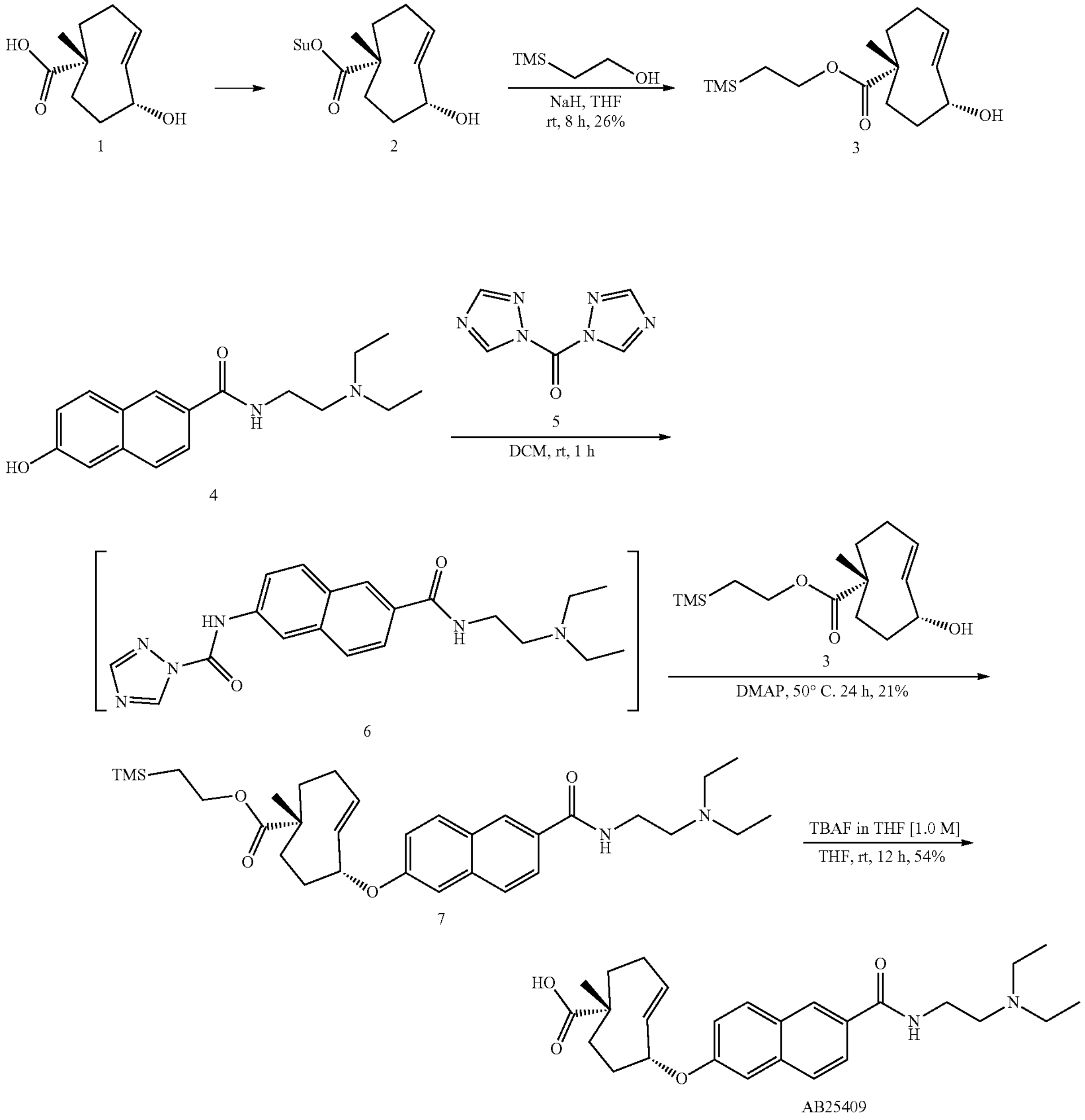

General Procedure for the Preparation of Compound 2. Compound 2 was prepared according to the literature procedure (Chem. Sci., 2021, 12, 1259).

General Procedure for the Preparation of Compound 3. To a flame dried round bottom flask was charged sodium hydride (60%, 399 mg, 9.96 mmol, 3.0 eq.) and dry THF (10 mL). The mixture was cooled to 0° C. and TMS-ethanol (3.33 mL, 23.2 mmol, 7.0 eq) was added dropwise at 0° C. The mixture was stirred for 30 min and a solution of compound 2 (934 mg, 3.32 mmol, 1 eq.) in anhydrous THF (3 mL) was added slowly via a syringe at 0° C. under nitrogen atmosphere. The reaction was warmed to rt and the stirring was continued for 8 h. The reaction was monitored by TLC for consumption of starting material. The reaction was quenched by pouring the reaction mixture into ice water (20 mL) and extracted with ethyl acetate (3×50 mL). The combined extracts were washed with sat. $NH_4Cl$ and dried over $Na_2SO_4$. After concentration, the residue was purified by flash chromatography using a gradient of ethyl acetate in hexanes (0-20%) to give compound 3 mixed with TMS-ethanol. The compound was then kept on high vacuum at 40° C. for 30 min to give compound 3 (405 mg, 26%). TLC: PE/EA=1/4. Rf (compound 2)=0.2. Rf (product, 3)=0.5

General Procedure for the Preparation of Compound 7. To a solution of compound 4 (109 mg, 0.38 mmol, 1.0 eq) in dry DCM (2 mL) was added compound 5 (63 mg, 0.38 mmol, 1.0 eq). The reaction mixture was stirred for 1 h. The LCMS analysis of reaction mixture showed a peak at m/z=381.90 which confirms the formation of intermediate compound 6. To the above reaction mixture was added DMAP (93 mg, 0.76 mmol, 2.0 eq) followed with a solution of compound 3 (108 mg, 0.38 mmol, 1.0 eq.) in THF (1 mL). The resulting reaction mixture was heated at 50° C. for 24 h. The reaction was monitored by HPLC and LCMS. The reaction mixture was concentrated to give a crude, which was purified by silica gel flash chromatography using a gradient of MeOH in DCM (0-5%) to give compound 7 (47 mg, 21%). TLC: MeOH/DCM=0.05/1. Rf (compound 4)=0.2. Rf (compound 6)=0.3. Rf (product, 7)=0.4. LCMS of Compound 6:381.90 [M+H]+. LCMS of Compound 7:596.90 [M+H]+

General Procedure for the Preparation of Compound AB25409. To a solution of compound 7 (47 mg, 0.079 mmol, 1.0 eq) in THF (3 mL) was added TBAF (1.0 M in THF, 1.2 mL, 1.2 mmol, 15 eq). The reaction mixture was stirred at rt for 15 h. The reaction was monitored by LCMS and HPLC. The solvent was removed. The crude mixture was purified by preparative HPLC using 5 to 100% ACN in water with 0.1% TFA. After lyophilization, the desired compound AB25409 (21 mg, 54%) was obtained as light yellow solid. LCMS: 497.0 [M+H]+; $^1$H NMR (400 MHz, CD3OD) δ 9.85 (s, 1H), 8.34 (d, J=8.2 Hz, 1H), 8.20 (s, 1H), 8.14 (d, J=8.4 Hz, 1H), 8.07 (d, J=9.0 Hz, 1H), 7.86 (d, J=8.4 Hz, 1H), 5.99-6.14 (m, 1H), 5.71-5.77 (m, 1H), 5.29 (s, 1H), 3.86 (br t, J=5.9 Hz, 2H), 3.45 (br t, J=5.4 Hz, 2H), 3.30-3.35 (m, 4H), 2.27-2.31 (m, 2H), 2.05-2.23 (m, 3H), 1.70-2.02 (m, 3H), 1.36 (t, J=7.3 Hz, 6H), 1.15 (s, 3H) ppm.

Example 12

TCO-Spacelink-Etoposide

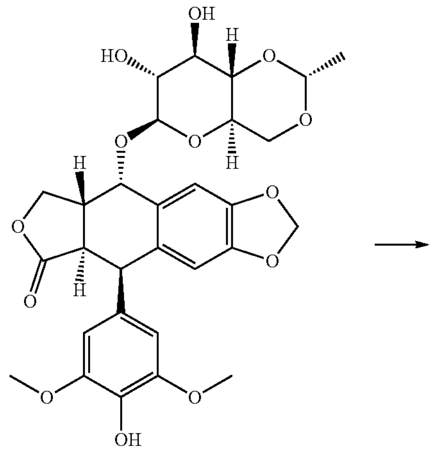

Etoposide

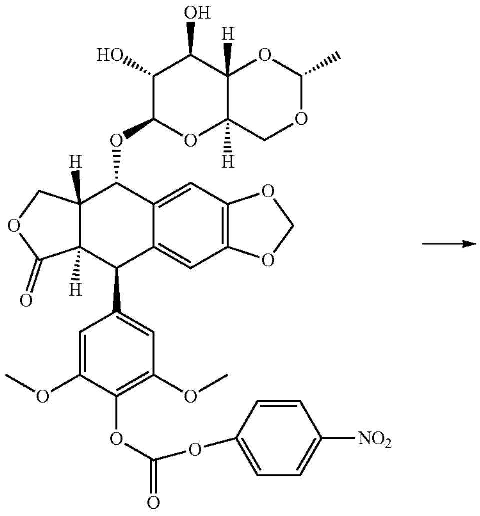

1

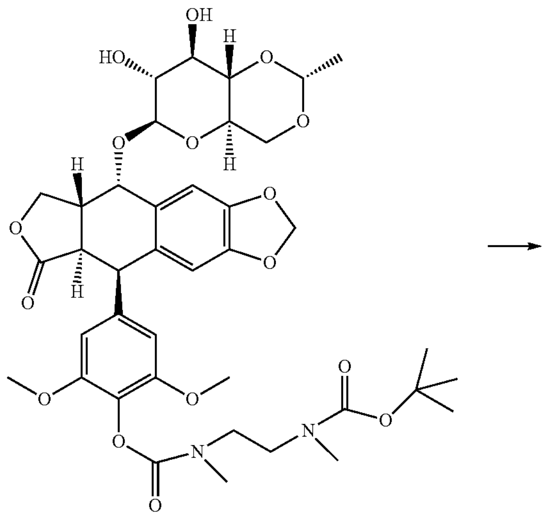

2

-continued

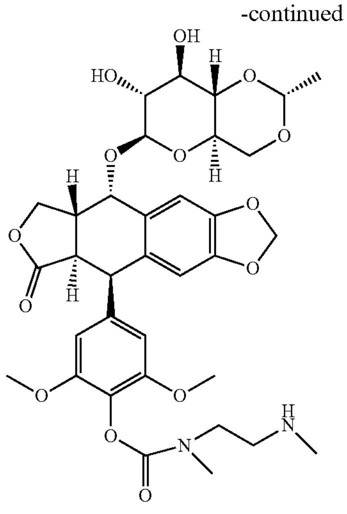

3

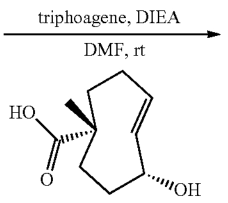

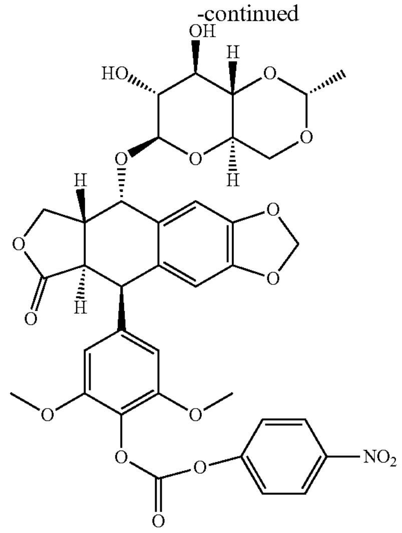

1

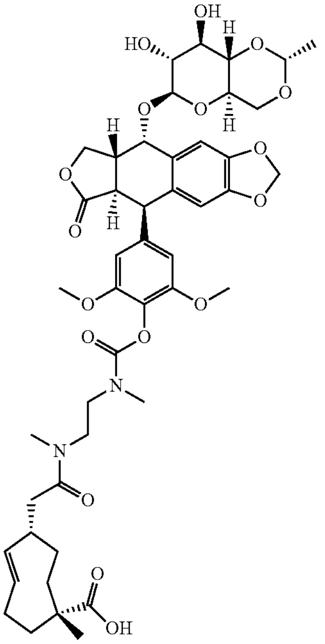

4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl (4-nitrophenyl) carbonate. To a solution of Etoposide (1.0 g, 1.7 mmol) and TEA (2.5 g, 25 mmol) in anhydrous THF (35 mL) was added a solution of, 4-nitrophenyl chloroformate (0.39 g, 1.95 mmol) in anhydrous THF (15 mL). The reaction mixture was stirred at room temperature overnight. The mixture was filtered and concentrated under reduced pressure. The residue was' purified by flash column chromatography (silica gel, DCM/$CH_3CN$ 2/1) to give compound 1 (0.78 g, 60% yield). LCMS: (m/z, C36H35NO17)=754.2 $[M+H]^+$; observe 754.1.

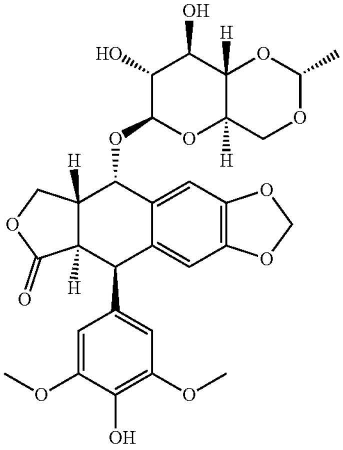

Etoposide

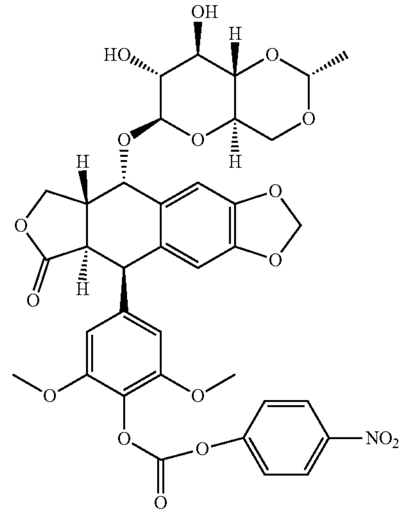

1

-continued

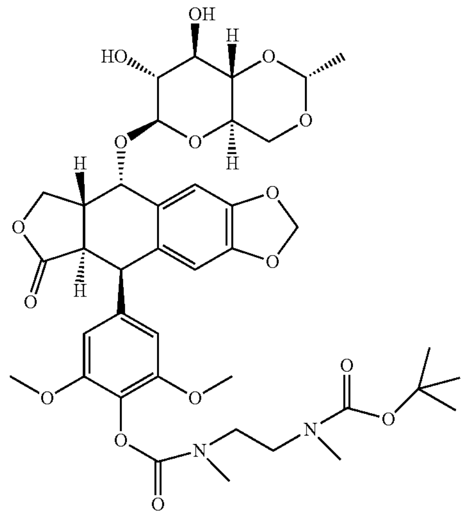

2

Chemical Formula: $C_{39}H_{50}N_2O_{15}$
Exact Mass: 802.32
Molecular Weight: 802.83 tert-butyl (4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl) ethane-1,2-diylbis(methylcarbamate). To a solution of etoposide carbonate compound 1 (1.2 g, 1.6 mmol) in DMF (10 mL) was added N-Boc, N,N'-dimethyl-ethylenediamine (450 mg, 2.37 mmol), DIPEA (0.68 mL, 3.98 mmol), and DMAP (250 mg, 2.04 mmol) and the reaction mixture was stirred at 60° C. for 3 hrs. The mixture was purified by reverse phase chromatography (C18, ACN/$H_2O$ (FA) 0%-100%) to give compound 2 (650 mg, yield 51%). LCMS: (m/z, C39H50N2O16)=825.3 [M+Na]$^+$; observe 826.1.

-continued

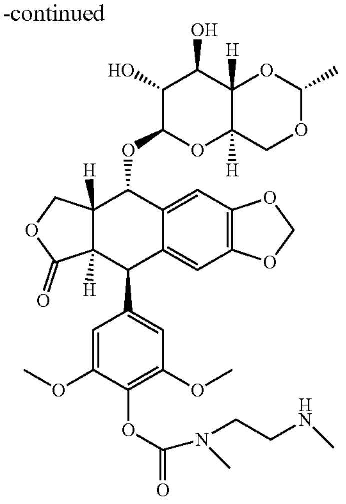

3

4-((5R,5aR,8aR,9S)-9-(((2R,4aR,6R,7R,8R,8aS)-7,8-dihydroxy-2-methylhexahydropyrano[3,2-d][1,3]dioxin-6-yl)oxy)-6-oxo-5,5a,6,8,8a,9-hexahydrofuro[3',4':6,7]naphtho[2,3-d][1,3]dioxol-5-yl)-2,6-dimethoxyphenyl methyl(2-(methylamino)ethyl)carbamate. To a solution of compound 2 (650 mg, 0.81 mmol) in DCM (10 mL) cooled in an ice-water bath was added TFA (1 mL). The mixture was stirred at 0° C. for 6 hrs. The reaction mixture was concentrated under vacuum. The residue was purified by reverse phase chromatography (C18, ACN/$H_2O$ (FA) 0%-100%) to give compound 3 (350 mg, yield 61%). LCMS: (m/z, C34H42N2O14)=703.3 [M+H]$^+$; observe 703.1.

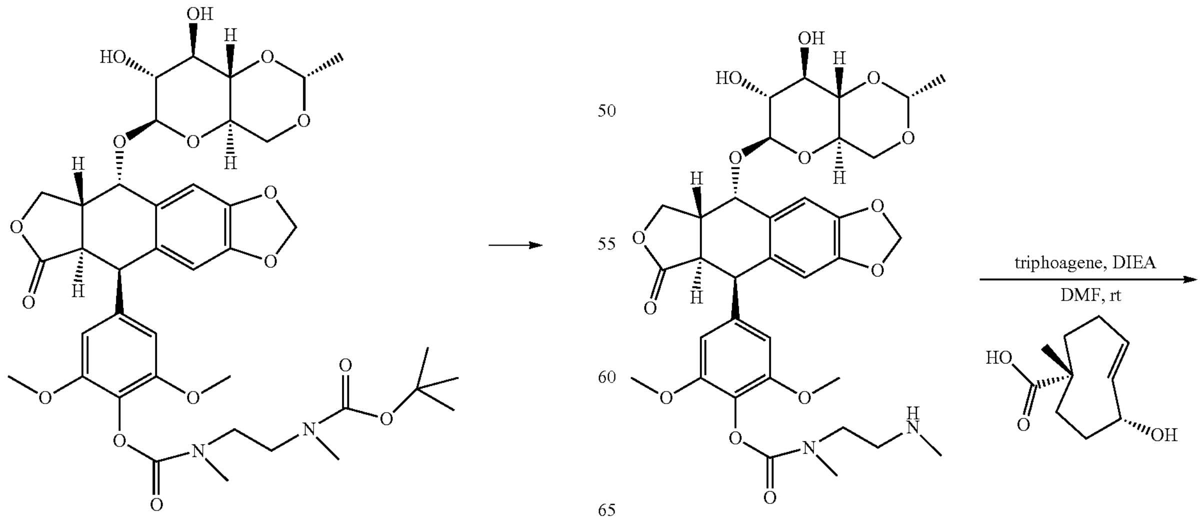

2 3

-continued

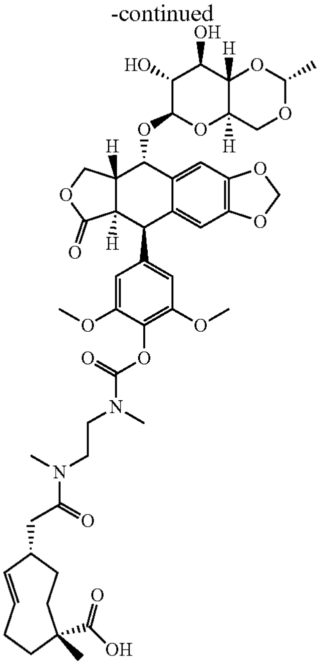

TCO-spacelink-Etoposide. To a solution of TCO (80 mg, 0.434 mmoL) in THF (5 mL) was added Triphosgene (52.5 mg, 0.177 mmoL) and DMAP (130 mg, 1.07 mmoL). The mixture was stirred at room temperature for 30 mins. The mixture was added to a solution of compound 3 (300 mg, 0.427 mmol) and DIPEA (117 mg, 0.9 mmol) in DMF (2 mL) and stirred at room temperature for 5 mins. The mixture was warmed to 50° C. and stirred for another 2 hrs. To the mixture was added EtOAc (20 mL) and HCl (10 mL, 1N in $H_2O$). The organic phase was separated and concentrated. The residue was purified by reverse phase chromatography (C18, ACN/$H_2O$ (FA) 0%-100%) to give TCO-spacelink-Etoposide (105 mg, yield 26.9%). LCMS: (m/z, C45H56N2O18)=911.4 $[M-H]^-$; observe 911.3.

Example 13

TCO(asp)-Exatecan

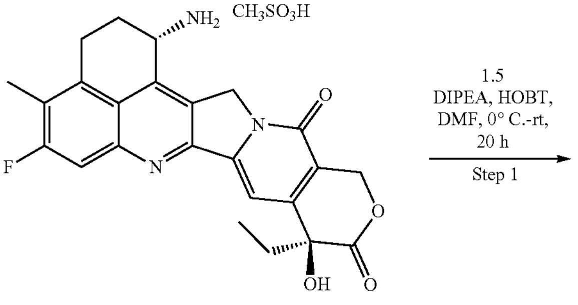

M Wt: 531.5

-continued

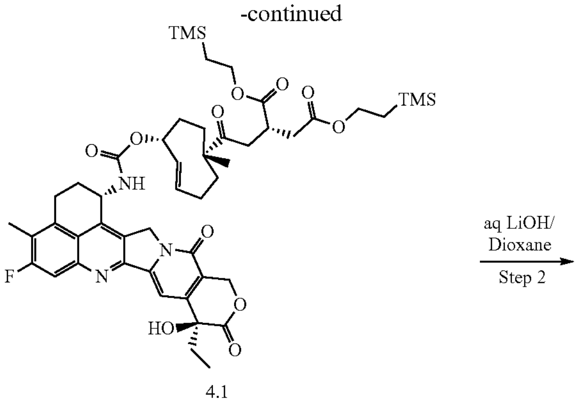

4.1
M Wt: 961.24

TCO(asp)-Exatecan bis(2-(trimethylsilyl)ethyl) ((6R,E)-6-((((1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl) carbamoyl)oxy)-1-methylcyclooct-4-ene-1-carbonyl)-L-aspartate (4.1). Step 1: Compound 1.5 (250 mg, 0.376 mmol, 1.0 eq) was dissolved in DMF (~5 mL) and cooled to 0° C. in an ice-water bath. To the solution was added Exetecan mesylate (220 mg, 0.414 mmol, 1.1 eq, Advanced Chemblocks Cat #10484, Lot 100981), DIPEA (200 μL, 1.1 mmol, 3 eq), and wetted HOBt (144 mg, 0.752 mmol, 2 eq, ~80% purity). The resulting slurry was allowed to warm to room temperature under ambient conditions. After 20 hours, analysis of the reaction by LCMS indicated near complete consumption of the starting materials. The reaction was partitioned with EtOAc and water. The organic phase was washed with water (2×), aq ammonium chloride (1×) and brine. There was some insoluble solid that was removed by filtration. The organic phase was dried with sodium sulfate, filtered and concentrated. The resulting dark brown/black oily residue was dissolved in a minimal amount of DCM and loaded onto a hexane flushed silca gel column (24 g, gold-capped ISCO) and eluted with 0-100% EtOAc in hexanes to afford the desired compound as a sticky grey/green solid (240 mg, 66% yield). (+ESI)$[M+H]^-$=962.2.

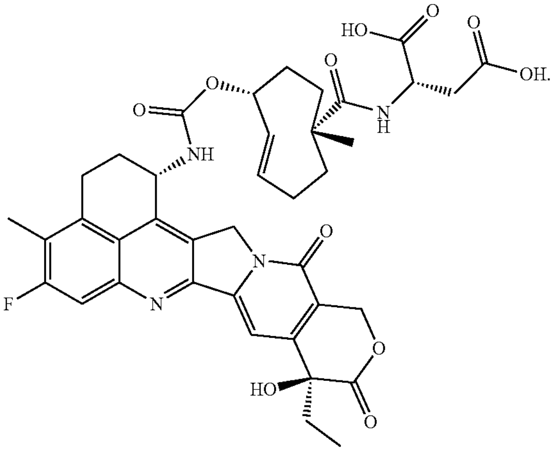

((6R,E)-6-((((1S,9S)-5-fluoro-9-hydroxy-4,9-dimethyl-10,13-dioxo-2,3,9,10,13,15-hexahydro-1H,12H-benzo[de]pyrano[3',4':6,7]indolizino[1,2-b]quinolin-1-yl)carbamoyl)

oxy)-1-methylcyclooct-4-ene-1-carbonyl)-L-aspartic acid (TCO(asp)-Exetecan). Step 2: Compound 4.1 (150 mg, 0.156 mmol, 1.0 eq) was dissolved in 1,4-dioxane (~5 mL). To the solution was added 2.0 M aq LiOH (500 μL, 1.00 mmol, 6.4 eq). Analysis after 1 hour by LCMS indicates the presence of starting material, monoester intermediate, product and by-product. An additional 500 μL of the same LiOH solution was added. After another 30 minutes, LCMS indicated the starting material was consumed and the reaction was an approximate equal ratio of desired compound and side-product. The reaction mixture was acidified first with acetic acid and then with dilute HCl to adjust the pH to 1-2. The product was extracted with EtOAc (5×). The organic extracts were combined, dried with sodium sulfate, filtered and concentrated. The off-white solid was subject to purification by prepHPLC which yielded two separate compounds with identical mass spectra and similar $^{1}H$ NMR spectra. The early eluting peak was labeled as peak 2 (16 mg, 13% yield). (−ESI)[M−H]−=759.4. HPLC (tr=8.73 min). The late eluting peak was labeled as peak 1 (20 mg, 17% yield). (−ESI)[M−H]−=759.4. HPLC (tr=8.96 min).

Example 14

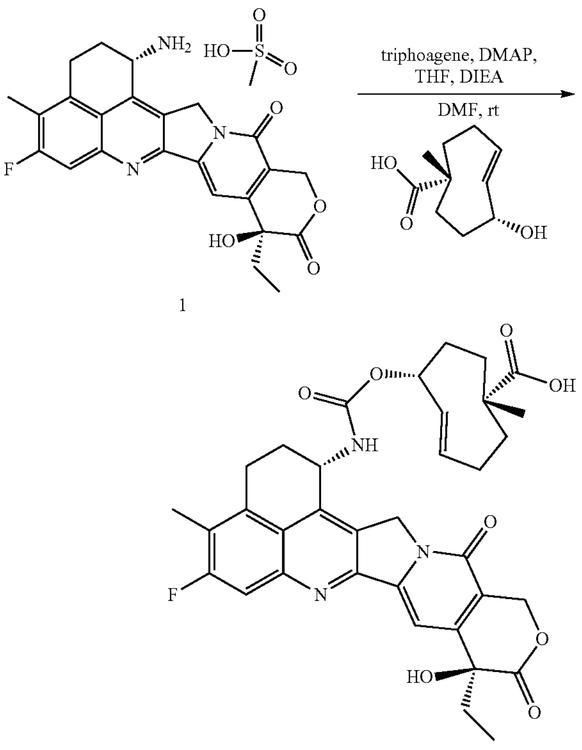

1

TCO-Exatecan. To a mixture of triphosgene (177 mg, 0.6 mmol) in THF (10 mL) was added (1R,6R,E)-6-hydroxy-1-methylcyclooct-4-ene-1-carboxylic acid (220 mg, 1.20 mmol) and DMAP (292 mg, 2.40 mmol). The mixture was stirred at room temperature for 30 mins. The mixture was added to a mixture of compound 1 (700 mg, 1.32 mmol) and DIPEA (510 mg, 3.96 mmol) in DMF (10 mL). The resulting mixture was stirred at room temperature for 12 hours. The mixture was purified by PREP-HPLC (CH3CN/H2O(FA)) 0% to 70%) to give desired product (110 mg, yield 14%). LCMS: (m/z, C35H36FN3O8)=646.3 [M+H]+.

Example C1

In-Vivo Imaging of SQL70-Targeted Fab-TCO Conjugate.

Monoclonal antibodies and antibody drug conjugates are widely prescribed for treatment of different types of cancer. The therapeutic potential of these drugs is limited by their systemic toxicity. Here, we evaluate a targeted version of a biologic drug, termed TCO-Fab, that is intravenously (IV) administered and locally retained upon reacting with a subcutaneously (SC) injected targeting biopolymer.

Study Objective

The goal of this study is to provide a proof-of-concept for using a biopolymer-targeting agent in combination with an appropriately functionalized biologic drug. The biologic drug will be tracked to the injection site of the biopolymer using in vivo imaging.

Study Design

Six-week-old, female nu/nu mice were SC injected with 100 μL of SQL70 biopolymer (Group 1 and Group 2) or control biopolymer (Group 3, used as negative control) in the right flank.

One hour after the SQL70 biopolymer injection, animals were dosed IV via tail vein injections (TVI) with TCO-Fab-Cy5.5 at 10 mg/kg (Group 1), or Fab-Cy5.5 at 10 mg/kg (Group 2, as a negative control).

One hour after the control biopolymer, animals were dosed via TVI with TCO-Fab-Cy5.5 at 10 mg/kg (Group 3) as a negative control. The three treatment groups are detailed in Table 1.

TABLE 1

| Treatment Groups | | | | |
|---|---|---|---|---|
| Group | Subcutaneous Injection on Day 1 | IV Drug | Dose Level (mg/kg/dose) | Dosing Day |
| 1 | 100 μL SQL70 | TCO-Fab-Cy5.5 | 10 | 1 |
| 2 | 100 μL SQL70 | Fab-Cy5.5 | 10 | 1 |
| 3 | 100 μL Control biopolymer | TCO-Fab-Cy5.5 | 10 | 1 |

Test Articles a. TCO-Fab-Cy5.5—(Ranibizumab-Cy5.5-TCO Conjugate)

Supplier: |Storage: 4° C., protected from light

Description: clear solution with red color.

Formulation: Protein concentration as indicated in 25 mM sodium citrate, 100 mM sodium chloride, pH 5.5; sterile; ready for injection.

b. Fab-Cy5.5—(Ranibizumab-Cy5.5 Conjugate)

Supplier: |Storage: 4° C., protected from light

Description: clear solution with blue color.

Formulation: Protein concentration as indicated in 25 mM sodium citrate, 100 mM sodium chloride, pH 5.5; sterile; ready for injection.

c. SQL70 Biopolymer

A tetrazine-modified sodium hyaluronate modified as in the formula

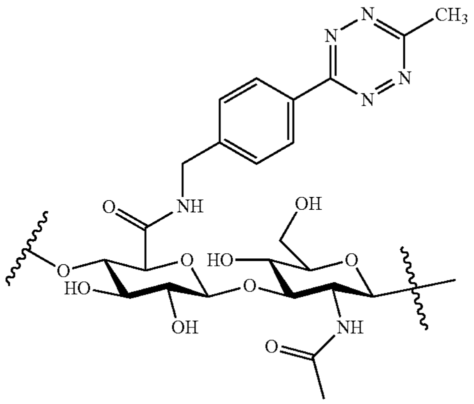

having ~10-15 kD MW and ~30% modification

Supplier: |Storage: 4° C., protected from light

Description: dark pink injectable liquid

Formulation: Sterile and already formulated in sodium chloride/sodium phosphate buffer a 63.2 mg/mL.

d. Control Biopolymer (Hyaluronic Acid)

Supplier: |Storage: 4° C.

Description: White hygroscopic solid.

Formulation: One time formulation in saline at pH 7.4 (63.2 mg/mL concentration) will be required. The product will be filtered through a 0.2-μm syringe filter inside a biohazard hood/under aseptic conditions. Once formulated, the control biopolymer is stable at 4° C. Please prepare fresh or up to 1 day ahead before use.

Dosing

Test articles and vehicle solution were administrated at indicated doses, routes and times, as described in Table 1. Dosing volumes were determined based on actual BWs of individual mice on the previous measurement day.

Live Imaging

Mice were imaged after biopolymer injection to determine baseline values. Mice were imaged at 1 h, 4 h, 24 h and 72 h post the IV injection. (NOTE: the timing is based on the IV injection of the different test articles and not the SC injection of the biopolymers.)

Fluorescent filters used were 680 nm excitation and 720 nm emission for Cy5.5.

At 72 hours post the IV injection (once the last live imaging time point has been completed), tissues were removed from the injection site for ex vivo imaging. The biopolymer injection site was defined as the region of interest for each animal.

Fluorescent filters used will be 680 nm excitation and 720 nm emission for Cy5.5.

Mice had no adverse reactions to the therapeutic. All were healthy and active throughout the study. One mouse in Group 1 (10 mg/kg TCO-Fab-Cy5.5) showed a signal at the site of the SQL70 injection versus the subjects of Group 2 and Group 3 (FIG. 1). Fluorescent signals can be seen in the liver, kidneys and bladder as the drug clears the body.

The invention claimed is:
1. A compound:
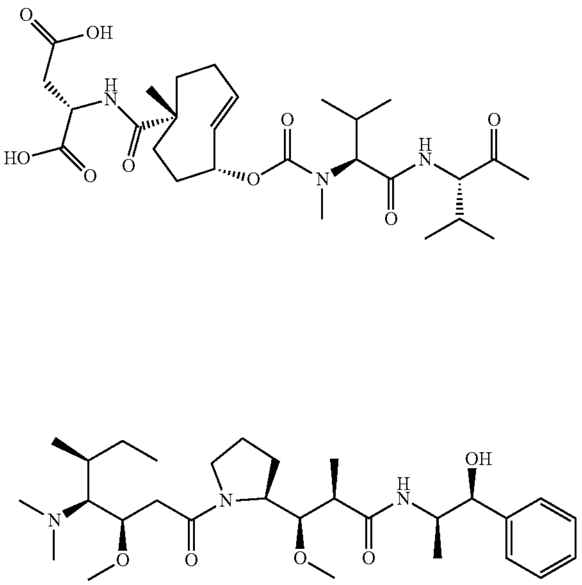
or a pharmaceutically acceptable salt thereof.
2. A pharmaceutical composition comprising the compound of claim 1, or a pharmaceutically acceptable salt thereof, and a pharmaceutically acceptable carrier.
3. A compound:
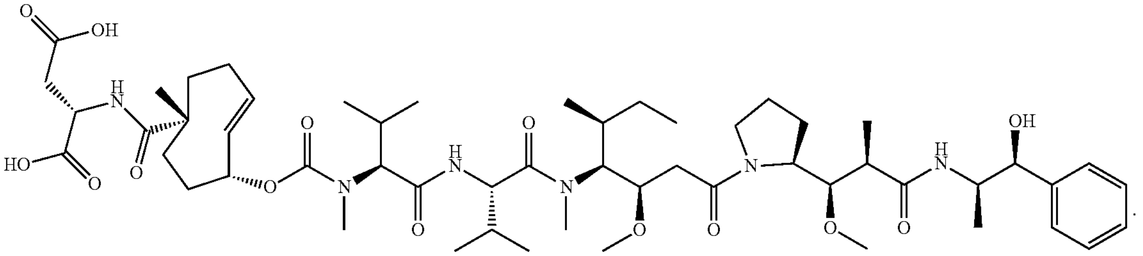

4. A pharmaceutical composition comprising the compound of claim 3 and a pharmaceutically acceptable carrier.

* * * * *

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Gly Phe Leu Gly
1


<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Ala Leu Ala Leu
1
```